(12) United States Patent
Fields et al.

(10) Patent No.: US 12,180,535 B2
(45) Date of Patent: Dec. 31, 2024

(54) TAGGING NUCLEIC ACIDS FOR SEQUENCE ASSEMBLY

(71) Applicant: Dovetail Genomics, LLC, Scotts Valley, CA (US)

(72) Inventors: Andrew Fields, Santa Cruz, CA (US); Paul Hartley, San Jose, CA (US); Nicholas Putnam, Santa Cruz, CA (US); Brandon Rice, Santa Cruz, CA (US); Jonathan Stites, Santa Cruz, CA (US)

(73) Assignee: DOVETAIL GENOMICS, LLC, Santa Cruz, CA (US)

(*) Notice: Subject to any disclaimer, the term of this patent is extended or adjusted under 35 U.S.C. 154(b) by 1184 days.

(21) Appl. No.: 16/685,855

(22) Filed: Nov. 15, 2019

(65) Prior Publication Data

US 2020/0283823 A1  Sep. 10, 2020

Related U.S. Application Data

(63) Continuation of application No. 15/329,414, filed as application No. PCT/US2015/043327 on Jul. 31, 2015, now Pat. No. 10,526,641.

(60) Provisional application No. 62/032,166, filed on Aug. 1, 2014, provisional application No. 62/032,181, filed on Aug. 1, 2014, provisional application No. 62/032,139, filed on Aug. 1, 2014, provisional application No. 62/032,221, filed on Aug. 1, 2014.

(51) Int. Cl.
*C12Q 1/6806* (2018.01)
*C12Q 1/6874* (2018.01)

(52) U.S. Cl.
CPC ......... *C12Q 1/6806* (2013.01); *C12Q 1/6874* (2013.01)

(58) Field of Classification Search
None
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,988,617 A | 1/1991 | Landegren et al. |
| 5,143,854 A | 9/1992 | Pirrung et al. |
| 5,234,809 A | 8/1993 | Boom et al. |
| 5,242,794 A | 9/1993 | Whiteley et al. |
| 5,348,853 A | 9/1994 | Wang et al. |
| 5,476,930 A | 12/1995 | Letsinger et al. |
| 5,494,810 A | 2/1996 | Barany et al. |
| 5,567,583 A | 10/1996 | Wang et al. |
| 5,571,639 A | 11/1996 | Hubbell et al. |
| 5,593,839 A | 1/1997 | Hubbell et al. |
| 5,705,628 A | 1/1998 | Hawkins |
| 5,780,613 A | 7/1998 | Letsinger et al. |
| 5,786,146 A | 7/1998 | Herman et al. |
| 5,837,832 A | 11/1998 | Chee et al. |
| 5,989,823 A | 11/1999 | Jayasena et al. |
| 5,994,056 A | 11/1999 | Higuchi |
| 6,033,854 A | 3/2000 | Kurnit et al. |
| 6,110,709 A | 8/2000 | Ausubel et al. |
| 6,117,635 A | 9/2000 | Nazarenko et al. |
| 6,171,785 B1 | 1/2001 | Higuchi |
| 6,174,670 B1 | 1/2001 | Wittwer et al. |
| 6,225,109 B1 | 5/2001 | Juncosa et al. |
| 6,287,766 B1 | 9/2001 | Nolan et al. |
| 6,326,145 B1 | 12/2001 | Whitcombe et al. |
| 6,416,950 B1 | 7/2002 | Lohse et al. |
| 6,449,562 B1 | 9/2002 | Chandler et al. |
| 6,582,938 B1 | 6/2003 | Su et al. |
| 6,787,308 B2 | 9/2004 | Balasubramanian et al. |
| 6,833,246 B2 | 12/2004 | Balasubramanian |
| 6,897,023 B2 | 5/2005 | Fu et al. |
| 6,969,488 B2 | 11/2005 | Bridgham et al. |
| 7,001,724 B1 | 2/2006 | Greenfield |
| 7,361,468 B2 | 4/2008 | Liu et al. |
| 7,414,117 B2 | 8/2008 | Saito et al. |

(Continued)

FOREIGN PATENT DOCUMENTS

| | | |
|---|---|---|
| AU | 2012222108 A1 | 7/2013 |
| DE | 10149786 A1 | 7/2003 |

(Continued)

OTHER PUBLICATIONS

Adams, et al. The Genome Sequence of *Drosophila melanogaster*. Science Mar. 24, 2000, 287.5461: 2185-2195.

(Continued)

*Primary Examiner* — Nancy J Leith

(74) *Attorney, Agent, or Firm* — WILSON SONSINI GOODRICH & ROSATI

(57) ABSTRACT

Various approaches for generating long-distance contiguity information to facilitate contig assembly and phase determination are disclosed. Nucleic acids are assembled into complexes using binding moieties such that, when the nucleic acid backbones are cleaved, the ensuing fragments remain bound. Exposed ends are tagged and ligated either to one another or to tagging moieties such as oligo labels. Ligated junctions are sequenced, and the sequence information is used to assemble contigs into common scaffolds or to assign phase information. Various approaches to tagging the exposed ends are presented.

23 Claims, 36 Drawing Sheets

Specification includes a Sequence Listing.

(56) References Cited

U.S. PATENT DOCUMENTS

| | | |
|---|---|---|
| 7,425,415 B2 | 9/2008 | Pfeifer et al. |
| 7,709,179 B2 | 5/2010 | Iwashita |
| 7,709,197 B2 | 5/2010 | Drmanac |
| 7,901,891 B2 | 3/2011 | Drmanac |
| 7,985,546 B2 | 7/2011 | Church et al. |
| 8,058,004 B2 | 11/2011 | Oleinikov |
| 8,071,296 B2 | 12/2011 | Ruan et al. |
| 8,076,070 B2 | 12/2011 | Chen et al. |
| 8,153,373 B2 | 4/2012 | De Laat et al. |
| 8,278,112 B2 | 10/2012 | Shokat et al. |
| 8,367,322 B2 | 2/2013 | Barany et al. |
| 8,642,295 B2 | 2/2014 | De Laat et al. |
| 8,673,562 B2 | 3/2014 | Drmanac et al. |
| 8,741,577 B2 | 6/2014 | Graneli et al. |
| 8,841,075 B1 | 9/2014 | Borner et al. |
| 9,273,309 B2 | 3/2016 | Dekker et al. |
| 9,411,930 B2 | 8/2016 | Green, Jr. et al. |
| 9,434,985 B2 | 9/2016 | Dekker et al. |
| 9,688,981 B2 | 6/2017 | Dekker et al. |
| 9,708,648 B2 | 7/2017 | Dekker et al. |
| 9,715,573 B2 | 7/2017 | Putnam et al. |
| 9,910,955 B2 | 3/2018 | Green, Jr. et al. |
| 10,059,989 B2 | 8/2018 | Giresi et al. |
| 10,066,227 B2 | 9/2018 | Dekker et al. |
| 10,089,437 B2 | 10/2018 | Green et al. |
| 10,318,706 B2 * | 6/2019 | Putnam ............... C12Q 1/6874 |
| 10,457,934 B2 | 10/2019 | Green et al. |
| 10,526,641 B2 | 1/2020 | Fields et al. |
| 10,529,443 B2 | 1/2020 | Green, Jr. et al. |
| 10,745,744 B2 | 8/2020 | Dekker et al. |
| 10,825,553 B2 | 11/2020 | Green, Jr. et al. |
| 10,947,579 B2 * | 3/2021 | Troll ....................... C40B 40/06 |
| 10,975,417 B2 | 4/2021 | Green, Jr. et al. |
| 11,081,209 B2 | 8/2021 | Green, Jr. et al. |
| 11,091,758 B2 | 8/2021 | Rokhsar et al. |
| 11,326,159 B2 | 5/2022 | Rokhsar |
| 11,535,844 B2 | 12/2022 | Dekker et al. |
| 11,600,361 B2 * | 3/2023 | Putnam ................ G16B 30/00 |
| 2002/0012930 A1 | 1/2002 | Rothberg et al. |
| 2002/0190663 A1 | 12/2002 | Rasmussen |
| 2003/0022207 A1 | 1/2003 | Balasubramanian et al. |
| 2003/0044781 A1 | 3/2003 | Korlach et al. |
| 2003/0064398 A1 | 4/2003 | Barnes |
| 2003/0068629 A1 | 4/2003 | Rothberg et al. |
| 2003/0100102 A1 | 5/2003 | Rothberg et al. |
| 2003/0148344 A1 | 8/2003 | Rothberg et al. |
| 2003/0170689 A1 | 9/2003 | Stamatoyannopoulos et al. |
| 2003/0228627 A1 | 12/2003 | Emerson et al. |
| 2004/0106110 A1 | 6/2004 | Balasubramanian et al. |
| 2004/0197779 A1 | 10/2004 | Apffel |
| 2004/0248161 A1 | 12/2004 | Rothberg et al. |
| 2005/0079510 A1 | 4/2005 | Berka et al. |
| 2005/0100932 A1 | 5/2005 | Lapidus et al. |
| 2005/0124022 A1 | 6/2005 | Srinivasan et al. |
| 2005/0130161 A1 | 6/2005 | Fraser et al. |
| 2005/0260625 A1 | 11/2005 | Wang |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |
| 2006/0040297 A1 | 2/2006 | Leamon et al. |
| 2006/0078909 A1 | 4/2006 | Srinivasan et al. |
| 2006/0078937 A1 | 4/2006 | Korlach et al. |
| 2006/0252061 A1 | 11/2006 | Zabeau et al. |
| 2007/0172839 A1 | 7/2007 | Smith et al. |
| 2007/0231817 A1 | 10/2007 | De Laat et al. |
| 2007/0277251 A1 | 11/2007 | Wartiovaara et al. |
| 2008/0233101 A1 | 9/2008 | Sauer |
| 2009/0111115 A1 | 4/2009 | Drmanac et al. |
| 2009/0186352 A1 | 7/2009 | Akoulitchev et al. |
| 2009/0191598 A1 | 7/2009 | Ruan et al. |
| 2009/0233291 A1 | 9/2009 | Chen et al. |
| 2009/0269771 A1 | 10/2009 | Schroeder |
| 2009/0298064 A1 | 12/2009 | Batzoglou et al. |
| 2010/0062947 A1 | 3/2010 | De Laat et al. |
| 2010/0081141 A1 | 4/2010 | Chen et al. |
| 2010/0093986 A1 | 4/2010 | Zwick et al. |
| 2010/0130373 A1 | 5/2010 | Dekker et al. |
| 2011/0033854 A1 | 2/2011 | Drmanac et al. |
| 2011/0256593 A1 | 10/2011 | Hsieh et al. |
| 2011/0287947 A1 | 11/2011 | Chen et al. |
| 2011/0300537 A1 | 12/2011 | Slepnev |
| 2011/0306504 A1 | 12/2011 | Xiao et al. |
| 2012/0197533 A1 | 8/2012 | Nazarenko et al. |
| 2012/0302449 A1 | 11/2012 | Dong et al. |
| 2012/0330559 A1 | 12/2012 | Jiang et al. |
| 2013/0005585 A1 | 1/2013 | Anderson et al. |
| 2013/0045872 A1 | 2/2013 | Zhou et al. |
| 2013/0084574 A1 | 4/2013 | Dong et al. |
| 2013/0096009 A1 | 4/2013 | Dekker et al. |
| 2013/0183672 A1 | 7/2013 | De Laat et al. |
| 2013/0203605 A1 | 8/2013 | Shendure et al. |
| 2013/0310548 A1 | 11/2013 | Park |
| 2014/0031241 A1 | 1/2014 | Nicol et al. |
| 2014/0057799 A1 | 2/2014 | Johnson et al. |
| 2014/0141982 A1 | 5/2014 | Jacobson et al. |
| 2014/0220587 A1 | 8/2014 | Green, Jr. et al. |
| 2015/0363550 A1 | 12/2015 | Green, Jr. et al. |
| 2018/0080021 A1 | 3/2018 | Reuter et al. |
| 2018/0119203 A1 | 5/2018 | Rice et al. |

FOREIGN PATENT DOCUMENTS

| | | |
|---|---|---|
| DE | 10214395 A1 | 10/2003 |
| DE | 10356837 A1 | 6/2005 |
| DE | 102004009704 A1 | 9/2005 |
| DE | 102004025744 A1 | 12/2005 |
| DE | 102004025745 A1 | 12/2005 |
| DE | 102004025746 A1 | 12/2005 |
| DE | 102004025694 A1 | 2/2006 |
| DE | 102004025695 A1 | 2/2006 |
| DE | 102004025696 A1 | 2/2006 |
| EP | 0476014 A1 | 3/1992 |
| EP | 0624059 A1 | 11/1994 |
| EP | 0717113 A2 | 6/1996 |
| EP | 0728520 A1 | 8/1996 |
| EP | 1967582 A1 | 9/2008 |
| EP | 2083090 A1 | 7/2009 |
| EP | 2624059 A1 | 8/2013 |
| EP | 2811022 A1 | 12/2014 |
| EP | 2951319 B1 | 3/2021 |
| GB | 2519255 A | 4/2015 |
| JP | 2008092904 A | 4/2008 |
| JP | 2009219451 A | 10/2009 |
| JP | 2014506788 A | 3/2014 |
| JP | 2016506733 A | 3/2016 |
| JP | 2019088295 A | 6/2019 |
| WO | WO-9015070 A1 | 12/1990 |
| WO | WO-9210092 A1 | 6/1992 |
| WO | WO-9309668 A1 | 5/1993 |
| WO | WO-9511995 A1 | 5/1995 |
| WO | WO-9729212 A1 | 8/1997 |
| WO | WO-9841651 A1 | 9/1998 |
| WO | WO-0014281 A2 | 3/2000 |
| WO | WO-02088382 A2 | 11/2002 |
| WO | WO-02103046 A2 | 12/2002 |
| WO | WO-03020968 A2 | 3/2003 |
| WO | WO-03031947 A2 | 4/2003 |
| WO | WO-03042657 A2 | 5/2003 |
| WO | WO-2005001113 A2 | 1/2005 |
| WO | WO-2005005655 A1 | 1/2005 |
| WO | WO-2005005657 A1 | 1/2005 |
| WO | WO-2005044836 A2 | 5/2005 |
| WO | WO-2006040550 A1 | 4/2006 |
| WO | WO-2007004057 A2 | 1/2007 |
| WO | WO-2007093819 A2 | 8/2007 |
| WO | WO-2008008845 A2 | 1/2008 |
| WO | WO-2008024473 A2 | 2/2008 |
| WO | WO-2008127281 A2 | 10/2008 |
| WO | WO-2008143903 A2 | 11/2008 |
| WO | WO-2009053039 A1 | 4/2009 |
| WO | WO-2009147386 A1 | 12/2009 |
| WO | WO-2010036323 A2 | 4/2010 |
| WO | WO-2011056872 A2 | 5/2011 |

(56) References Cited

FOREIGN PATENT DOCUMENTS

| | | |
|---|---|---|
| WO | WO-2011106546 A1 | 9/2011 |
| WO | WO-2012005595 A2 | 1/2012 |
| WO | WO-2012045012 A2 | 4/2012 |
| WO | WO-2012047726 A1 | 4/2012 |
| WO | WO-2012054873 A2 | 4/2012 |
| WO | WO-2012106546 A2 | 8/2012 |
| WO | WO-2012142531 A2 | 10/2012 |
| WO | WO-2012142611 A2 | 10/2012 |
| WO | WO-2012150317 A1 | 11/2012 |
| WO | WO-2013078470 A2 | 5/2013 |
| WO | WO-2014012010 A1 | 1/2014 |
| WO | WO-2014047561 A1 | 3/2014 |
| WO | WO-2014121091 A1 | 8/2014 |
| WO | WO-2015089243 A1 | 6/2015 |
| WO | WO-2015123588 A1 | 8/2015 |
| WO | WO-2016019360 A1 | 2/2016 |
| WO | WO-2016044313 A1 | 3/2016 |
| WO | WO-2016061517 A2 | 4/2016 |
| WO | WO-2016089920 A1 | 6/2016 |
| WO | WO-2016134034 A1 | 8/2016 |
| WO | WO-2016154540 A1 | 9/2016 |
| WO | WO-2016164313 A1 | 10/2016 |
| WO | WO-2016207647 A1 | 12/2016 |
| WO | WO-2016207653 A1 | 12/2016 |
| WO | WO-2016207661 A1 | 12/2016 |
| WO | WO-2017070123 A1 | 4/2017 |
| WO | WO-2017147279 A1 | 8/2017 |
| WO | WO-2017197300 A1 | 11/2017 |
| WO | WO-2018195091 A1 | 10/2018 |
| WO | WO-2019094636 A1 | 5/2019 |
| WO | WO-2019152543 A1 | 8/2019 |
| WO | WO-2020047002 A1 | 3/2020 |
| WO | WO-2020223539 A1 | 11/2020 |
| WO | WO-2020264185 A1 | 12/2020 |
| WO | WO-2022147129 A1 | 7/2022 |
| WO | WO-2023091592 A1 | 5/2023 |
| WO | WO-2023146922 A2 | 8/2023 |
| WO | WO-2023220142 A1 | 11/2023 |

OTHER PUBLICATIONS

Adey, A. et al. In vitro, long-range sequence information for 19 de novo genome assembly via transposase contiguity. Genome Res., 24(12):2041-2049, Dec. 2014.
Alkan, C. et al. Limitations of next-generation genome sequence assembly. Nat. Methods, 8(1):61-65, Jan. 2011.
Allison 2007 Fundamental Molecular Biology. Wiley-Blackwell, Chapter 8, pp. 1-15.
Altschul, et al. Gapped BLAST and PSI-BLAST: a new generation of protein database search programs. Nucleic Acids Res 25:3389-3402 (1977).
Amini, S. et al. Haplotype-resolved whole-genome sequencing by contiguity-preserving transposition and combinatorial indexing. Nat. Genet., 46(12):1343-1349, Dec. 2014.
Ausubel, et al., eds. 1993. Current Protocols in Molecular Biology. Part 1: E. coli, plasmids, and bacteriophages, pp. 1-15.
Bansal et al., Hapcut: an efficient and accurate algorithm for the haplotype assembly problem, Bioinformatics, 24(16): i153-i159 (Aug. 9, 2008).
Belton et al. Hi-C: a comprehensive technique to capture the conformation of genomes. Methods 58(3):268-276 (Nov. 1, 2012).
Blander, G. et al.SIRT1 Shows No Substrate Specificity in Vitro. Journal of biological Chemistry (2005) vol. 280, p. 9780-9785.
Blecher-Gonen, Ronnie et al. High-throughput chromatin immunoprecipitation for genome-wide mapping of in vivo protein-DNA interactions and epigenomic states. Nature Protocols, 8(3):539-554 (Feb. 21, 2013).
Bolger, A.M. et al. Trimmomatic: a flexible trimmer for Illumina sequence data. Bioinformatics, 30(15):2114-2120, Aug. 2014.
Bradnam, K.R. et al. Assemblathon 2: evaluating de novo methods of genome assembly in three vertebrate species. Gigascience, 2(1):10, 2013.

Burton, et al. Chromosome-scale scaffolding of de novo genome assemblies based on chromatin interactions. Nat. Biotechnol. 2013, 31: 1119-1125.
Cai et al., "SATB1 packages densely looped transcriptionally active chromatin for coordinated expression of cytokine genes," Nature Genetics, 2006, vol. 38, No. 11, pp. 1278-1288.
Chapman, et al. Meraculous: de novo genome assembly with short paired-end reads. PloS one. 2011, 6.8: e23501.
Constans, A. All in the Family SCIENTIST 13: 36 (2003).
Constans. Beyond Sanger: Toward the $1,000 Genome—The Scientist—Magazine of the Life Sciences. The Scientist. Jun. 30, 2003; 17(13):36.
International Search Report and Written Opinion, PCT/US2014/069642 dated Mar. 31, 2015, pp. 1-10.
Cortese, J. Array of options. SCIENTIST. 2000, 14.11: 26.
Cortese, J. The array of today. SCIENTIST. 2000, 14.17: 25.
De Koning, A.P. et al. Repetitive elements may comprise over two-thirds of the human genome. PLoS Genet., 7(12):e1002384, Dec. 2011.
Dekker et al., A closer look at long-range chromosomal interactions. TRENDS in Biochemical Science (Jun. 2003) 28(6):277-280.
Dekker et al., "Capturing chromosome conformation," Science, 2002, vol. 295, pp. 1306-1311.
Dixon, J. R. et al. Topological domains in mammalian genomes identified by analysis of chromatin interactions. Nature, 485(7398):376-380, May 2012.
Dostie et al., "Chromosome Conformation Capture Carbon Copy (5C): a massively parallel solution for mapping interaction between genomic elements," Genome research, 2006, vol. 16, No. 10, pp. 1299-1309.
Dower, et al. Recombinant and synthetic randomized peptide libraries. Ann. Rep. Med. Chem. 1991, 26:271-280.
Drmanac, et al. Human Genome Sequencing Using Unchained Base Reads on Self-Assembling DNA Nanoarrays. Science Jan. 1, 2010, 327.5961: 78-81.
Drmanac et al. Human genome sequencing using unchained base reads on self-assembling DNA nanoarrays. Science. 327: 78-81 (2010).
Eisenstein, Oxford Nanopore announcement sets sequencing sector abuzz. Nat Biotechnol. 30(4): 295-296 (2012).
Ekins, R. et al. Microarrays: Their Origins and applications. Trends in Biotechnology, 17(6); 217-218 (Jun. 1999).
Fan et al. "A versatile assay for high-throughput gene expression profiling on universal array matrices." Genome Research, 2004, vol. 14 No. 5 pp. 878-885.
Fangman, et al. Activation of replication origins within yeast chromosomes, Annual Review of Cell Biology, 7(1); 375-402 (1991).
Ferraiuolo, M.A. et al. From cells to chromatin: capturing snapshots of genome organization with 5C technology. Methods. Nov. 2012;58(3):255-67. Epub Nov. 5, 2012.
Flot, JF et al. Contact genomics: scaffolding and phasing (meta) genomes using chromosome 3D physical signatures. FEBS Letters 589 (2015) 2966-2974.
Fodor, et al. Light-directed, spatially addressable parallel chemical synthesis. Science. Feb. 15, 1991, 251.4995: 767-773.
Fullwood, et al. "ChIP-Based Methods for the Identification of Long-Range Chromatin Interactions" Journal of Cellular Biochemistry, vol. 107, No. 1, pp. 30-39, May 2009.
Fullwood, et al. Next Generation DNA sequencing of paired-end tags (PET) for transcriptome and genome analyses. Genome Research. 19(4):521-532 (Apr. 2009).
Fullwood, MJ. Et al. Chromatin interaction analysis using paired-end tag sequencing. Jan. 2010. Curr. Prot. In Mol. Biol. Chapter 21; unit 21 .15.1-25.
Fyodorov, et al. Chromatin assembly in vitro with purified recombinant ACF and NAP-1. Methods in enzymology. 2002, 371: 499-515.
Garaj, et al. Graphene as a sub-nanometer trans-electrode membrane. Nature. Sep. 9, 2010, 467.7312: 190-193.
Garstecki et al., Formation of bubbles and droplets in microfluidic systems. Technical sciences 53(4): 69 (2005).

(56) References Cited

OTHER PUBLICATIONS

GE Healthcare: Instructions 71-7106-00AF Activated Thiol Sepharose 4B (pp. 1-12) (Jul. 2008).
Gilmour, David S., et al. Detecting protein-DNA interactions in vivo: distribution of RNA polymerase on specific bacterial genes. Proceedings of the National Academy of Sciences. (1984) 81(14): 4275-4279.
Gish et al. Identification of protein coding regions by database similarity search. Nature Genetics 3:266-272 (1993).
Gnerre, S. et al. High-quality draft assemblies of mammalian genomes from massively parallel sequence data. Proc. Natl. Acad. Sci. U.S.A., 108 (4):1513-1518, Jan. 2011.
Goodwin, S. et al. Oxford nanopore sequencing and de novo assembly of a eukaryotic genome. bioRxiv, pp. 1-28 (Jul. 15, 2015).
Green R.E. et al. Three crocodilian genomes reveal ancestral patterns of evolution among archosaurs. Science, 346(6215):1254449 (1-11) (Dec. 12, 2014).
Grunenwald et al., "Rapid, high-throughput library preparation for next-generation sequencing" 2010 Nature Methods, vol. 7.
Gwynne, P. et al. Microarray analysis: the next revolution in molecular biology. Science. pp. 1-6 (Aug. 6, 1999).
Haussler, D., et al. Genome 10K: a proposal to obtain whole-genome sequence for 10,000 vertebrate species. J. Hered., 100(6):659-674, 2009.
Heid, C.A. et al. Real time quantitative PCR. Genome Research, 6(10): 986-994 (1996).
Herschleb, J. et al. Pulsed-field gel electrophoresis. Pulsed-field gel electrophoresis. Nature Protocols 2(3):677-84 (Mar. 29, 2007).
Hesselberth, Jay R. et al. Global mapping of protein-DNA interaction in vivo by digital genomic footprinting, Nature Methods 6(4): 283-289 (Apr. 2009).
International Application No. PCT/US16/57557 International Search Report and Written Opinion dated Mar. 10, 2017.
International Application No. PCT/US17/32466 International Search Report and Written Opinion dated Aug. 22, 2017.
International Application No. PCT/US2014/014184 International Search Report and Written Opinion dated Apr. 23, 2014.
International Application No. PCT/US2015/043327 International Preliminary Report on Patentability dated Feb. 7, 2017.
International Application No. PCT/US2016/018295 International Preliminary Report on Patentability dated Aug. 31, 2017 .
International Application No. PCT/US2016/018295 International Search Report dated Aug. 4, 2016.
International Application No. PCT/US2016/024225 International Preliminary Report on Patentability dated Sep. 26, 2017.
International Application No. PCT/US2016/024225 International Search Report dated Jul. 10, 2016.
International Application No. PCT/US2016/057557 International Preliminary Report on Patentability dated May 3, 2018.
International Human Genome Sequencing Consortium. Finishing the euchromatic sequence of the human genome. Nature, 431(7011):931-945, Oct. 2004.
International Preliminary Report on Patentability and Written Opinion, PCT/US2014/069642, dated Jun. 23, 2016.
Jansen, et al. Nucleosome Positioning in *Saccharomyces cerevisiae*. Microbiology and Molecular Biology Reviews, Jun. 2011, pp. 301-320.
Kalhor, R. et al. Genome architectures revealed by tethered chromosome conformation capture and population-based modeling, Nature Biotechnology, 30(1): 90-98 (Jan. 2012).
Kaplan, N. et al. High-throughput genome scaffolding from in vivo DNA interaction frequency. Nat. Biotechnol., 31(12):1143-1147 (Dec. 2013).
Kidd, J. M. et al. Mapping and sequencing of structural variation from eight human genomes. Nature, 453(7191):56-64, May 2008.
Kitzman, Jacob O. et al. Haplotype-resolved genome sequencing of a Gujarati Indian individual, Nature Biotechnology, 29(1): 59-63 (Jan. 2011).
Koren, S. et al. Hybrid error correction and de novo assembly of single-molecule sequencing reads. Nature biotechnology, 30(7):693-700, 2012.
Kotoulas, S. et al. The chipping forecast. Special supplement to Nature Genetics vol. 21; pp. 1-6 (1999).
Kundu et al. Activator-dependent transcription from chromatin in vitro involving targeted histone acetylation by p300. Molecular cell. 2000, 6.3: 551-561.
Lasken, Roger S. et al. Mechanism of chimera formation during the Multiple Displacement Amplification reaction. BMC biotechnology. 7(19):1-11 (Apr. 12, 2007).
Lee, T.I. et al. Chromatin immunoprecipitation and microarray-based analysis of protein location, Nature Protocols 1(2): 729-748 (2006).
Lemieux, B. et al. Overview of DNA chip technology. Molecular Breeding 4: 277-289 (1998).
Levene, M.J. et al., Zero-Mode Waveguides for Single-Molecule Analysis at High Concentrations, Science, 299(5607):682-686 (Jan. 31, 2003).
Lieberman-Aiden, E. et al. Comprehensive mapping of long-range interactions reveals folding principles of the human genome. Science, 326(5950):289-293, Oct. 2009.
Liu, B. et al. COPE: an accurate k-mer-based pair-end reads connection tool to facilitate genome assembly. Bioinformatics, 28(22): 2870-2874 (Oct. 8, 2012).
Lupski, James R. et al. Whole-genome sequencing in a patient with Charcot-Marie-Tooth neuropathy. New England Journal of Medicine, 362(13): 1181-1191 (Apr. 1, 2010).
Lusser, Alexandra et al. Strategies for the reconstitution of chromatin. Nature Methods, 1(1):19-26 (Oct. 2004).
Ma, H. et al. Application of Real-time Polymerase Chain Reaction (RT-PCR), The Journal of American Science, 2 (3):1-15 (Aug. 10, 2006).
Madden et al., Applications of network BLAST server. Methods Enzymol. 266:131-141 (1996).
Maniatis, et al. Molecular Cloning: A Laboratory Manual, Cold Spring Harbor, N.Y., pp. 280-281 (1982).
Margulies, M. et al. Genome sequencing in open microfabricated high density picolitre reactors. Nature 437(7057):376-380 (Sep. 15, 2005).
Marie-Nelly, H. et al. High-quality genome (re)assembly using chromosomal contact data. Nature Communications 5:5695 (Dec. 17, 2014).
Marshall, A. et al. DNA chips: an array of possibilities. Nature Biotechnology, 16(1): 27-31 (Jan. 1998).
Mary, I. et al. Metaproteomic and metagenomic analyses of defined oceanic microbial populations using microwave cell fixation and flow cytometric sorting. FEMS Microbiol Ecol. 74(1):10-18 (Oct. 2010). E-Pub. Jul. 5, 2010.
Meyer, M. et al. Illumina sequencing library preparation for highly multiplexed target capture and sequencing. Cold Spring Harb Protoc, 2010(6):pdb.prot5448 (Jun. 2010).
Miller et al. A Simple salting out procedure for extracting DNA from human nucleated cells. Nucleic Acids Research vol. 16, No. 3, 1215 (1988).
Morrison, AJ et al. Retinoblastoma Protein Transcriptional Repression through Histone Deacetylation of a Single Nucleosome. Molecular and Cellular biology 22(3);856-865 (Feb. 2002).
Myers, E.W. et al. A Whole-Genome Assembly of *Drosophila*. Science, 287(5461):2196-2204 (Mar. 24, 2000).
Nazarenko, I.A. et al. A closed tube format for amplification and detection of DNA based on energy transfer. Nucleic acids research, 25(12):2516-2521 (Jun. 15, 1997).
PCT/US2014/014184 International Preliminary Report on Patentability dated Aug. 13, 2015.
Peng, Z. et al. Generation of long insert pairs using a Cre-LoxP Inverse PCR approach, PLoS One, 7(1): e29437 (2012) E-Pub Jan. 9, 2012.
Peters, B.A. et al. Accurate whole-genome sequencing and haplotyping from 10 to 20 human cells. Nature, 487(7406):190-195 (Jul. 11, 2012).

(56) References Cited

OTHER PUBLICATIONS

Putnam, N. H. et al. Supplemental Material—Chromosome-scale shotgun assembly using an in vitro method for long-range linkage. Genome Research 26:342-350 (2016). E-Pub Feb. 4, 2016.
Putnam, N.H. et al. Chromosome-scale shotgun assembly using an in vitro method for long-range linkage. arXiv:1502.05331[q-bio. GN] pp. 1-25. Feb. 18, 2015 (Retrieved from the Internet Oct. 8, 2015).
Putnam, Nicholas H. et al. Chromosome-scale shotgun assembly using an in vitro method for long-range linkage. Genome Research, 26(3):342-350 (Mar. 2016).
Quail, M.A. et al. A tale of three next generation sequencing platforms: comparison of Ion Torrent, Pacific Biosciences and Illumina MiSeq sequencers. BMC Genomics, 13:341 (Jul. 24, 2012).
Rios, J. et al. Identification by whole-genome resequencing of gene defect responsible for severe hypercholesterolemia. Human Molecular Genetics, 19(22): 4313-4318 (Nov. 15, 2010). E-Pub Aug. 18, 2010).
Rozowsky, J. et al. AlleleSeq: analysis of allele-specific expression and binding in a network framework. Mol. Syst. Biol., 7:522; pp. 1-15 (Aug. 2, 2011).
Salzberg, S.L. et al. Gage: A critical evaluation of genome assemblies and assembly algorithms. Genome Res., 22(3):557-567 (Mar. 2012). E-Pub Jan. 6, 2012.
Sambrook, et al. Mixed Oligonucleotide-primed Amplification of cDNA (MOPAC). Cold Spring Harbor Protocols, pp. 1-30 (2006).
Schena M. (ed.), Microarray Biochip Technology (2000). A biotechniques Books Publication. Eaton Publishing, pp. 1-44. ISBN-10: 1881299376 ISBN-13: 978-1881299370.
Schena, M. et al. PCR applications: protocols for functional genomics. Chapter 28: Parallel analysis with biological chips. Eds. Michael A. Innis, David H. Gelfand, John J. Sninsky. Academic Press. ISBN: 0-12-372185-7. pp. 445-456 (1999) .
Schena, Mark et al. Genes, genomes, and chips. DNA microarrays: A practical approach. Oxford University Press, pp. 1-18 (1999); ISBN-10: 1881299376 ISBN-13: 978-1881299370.
Schloss, P.D. et al. A statistical toolbox for metagenomics: assessing functional diversity in microbial communities, BMC Bioinformatics 9(34):1-15 (Jan. 23, 2008).
Schmidt, D. et al. ChIP-seq: using high-throughput sequencing to discover protein-DNA interactions. Methods 48(3): 240-248(Jul. 2009).
Schutze, T. et al. A calibrated diversity assay for nucleic acid libraries using DiStRO—a Diversity Standard of Random Oligonucleotides. Nucleic Acids Research, 38(4):e23 (pp. 1-5) Mar. 2010; epub Dec. 3, 2009.
Schwartz, D.C. et al. Separation of yeast chromosome-sized DNAs by pulsed field gradient gel electrophoresis. Cell 37(1): 67-75 (May 1984).
Selvaraj, S. et al. Whole-genome haplotype reconstruction using proximity-ligation and shotgun sequencing. Nature Biotechnology, 31(12):1111-1118 (Dec. 2013).
Selvaraj, S. et al. Complete haplotype phasing of the MHC and KIR loci with targeted HaploSeq. BMC Genomics 16:900, pp. 1-7 (Nov. 5, 2015).
Combined Search and Examination Report under Sections 17 & 18(3), Great Britain Patent Application No. GB1520448.0, dated May 31, 2016.
Sexton et al., Sensitive detection of chromatin coassociations using enhanced chromosome conformation capture on chip. Nature Protocols. 7(7):1335-1350 (2012).
Shalon, D. et al. A DNA microarray system for analyzing complex DNA samples using two-color fluorescent probe hybridization. Genome research, 6(7): 639-645 (Jul. 1996).
Shedlock, A.M. et al. Phylogenomics of nonavian reptiles and the structure of the ancestral amniote genome. Proc. Natl. Acad. Sci. U.S.A., 104(8):2767-2772 (Feb. 20, 2007). E-Pub Feb. 16, 2007.
Sheridan, C. Milestone approval lifts Illumina's NGS from research into clinic. Nature Biotechnology, 32(2):111-112 (Feb. 2014).
Shiio Y., et al. Quantitative proteome analysis using isotope-coded affinity tags and mass spectrometry. Nature Protocols, 1(1): 139-145 (2006).
Sigma Protein A immobilized product sheet (Published Mar. 2001) accessed on Apr. 14, 2016.
Simpson, et al. Efficient de novo assembly of large genomes using compressed data structures. Genome Res. Mar. 2012; 22(3): 549-556.
Solomon, M.J. et al. Formaldehyde-mediated DNA-protein crosslinking: a probe for in vivo chromatin structures. Proceedings of the National Academy of Sciences, 82(19): 6470-6474 (Oct. 1985).
Solomon, M.J. et al. Mapping protein-DNA interactions in vivo with formaldehyde: evidence that histone H4 is retained on a highly transcribed gene. Cell, 53(6):937-947 (Jun. 17, 1988).
Soni, et al. Progress toward ultrafast DNA sequencing using solid-state nanopores. Clin Chem, 53(11):1996-2001 (Nov. 2007). Epub Sep. 21, 2007.
Splinter, E. 3C Technology: Analyzing the Spatial Organization of Genomic Loci In Vivo Methods in Enzymology, 375:493-507 (2004).
Splinter, E. et al. Determining long-range chromatin interactions for selected genomic sites using 4C-seq technology: from fixation to computation. Methods. Nov. 2012;58(3):221-30. (Epub May 17, 2012).
Stadhouders et al., Multiplexed chromosome conformation capture sequencing for rapid genome-scale high-resolution detection of long-range chromatin interactions. Nature Protocols. 8(3):509-524 (2013).
Storek, Michael J. et al. High-resolution footprinting of sequence-specific protein-DNA contacts, Nature Biotechnology, 20(2):183-186 (Feb. 1, 2002).
Syed, F. et al. Optimized library preparation method for next-generation sequencing. Application Note Abstract, Nature Methods 6:i-ii (Oct. 2009).
Tanizawa, H. et al., Mapping of long-range associations throughout the fission yeast genome reveals global genome organization linked to transcriptional regulation. Nucleic Acid Research, 38(22):8164-8177 (Dec. 2010). Epub Oct. 28, 2010.
Teague, B. et al. High-resolution human genome structure by single-molecule analysis. Proceedings of the National Academy of Sciences, 107(24): 10848-10853 (Jun. 15, 2010).
Torjensen, I. Genomes of 100,000 people will be sequenced to create an open access research resource. BMJ, 347:f6690 (Nov. 6, 2013).
Tuzun, E. et al. Fine-scale structural variation of the human genome. Nat. Genet., 37(7):727-732 (Jul. 2005). Epub May 15, 2005.
Tyagi, S. et al. Molecular beacons: probes that fluoresce upon hybridization. Nature Biotechnology, 14(3):303-308 (Mar. 1996).
Umbarger, M.A. Chromosome conformation capture assays in bacteria. Methods 58(3):212-220 (Nov. 2012).
U.S. Appl. No. 14/764,945 Non-Final Office Action dated Sep. 22, 2017.
U.S. Appl. No. 15/045,818 Non-Final Office Action dated Jan. 30, 2017.
U.S. Appl. No. 15/045,818 Non-final Office Action dated Sep. 1, 2016.
U.S. Appl. No. 15/045,818 Notice of Allowance dated May 19, 2017.
U.S. Appl. No. 15/137,988 Notice of Allowance dated Mar. 15, 2017.
U.S. Appl. No. 15/167,880 Non-Final Office Action dated Jul. 3, 2017.
U.S. Appl. No. 15/167,880 Notice of Allowance dated Oct. 26, 2017.
U.S. Appl. No. 15/329,414 Final Office Action dated May 14, 2019.
U.S. Appl. No. 15/329,414 Final Office Action dated Oct. 9, 2018.
U.S. Appl. No. 15/329,414 Non-Final Office Action dated May 2, 2018.
U.S. Appl. No. 15/649,268 Final Office Action dated Apr. 18, 2018.
U.S. Appl. No. 15/649,268 Non-Final Office Action dated Oct. 20, 2017.
U.S. Appl. No. 14/170,339 Non-Final Office Action dated Oct. 20, 2014.

(56) References Cited

OTHER PUBLICATIONS

U.S. Appl. No. 14/170,339 Restriction Requirement dated Mar. 14, 2014.
Venter, J.C. et al. The sequence of the human genome. Science, 291(5507):1304-1351 (Feb. 16, 2001).
Voskoboynik, A. et al. The genome sequence of the colonial chordate, Botryllus schlosseri. eLife, 2:e00569 (2013). doi: 10.7554/eLife.00569. Epub Jul. 2, 2013.
Weisenfeld N.I., et al. Comprehensive variation discovery in single human genomes. Nat. Genet. 46(12):1350-1355 (Dec. 2014).
Whitcombe, D. et al. Detection of PCR Products Using Self-probing Amplicons and Fluorescence. Nature Biotechnology, 17(8):804-807 (Aug. 1999).
Williams, et al. Amplification of complex gene libraries by emulsion PCR. Nature Methods. 2006;3(7):545-50.
Williams, L.J. Paired-end sequencing of Fosmid libraries by Illumina. Genome Res., 22(11):2241-2249 (Nov. 2012). Epub Jul. 16, 2012.
Wing, R.D., et al. An improved method of plant megabase DNA isolation in agarose microbeads suitable for physical mapping and YAC cloning. The Plant Journal, 4(5):893-898 (1993).
Wu, C.C. et al. Long-span, mate-pair scaffolding and other methods for faster next-generation sequencing library creation. Nat. Methods, 9(9; Advertising Feature):i-ii (Sep. 2012).
Wu, T.D. et al. GMAP: a genomic mapping and alignment program for mRNA and EST sequences. Bioinformatics, 21(9):1859-1875, May 1, 2005. Epub Feb. 22, 2005.
Xie et al. De Novo Plant Genome Assembly Based on Chromatin Interactions: A Case Study of *Arabidopsis thaliana*. Mol Plant 8(3):489-92 (2015).
Zhang, et al. A greedy algorithm for aligning DNA sequences. J Comput Biol. Feb.-Apr. 2000;7(1-2):203-14.
Zhang, J. et al. PowerBLAST: A New Network BLAST Application for Interactive or Automated Sequence Analysis and Annotation Genome Res., vol. 7, pp. 649-656, (1997).
Zhou, S. et al. A single molecule scaffold for the maize genome. PLoS Genetics, 5(11): e1000711; pp. 1-14 (Nov. 20, 2009).
Zinchenko, A. et al. Compaction of Single-Chain DNA by Histone-Inspired Nanoparticles. Physical Review Letters, 95(22); 228101 (2005).
Constans A., "Microarrays in Microtubes," Scientist. 2003 17.13:36.
Dejica Vm, et al. Cleavage of type II collagen by cathepsin K in human osteoarthritic cartilage. Am J Pathol. Jul. 2008; 173(1):161-9. Epub May 29, 2008.
Enoiu et al., Repair of cisplatin-induced DNA interstand crosslinks by a replication-independent pathway involving transcription-coupled repair and translesion synthesis. Nucleic Acids Research, 40(18):8953-8964 (2012).
Higashi-Fujime S, et al. Muscle actin cleaved by proteinase K: its polymerization and in vitro motility. J Biochem. 112(4):568-572 (1992).
Kalhor et al., "Genome architectures revealed by tethered chromosome conformation capture and population-based modeling," Nature Biotechnology, 2012, 30(1): 90-98.
Korbel et al., Genome assembly and haplotyping with Hi-C. Nat Biotechnol. 31(12):1099-1101 (2013).
Mornet et al., Proteolysis and the domain organization of myosin subfragment 1. Proc Natl Acad Sci USA. 81(3):736-739 (1984).
Nagaki et al., Chromatin immunoprecipitation reveals that the 180-bp satellite repeat is the key functional DNA element of Arabidopsis thaliana centromeres. Genetics. 163(3):1221-1225 (2003).
O'Neill Lp, Turner Bm. Immunoprecipitation of native chromatin: NChIP. Methods. Sep. 2003;31(1):76-82.
Putnam et al. Chromosome-scale shotgun assembly using an in vitro method for long-range linkage. ARXIV.ORG, Cornell University Library XP080803553, pp. 1-25 (2015).
Risca et al., Unraveling the 3D genome: genomics tools for multi-scale exploration. Trends Genet. 31(7): 357-372 (2015).
Rizzo et al., Standardized collection of MNase-seq experiments enables unbiased dataset comparisons. BMC Mol Biol. 6:13:15, pp. 1-10 (2012).
Troll et al. Structural Variation Detection by Proximity Ligation from Formalin-Fixed, Paraffin- Embedded Tumor Tissue. J Mol Diagn. 21(3):375-383 (2019).
Tyagi S, et al. Molecular beacons: hybridization probes for detection of nucleic acids in homogeneous solutions. In: Kessler, C. (eds) Nonradioactive Analysis of Biomolecules. Springer Lab Manuals. Springer, Berlin, Heidelberg. 2000.
Goh et al., Chromatin Interaction Analysis with Paired-End Tag Sequencing (ChIA-PET) for mapping chromatin interactions and understanding transcription regulation. J Vis Exp. (62):3770 (2012).
Monson-Miller et al., Reference genome-independent assessment of mutation density using restriction enzyme-phased sequencing. BMC Genomics. 13:72 (2012).
Vakoc et al., Proximity among distant regulatory elements at the beta-globin locus requires GATA-1 and FOG-1. Mol Cell. 17(3):453-462 (2005).
Corn, Robert M., Programmable Self-Assembly of DNA-dendrimer and DNA-fullerene Nanostructures. AFRL-IF-RS-TR-2004-287, Final Technical Report (pp. 1-106) (2004).
Dower, William J, et al., Recombinant and Synthetic Randomized Peptide Libraries. Annual Reports in Medicinal Chemistry 26:271-280 (1991).
Fullwood, et al. An oestrogen-receptor-alpha-bound human chromatin interactome. Nature 462(7269):58-64 (2009).
Hsieh et al., Mapping nucleosome resolution chromosome folding in yeast by Micro-C. Cell. 162(1):108-119 (2015).
Juric et al., MAPS: Model-based analysis of long-range chromatin interactions from PLAC-seq and HiChIP experiments. PLoS Comput Biol. 15(4):e1006982, pp. 1-24 (2019).
Krietenstein et al., Ultrastructural details of mammalian chromosome architecture. bioRxiv preprint 639922, pp. 1-15 (2019). https://www.biorxiv.org/content/10.1101/639922v1 http://dx.doi_org/10.1101/639922.
Li et al., OCEAN-C: mapping hubs of open chromatin interactions across the genome reveals gene regulatory networks. Genome Biol. 19(1):54, pp. 1-14 (2018).
Li, Guoqiang et al. Simultaneous profiling of DNA methylation and chromatin architecture in mixed populations and in single Cells. bioRxiv pp. 1-35 (2018).
Ma et al., Using DNase Hi-C techniques to map global and local three-dimensional genome architecture at high resolution. bioRxiv preprint184846, pp. 1-55 (2018).
Mifsud et al., Mapping long-range promoter contacts in human cells with high-resolution capture Hi-C. Nat Genet. 47(6):598-606 (2015).
Phimister, Bette, et al., The Chipping Forecast. Nature Genetics 21:61 (pp. 1-4) (1999).
Ramani et al., Mapping 3D genome architecture through in situ DNase Hi-C. Nat Protoc. 11(11):2104-2121 (2016).
Ramani, et al. Massively multiplex single-cell Hi-C. Nat Methods. Mar. 2017; 14(3): 263-266. Published online Jan. 3, 20170.
Schmitt, Anthony D et al. A Compendium of Chromatin Contact Maps Reveals Spatially Active Regions in the Human Genome. Cell Reports 17(8):2042-2059 (2016).
Wang et al., The 3D Genome Browser: a web-based browser for visualizing 3D genome organization and long-range chromatin interactions. Genome Biol. 19(1):151, pp. 1-12 (2018).

* cited by examiner

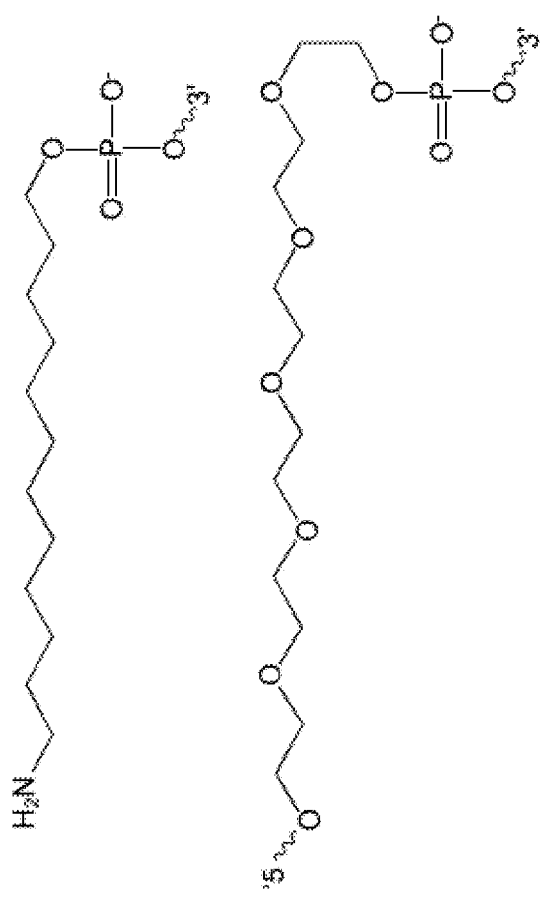
FIG. 6A.1

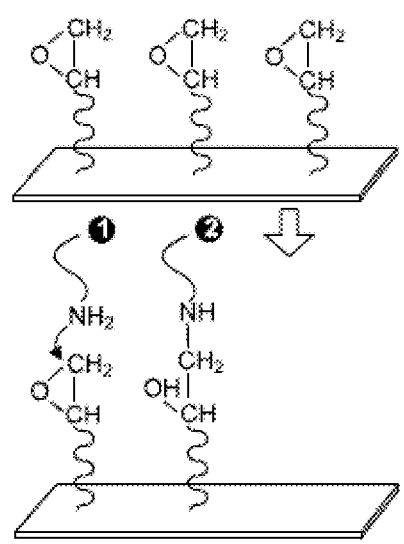
*FIG. 6A.2*
| 5'-ACACTCTTTCCCTACACGACGCTCTTCCGATCT-3'OH (SEQ ID NO: 1)
| 5'-AAAAAGATATCACGTACGTACGTACGTACGT-3'OH (SEQ ID NO: 2)
*FIG. 6A.3*

FIG. 6A.4

(SEQ ID NO: 3)
5'-AAAAAGATATCACTACGTACGTACGTACGTNNNNNNNNNNNNNNNNNNNNNNNNNNNNAAGATCCGGATCGGAAGAGCGTCGTGTAGGGAAAGAGTGT-3'OH (SEQ ID NO: 1)
5'-ACACTCTTTCCCTACACGACGCTCTTCCGATCT-3'OH (SEQ ID NO: 2)
3'OH-TGTGAGAAAGGGATGTGCTGCGAGAAGGCTAGANNNNNNNNNNNNNNNNNNNNNNNNNNNNTTCATGCATGCATGCATGCACTATGCACTATAGAAAAA-5'

5'-AAAAAGATATCACGTACGTACGTACGTACGT-3'OH (SEQ ID NO: 3)

FIG. 6A.5

(SEQ ID NO: 4)
5'-ACACTCTTTCCCTACACGACGCTCTTCCGATCTNNNNNNNNNNNNNNNNNNNNNNNNNACGTACGTACGTACGTACGTGATATCTTTTT-3'OH
3'OH-TGTGAGAAAGGGATGTGCTGCGAGAAGGCTAGANNNNNNNNNNNNNNNNNNNNNNNNNTGCATGCATGCATGCATGCACTATAGAAAAA-5' (SEQ ID NO: 2)

5'-AAAAAGATATCACGTACGTACGTACGTACGT-3'OH (SEQ ID NO: 3)

FIG. 6A.6

(SEQ ID NO: 4)
5'-ACACTCTTTCCCTACACGACGCTCTTCCGATCTNNNNNNNNNNNNNNNNNNNNNNNNNACGTACGTACGTACGTACGTGATATCTTTTT-3'OH

5'-AAAAAGATATCACGTACGTACGTACGTACGT-3'OH (SEQ ID NO: 3)

FIG. 6A.7

5'- ACACTCTTTCCCTACACGACGCTCTTCCGATCTNNNNNNNNNNNNN -N
      (SEQ ID NO: 4)
3'- TGTGAGAAAGGGATGTGCTGCGAGAAGGCTAGANNNNNNNNNNNNN -N
      (SEQ ID NO: 2)
5'- AAAAAGATATCACGTACGTACGTACGTACGT-3'OH
3'OH-TTTTTCTATAGTGCATGCATGCATGCATGCANN NNNNNN N

FIG. 6A.8

5'- ACACTCTTTCCCTACACGACGCTCTTCCGATCTNNNNNNNNNNNNN -N
      (SEQ ID NO: 4)
3'- TGTGAGAAAGGGATGTGCTGCGAGAAGGCTAGANNNNNNNNNNNNN -N
      (SEQ ID NO: 3)
5'- AAAAAGATATCACGTACGTACGTACGTACGTNN-3'OH
3'OH-TTTTTCTATAGTGCATGCATGCATGCATGCANN NNNNNN N

FIG. 6A.9

5'- ACACTCTTTCCCTACACGACGCTCTTCCGATCTNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNACGTACGTACGTACGTGAATCTTTT-3'OH
      (SEQ ID NO: 4)
5'- AAAAAGATACCTACGTACCTACGTACGTCATCCGAAGAGCGTCGTGTAGGGAAAGAGTGT-3'OH
      (SEQ ID NO: 3)

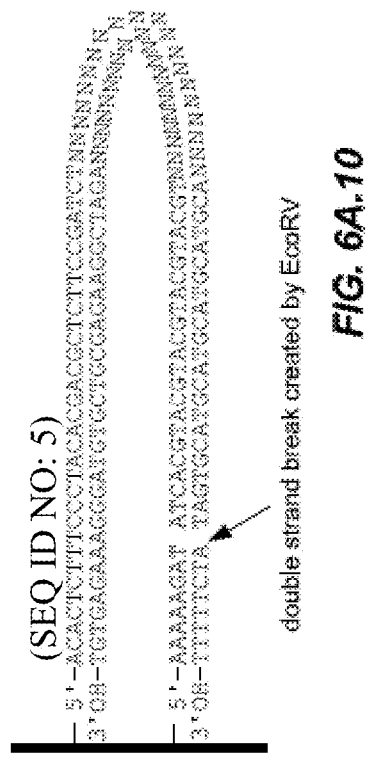
FIG. 6A.10
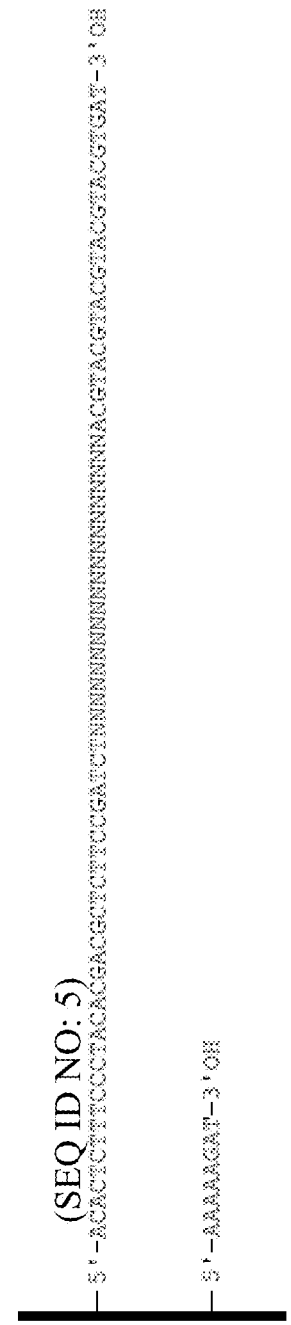
FIG. 6A.11

(SEQ ID NO: 6)
5'-P-NNNNNN
HO-3'-TGCATGCATGCATGCATCCACTANNNNNN

FIG. 6B.1

(SEQ ID NO: 6)
HO-3'-TGCATGCATGCATGCATCCACTANNNNNN (SEQ ID NO: 7)
5'-ACACTCTTTCCCTACACGACGCTCTTCCGATCTNNNNNNNNNNNNNNNNNACGTACGTACGTACGTGATNNNNNNN-3'OH

FIG. 6B.2

(SEQ ID NO: 7)
5'-ACACTCTTTCCCTACACGACGCTCTTCCGATCTNNNNNNNNNNNNNNNNNACGTACGTACGTACGTGATNNNNNNN-3'OH
3'-TGTGAGAAAGGGATGTGCTGCGAGAAGGCTAGANNNNNNNNNNNNNNNNTGCATGCATGCATGCACTANNNNNNN-5'

(SEQ ID NO: 8)

FIG. 6B.3

(SEQ ID NO: 7)
5'-ACACTCTTTCCCTACACGACGCTCTTCCGATCTNNNNNNNNNNNNNNNNNACGTACGTACGTACGTGATNNNNNNN-3'OH
3'-TGTGAGAAAGGGATGTGCTGCGAGAAGGCTAGANNNNNNNNNNNNNNNNTGCATGCATGCATGCACTANNNNNNN-5'

(SEQ ID NO: 8)

FIG. 6B.4

(SEQ ID NO: 9)
5'-ACACTCTTTCCCTACACGACGCTCTTCCGATCTNNNNNNNNNNNNNNNNNACGTACGTACGTACGTGATNNNNNNNA-3'OH
3'-TGTGAGAAAGGGATGTGCTGCGAGAAGGCTAGANNNNNNNNNNNNNNNNNTGCATGCATGCATGCACTANNNNNNN-5'

(SEQ ID NO: 8)

FIG. 6B.5

5'-ACACTCTTTCCCTACACGACGCTCTTCCGATCTNNNNNNNNNNNNNNACGTACGTACGTGATNNNNNNA-3'OH (SEQ ID NO: 9)

3'HO-TGTGAGAAAGGGATGTGCTGCGAGAAGGCTAGANNNNNNNNNNNNTGCATGCATGCACTANNNNNN-5' (SEQ ID NO: 8)

5'P-AGATCGGAAGAGCACACGTCTGAACTCCAGTCAC-3'OH (SEQ ID NO: 10)

3'HO-TTCTAGCCTTCTCGTGTGCAGACTTGAGGTCAGTG-5' (SEQ ID NO: 11)

FIG. 6B.6

5'-ACACTCTTTCCCTACACGACGCTCTTCCGATCTNNNNNNNNNNNNNNNNNNAGTACGTACGTGATNNNNNNNA-3'

AGATCGGAAGAGCACACGTCTGAACTCCAGTCAC-3'OH (SEQ ID NO: 12)

3'HO-TGTGAGAAAGGGATGTGCTGCGAGAAGGCTAGANNNNNNNNNNNNNNNNNNTCATGCATGCACTANNNNNNNN

TTCTAGCCTTCTCGTGTGCAGACTTGAGGTCAGTG-5' (SEQ ID NO: 13)

FIG. 6B.7

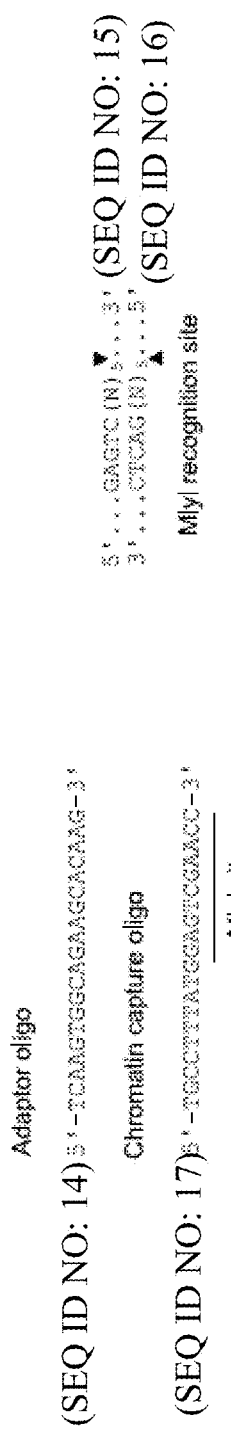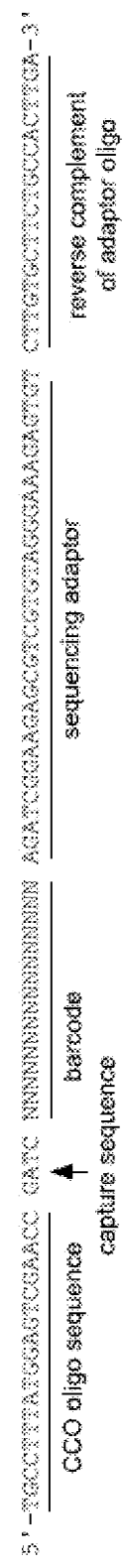

Adaptor oligo
(SEQ ID NO: 14) 5'-TCAAGTGCAGAAGCAAG-3'
Chromatin capture oligo
(SEQ ID NO: 17) 5'-TGCCTTATGGAGTCGAACC-3'
                              MlyI site 5'-...GAGTC(N)5...-3' (SEQ ID NO: 15)
3'-...CTCAG(N)5...-5' (SEQ ID NO: 16)
       MlyI recognition site

FIG. 11A (SEQ ID NO: 18)
5'-TGCCTTATGGAGTCGAACC GATC NNNNNNNNNNNN AGATCGGAAGAGCGTCGTGTAGGGAAAGAGTGT CTTGTTGCTTCTGCACTTGA-3'
   CCO oligo sequence      barcode         sequencing adaptor                    reverse complement
   capture sequence                                                              of adaptor oligo

FIG. 11B

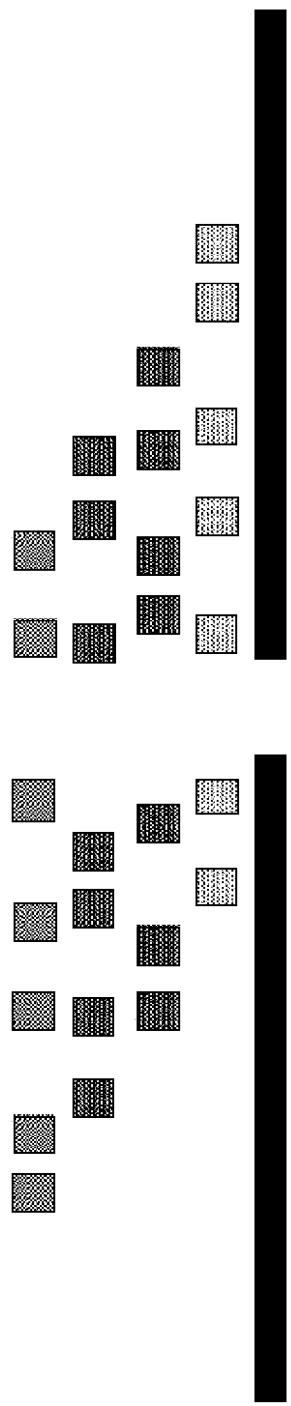
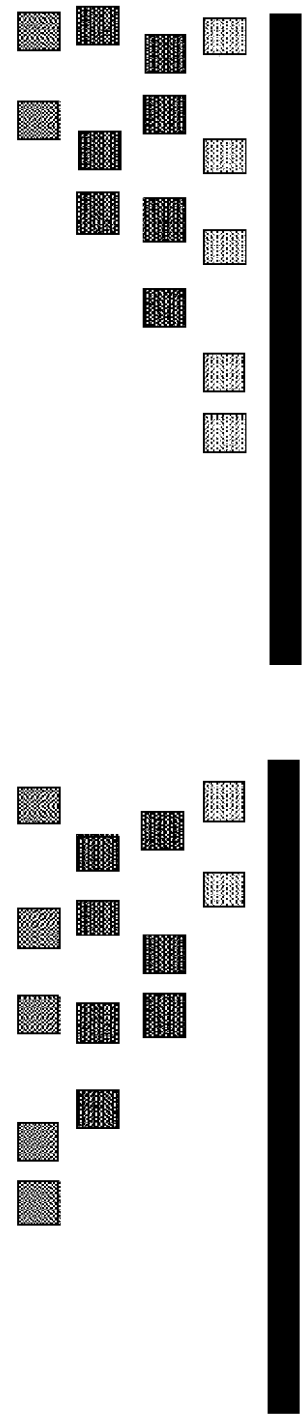

(SEQ ID NO: 22) 5'-P-GATCNNNNNNNNNN
                HO-3'-NNNNNNNNNN (SEQ ID NO: 22) 5'-P-GATCNNNNNNNNNN
(SEQ ID NO: 23) HO-3'-CTAGNNNNNNNNNN

} FIG. 14A

(SEQ ID NO: 22) 5'-P-GATCNNNNNNNNNN
(SEQ ID NO: 24) HO-3'-ACTAGNNNNNNNNNN

FIG. 14B

(SEQ ID NO: 25) 5'-ATGCATGCACTANNNNNNNNNNT-3'-OH    (SEQ ID NO: 22) 5'-P-GATCNNNNNNNNNN
                3'-OH-NNNNNNNNNN -5'                 (SEQ ID NO: 24) HO-3'-ACTAGNNNNNNNNNN

FIG. 14C

(SEQ ID NO: 26) 5'-ATGCATGCACTANNNNNNNNNNTGATCNNNNNNNNNN
(SEQ ID NO: 27) 3'-OH-NNNNNNNNNNACTAGNNNNNNNNNN

FIG. 14D

RCA extension:
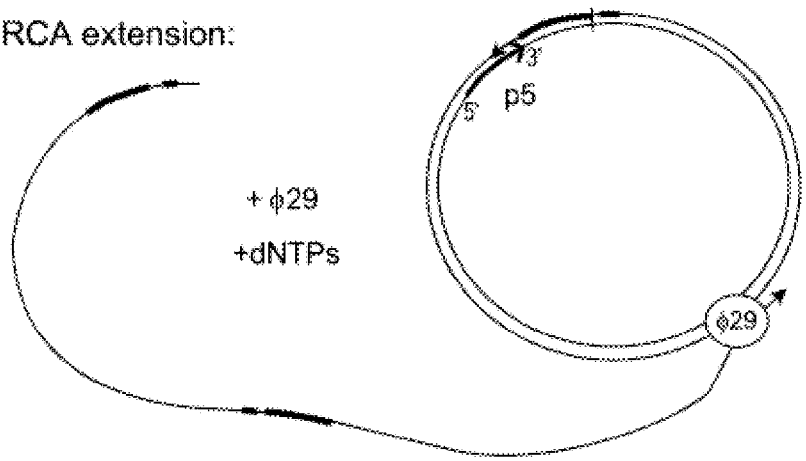
FIG. 16E
Second strand synthesis on linear RCA product:
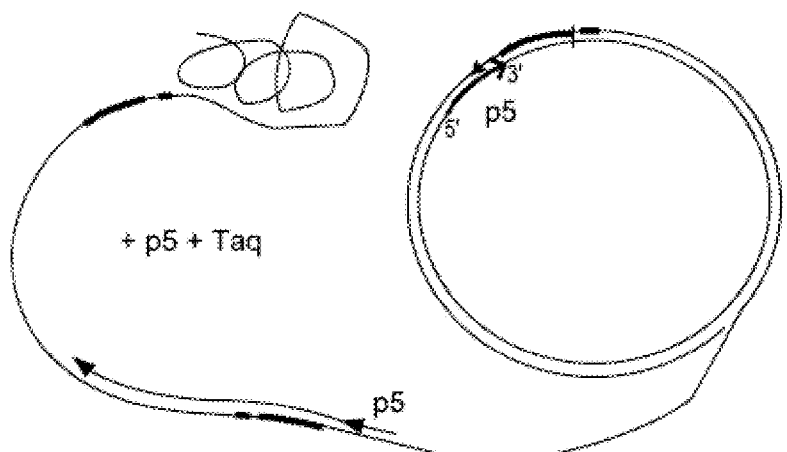
FIG. 16F
Combine barcode balls, gDNA chromatin assemblies, DNA ligase and MboII enzyme. MboII opens the barcode-ball cloning site asymmetrically:
```
5' -PPPPPPPPPPPPPPPPBBBBBBBBBBBBBBBBBT NNNNNNNNTCTTC--- 3'   (SEQ ID NO: 28)
3' -............................     A        AGAAG--- 5'
                                            CCTC--- 3'
                                          AGTCG--- 5'
```
FIG. 16G

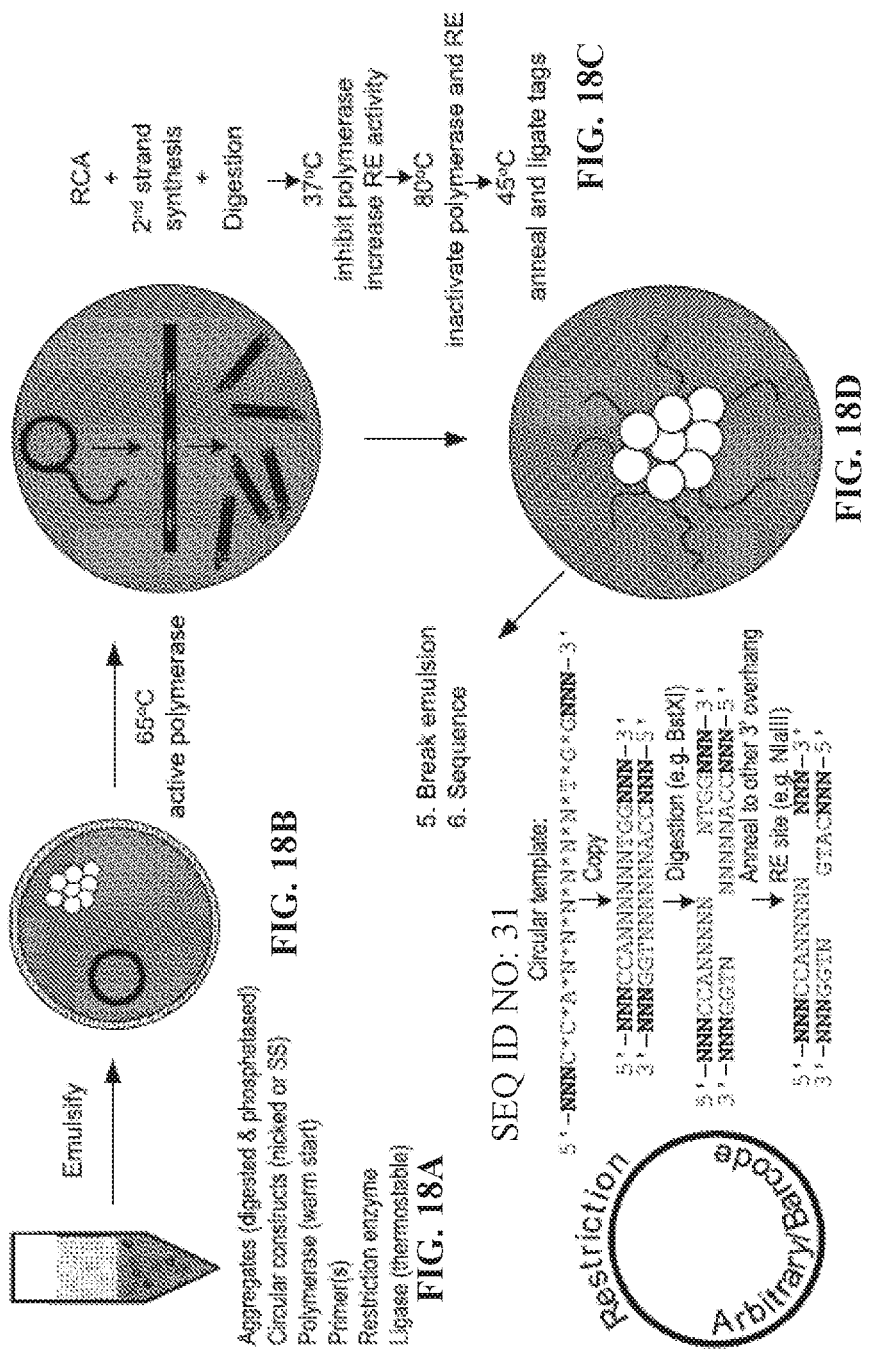

Heterozygous SNPs between read pairs

|  | Read pairs with correctly phased SNPs | Read pairs with incorrectly phased SNPs | Read pairs without either allele | Percent of read pairs with correct phase (excluding errors) |
|---|---|---|---|---|
| Insert < 500 | 467 | 8 | 16 | 98.32% |
| 500 < Insert < 1kb | 17 | 0 | 0 | 100.0% |
| 1kb < Insert < 10Mb | 64 | 3 | 1 | 95.52% |
| 10kb < Insert < 100Mb | 23 | 0 | 2 | 100.0% |
| 100kb < Insert < 1Mb | 0 | 1 | 0 | 0.0% |
| Insert > 1Mb | 18 | 23 | 4 | 43.9% |

*FIG. 24*

Sequentially applied categories of read pairs

| Library | Nanotin (NA 12878) | RC HiSeq (NA 12878) | TCC (NA 12878) |
|---|---|---|---|
| Unmapped | 5.436 % | 11.309 % | 25.054 % |
| Duplicates | 0.268 % | 30.081 % | 0.73 % |
| Mapq < 20 | 26.522 % | 11.607 % | 31.501 % |
| Different Scaffold | 50.931 % | 11.466 % | 12.793 % |
| Insert > 500kb | 2.921 % | 0.664 % | 11.923 % |
| Insert < 2kb | 11.747 % | 31.294 % | 5.821 % |
| 2kb < Insert < 10kb | 1.303 % | 2.014 % | 2.269 % |
| 10kb < Insert < 1000kb | 0.846 % | 1.55 % | 5.217 % |
| 100kb < Insert < 500kb | 0.026 % | 0.016 % | 4.692 % |

*FIG. 25*

SEQUENCE LISTING

```
<160> NUMBER OF SEQ ID NOS: 34

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acactctttc cctacacgac gctcttccga tct                                    33

<210> SEQ ID NO 2
<211> LENGTH: 31
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaaagatat cacgtacgta cgtacgtacg t                              31

<210> SEQ ID NO 3
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(51)
<223> OTHER INFORMATION: a, c, t, g, unknown or other

<400> SEQUENCE: 3
aaaaagatat cacgtacgta cgtacgtacg tnnnnnnnnn nnnnnnnnnn nagatcggaa    60
gagcgtcgtg tagggaaaga gtgt                                          84

<210> SEQ ID NO 4
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(53)
<223> OTHER INFORMATION: a, c, t, g, unknown or other

<400> SEQUENCE: 4
acactctttc cctacacgac gctcttccga tctnnnnnnn nnnnnnnnnn nnnacgtacg    60
tacgtacgta cgtgatatct tttt                                          84

<210> SEQ ID NO 5
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(53)
<223> OTHER INFORMATION: a, c, t, g, unknown or other

<400> SEQUENCE: 5
acactctttc cctacacgac gctcttccga tctnnnnnnn nnnnnnnnnn nnnacgtacg    60
tacgtacgta cgtgat                                                   76

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
```

-continued

```
<400> SEQUENCE: 6
nnnnnnatca cgtacgtacg tacgtacgt                                    29

<210> SEQ ID NO 7
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(53)
<223> OTHER INFORMATION: a, c, t, g, unknown or other
<220> FEATURE:
<221> NAME/KEY: modified_base
<222> LOCATION: (77)..(82)
<223> OTHER INFORMATION: a, c, t, g, unknown or other

<400> SEQUENCE: 7
acactctttc cctacacgac gctcttccga tctnnnnnnn nnnnnnnnnn nnnacgtacg   60
tacgtacgta cgtgatnnnn nn                                           82

<210> SEQ ID NO 8
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (30)..(49)
<223> OTHER INFORMATION: a, c, t, g, unknown or other

<400> SEQUENCE: 8
nnnnnnatca cgtacgtacg tacgtacgtn nnnnnnnnnn nnnnnnnnna gatcggaaga   60
gcgtcgtgta gggaaagagt gt                                           82

<210> SEQ ID NO 9
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(53)
<223> OTHER INFORMATION: a, c, t, g, unknown or other
<220> FEATURE:
<221> NAME/KEY: modified_base
<222> LOCATION: (77)..(82)
<223> OTHER INFORMATION: a, c, t, g, unknown or other

<400> SEQUENCE: 9
acactctttc cctacacgac gctcttccga tctnnnnnnn nnnnnnnnnn nnnacgtacg   60
tacgtacgta cgtgatnnnn nna                                          83

<210> SEQ ID NO 10
<211> LENGTH: 34
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 10
agatcggaag agcacacgtc tgaactccag tcac                               34

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtgactggag ttcagacgtg tgctcttccg atctt                              35

<210> SEQ ID NO 12
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (34)..(53)
<223> OTHER INFORMATION: a, c, t, g, unknown or other
<220> FEATURE:
<221> NAME/KEY: modified_base
<222> LOCATION: (77)..(82)
<223> OTHER INFORMATION: a, c, t, g, unknown or other

<400> SEQUENCE: 12
acactctttc cctacacgac gctcttccga tctnnnnnnn nnnnnnnnnn nnnacgtacg   60
tacgtacgta cgtgatnnnn nnaagatcgg aagagcacac gtctgaactc cagtcac     117

<210> SEQ ID NO 13
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (36)..(41)
<223> OTHER INFORMATION: a, c, t, g, unknown or other
<220> FEATURE:
<221> NAME/KEY: modified_base
<222> LOCATION: (65)..(84)
<223> OTHER INFORMATION: a, c, t, g, unknown or other

<400> SEQUENCE: 13
gtgactggag ttcagacgtg tgctcttccg atcttnnnnn natcacgtac gtacgtacgt   60
acgtnnnnnn nnnnnnnnnn nnnnagatcg gaagagcgtc gtgtagggaa agagtgt     117

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tcaagtggca gaagcacaag                                               20
```

```
<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 15 gagtcnnnnn                                                              10

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 16 nnnnngactc                                                              10

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tgcctttatg gagtcgaacc                                                   20

<210> SEQ ID NO 18
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(40)
<223> OTHER INFORMATION: a, c, t, g, unknown or other

<400> SEQUENCE: 18
tgcctttatg gagtcgaacc gatcnnnnnn nnnnnnnnnn agatcggaag agcgtcgtgt       60
agggaaagag tgtcttgtgc ttctgccact tga                                    93

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cttgtgcttc tgccacttga                                                   20
```

```
<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgcctttatg gagtcgaacc gatc                                            24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gatcggttcg actccataaa ggca                                            24

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(14)
<223> OTHER INFORMATION: a, c, t, g, unknown or other

<400> SEQUENCE: 22
gatcnnnnnn nnnn                                                       14

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, t, g, unknown or other

<400> SEQUENCE: 23
nnnnnnnnnn gatc                                                       14

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, t, g, unknown or other

<400> SEQUENCE: 24
nnnnnnnnnn gatca                                                      15
```

-continued

```
<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(24)
<223> OTHER INFORMATION: a, c, t, g, unknown or other

<400> SEQUENCE: 25
atgcatgcac tannnnnnnn nnnnt                                             25

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(24)
<223> OTHER INFORMATION: a, c, t, g, unknown or other
<220> FEATURE:
<221> NAME/KEY: modified_base
<222> LOCATION: (30)..(39)
<223> OTHER INFORMATION: a, c, t, g, unknown or other

<400> SEQUENCE: 26
atgcatgcac tannnnnnnn nnnntgatcn nnnnnnnn                                39

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, t, g, unknown or other
<220> FEATURE:
<221> NAME/KEY: modified_base
<222> LOCATION: (16)..(27)
<223> OTHER INFORMATION: a, c, t, g, unknown or other

<400> SEQUENCE: 27
nnnnnnnnnn gatcannnnn nnnnnnn                                           27

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, c, t, g, unknown or other

<400> SEQUENCE: 28
nnnnnnntct tc                                                           12

<210> SEQ ID NO 29
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, c, t, g, unknown or other

<400> SEQUENCE: 29
nnnnnnntct tcaagctt                                                 18

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aagcttgaag a                                                        11

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: modified_base
<222> LOCATION: (16)..(18)
<223> OTHER INFORMATION: a, c, t, g, unknown or other

<400> SEQUENCE: 31
nnnccannnn nntggnnn                                                 18

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aagctagctt                                                          10

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (8)..(10)
```

```
<223> OTHER INFORMATION: a, c, t, g, unknown or other

<400> SEQUENCE: 33 nnngatcnnn                                                                    10

<210> SEQ ID NO 34
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aagctaagct                                                                    10
```

TAGGING NUCLEIC ACIDS FOR SEQUENCE ASSEMBLY

CROSS-REFERENCE TO RELATED APPLICATIONS

The present application is a continuation of U.S. application Ser. No. 15/329,414, filed on Jan. 26, 2017, which is the U.S. National Phase Entry of International Application No. PCT/US2015/043327, filed on Jul. 31, 2015, which claims priority to U.S. Provisional Application Ser. No. 62/032,139, filed Aug. 1, 2014, U.S. Provisional Application Ser. No. 62/032,166, filed Aug. 1, 2014, U.S. Provisional Application Ser. No. 62/032,181, filed Aug. 1, 2014, and U.S. Provisional Application Ser. No. 62/032,221, filed Aug. 1, 2014, the contents of each are incorporated herein by reference in their entireties.

SEQUENCE LISTING

This instant application contains a Sequence Listing which has been submitted in ASCII format via EFS-Web and is hereby incorporated by reference in its entirety. Said ASCII copy, created on Nov. 15, 2019, is named "45299704301_SL.txt" and is 11,872 bytes in size.

BACKGROUND

Existing sequencing technologies allow for the inexpensive production for short reads amounting to gigabases of DNA, but it remains challenging to generate accurate de novo genome assemblies from these reads alone due to genomic complexities such as repetitive regions or ambiguity in placement and orientation of a sequence of DNA on an assembly scaffold. It remains difficult in theory and in practice to produce high-quality, highly contiguous genome sequences. The robust and efficient acquisition of long-range DNA sequence information has been a long-standing goal for genomics and other DNA analyses since the advent of high-throughput sequencing. The present disclosure provides methods and compositions to associate polynucleotide segments to acquire long-range DNA sequence information, which can be used for applications such as genomic assembly and haplotype phasing.

SUMMARY

Embodiments disclosed herein relate to compositions, methods, kits, and computer devices related to the use of clonal clusters to capture and mark nucleic acid molecules, such as nucleic acid molecules in DNA complexes such as chromatin aggregates.

A persistent shortcoming of much of the next generation sequencing (NGS) data is the inability to span large repetitive regions of genomes due to short read lengths and relatively small insert sizes. This deficiency significantly affects de novo assembly. Contigs separated by long repetitive regions cannot be linked or re-sequenced, since the nature and placement of genomic rearrangements are uncertain. Further, since variants cannot be confidently associated with haplotypes over long-distances, phasing information is indeterminable. The disclosure can address all of these problems simultaneously by generating extremely long-range read pairs (XLRPs) or commonly tagged extremely long distance sequence reads that span genomic distances on the order of hundreds of kilobases, and up to megabases with the appropriate input DNA and that originate from a common DNA molecule. Such data can be invaluable for overcoming the substantial barriers presented by large repetitive regions in genomes, including centromeres; enable cost-effective de novo assembly; and produce re-sequencing data of sufficient integrity and accuracy for personalized medicine.

Of significant importance is the use of reconstituted chromatin in forming associations among very distant, but molecularly-linked, segments of DNA. The disclosure enables distant segments to be brought together and covalently linked by chromatin conformation, thereby physically connecting previously distant portions of the DNA molecule. Subsequent processing can allow for the sequence of the associated segments to be ascertained, yielding read pairs whose separation on the genome extends up to the full length of the input DNA molecules. Since the read pairs are derived from the same molecule, these pairs also contain phase information.

In some embodiments, the disclosure provides methods that produce high quality assemblies with far less data than previously required. For example, the methods disclosed herein provide for genomic assembly from only two lanes of Illumina HiSeq data.

In other embodiments, the disclosure provides methods that generate chromosome-level phasing using a long-distance read pair approach. For example, the methods disclosed herein can phase 90% or more of the heterozygous single nucleotide polymorphisms (SNPs) for that individual to an accuracy of at least 99% or greater. This accuracy is on par with phasing produced by substantially more costly and laborious methods.

In some aspects, the present disclosure provides methods for generating labeled polynucleotides from a first DNA molecule. In some cases, the first DNA molecule comprises a first sequence segment and a second sequence segment. In certain cases, the method comprises: a. crosslinking the first sequence segment and the second sequence segment outside of a cell; b. adding the first sequence segment and the second sequence segment to a first resolved locus comprising a plurality of binding probes, wherein the plurality of binding probes are produced on the first resolved locus using bridge amplification; and generating a first labeled polynucleotide comprising a first label and a first complement sequence, and a second labeled polynucleotide comprising a second label and a second complement sequence, wherein the first complement sequence is complementary to the first sequence segment and the second complement sequence is complementary to the second sequence segment.

In other aspects, the present disclosure provides methods for generating labeled polynucleotides from a first DNA molecule. In some cases, the first DNA molecule comprises a first sequence segment and a second sequence segment. In certain cases, the method comprises: a. crosslinking the first sequence segment and the second sequence segment outside of a cell; b. adding the first sequence segment and the second sequence segment to a first resolved locus comprising a plurality of binding probes, wherein the binding probes are feature oligonucleotides immobilized on the first resolved locus at a 5' end; and c. generating a first labeled polynucleotide comprising a first label and a first complement sequence, and a second labeled polynucleotide comprising a second label and a second complement sequence, wherein the first complement sequence is complementary to the first sequence segment and the second complement sequence is complementary to the second sequence segment.

In some cases, the first labeled polynucleotide is generated by extending the first sequence segment using the binding probe as a template. In various cases, the first and the second label are identical. In many cases, the method comprises severing the first DNA molecule. In certain cases, the method comprises linking a sequencing adaptor to the first labeled polynucleotide and the second labeled polynucleotide. In further cases, the method comprises obtaining sequence information of the first labeled polynucleotide and the second labeled polynucleotide. In some cases, the method comprises using the sequence information to associate the first sequence segment and the second sequence segment. In various cases, the method comprises using the sequence information to assemble a plurality of contigs. In many cases, the method comprises using the sequence information to assemble the first DNA molecule. In further cases, the method comprises using the sequence information to assemble a genome. In some embodiments, the first sequence segment and the second sequence segment is cross-linked to a plurality of association molecules. In various cases, the association molecules comprise amino acids. In further cases, the association molecules comprise peptides or proteins. In other cases, the association molecules comprise histones. In certain cases, the association molecules are from a different source than the first DNA molecule. In some cases, the first resolved locus is located on a substrate. In certain cases, the substrate comprises a solid support. In further cases, the substrate is a microarray. In some cases, the substrate comprises more than 10,000 resolved loci. In certain cases, the first resolved locus comprises a unique binding probe that is not found in any other resolved locus on the substrate. In various cases, each of the resolved loci comprises a unique binding probe that is not found in any other resolved locus on the substrate. In many cases, the binding probes are feature oligonucleotides. In further cases, the feature oligonucleotides comprise one or more elements selected from the group consisting of a linker, a primer, a barcode and a capture sequence. In some embodiments, the barcode represents the first resolved locus. In certain embodiments, the capture sequence can hybridize to the first sequence segment.

In further aspects, the present disclosure provides compositions comprising: a first sequence segment and a second sequence segment; a plurality of association molecules cross-linked to the first and the second sequence segment; and a first binding probe attached to the first sequence segment, wherein the first binding probe is immobilized on a first resolved locus. In some cases, the composition comprises a polymerase, wherein the polymerase is bound to the first binding probe. In certain cases, the first sequence segment is hybridized to the first binding probe. In further cases, the first sequence segment is ligated to the first binding probe. In some cases, the second sequence segment is hybridized to a second binding probe. In certain cases, the first binding probe and the second binding probe are identical. In various cases, the first sequence segment and the second sequence segment are part of a same DNA molecule. In other cases, the first sequence segment and the second sequence segment are part of different DNA molecule. In some embodiments, the association molecules comprise amino acids. In further embodiments, the association molecules comprise peptides or proteins. In certain embodiments, the association molecules comprise histones. In other embodiments, the association molecules comprise nanoparticles. In some cases, the nanoparticle is a platinum-based nanoparticle. In other cases, the nanoparticle is a DNA intercalator, or any derivatives thereof. In further cases, the nanoparticle is a bisintercalator, or any derivatives thereof.

In some cases, the first resolved locus comprises a plurality of binding probes. In certain cases, greater than 90% of the binding probes in the first resolved locus comprise an identical label. In many cases, greater than 90% of the binding probes in the first resolved locus are identical. In various cases, the first binding probe is a feature oligonucleotide. In further cases, the feature oligonucleotide is immobilized on the first resolved locus at a 5' end. In some cases, the feature oligonucleotide comprises one or more elements selected from the group consisting of a linker, a primer, a sequence adaptor, a barcode and a capture sequence. In certain cases, the first resolved locus comprises a plurality of feature oligonucleotides. In many cases, greater than 90% of the feature oligonucleotides in the first resolved locus comprise a same barcode. In various cases, greater than 90% of the feature oligonucleotides in the first resolved locus comprise a sequence adaptor. In some embodiments, the first resolved locus is located on a substrate. In certain embodiments, the substrate comprises a solid support. In further embodiments, the substrate is a microarray. In various embodiments, the substrate comprises more than 10,000 resolved loci. In some cases, the first resolved locus comprises a unique binding probe that is not found in any other resolved locus on the substrate. In further cases, each of the resolved loci comprises a unique binding probe that is not found in any other resolved locus on the substrate.

In some aspects, the present disclosure provides a method of mapping a sequence to a nucleic acid molecule, comprising the steps of obtaining a nucleic acid sample comprising a first nucleic acid molecule comprising a first region and a second region; contacting the nucleic acid sample with a binding agent such that the first region and the second region of the first nucleic acid molecule are redundantly bound independently of a phosphodiester backbone of the first nucleic acid molecule; digesting the nucleic acid sample to produce at least one double strand break of known end sequence between the first region and the second region of the first nucleic acid molecule; contacting the nucleic acid sample to a population of oligonucleotides comprising a first plurality of oligonucleotides, wherein each of the first plurality of oligonucleotides comprises a) a 3' annealing region capable of annealing to the double strand break, and b) a first molecular tag sequence 5' of the annealing region, and wherein at least one of the plurality of oligonucleotides anneals to at least one double strand break of the first nucleic acid molecule; ligating the nucleic acid sample to at least one oligonucleotide of the population of oligonucleotides; separating the binding agent from the first nucleic acid molecule; and sequencing the molecular tag region of the oligonucleotide and the ligated adjacent sequence; wherein a first sequence comprising the first molecular tag corresponds to a sequence of the first nucleic acid molecule. In some cases, a second sequence comprising the first molecular tag corresponds to a sequence of the first nucleic acid molecule. In certain cases, the nucleic acid sample comprises a second nucleic acid molecule comprising a third region and a fourth region. In further cases, the nucleic acid sample is subjected to fragmentation prior to contacting with the binding agent. In some cases, the fragmentation comprises at least one treatment selected from the list consisting of sonication, shearing, partial nonspecific endonuclease treatment, and partial specific endonuclease treatment. In various cases, the population of oligonucleotides comprises a second plurality of oligonucleotides, wherein each of the second plurality of oligonucleotides comprises a) a 3' annealing region capable of annealing to the double strand break, and b) a second molecular tag sequence 5' of the annealing region, having a sequence different from that of the first molecular tag. In some cases, the second plurality of oligonucleotides is spatially separate from the first plurality of oligonucleotides. In certain cases, the population of oligonucleotides is attached to a solid surface. In further cases, the solid surface is a nucleic acid array. In other cases, the solid surface is a surface of a population of beads, and wherein the surface of each bead comprises a single plurality of oligonucleotides. In further cases, the nucleic acid sample comprises a second nucleic acid comprising a third and a fourth region. In certain cases, a plurality of sequence reads are generated, and all reads comprising a first molecular tag map to a first nucleic acid molecule, and all reads comprising a second molecular tag map to a second nucleic acid molecule.

Methods and compositions disclosed herein are related to the use of clonal oligonucleotide clusters to tag individual nucleic acid molecules. In one aspect, the methods disclosed herein are performed as follows. A nucleic acid sample is obtained. A partial list of nucleic acid samples comprises a cell or cell population sample, a sample from a human, an environmental sample, a sample comprising nucleic acids from a plurality of organisms, a reverse-transcribed ribonucleic acid sample, or an archaeological sample. Nucleic acids are extracted, and in some cases separated from native chromatin. In certain cases, native chromatin is retained. In further cases, the nucleic acids are fragmented, such as by shearing, sonication, nonspecific endonuclease treatment, or specific endonuclease treatment. In various cases, the fragmentation is partial, while in other cases the fragmentation is total or no fragmentation is performed. In some cases, the nucleic acid sample is treated with a binding agent, comprising a constituent such as a nucleic acid binding protein, for example a histone or a modified non-specific transcription factor or other general nucleic acid biding agent. In some cases, the binding agent is at least one of protamine, spermine, spermidine or other positively charged molecules. In certain cases, the DNA-binding agent complexes are fixed, for example by cross-linking. Exemplary cross-linking agents are formaldehyde and psoralen. In many cases, formaldehyde is used. In other cases, no cross-linking is performed. The sample is contacted with a restriction endonuclease. A number of restriction endonucleases are consistent with the methods disclosed herein. In certain embodiments, the restriction endonuclease is MboI, while in many embodiments any one or more of the restrictions endonucleases recited herein or known to those in the art are used. In some embodiments, restriction endonuclease is allowed to fully digest its substrate, while in other embodiments digestion is partial. In some cases, fragmented DNA is attached to DNA comprising a specific sequence, such as an adaptor having a sequence selected to bind to a capture sequence on a solid support, or bound to a molecular tag or barcode, or both selected to bind to a capture sequence on a solid support and bound to a molecular tag or barcode. The fixed, digested sample is contacted to a plurality of populations of oligonucleotides attached to a solid substrate. Cases of solid substrate include a flat glass surface and round nano- or microparticles. In certain cases, 1 to 10 spacer groups are present between an oligonucleotide and substrate. Cases of spacer groups are triethylene glycol and hexaethylene glycol. In some cases, each population of oligonucleotides comprises a 3' region, which in various cases is capable of annealing to a complementary end generated by the restriction endonuclease treatment, for example, of a nucleic acid complex. In further cases, the nucleic acid complex is capable of ligation to the complementary end generated by restriction endonuclease treatment. Adjacent to the 3' end is a molecular tag sequence that in certain cases is unique to a given population of oligonucleotide clusters. In some cases, there are multiple oligonucleotides having the same molecular tag sequence, all belonging to one cluster. In various cases, a molecular tag is not unique to a single cluster or oligonucleotide population; rather there is uniformity among molecular tags in a single population or locus, and there is sufficient diversity among molecular tag sequences such that overlapping nucleic acid molecules in distinct nucleic acid complexes are unlikely to be tagged with identical molecular tags or barcodes. In some embodiments, adjacent to the molecular tag sequence is DNA sequence that functions as a spacer between the solid substrate and molecular tag. The DNA-bound digested, treated sample is allowed to anneal to the plurality of populations of oligonucleotides. In certain embodiments, the DNA sample has 5' phosphates. In further embodiments, the DNA sample with 5' phosphates is allowed to anneal to the population of oligonucleotides and subsequently covalently linked with DNA ligase. In many cases, the sample is contacted with the oligonucleotides such that only one DNA complex will contact a given uniform population of oligonucleotides. In various cases, more than one DNA complex may contact a given uniform population of oligonucleotides. In further cases, multiple complementary ends of a single DNA complex, such as DNA bound in native chromatin, DNA bound in assembled chromatin, DNA bound to histones or other chromatin component, DNA bound to a DNA-binding protein, DNA bound to a positively charged DNA binding agent, DNA bound to a nanoparticle having a positively charged coating or surface, will each direct polynucleotide extension from the DNA complex, using as template the oligonucleotide or oligonucleotides in the cluster to which the DNA complex has annealed. After DNA polymerization, the original oligonucleotides will be double stranded and attached to DNA from the sample. Any protein such as histones attached to the DNA sample is removed. A method to remove protein includes heat, detergent and protease treatment. In some cases, the free end of the DNA sample is attached to a common double stranded DNA sequence. Mechanisms for attaching include creating a blunt end in the free end of the DNA sample, adenylating the 3' end of the blunt ends and attaching the common DNA sequence with a 3' thymidine overhang to the free end of the DNA sample. The oligonucleotides having both molecular tag or barcode sequence and sequence derived from the DNA complex to which they were bound are then separated from the DNA binding agent of the DNA complex. The processed DNA is prepared for analysis by DNA sequencing analysis. One preparation method involves melting hydrogen bonding (denaturation) between DNA strands. In certain cases, the separation is effected by heat treatment, ionic treatment or other treatment to separate annealed nucleic acids. In some cases, the oligonucleotides are then washed to remove any unbound DNA complexes. In further cases, the oligonucleotides are cleaved from the surface. In some cases, the cleavage is directed by the sequence of the oligonucleotide surface attachment region of the oligonucleotide, for example in combination with a restriction endonuclease. In certain cases, the cleavage is accomplished chemically. In various cases, the cleaved oligonucleotides are sorted by their tagged incorporated nucleotides such that oligonucleotides to which no DNA complex sequence-directed nucleotide addition has occurred are removed. In some embodiments, this sorting is effected by contacting with avidin, strepatavidin, or avidin and streptavidin. In certain embodiments, the isolated oligonucleotides are then sequenced. Any number of sequencing techniques is consistent with the methods disclosed herein. In some cases, the sequencing is effected by constructing a sequencing library, for example by adding end-adapters, and sequencing using Illumina sequencing by synthesis technology. In certain cases, the end-adapters are included in the oligonucleotides and/or attached the free end of the DNA sample which is attached to the oligonucleotides. A number of sequencing techniques are listed herein, and in various embodiments each is consistent with the methods disclosed herein. Sequence information is analyzed to identify the molecular tag of each read. In many cases, sequences sharing a common molecular tag are assigned to a common 'bin,' corresponding to a DNA complex from which they originated. In some cases, the non-original oligonucleotide sequence of a given bin, originating from a common DNA complex, is assigned to a common phase of a single nucleic acid molecule of the original sample. In various cases, more than one DNA complex may anneal to a single oligonucleotide population. In certain cases, resolution of a sequence read to one or another original nucleic acid molecule may be aided by consulting sequence contig information, such as information separately obtained from previously existing data, or concurrently or independently generated. In further cases, DNA complexes are split into pools (in some embodiments as few as 2 pools, or 3, 4, 5, 6, 7, 8, 9, 10, 20, 30, 40, 50, 60, 70, 80, 90, up to 96, or more than 96, such as 100, 200, 300, 384, 400, or more than 400) and each pool has free nucleic acid ends tagged with a barcode that is ligated on to the pool or otherwise attached to the free end of the DNA complex in that pool. In many cases, a barcode tag is unique to that pool. Then, these pools are rejoined and mixed into a single solution prior to performing the oligonucleotide-mediated tagging. This dual tag system lessens the probability of having two complexes genomically overlapping redundantly, indistinguishably tagged, which in some cases leads to indistinguishable and overlapping segments on a single locus due to the pool barcodes. Sequence contig information may be obtained from any number of sources disclosed herein, such as the National Center for Biotechnology Information, the Joint Genome Institute, the Eukaryotic Pathogen Database, or any number of other genome sequence databases. In these embodiments, sequence reads are first mapped to a bin and then assigned to a contig or group of contigs for which some chromosomal or other mapping information is available. Reads are then assigned to a single phase of a common molecule only if they map to a common general contig position in light of independently evaluated contig information.

Disclosed herein are methods, compositions, kits and computer systems related to labeling DNA complexes, such that molecular phase information is recovered and in some cases used to assemble contigs. In some aspects, the present disclosure provides methods comprising: a. crosslinking a first DNA molecule to yield a DNA complex; b. severing the DNA complex to form a plurality of sequence segments comprising a first sequence segment and a second sequence segment, wherein the first sequence segment comprises a first segment end and the second sequence segment comprises a second segment end; and c. attaching a first label to the first segment end and a second label to the second segment end. In some cases, the first label and the second label are identical. In other cases, the first label and the second label are different. In many cases, the first label and the second label are polynucleotides. In certain cases, the first label and the second label each comprise one or more elements selected from the group consisting of a linker, a barcode and an adaptor. In some cases, the first label comprises a first adaptor and the second label comprises a second adaptor. In certain cases, the first adaptor is hybridized to a first binding probe on a resolved locus. In further cases, the resolved locus comprises greater than 10,000 binding probes. In many cases, greater than 90% of the binding probes on the resolved locus are identical. In various cases, the first segment end and the second segment end comprise blunt ends. In other cases, the first segment end and the second segment end comprise overhang sequences. Some embodiments comprise filling in the overhang sequences to generate blunt ends. Certain embodiments comprise adding a first single nucleotide to the first segment end and a second single nucleotide to the second segment end. In some cases, the first and the second single nucleotides are added to the first and the second segment ends using a DNA polymerase that lacks 3'-5' exonuclease activity. In certain cases, the first and the second single nucleotide are both adenosine. In various cases, the first label and the second label are attached to the first and the second segment ends using TA-based ligation. In many cases, the first label comprises a first barcode and the second label comprises a second barcode. In some cases, the first barcode and the second barcode are identical. Some embodiments comprise associating the first sequence segment and the second sequence segment based on the first barcode and the second barcode. Certain embodiments comprise ligating a barcoded aggregate to the DNA complex. In some cases, the barcoded aggregate comprises a plurality of barcoded polynucleotides and a plurality of aggregate molecules. In certain cases, the barcoded polynucleotides are ligated to the first sequence segment and the second sequence segment. Some embodiments comprise amplifying the first sequence segment and the second sequence segment using the barcoded polynucleotides as templates. In some cases, the barcoded polynucleotides comprise the first and the second label. In certain cases, the barcoded polynucleotides are generated using Rolling Circle Amplification (RCA). In various cases, the aggregate molecules comprise amino acids. In many cases, the aggregate molecules comprise peptides or proteins. In further cases, the aggregate molecules comprise histones. In other cases, the aggregate molecules comprise nanoparticles. In some cases, the nanoparticle is a platinum-based nanoparticle. In other cases, the nanoparticle is a DNA intercalator, or any derivatives thereof. In further cases, the nanoparticle is a bisintercalator, or any derivatives thereof.

In some cases, the first DNA molecule is cross-linked to a plurality of association molecules. In various cases, the association molecules comprise amino acids. In many cases, the association molecules comprise peptides or proteins. In further cases, the association molecules comprise histones. In other cases, the association molecules comprise nanoparticles. In some cases, the nanoparticle is a platinum-based nanoparticle. In other cases, the nanoparticle is a DNA intercalator, or any derivatives thereof. In further cases, the nanoparticle is a bisintercalator, or any derivatives thereof. In certain cases, the association molecules are from a different source than the first DNA molecule. Some embodiments comprise linking a sequencing adaptor to the first sequence segment and the second sequence segment. Certain embodiments comprise obtaining sequence information of the first sequence segment and the second sequence segment. Various embodiments comprise using the sequence information to associate the first sequence segment and the second sequence segment. Many embodiments comprise using the sequence information to assemble a plurality of contigs. Some embodiments comprise using the sequence information to assemble the first DNA molecule. Further embodiments comprise using the sequence information to assemble a genome.

The present disclosure provides compositions comprising: a first sequence segment and a second sequence segment; a plurality of association molecules cross-linked to the first and the second sequence segment; and a first label attached to the first sequence segment and a second label attached to the second sequence segment. In some cases, the first and the second labels are identical. In other cases, the first and the second labels are different. In certain cases, the association molecules comprise amino acids. In many cases, the association molecules comprise peptides or proteins. In various cases, the association molecules comprise histones. In other cases, the association molecules comprise nanoparticles. In some cases, the nanoparticle is a platinum-based nanoparticle. In other cases, the nanoparticle is a DNA intercalator, or any derivatives thereof. In further cases, the nanoparticle is a bisintercalator, or any derivatives thereof. In some cases, the association molecules are from a different source than the first DNA molecule. In certain cases, the first and the second sequence segments are produced by severing a first DNA molecule. In various cases, the first label is ligated to the first sequence segment and the second label is ligated to the second sequence segment. In many cases, the first label and the second label are polynucleotides. In further cases, the first label and the second label each comprise one or more elements selected from the group consisting of a linker, a barcode and an adaptor. In some cases, the first label comprises a first adaptor and the second label comprises a second adaptor. In certain cases, the first adaptor is further hybridized to a binding probe on a resolved locus. In further cases, the resolved locus comprises greater than 10,000 binding probes. In many cases, greater than 90% of the binding probes on the resolved loci are identical.

The present disclosure provides compositions comprising: a plurality of barcoded polynucleotides each comprising a label; and a plurality of aggregate molecules attached to the plurality of barcoded polynucleotides. In some cases, all of the labels in the barcoded polynucleotides are identical. In certain cases, the aggregate molecules comprise amino acids. In various cases, the aggregate molecules comprise peptides or proteins. In further cases, the aggregate molecules comprise histones. In other cases, the aggregate molecules comprise nanoparticles. In some cases, the nanoparticle is a platinum-based nanoparticle. In other cases, the nanoparticle is a DNA intercalator, or any derivatives thereof. In further cases, the nanoparticle is a bisintercalator, or any derivatives thereof. In some cases, the barcoded polynucleotides are further ligated to a DNA complex. In certain cases, the DNA complex comprises a first sequence segment and a second sequence segment cross-linked to a plurality of association molecules. In various cases, the first sequence segment and the second sequence segment are each ligated to the barcoded polynucleotides. In certain cases, the association molecules comprise amino acids. In various cases, the association molecules comprise peptides or proteins. In further cases, the association molecules comprise histones. In other cases, the association molecules comprise nanoparticles. In some cases, the nanoparticle is a platinum-based nanoparticle. In other cases, the nanoparticle is a DNA intercalator, or any derivatives thereof. In further cases, the nanoparticle is a bisintercalator, or any derivatives thereof.

The present disclosure provides compositions comprising a first complex comprising a population of nucleic acid sequence units, wherein each sequence unit comprises a primer binding site and a sequence tag unique to that sequence unit, and at least one DNA binding agent bound to at least two of the nucleic acid sequence units, wherein at least two of the nucleic acid sequence units are not covalently bound through a phosphodiester backbone. In some cases, the DNA binding agent is cross-linked to the at least two of the nucleic acid sequences. In certain cases, the first complex is covalently bound through at least one phosphodiester backbone to a second complex comprising a DNA binding agent bound to at least two nucleic acid molecules comprising nucleic acid sequence of a target nucleic acid sample.

The present disclosure provides methods, compositions, kits and computer systems related to DNA characterization, such that molecular phase information can be recovered and in some cases used to assemble contigs.

The present disclosure also provides methods for associating a first sequence segment and a second sequence segment. In some cases, the methods comprise: crosslinking a DNA library comprising a first DNA molecule, wherein the first DNA molecule comprises the first sequence segment and the second sequence segment; isolating the first sequence segment and the second sequence segment in a first reaction volume; and attaching a first label to the first sequence segment and a second label to the second sequence segment.

The present disclosure further provides methods for associating a first sequence segment and a second sequence segment, the method comprising: crosslinking a DNA library comprising a first DNA molecule, wherein the first DNA molecule comprises the first sequence segment and the second sequence segment; isolating the first sequence segment and the second sequence segment in a first reaction volume; and linking the first sequence segment and the second sequence segment. In some cases, the methods comprise releasing the first sequence segment and the second sequence segment from the crosslinking. In certain cases, the methods comprise severing the first DNA molecule. In various cases, the methods comprise linking a sequencing adaptor to the first labeled polynucleotide and the second labeled polynucleotide. In further cases, the methods comprise obtaining sequence information of the first labeled polynucleotide and the second labeled polynucleotide. In certain cases, the methods comprise using the sequence information to associate the first sequence segment and the second sequence segment. In some cases, the methods comprise using the sequence information to assemble a plurality of contigs. In various cases, the methods comprise using the sequence information to assemble the first DNA molecule. In further cases, the methods comprise using the sequence information to assemble a genome. In some cases, the first reaction volume is an aqueous droplet. In certain cases, the first sequence segment and the second sequence segment are isolated in the reaction volume using a microfluidic device. In various cases, the first reaction volume does not comprise any other DNA molecule. In many cases, the first sequence segment and the second sequence segment are cross-linked outside of a cell. In further cases, the first sequence segment and the second sequence segment are cross-linked to a plurality of association molecules. In certain cases, the association molecules comprise amino acids. In various cases, the association molecules comprise peptides or proteins. In further cases, the association molecules comprise histones. In other cases, the association molecules comprise nanoparticles. In some cases, the nanoparticle is a platinum-based nanoparticle. In other cases, the nanoparticle is a DNA intercalator, or any derivatives thereof. In further cases, the nanoparticle is a bisintercalator, or any derivatives thereof. In some cases, the association molecules are from a different source than the first DNA molecule. In some embodiments, the first label and the second label are identical. In other embodiments, the first label and the second label are different. In certain embodiments, the first label and the second label are polynucleotides. In various embodiments, the first label and the second label each comprise one or more elements selected from the group consisting of a primer, a barcode and a restriction site. In further embodiments, the first label and the second label each comprise a barcode. In some cases, the first label and the second label are produced in the first reaction volume. In certain cases, the first label and the second label are produced using PCR. In further cases, the first label and the second label are produced using Rolling Circle Amplification (RCA).

The present disclosure provides an aqueous droplet comprising: a nucleic acid molecule comprising a first sequence segment and a second sequence segment; and plurality of association molecules cross-linked to the first and the second sequence segments. In some cases, the compositions comprise an amplification template. In certain cases, the amplification template is linear. In other cases, the amplification template is circular. In some cases, the compositions comprise a polymerase. In certain cases, compositions comprise a primer. In further cases, the compositions comprise a restriction enzyme. In various cases, the compositions comprise a ligase. In some embodiments, the aqueous droplet is surrounded by an oil or an organic phase. In certain embodiments, the aqueous droplet is within a microfluidic device. In certain cases, the association molecules comprise amino acids. In many cases, the association molecules comprise peptides or proteins. In further cases, the association molecules comprise histones. In other cases, the association molecules comprise nanoparticles. In some cases, the nanoparticle is a platinum-based nanoparticle. In other cases, the nanoparticle is a DNA intercalator, or any derivatives thereof. In further cases, the nanoparticle is a bisintercalator, or any derivatives thereof. In some embodiments, the association molecules are from a different source than the first DNA molecule. In other embodiments, the association molecules are from the same source as the first DNA molecule. In some cases, the histones are from a different source than the first and the second sequence segments. In other cases, the histones are from the same source as the first and the second sequence segments.

The present disclosure also provides compositions comprising an emulsion of a plurality of aqueous droplets, wherein a first droplet comprises: a first nucleic acid, wherein the first nucleic acid molecule comprises a first region and a second region; an oligonucleotide comprising an end sequence capable of annealing to the double-stranded break of known sequence; and a molecular tag sequence; and wherein a first droplet is enveloped by an immiscible layer. In some cases, the first nucleic acid is complexed with a binding agent, wherein the first region and the second region of the first nucleic acid molecule are bound independently of a phosphodiester backbone of the first nucleic acid molecule; and wherein a double-stranded break of known end sequence is introduced between the first region and the second region of the first nucleic acid molecule. In certain cases, the first nucleic acid is covalently bound to the binding agent. In various cases, the first droplet comprises a single covalently bound molecule. In many cases, the oligonucleotide is double-stranded. In further cases, the oligonucleotide comprises biotin. In some cases, the molecular tag sequence of the oligonucleotide is not present in a second droplet. In certain cases, the droplet comprises a ligase. In some further cases, the droplet comprises ATP. In some many cases, the droplet comprises a nucleic acid polymerase. In various cases, the polymerase is BstXI. In certain cases, the droplet comprises a plurality of dNTP. In some cases, the plurality of dNTP comprises at least one biotinylated dNTP. In further cases, the droplet comprises a restriction endonuclease. In some cases, the restriction endonuclease cleaves a double-stranded nucleic acid to produce a double-stranded break of known end sequence. In other cases, the restriction endonuclease is inactive. In certain cases, the restriction endonuclease is NlaIII.

The present disclosure provides a method of assembling a plurality of contigs. In some cases, the method comprises: generating a plurality of read-pairs from a single DNA molecule, wherein said single DNA molecule is cross-linked to a plurality of nanoparticles; and assembling the contigs using the read-pairs, wherein at least 1% of the read-pairs span a distance of at least 50 kB on the single DNA molecule. In certain cases, at least 10% of the read-pairs span a distance of at least 50 kB on the single DNA molecule. In particular cases, at least 1% of the read-pairs span a distance of at least 100 kB on the single DNA molecule. In further cases, the read-pairs are generated within 7 days. In some cases, the nanoparticle is a platinum-based nanoparticle. In certain cases, the platinum-based nanoparticle is selected from the group consisting of cisplatin, oxaliplatin, and transplatin. In other cases, the nanoparticle is a DNA intercalator. In some cases, the DNA intercalator is a bis-intercalator. In further cases, the bis-intercalator is bisacridine. In some cases, the crosslinking is reversible. In certain cases, the crosslinking is reversed using heat. In other cases, the crosslinking is reversed using a chemical agent such as thiourea.

In other cases, the method comprises: generating a plurality of read-pairs from the single DNA molecule outside of a cell; and assembling the contigs using the read-pairs, wherein at least 1% of the read-pairs span a distance of at least 50 kB on the single DNA molecule. In certain cases, at least 1% of the read-pairs span a distance of at least 100 kB on the single DNA molecule. In further cases, at least 1% of the read-pairs span a distance of at least 500 kB on the single DNA molecule. In some cases, the nanoparticle is a platinum-based nanoparticle. In certain cases, the platinum-based nanoparticle is selected from the group consisting of cisplatin, oxaliplatin, and transplatin. In other cases, the nanoparticle is a DNA intercalator. In some cases, the DNA intercalator is a bis-intercalator. In further cases, the bis-intercalator is bisacridine. In some cases, the crosslinking is reversible. In certain cases, the crosslinking is reversed using heat. In other cases, the crosslinking is reversed using a chemical agent such as thiourea.

The present disclosure provides a method of haplotype phasing. In some cases, the method comprises: generating a plurality of read-pairs from a single DNA molecule, wherein said single DNA molecule is cross-linked to a plurality of nanoparticles; and assembling a plurality of contigs of the DNA molecule using the read-pairs, wherein at least 1% of the read-pairs spans a distance of at least 50 kB on the single DNA molecule, and wherein the haplotype phasing is performed at greater than 70% accuracy. In certain cases, at least 10% of the read-pairs span a distance of at least 50 kB on the single DNA molecule. In further cases, at least 1% of the read-pairs span a distance of at least 100 kB on the single DNA molecule. In various cases, the haplotype phasing is performed at greater than 90% accuracy. In some cases, the nanoparticle is a platinum-based nanoparticle. In certain cases, the platinum-based nanoparticle is selected from the group consisting of cisplatin, oxaliplatin, and transplatin. In other cases, the nanoparticle is a DNA intercalator. In some cases, the DNA intercalator is a bis-intercalator. In further cases, the bis-intercalator is bisacridine. In some cases, the crosslinking is reversible. In certain cases, the crosslinking is reversed using heat. In other cases, the crosslinking is reversed using a chemical agent such as thiourea.

The method comprises: generating a plurality of read-pairs from a single DNA molecule, wherein said single DNA molecule is cross-linked to a plurality of nanoparticles outside of a cell; and assembling a plurality of contigs of the DNA molecule using the read-pairs, wherein at least 1% of the read-pairs spans a distance of at least 30 kB on the single DNA molecule, and wherein the haplotype phasing is performed at greater than 70% accuracy. In certain cases, at least 10% of the read-pairs span a distance of at least 30 kB on the single DNA molecule. In further cases, at least 1% of the read-pairs span a distance of at least 50 kB on the single DNA molecule. In various cases, the haplotype phasing is performed at greater than 90% accuracy. In some cases, the nanoparticle is a platinum-based nanoparticle. In certain cases, the platinum-based nanoparticle is selected from the group consisting of cisplatin, oxaliplatin, and transplatin. In other cases, the nanoparticle is a DNA intercalator. In some cases, the DNA intercalator is a bis-intercalator. In further cases, the bis-intercalator is bisacridine. In some cases, the crosslinking is reversible. In certain cases, the crosslinking is reversed using heat. In other cases, the crosslinking is reversed using a chemical agent such as thiourea.

The present disclosure provides a method of generating a first read-pair from a first DNA molecule. In some cases, the method comprises: (a) crosslinking the first DNA molecule to a plurality of nanoparticles outside of a cell, wherein the first DNA molecule comprises a first DNA segment and a second DNA segment; (b) linking the first DNA segment with the second DNA segment and thereby forming a linked DNA segment; and (c) sequencing the linked DNA segment and thereby obtaining the first read-pair. In certain cases, the first DNA molecule is cross-linked with a fixative agent. In various cases, the fixative agent is formaldehyde. In further cases, the first DNA segment and the second DNA segment are generated by severing the first DNA molecule. In certain cases, the method further comprises assembling a plurality of contigs using the first read-pair. In some cases, each of the first and the second DNA segment is connected to at least one affinity label and the linked DNA segment is captured using the affinity labels. In various cases, the method further comprises: (a) crosslinking a second plurality of nanoparticles to a second DNA molecule outside of a cell and thereby forming a second complex; (b) severing the second complex thereby generating a third DNA segment and a fourth segment; (c) linking the third DNA segment with the fourth DNA segment and thereby forming a second linked DNA segment; and (d) sequencing the second linked DNA segment and thereby obtaining a second read-pair. In certain cases, less than 40% of the DNA segments from the DNA molecules are linked with DNA segments from any other DNA molecule. In further cases, less than 20% of the DNA segments from the DNA molecules are linked with DNA segments from any other DNA molecule. In some cases, the nanoparticle is a platinum-based nanoparticle. In certain cases, the platinum-based nanoparticle is selected from the group consisting of cisplatin, oxaliplatin, and transplatin. In other cases, the nanoparticle is a DNA intercalator. In some cases, the DNA intercalator is a bis-intercalator. In further cases, the bis-intercalator is bisacridine. In some cases, the crosslinking is reversible. In certain cases, the crosslinking is reversed using heat. In other cases, the crosslinking is reversed using a chemical agent such as thiourea.

The present disclosure provides a method of generating a first read-pair from a first DNA molecule comprising a predetermined sequence. In some cases, the method comprises: (a) providing one or more DNA-binding molecules to the first DNA molecule, wherein the one or more DNA-binding molecules bind to the predetermined sequence; (b) crosslinking the first DNA molecule to a plurality of nanoparticles outside of a cell, wherein the first DNA molecule comprises a first DNA segment and a second DNA segment; (c) linking the first DNA segment with the second DNA segment and thereby forming a first linked DNA segment; and (d) sequencing the first linked DNA segment and thereby obtaining the first read-pair; wherein the probability that the predetermined sequence appears in the read-pair is affected by the binding of the DNA-binding molecule to the predetermined sequence. In certain cases, the DNA-binding molecule is a nucleic acid that can hybridize to the predetermined sequence. In some cases, the nucleic acid is RNA. In other cases, the nucleic acid is DNA. In further cases, the DNA-binding molecule is a small molecule. In some cases, the nanoparticle is a platinum-based nanoparticle. In certain cases, the platinum-based nanoparticle is selected from the group consisting of cisplatin, oxaliplatin, and transplatin. In other cases, the nanoparticle is a DNA intercalator. In some cases, the DNA intercalator is a bis-intercalator. In further cases, the bis-intercalator is bisacridine. In some cases, the crosslinking is reversible. In certain cases, the crosslinking is reversed using heat. In other cases, the crosslinking is reversed using a chemical agent such as thiourea. In some embodiments, the small molecule binds to the predetermined sequence with a binding affinity less than 100 µM. In further embodiments, the small molecule binds to the predetermined sequence with a binding affinity less than 1 µM. In some cases, the DNA-binding molecule is immobilized on a surface or a solid support. In certain cases, the probability that the predetermined sequence appears in the read-pair is decreased. In other cases, the probability that the predetermined sequence appears in the read-pair is increased.

The present disclosure provides a composition comprising a DNA fragment and a plurality of nanoparticles, wherein the nanoparticles are cross-linked to the DNA fragment in an in vitro complex, and wherein the in vitro complex is immobilized on a solid support. In other aspects, the present disclosure provides a composition comprising a DNA fragment, a plurality of nanoparticles, and a DNA-binding molecule, wherein the DNA-binding molecule is bound to a predetermined sequence of the DNA fragment, and wherein the nanoparticles are cross-linked to the DNA fragment. In some cases, the DNA-binding molecule is a nucleic acid that can hybridize to the predetermined sequence. In some cases, the nucleic acid is RNA. In other cases, the nucleic acid is DNA. In further cases, the DNA-binding molecule is a small molecule. In some cases, the nanoparticle is a platinum-based nanoparticle. In certain cases, the platinum-based nanoparticle is selected from the group consisting of cisplatin, oxaliplatin, and transplatin. In other cases, the nanoparticle is a DNA intercalator. In some cases, the DNA intercalator is a bis-intercalator. In further cases, the bis-intercalator is bisacridine. In some cases, the crosslinking is reversible. In certain cases, the crosslinking is reversed using heat. In other cases, the crosslinking is reversed using a chemical agent such as thiourea. In some embodiments, the small molecule binds to the predetermined sequence with a binding affinity less than 100 µM. In further embodiments, small molecule binds to the predetermined sequence with a binding affinity less than 1 µM. In certain cases, the nucleic acid is immobilized to a surface or a solid support.

In some cases, methods that produce fragments of genomic DNA up to megabase scale are used with the methods disclosed herein. Long DNA fragments can be generated to confirm the ability of the present methods to generate read pairs spanning the longest fragments offered by those extractions. In some cases, DNA fragments beyond 150 kbp in length are extracted and used to generate XLRP libraries.

The disclosure provides methods for greatly accelerating and improving de novo genome assembly. The methods disclosed herein utilize methods for data analysis that allow for rapid and inexpensive de novo assembly of genomes from one or more subjects. The disclosure further provides that the methods disclosed herein can be used in a variety of applications, including haplotype phasing, and metagenomics analysis.

The disclosure provides for a method for genome assembly comprising the steps of: generating a plurality of contigs; generating a plurality of read pairs from data produced by probing the physical layout of chromosomes, chromatin, or reconstituted chromatin; mapping or assembling the plurality of read pairs to the plurality of contigs; constructing an adjacency matrix of contigs using the read-mapping or assembly data; and analyzing the adjacency matrix to determine a path through the contigs that represent their order and/or orientation to the genome. In some cases, the disclosure provides that at least about 90% of the read pairs are weighted by taking a function of each read's distance to the edge of the contig so as to incorporate information about which read pairs indicate short-range contacts and which read pairs indicate longer-range contacts. In certain cases, the adjacency matrix is re-scaled to down-weight the high number of contacts on some contigs that represent promiscuous regions of the genome, such as conserved binding sites for one or more agents that regulate the scaffolding interactions of chromatin, like transcriptional repressor CTCF. In further cases, the disclosure provides for a method for the genome assembly of a human subject, whereby the plurality of contigs is generated from the human subject's DNA, and whereby the plurality of read pairs is generated from analyzing the human subject's chromosomes, chromatin, or reconstituted chromatin made from the subject's naked DNA.

The present disclosure provides a method for generating a plurality of contigs using a shotgun sequencing technique. In some cases, the method comprises: fragmenting long stretches of a subject's DNA into random fragments of indeterminate size; sequencing the fragments using high throughput sequencing methods to generate a plurality of sequencing reads; and assembling the sequencing reads so as to form a plurality of contigs.

The present disclosure provides a method for generating a plurality of read pairs by probing the physical layout of chromosomes, chromatin, or reconstituted chromatin using a chromatin capture technique. In some cases, the chromatin capture technique comprises: crosslinking chromosomes, chromatin, or reconstituted chromatin with a fixative agent, such as formaldehyde, to form DNA-protein cross links; cutting the cross-linked DNA-Protein with one or more restriction enzymes so as to generate a plurality of DNA-protein complexes comprising sticky ends; filling in the sticky ends with nucleotides containing one or more markers, such as biotin, to create blunt ends that are then ligated together; fragmenting the plurality of DNA-protein complexes into fragments; pulling down junction containing fragments by using the one or more of the markers; and sequencing the junction containing fragments using high throughput sequencing methods to generate a plurality of read pairs. In certain cases, the plurality of read pairs for the methods disclosed herein is generated from data produced by probing the physical layout of reconstituted chromatin.

The present disclosure provides a method for determining a plurality of read pairs by probing the physical layout of chromosomes or chromatin isolated from cultured cells or primary tissue. In some cases, the plurality of read pairs are determined by probing the physical layout of reconstituted chromatin formed by complexing naked DNA obtained from a sample of one or more subjects with isolated histones.

The present disclosure provides a method to determine haplotype phasing. In some cases, the method comprises a step of identifying one or more sites of heterozygosity in the plurality of read pairs, wherein phasing data for allelic variants are determined by identifying read pairs that comprise a pair of heterozygous sites.

The present disclosure provides a method for high-throughput bacterial genome assembly. In certain cases, the method comprises a step of generating a plurality of read pairs by probing the physical layout of a plurality of microbial chromosomes using a modified chromatin capture method, comprising the modified steps of: collecting microbes from an environment; adding a fixative agent, such as formaldehyde, so as to form cross-links within each microbial cell, and wherein read pairs mapping to different contigs indicate which contigs are from the same species.

The present disclosure provides a method for genome assembly. In certain cases, the method comprises: (a) generating a plurality of contigs; (b) determining a plurality of read pairs from data generated by probing the physical layout of chromosomes, chromatin, or reconstituted chromatin; (c) mapping the plurality of read pairs to the plurality of contigs; (d) constructing an adjacency matrix of contigs using the read-mapping data; and (e) analyzing the adjacency matrix to determine a path through the contigs that represent their order and/or orientation to the genome.

The present disclosure provides a method to generate a plurality of read pairs by probing the physical layout of chromosomes, chromatin, or reconstituted chromatin using a chromatin capture technique. In further cases, the chromatin capture technique comprises (a) crosslinking chromosomes, chromatin, or reconstituted chromatin with a fixative agent to form DNA-protein cross links; (b) cutting the cross-linked DNA-Protein with one or more restriction enzymes so as to generate a plurality of DNA-protein complexes comprising sticky ends; (c) filling in the sticky ends with nucleotides containing one or more markers to create blunt ends that are then ligated together; (d) shearing the plurality of DNA-protein complexes into fragments; (e) pulling down junction containing fragments by using one or more of the markers; and (f) sequencing the junction containing fragments using high throughput sequencing methods to generate a plurality of read pairs. In certain cases, the plurality of read pairs is determined by probing the physical layout of chromosomes or chromatin isolated from cultured cells or primary tissue. In some cases, the plurality of read pairs is determined by probing the physical layout of reconstituted chromatin formed by complexing naked DNA obtained from a sample of one or more subjects with isolated histones. In certain cases, at least about 50%, about 60%, about 70%, about 80%, about 90%, about 95% or about 99% or more of the plurality of read pairs are weighted by taking a function of the read's distance to the edge of the contig so as to incorporate a higher probability of shorter contacts than longer contacts. In various cases, the adjacency matrix is re-scaled to down-weight the high number of contacts on some contigs that represent promiscuous regions of the genome. In further cases, the promiscuous regions of the genome include one or more conserved binding sites for one or more agents that regulate the scaffolding interactions of chromatin. In some cases, the agent is transcriptional repressor CTCF.

The methods disclosed herein provide for the genome assembly of a human subject. In some cases, the plurality of contigs is generated from the human subject's DNA. In further cases, the plurality of read pairs is generated from analyzing the human subject's chromosomes, chromatin, or reconstituted chromatin made from the subject's naked DNA.

The present disclosure provides a method for determining haplotype phasing. In some cases, the method comprises identifying one or more sites of heterozygosity in the plurality of read pairs, wherein phasing data for allelic variants are determined by identifying read pairs that comprise a pair of heterozygous sites.

The present disclosure provides a method for metagenomics assemblies, wherein a plurality of read pairs is generated by probing the physical layout of a plurality of microbial chromosomes using a modified chromatin capture method. In certain cases, the method comprises: collecting microbes from an environment; and adding a fixative agent so as to form cross-links within each microbial cell, and wherein read pairs mapping to different contigs indicate which contigs are from the same species. In some cases, the fixative agent is formaldehyde.

Also disclosed herein is a method of generating a first read-pair from a first DNA molecule. In some aspects the method comprises one or more of: (a) binding the first DNA molecule to a plurality of binding moieties outside of a cell, wherein the first DNA molecule comprises a first DNA segment and a second DNA segment; (b) digesting the first DNA molecule such that the first DNA segment and the second DNA segment are not bound by a common phosphodiester backbone; (c) tagging an exposed end of the first DNA segment and an exposed end of the second DNA segment; (d) linking the first DNA segment to a nucleic acid binding partner thereby forming a linked DNA segment; and (e) sequencing the linked DNA segment and thereby obtaining the first read-pair, said first read pair comprising at least some first DNA segment sequence and at least some nucleic acid binding partner sequence. In some aspects the binding moieties are nanoparticles. 26. In some aspects the nanoparticles are platinum-based nanoparticles. In some aspects the nanoparticles are DNA intercalators. In some aspects the nucleic acid binding partner comprises the second DNA segment sequence. In some aspects the first DNA segment maps to a first contig and the second DNA segment maps to a second DNA contig. Some aspects further comprise assigning the first contig and the second contig to a common DNA scaffold. Some aspects further comprise assigning the first contig and the second contig to common DNA molecule. In some aspects the nucleic acid binding partner comprises an oligonucleotide tag sequence. In some aspects the oligonucleotide tag sequence is bound to a solid surface comprising a plurality of the oligonucleotide tag sequence. In some aspects the solid surface is a nucleic acid array. In some aspects the oligonucleotide tag sequence is cross-linked to a DNA binding moiety that comprises multiple copies of the oligonucleotide tag sequence. In some aspects the DNA binding moiety comprises reconstituted chromatin. In some aspects the DNA binding moiety comprises a nanoparticle. In some aspects the oligonucleotide tag sequence is contained in a vesicle.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2A illustrates where DNA is cross-linked and processed. FIG. 2B demonstrates where read-set data are mapped to assembled contigs, generated from random shotgun sequencing and assembly. FIG. 2C illustrates that after filtering and weighting, an adjacency matrix summarizing all inter-contig read-set data can be constructed. This matrix can be re-ordered to indicate the correct assembly path. As shown, most of the read set will map within a contig. Read-sets that map to different contigs provide data about which contigs are adjacent in a correct genome assembly.

FIG. 3A: Uncertainty in linkage results from read pairs that cannot bridge repetitive regions. FIG. 3B Uncertainty in placement of segment because read pairs cannot span bordering repeats.

FIG. 6A.1-11 provides details and a protocol for oligonucleotide synthesis, sequence and fixation to an array. At FIG. 6.A.1 is shown, from top to bottom, a 12-carbon group with an amino moiety for attachment to an epoxysilane glass surface; a hexaethyleglycol group intended for increasing the distance between a solid surface and the DNA sequence of an oligonucleotide attached to the surface; an exemplary Adaptor oligonucleotide (SEQ ID NO: 1); and an exemplary Chromatin Capture Oligonucleotide (CCO) (SEQ ID NO: 2). At FIG. 6A.2 is seen the structure and reaction with an amine of an epoxysilanized cover slip (image courtesy www.us.schott.com). Also at FIG. 6A.2 is shown an exemplary Adapter oligonucleotide and CCO, each linked to a solid surface, through linker molecules that are left out for clarity. At FIG. 6A.3 is seen an exemplary synthesized barcoded oligonucleotide. At FIG. 6A.4. is seen an exemplary barcoded oligonucleotide (SEQ ID NO: 3) annealed to an exemplary annealing primer (SEQ ID NO: 1) of the surface of FIG. 6A.3, above. At FIG. 6A.5, is seen strand extension with DNA Polymerase, Klenow of the structure at FIG. 6.A4. At FIG. 6A.6 is seen the structure (SEQ ID NO: 4) after removal of the original barcoded oligos following DNA synthesis. At FIG. 6A.7 is seen annealing of the CCO primer (SEQ ID NO: 2) to the synthesized strand (SEQ ID NO: 4). At FIG. 6A.8 is shown strand extension with a thermostable polymerase such as Taq (SEQ ID NO: 3 and SEQ ID NO: 4). At FIG. 6A.9 is seen the final product of one cycle of PCR after melting the duplexes (SEQ ID NO: 3 and SEQ ID NO: 4). At FIG. 6A.10 is seen formation of blunt ends from stable bridges formed by the amplification of the previous products (SEQ ID NO: 5). At FIG. 6A.11 is seen the platform ready to be ligated to an appropriately digested DNA complex after the blunt-ended double-stranded molecules generated previously are melted and strands not covalently linked to the structure are removed.

FIG. 6B.1-7 provides details of oligonucleotide extension, chromatin complex release and oligonucleotide cleavage. At FIG. 6B.1 is seen chromatin (as a DNA complex) prepared and ligated to a universal adapter (SEQ ID NO: 6). At FIG. 6B.2, chromatin (as a DNA complex) is ligated to a capture sequence (SEQ ID NO: 7). At FIG. 6B.3 the 3' end of the ligated chromatin is extended with a DNA polymerase such as Klenow fragment (SEQ ID NO: 8). At FIG. 6B.4, Chromatin is removed, as is some sequence distal to the ligation site. At FIG. 6B.5, the free 3' end is adenylated (SEQ ID NO: 9) with a polymerase such as Klenow (3'-5' exo-). At FIG. 6B.6, a sequencing adaptor is ligated by TA ligation with a DNA ligase such as T4 DNA ligase. The adaptor shown here is a P7 adaptor (SEQ ID NO: 10 and SEQ ID NO: 11). At FIG. 6B.7, PCR may now be performed to obtain sufficient quantities of product for high-throughput sequencing (SEQ ID NO: 12 and SEQ ID NO: 13).

FIG. 11A-D provides an example of an alternative oligo adapter scheme. FIG. 11A: An adapter oligo (top; SEQ ID NO: 14) and a chromatin capture oligo ('CCO', bottom; SEQ ID NO: 17) are presented. Each oligo comprises a 5' terminal group such as an amino group or a phosphate group, and 1 to 10 spacer groups 5' to the sequence indicated. The sequences provided herein are exemplary. Other oligonucleotides consistent with the disclosure and methods herein are contemplated (eg., SEQ ID NO: 15 and SEQ ID NO: 16). In some embodiments both oligos are fixed at their 5' ends to an array or other solid support. FIG. 11B A barcoded oligo is presented (SEQ ID NO: 18). The oligo comprises in a 5' position sequence identical to the chromatin capture oligo in (A), above, followed in the 3' direction by a capture sequence, a molecular tag sequence or barcode that varies among loci in an array, a sequencing adapter, and a sequence that comprises the reverse complement of the adapter oligo such that the adapter oligo can anneal thereto. FIG. 11C A product of bridge amplification as applied to the oligos in (A) and (B). The oligo in (B) hybridizes at its 3' end to the adapter oligo of (A). Nucleic acid synthesis off of the 3' OH of the adapter oligo of (A) and templated by the oligo in (B) creates the double-stranded DNA molecule as depicted herein (SEQ ID NO: 14 and 19-21), having a restriction endonuclease site generated within the CCO oligo. FIG. 11D The product in (C) is digested with the restriction endonuclease that cleaves the restriction site generated in (C), (which is depicted as an MlyI site, but for which other restriction sites and endonucleases are compatible alternatives), and the nucleic acids are melted to allow oligonucleotides not bound at a 5' end to the solid surface to be washed away. The resultant single-stranded oligonucleotides include a single-stranded CCO oligo having sequence for the restriction site and a free 3' OH, and a second oligo comprising, the 5' end, a junction with the surface, an adapter oligo sequence, molecular tag or barcode sequence, and a capture sequence that is selected to interact with the free double-strand breaks of appropriately prepared DNA complexes.

FIG. 13A-B provide illustrations of correctly and incorrectly oriented contigs. FIG. 13A depicts properly oriented contigs. A first and second contig are indicated by solid black bars at the bottom of the figure, while each of four read sets are indicated by four horizontal files, of boxes corresponding to the position to which each maps on a contig. The first and second contigs are oriented such that the distance among reads in each of the four read sets is minimized. FIG. 13B depicts incorrectly oriented contigs. A first and second contig are indicated by solid black bars, while each of four read sets are indicated by four horizontal files, of boxes corresponding to the position to which each maps on a contig. The first and second contigs are not oriented such that the distance among reads in each of the four read sets is minimized.

FIG. 14A-D provides an exemplary method for attaching universal adaptors to a DNA complex. Shown is a representation of cross-linked chromatin that has been digested with the restriction endonuclease MboI, which leaves a 5' single strand GATC overhang. The sequences and chromatin fragmentation method are used purely to demonstrate this method, and other sequences and/or fragmentation methods may be suitable. The grey circle is cross-linked chromatin with associated, MboI digested DNA. For clarity only one MboI end of DNA is shown, but there will be more than one. FIG. 14A demonstrates that enzymes are used to generate blunt ends. There are a number of ways to generate blunt ends. For example, a mixture of DNA polymerase and exonuclease can be used to fill in 3' recessed ends (SEQ ID NO: 23) and cut back 5' overhangs (SEQ ID NO: 22). Here, a DNA polymerase is used to fill in the recessed 3' end. FIG. 14B demonstrates Klenow (3'-5' exo-) used to adenylate the 3' end (SEQ ID NO: 24). FIG. 14C demonstrates that DNA Ligase is used to ligate an adapter by TA mediated ligation. The adapter (SEQ ID NO: 25) has 3 parts: 1) a single strand 3' or 5' overhang depending on the chromatin capture platform to be used; 2) a double stranded region that functions to form an adapter, but may also contain a barcode region; and 3) a 3' T overhang for TA ligation. The free 5' end may be optionally phosphorylated if required for ligation to a downstream capture platform. FIG. 14D demonstrates that chromatin is now ready for use with the appropriate chromatin capture platform (SEQ ID NO: 26 and SEQ ID NO: 27).

FIG. 15A provides a representative of a library of barcoded circular products. Each library constituent comprises a circular nucleic acid molecule having a 'forward' PCR primer site, followed by a random sequence of a set length (in the figure, the length is 17 bp) followed by a multiple cloning site. FIG. 15B shows the conversion of a circular library member into a linear double-stranded concatamer of the monomeric sequence. FIG. 15C shows the generation of a 'barcode ball' from the linear concatamer of 5B. Chromatin constituents or other DNA binding moieties are added to the linear concatamers, resulting in DNA-binder complex formation. The complexes may optionally be contacted with a cross-linking agent such as formaldehyde or psoralen. The DNA-binder complexes are treated with a restriction endonuclease to cleave concatamer sequence at exposed multiple cloning sites. Break points are treated with phosphatase or with ddTTP tailing to prevent later self-ligation of cleaved ends. FIG. 15D shows a barcode ball bound to a target sequence DNA-binding agent complex prepared with DNA breakpoints having overhangs complementary to those of the barcode ball. The barcode balls are mixed with the prepared target DNA complexes and treated with ligase. In some embodiments the barcode balls are provided in excess, to reduce the chance of two target DNA complexes binding to one another. Barcode balls, as mentioned above, are treated to prevent self or cross-ligation. FIG. 15E shows a Barcode ball-DNA complex ligation product. Multiple Barcode ball ends are ligated to multiple cleaved target DNA ends. FIG. 15F shows the production of a sequencing library from a Barcode ball DNA complex ligation product. A ligation product is sheared and end-repaired to form a population of linear DNA molecules, some of which comprise Barcode ball—target nucleic acid ligation junctions comprising primer binding sites and random sequence tags. A reverse adapter is ligated onto the population, and amplification and size selection is used to generate a suitable sequencing library comprising end labeled, size selected inserts comprising junction sequences.

FIG. 16A-G provide details of the concatamer synthesis process. FIG. 16A provides an exemplary 200 bp oligonucleotide capable of circularization with a p5 primer. The oligo comprises a primer binding site and a variable region as in FIG. 15A-E, above. FIG. 16B provides details of the junction of the circularized molecule. "p" and "B" are for schematic purposes and do not indicate actual bases in a sequence; rather these letters indicate the function of the bases at those positions. The MboI site is indicated (SEQ ID NO: 28). FIG. 16C provides an alternative sequence, having a HindIII site indicated (SEQ ID NO: 29 and SEQ ID NO: 30). FIG. 16D indicates how rolling strand synthesis may be initiated to generate concatamers. FIG. 16E shows extension of e rolling strand synthesis using phage29 polymerase and dNTPs. FIG. 16F indicates second strand synthesis using the p5 binding site that originally directed circularization.

FIG. 16G provide an exemplary composition for digesting the junction ends between concatamers in the complex.

FIG. 17A provides a three-part workflow for the generation of emulsion compositions, comprising: the following sections: 1. A sample comprising DNA-protein complexes is passed through a microfluidics device such that droplets comprising individual DNA-protein complexes are generated, separated by immiscible liquid; 2. Droplets may be thermally, chemically or otherwise manipulated; 3. To individual droplets are added reagents related to nucleic acid synthesis, restriction and ligation. FIG. 17B provides an alternative workflow for the generation of emulsion compositions, through which an emulsion comprising individual droplets, each comprising at least one DNA-protein complex per droplet is generated. A composition comprising DNA-protein complexes is provided in a volume with an immiscible liquid. The volume is subjected to blending, vortexing or otherwise agitated to form an emulsion of at least one DNA-complex per hydrophilic droplet in the emulsion.

FIG. 18A-E provides an exemplary workflow for the methods disclosed herein. FIG. 18A depicts a composition comprising DNA-protein complexes provided with a population of unique circular nucleic acid molecules encoding molecular tag oligonucleotides in a volume with an immiscible liquid. FIG. 18B depicts the composition being emulsified to generate droplets having a single DNA-protein complex, a single circular nucleic acid, and a composition comprising a heat-activatable DNA polymerase, a restriction endonuclease, a ligase, and reagents for the activity of these enzymes. FIG. 18C depicts the droplet being heated to activate the polymerase, leading to rolling-circle amplification of the sequence of the circular nucleic acid to form a multimeric repeat of the circular nucleic acid sequence. FIG. 18D depicts the droplet being cooled to increase restriction endonuclease activity, heated to inactivate both the polymerase and the restriction endonuclease, and cooled to a ligase active temperature. Newly released linear oligonucleotide fragments are annealed to the sticky ends of the DNA-protein complex and ligate thereto. The emulsion is then broken and ligated oligos are released for sequencing. FIG. 18E depicts a cartoon of the circular nucleic acid template, indicating presence of a restriction endonuclease site and of a bar code-containing region.

FIG. 19A demonstrates where DNA is cross-linked and processed to created biotinylated junction fragments for sequencing (e.g., SEQ ID NO: 34). FIG. 19B, FIG. 19C, and FIG. 19D provide contact map data on human chr14 for a variety of restriction enzymes. As shown, most contacts are local along the chromosome.

FIG. 24 illustrates the phasing accuracy for a sample with well-characterized haplotypes, NA12878, using the read pairs generated using nanoparticle-DNA complexes. Indicated distances are those between the SNPs being phased.

FIG. 25 provides characterization of the read pairs generated using nanoparticle-DNA complexes.

DETAILED DESCRIPTION

Figure 1:
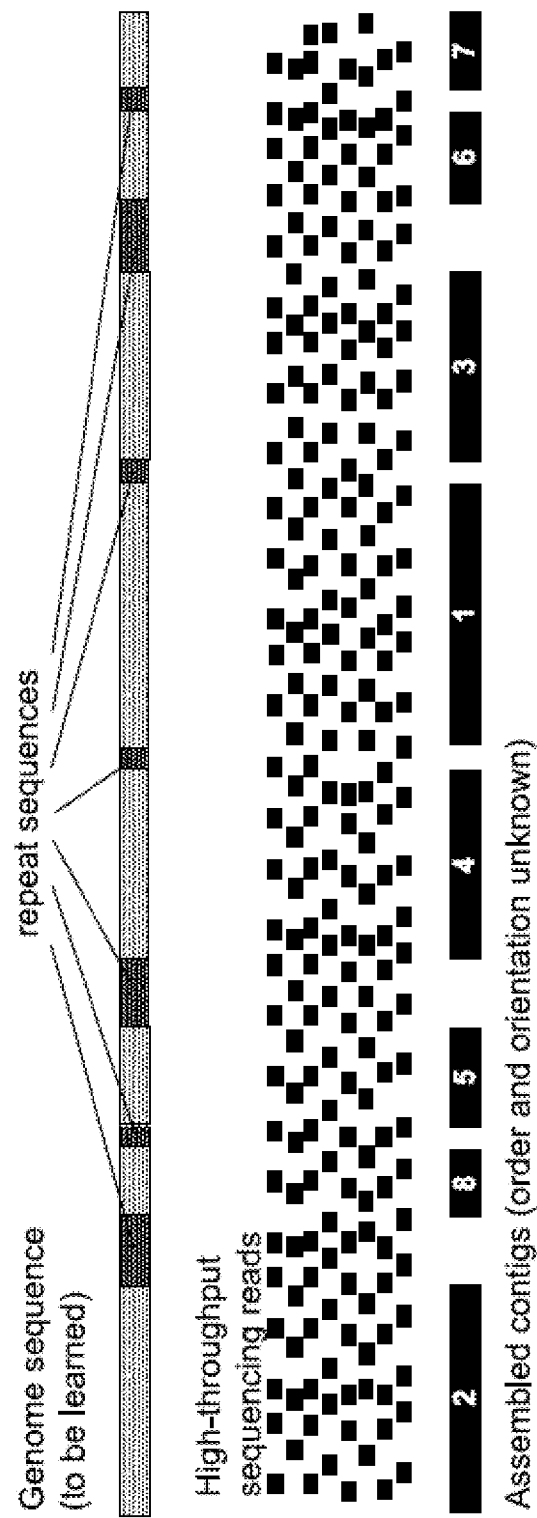
FIG. 1 presents an illustration of genome assembly using high-throughput sequencing reads. The genome to be assembled is shown (top). Typically, genomes have many repeat sequences that are difficult to assemble. Random, high-throughput sequence data from genomes (middle) are collected and assembled into "contigs" in regions that are unique in the genome (bottom). Contig assembly generally stops at the many repeat sequences. The final output is a set of thousands of contigs whose order and orientation relative to one another are not known. In the figure, they are arbitrarily numbered from longest to shortest.

Technological efforts to produce long-range DNA sequence information have largely been stymied by the difficulty of manipulating long DNA fragments, which are exceptionally fragile, and by the massive throughput required to analyze whole genomes. Some current efforts to address these shortcomings include the development of nanopore-based sequencing technology (Eisenstein, M. (2012). *Nat. Biotechnol*, 30(4), 295-6), sequencing of pools of diluted fosmid clones (Kitzman et al. (2011) *Nat. Biotechnol*, 29(1), 59-63), and the use of data from chromatin capture experiments (Burton et al. (2013) *Nat. Biotechnol*, 31(12), 1119-25; Selvaraj et al. (2013) *Nat. Biotechnol*, 31(12), 1111-8). These approaches are not yet developed enough to become routinely implemented in sequencing efforts.

De novo genomic assembly can be improved by incorporating long range DNA interaction data obtained by linking together distant DNA sequences. One method to form these linkages is to assemble chromatin in vitro with genomic DNA and proteins such as histones. The assembled chromatin can then be cross-linked to fix long range interactions, and the sequence of DNA found within each is identified. One way to identify DNA sequences in an aggregate is to digest and re-ligate DNA, followed by identification of non-contiguous DNA sequences via sequencing. This approach, however, is limited by its capacity to identify only one pair of DNA sequences with an aggregate.

The present disclosure provides robust, cost-effective, and sample-efficient methods for producing long range sequence information, such as physical linkage information for assembled contigs that are bound by repetitive, hard to assemble sequence regions. The methods disclosed herein address previous shortcomings while producing sequence information or physical linkage information over comparatively vast genomic distances (up to megabases) due to the stabilization offered by chromatin and cross-linking. Furthermore, the methods disclosed herein may be realized with numerous distinct platforms, each with strengths and weaknesses for particular applications or targeted outcomes.

The present disclosure provides methods for identifying DNA sequences within a chromatin aggregate by associating the ends of DNA with reverse complementary sequences. In some cases, the chromatin is digested with a restriction enzyme, which may leave short overhangs of the restriction enzyme recognition site, and the DNA may be captured on a chromatin capture platform (e.g. a DNA microarray) using a sequence that is the reverse complement of the restriction enzyme recognition site. In further examples, a common adaptor is attached to the ends of DNA in the digested chromatin aggregate to allow for more powerful and flexible approaches towards analyzing the identity of DNA within individual aggregates. There are several advantages of attaching an adaptor to the chromatin aggregates. The capture sequence for hybridizing to the chromatin aggregate can be standardized across chromatin preparations and platforms. For instance, only one platform design may be needed and different methods for fragmenting the chromatin (e.g. using different restriction enzymes) may be employed. The adaptor may also be designed to comprise a unique barcode, which may allow for efficient use of the bandwidth of the chromatin capture platform. For example, several distinct in vitro chromatin assemblies may be prepared and attached to an adaptor with a unique barcode, so that the distinct chromatin assemblies may be applied to a same chromatin capture platform and still be identified in downstream analysis based on the barcode sequence. Alternatively, one in vitro chromatin assembly may be prepared and split into multiple aliquots, which are each linked to a chromatin adaptor with a unique barcode. In some cases, the aliquots are mixed backed together and applied to a same chromatin capture platform, but the distinct chromatin aggregates that share the same barcode can still be identified. The use of the adaptors may also negate the bias caused by digesting the chromatin aggregate with a restriction enzyme that has a non-palindromic recognition site, wherein only one of the single-strand overhangs is captured on the chromatin capture platform. In some cases, the adaptors are designed such that the capture sequence(s) has a desired melting temperature (Tm). In further examples, a protective moiety (e.g. a phosphorothioate bond) is introduced into the adaptor to protect the short overhangs on the chromatin from exonuclease activity.

Knowledge of all DNA sequences within a chromatin aggregate would prove more powerful for accurate de novo genome assembly. A method for the identifying DNA sequences in an aggregate can be achieved by attaching a unique label (e.g. a barcode) to the sequences found within the aggregate. DNA sequencing of the labeled sequences may reveal the nature of these sequences and help group them together according to the barcode attached to them. The present disclosure provides methods and compositions for attaching barcodes to DNA sequences that may be found within a chromatin aggregate.

The present disclosure also provides methods for carrying out massively-parallel barcoding of individual DNA molecules. In some cases, libraries of barcode aggregates (also referred to as "barcode balls) each comprising multiple copies of a barcode tag, which is unique for each barcode aggregate, are used to attach barcode tags to the ends of DNA. In some cases, each individual DNA molecule is labeled with a unique barcode tag and DNA segments labeled with a common barcode tag are identified.

As used herein and in the appended claims, the singular forms "a," "and," and "the" include plural referents unless the context clearly dictates otherwise. Thus, for example, reference to "contig" includes a plurality of such contigs and reference to "probing the physical layout of chromosomes" includes reference to one or more methods for probing the physical layout of chromosomes and equivalents thereof known to those skilled in the art, and so forth.

Also, the use of "and" means "and/or" unless stated otherwise. Similarly, "comprise," "comprises," "comprising" "include," "includes," and "including" are interchangeable and not intended to be limiting, and refer to the nonexclusive presence of the recited element, leaving open the possibility that additional elements are present.

It is to be further understood that where descriptions of various embodiments use the term "comprising," those skilled in the art would understand that in some specific instances, an embodiment can be alternatively described using language "consisting essentially of" or "consisting of."

The term "read" or "sequencing read" as used herein, refers to a fragment of DNA sequence information in which the sequence has been determined.

The term "contigs" as used herein, refers to contiguous regions of DNA sequence. "Contigs" can be determined by any number methods known in the art, such as, by comparing sequencing reads for overlapping sequences, and/or by comparing sequencing reads against a databases of known sequences in order to identify which sequencing reads have a high probability of being contiguous. For many genomes and other large-scale sequencing projects, contigs are available and can be readily obtained, but physical linkage information regarding whether two or more contigs represent sequence from a single physical nucleic acid molecule, and how the contigs are to be positioned relative to one another, is difficult to obtain. This difficulty is largely due to the presence of repetitive regions comprising sequence information that does not uniquely map to any single contig.

The term "subject" as used herein can refer to any eukaryotic or prokaryotic (eubacterial or archaeal) organism. For example, a subject can be a mammal, such as a human.

The terms "nucleic" or "polynucleotide" as used herein can refer to deoxyribonucleotides (DNA) or ribonucleotides (RNA) and polymers thereof, in either single- or double-stranded form. Unless specifically limited, the term encompasses nucleic acid molecules containing known analogues of naturally occurring nucleotides that have similar binding properties as the reference nucleotides and/or are metabolized in a manner similar to naturally occurring nucleotides.

The term "naked DNA" as used herein can refer to DNA that is substantially free of complexed proteins. For example, it can refer to DNA complexed with less than about 50%, about 40%, about 30%, about 20%, about 10%, about 5%, or about 1% of the endogenous proteins found in the cell nucleus.

The term "reconstituted chromatin" as used herein can refer to forming chromatin formed by complexing isolated nuclear proteins to naked DNA.

The term "nanoparticles" as used herein can refer to nanometer-scale spheres that can be modified to bind DNA. The nanoparticles can be positively charged on the surface (e.g. by coating with amine-containing molecules). See Zinchenko, A. et al. (2005) "Compaction of Single-Chain DNA by Histone-Inspired Nanoparticles" *Physical Review Letters,* 95(22), 228101, which is herein incorporated by reference in its entirety. In some cases, the nanoparticle is a platinum-based nanoparticle, such cisplatin, oxaliplatin, satraplatin, picoplatin, nedaplatin, triplatin, lipoplatin, transplatin, carboplatin or any other platinum-based DNA-binding nanoparticle, or derivatives thereof. In other cases, the nanoparticle can be a DNA intercalator (e.g. berberine, chlorambucil, ethidium bromide, mitoxantrone, proflavine, daunomycin, doxorubicin, thalidomide, nimustine, tirapazamine, carmustine, angelicin, daunorubicin, carminomycin, aclacinomycin, chlorambucil, cyclophosphamide, methotrexate, 5-uracil, arabinosyl cytosine, mitomycin, procarbazine, vinblastine, vincristine, plicamycin (Mithracin®), daptomycin (Cubicin®) anthracycline, furocoumarins, psoralen), or any derivatives thereof. In further cases, the nanoparticle can be a bisintercalator (e.g. bisacridine, echinomycin), or any derivatives thereof.

The term "read set", "read-set", "read pair", or "read-pair" as used herein can refer to two or more elements, or a library of elements, that are linked to provide sequence information. In some cases, the number of read-sets or read-pairs can refer to the number of mappable read-sets or read-pairs. In other cases, the number of read-sets or read-pairs can refer to the total number of generated read-sets or read-pairs. In some cases, the linked elements in a read-set or read-pair can share a common label such as a barcode.

The term "bridge amplification" as used herein can refer to an amplification reaction where one or more of template and primer molecules are immobilized on a support, thereby forming a bridge-like structure during amplification. An example of bridge amplification is described in U.S. Pat. No. 8,652,810, which is herein incorporated by reference in its entirety.

The term "about" as used herein to describe a number, unless otherwise specified, refers to that number plus or minus 10%.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

In some cases, the methods disclosed herein take advantage of the ability to cross-link sequences segments, such as in endogenous or reconstituted chromatin or other protein-polynucleotide complexes, in a way that physically connects different parts of a longer polynucleotide through chemical linkage. When the cross-linked polynucleotide complexes are formed, the polynucleotide is in a compact and stable cross-linked form and behaves as a polymer unit, which can be manipulated without fear of shearing the polynucleotide.

In some cases, the methods disclosed herein labels these cross-linked polynucleotide complexes using an oligonucleotide array (e.g. DNA microarray) in order to identify polynucleotide fragments that are related by physical linkage and/or proximity. In some cases, this information is useful for applications such as genomic assembly and/or haplotype phasing.

In some cases, the methods disclosed herein are used to label and/or associate polynucleotides or sequence segments thereof, and to utilize that data for various applications. In some cases, the disclosure provides methods that produce a highly contiguous and accurate human genomic assembly with less than about 10,000, about 20,000, about 50,000, about 100,000, about 200,000, about 500,000, about 1 million, about 2 million, about 5 million, about 10 million, about 20 million, about 30 million, about 40 million, about 50 million, about 60 million, about 70 million, about 80 million, about 90 million, about 100 million, about 200 million, about 300 million, about 400 million, about 500 million, about 600 million, about 700 million, about 800 million, about 900 million, or about 1 billion read pairs. In some cases, the disclosure provides methods that phase, or assign physical linkage information to, about 50%, 60%, 70%, 75%, 80%, 85%, 90%, 91%, 92%, 93%, 94%, 95%, 96%, 97%, 98%, 99% or more of heterozygous variants in a human genome with about 50%, 60%, 70%, 75%, 80%, 85%, 90%, 91%, 92%, 93%, 94%, 95%, 96%, 97%, 98%, 99%, or greater accuracy.

Figure 5:
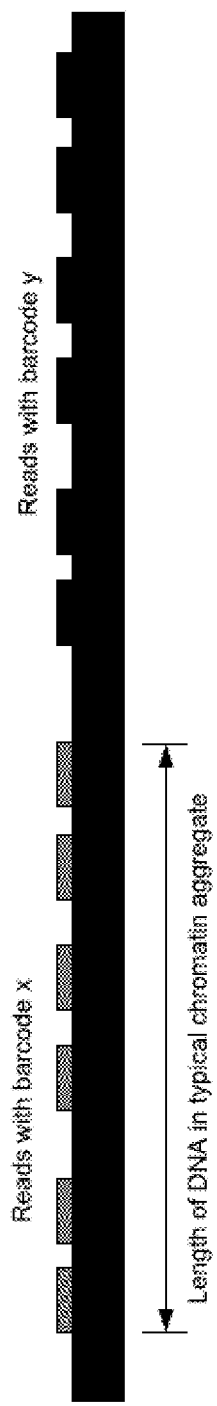
FIG. 5 provides a sequencing product of a typical chromatin aggregate. Reads with a barcode corresponding to the feature to which a chromatin aggregate bound are distributed throughout the length of the nucleic acid molecule incorporated into the chromatin fragment.

In some embodiments read pairs comprise two distinct sequences of a target nucleic acid sample. In some embodiments, a read pair comprises a sequence read of a target nucleic acid sample in combination with a sequence read of a molecular tag, such that all target nucleic acid sample reads corresponding to a common molecular tag sequence map to the same nucleic acid molecule within a target nucleic acid sample. Accordingly, in some embodiments molecular tag sequence is used to sort target nucleic acid sample reads into 'tagged bins,' which in some embodiments each correspond to a single molecule of a target nucleic acid sample. As seen in FIG. 5, commonly tagged reads can thus be mapped to a single nucleic acid molecule or molecular fragment.

In some cases, a nucleic acid sample is incompletely fragmented such that multiple copies of homologous nucleic acids are fragmented differentially with respect to one another, in some cases resulting in overlapping fragments having identical sequence in their positions of overlap but having non-identical molecular ends. In some cases, molecular tagged sequences that map to each individual molecular fragment, such as overlapping sequence spanning at least one polymorphism that may differ among homologous chromosome pairs. In such cases, by comparing the sequence at the position that may differ among homologous chromosome pairs, one may determine whether the overlapping sequences represent sequence from the sample phase that is the same physically linked chromosome or original nucleic acid of the sample.

Further, the range of the associated sequence segments generated by the disclosure can be extended to span much larger genomic distances. The assembly can be produced from a standard shotgun library in addition to a library of associated sequence segments (i.e. a read-set). In some cases, the sequence segments is associated based on a label. In further cases, the sequence segments labeled with a common label are associated to one another, and optionally binned together to form a "read-set". In some cases, the label is a barcode sequence.

In some cases, the disclosure provides software that utilizes both the standard shotgun library and the read-set. In some cases, the phased variants are produced with a single long-range read pair library. In further cases, the reads are mapped to a reference genome and used to assign variants to one of the individual's two parental chromosomes. Further, the disclosure provides methods for the extraction of even larger DNA fragments using known techniques, so as to generate exceptionally long reads.

Figure 3A:
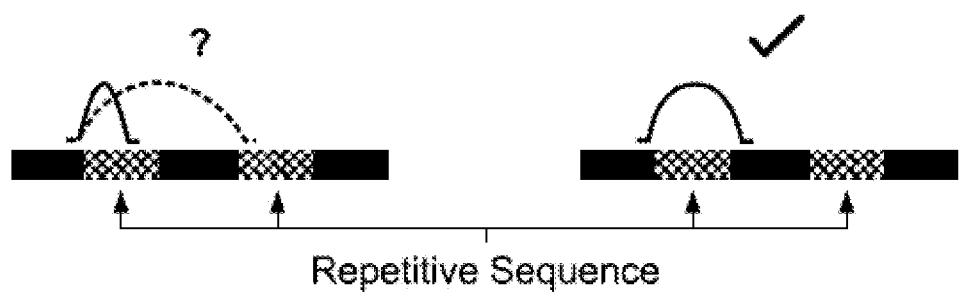
FIG. 3A-B provides an illustration of the ambiguities that arise in genomic assembly and alignment from repetitive regions in the genome.
Figure 3B:
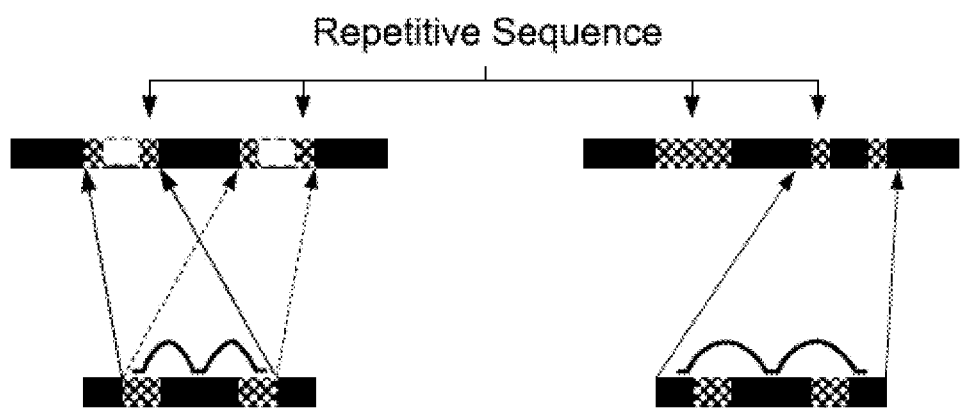
Figure 4:
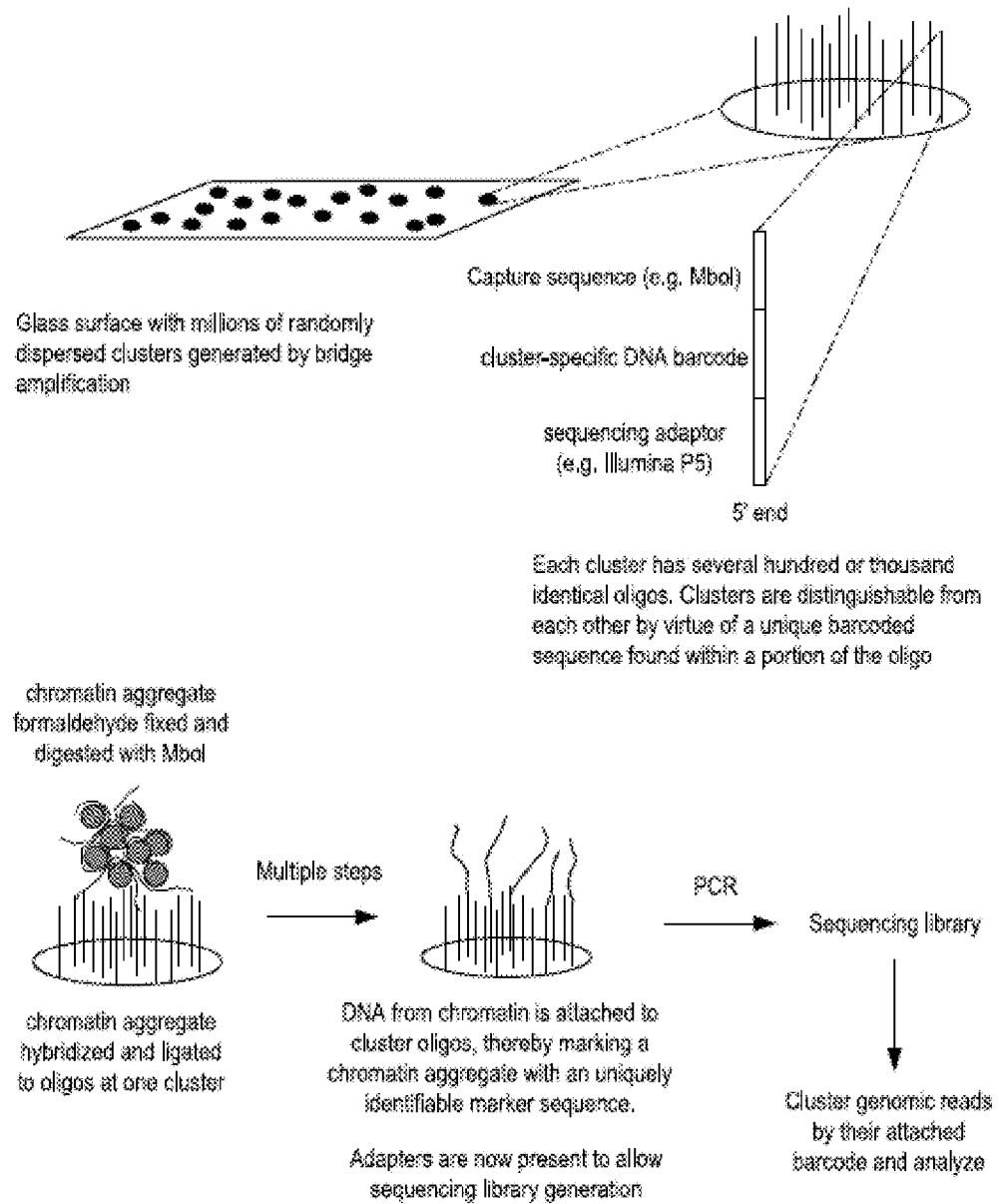
FIG. 4 provides an example of compositions and devices involved in the implementation of methods disclosed herein. (Upper left) A glass surface having a plurality of oligonucleotide clusters is provided. Each cluster independently comprises a plurality of identical oligos, each comprising, from 5' to 3', a 5' attachment site to the plate, a sequencing adapter sequence (an example of which is the Illumina P5 adapter, but other adapters are similarly consistent with the disclosure herein), a cluster-specific molecular tag or barcode, and at the 3' end, a capture sequence (an example of which is an MboI sequence). In some embodiments, clusters are characterized by each having a unique molecular tag, while in some embodiments a molecular tag or barcode is common to two or more clusters. A DNA complex, such as a chromatin aggregate fixed with formaldehyde and digested with MboI as shown, is hybridized and ligated to oligos at a cluster, as shown at lower left. (Lower middle) Following ligation of DNA complex complementary ends to oligos of a cluster, the complex is removed from the cluster such that ligated free ends of the DNA complex remain attached to the cluster. Free DNA ends are repaired if sheared and a second library adapter is ligated or otherwise added to the free ends in some embodiments. (Lower Right) PCR is performed using primers that anneal to the original 5' sequencing adapter and to the second library adapter ligated or otherwise added thereto. The library is sequenced, and the sequence reads are analyzed as disclosed herein.

The mechanism that repeat sequences obstruct assembly and alignment processes is a consequence of ambiguity (FIG. 3). In the case of large repetitive regions, the difficulty is one of span. If a read or read-set is not long enough to span a repetitive region, one cannot confidently connect regions bordering the repetitive element. In the case of smaller repetitive elements the problem is primarily placement. When a region is flanked by two repetitive elements that are common in the genome, determining its exact placement becomes difficult if not impossible due to the similarity of the flanking elements to all others of their class. In both cases it is the lack of distinguishing information in the repeat that makes the identification, and thus placement of a particular repeat challenging. What is needed is the ability to experimentally establish connection between unique segments hemmed or separated by repetitive regions.

The methods provided herein can greatly advance the field of genomics by overcoming the substantial barriers posed by these repetitive regions and can thereby enable important advances in many domains of genomic analysis. To perform a de novo assembly with previous technologies, one must either settle for an assembly fragmented into many small scaffolds or commit substantial time and resources to producing a large-insert library or using other approaches to generate a more contiguous assembly. Such approaches may include acquiring very deep sequencing coverage, constructing BAC or fosmid libraries, optical mapping, or, most likely, some combination of these and other techniques. The intense resource and time requirements put such approaches out of reach for most small labs and prevents studying non-model organisms. Since the methods described herein can produce very long-range read-sets, de novo assembly may be achieved with a single sequencing run. This cuts assembly costs by orders of magnitude and shorten the time required from months or years to weeks. In some cases, the methods disclosed herein allow for generating a plurality of read-sets in less than 14 days, less than 13 days, less than 12 days, less than 11 days, less than 10 days, less than 9 days, less than 8 days, less than 7 days, less than 6 days, less than 5 days, less than 4 days, less than 3 days, less than 2 days, less than 1 day or in a range between any two of foregoing specified time periods. In some cases, the methods allow for generating a plurality of read-sets in about 10 days to 14 days. Building genomes for even the most niche of organisms would become routine, phylogenetic analyses would suffer no lack of comparisons, and projects such as Genome 10k could be realized.

The methods described herein allow for assignment of previously provided, previously generated, or de novo synthesized contig information into physical linkage groups such as chromosomes or shorter contiguous nucleic acid molecules. Similarly, the methods disclosed herein allow said contigs to be positioned relative to one another in linear order along a physical nucleic acid molecule. Similarly, the methods disclosed herein allow said contigs to be oriented relative to one another in linear order along a physical nucleic acid molecule.

Similarly, the methods disclosed herein can provide advances in structural and phasing analyses for medical purposes. There is astounding heterogeneity among cancers, individuals with the same type of cancer, or even within the same tumor. Teasing out the causative from consequential effects requires very high precision and throughput at a low per-sample cost. In the domain of personalized medicine, one of the gold standards of genomic care is a sequenced genome with all variants thoroughly characterized and phased, including large and small structural rearrangements and novel mutations. To achieve this with previous technologies demands effort akin to that required for a de novo assembly, which is currently too expensive and laborious to be a routine medical procedure. In some cases, the methods disclosed herein rapidly produce complete, accurate genomes at low cost and thereby yield many highly sought capabilities in the study and treatment of human disease.

Further, applying the methods disclosed herein to phasing can combine the convenience of statistical approaches with the accuracy of familial analysis, providing savings—money, labor, and samples—greater than those using either method alone. De novo variant phasing, a highly desirable phasing analysis that is prohibitive with previous technologies, can be performed readily using the methods disclosed herein. This is particularly important as the vast majority of human variation is rare (less than 5% minor allele frequency). Phasing information is valuable for population genetic studies that gain significant advantages from networks of highly connected haplotypes (collections of variants assigned to a single chromosome), relative to unlinked genotypes. Haplotype information may enable higher resolution studies of historical changes in population size, migrations, and exchange between subpopulations, and allows us to trace specific variants back to particular parents and grandparents. This in turn clarifies the genetic transmission of variants associated with disease, and the interplay between variants when brought together in a single individual. In further cases, the methods of the disclosure enable the preparation, sequencing, and analysis of extremely long range read-set (XLRS) or extremely long range read-pair (XLRP) libraries.

In some embodiments of the disclosure, a tissue or a DNA sample from a subject is provided and the method returns an assembled genome, alignments with called variants (including large structural variants), phased variant calls, or any additional analyses. In other embodiments, the methods disclosed herein provide XLRP libraries directly for the individual.

In various embodiments, the methods disclosed herein generates extremely long-range read pairs separated by large distances. The upper limit of this distance may be improved by the ability to collect DNA samples of large size. In some cases, the read pairs span up to 50, 60, 70, 80, 90, 100, 125, 150, 175, 200, 225, 250, 300, 400, 500, 600, 700, 800, 900, 1000, 1500, 2000, 2500, 3000, 4000, 5000 kbp or more in genomic distance. In some cases, the read pairs span up to 500 kbp in genomic distance. In other cases, the read pairs span up to 2000 kbp in genomic distance. The methods disclosed herein can integrate and build upon standard techniques in molecular biology, and are further well-suited for increases in efficiency, specificity, and genomic coverage. In some cases, the read pairs are generated in less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, or 90 days. In some cases, the read pairs are generated in less than about 14 days. In further cases, the read pairs are generated in less about 10 days. In some cases, the methods of the present disclosure provide greater than about 5%, about 10%, about 15%, about 20%, about 30%, about 40%, about 50%, about 60%, about 70%, about 80%, about 90%, about 95%, about 99%, or about 100% of the read pairs with at least about 50%, about 60%, about 70%, about 80%, about 90%, about 95%, about 99%, or about 100% accuracy in correctly ordering and/or orientating the plurality of contigs. In some cases, the methods provide about 90 to 100% accuracy in correctly ordering and/or orientating the plurality of contigs.

In other embodiments, the methods disclosed herein are used with currently employed sequencing technology. In some cases, the methods are used in combination with well-tested and/or widely deployed sequencing instruments. In further embodiments, the methods disclosed herein are used with technologies and approaches derived from currently employed sequencing technology.

The methods disclosed herein can dramatically simplify de novo genomic assembly for a wide range of organisms. Using previous technologies, such assemblies are currently limited by the short inserts of economical mate-pair libraries. While it may be possible to generate read pairs at genomic distances up to the 40-50 kbp accessible with fosmids, these are expensive, cumbersome, and too short to span the longest repetitive stretches, including those within centromeres, which in humans range in size from 300 kbp to 5 Mbp. In some cases, the methods disclosed herein provide read pairs capable of spanning large distances (e.g., megabases or longer) and thereby overcome these scaffold integrity challenges. Accordingly, producing chromosome-level assemblies may be routine by utilizing the methods disclosed herein. Similarly, the acquisition of long-range phasing information can provide tremendous additional power to population genomic, phylogenetic, and disease studies. In certain cases, the methods disclosed herein enable accurate phasing for large numbers of individuals, thus extending the breadth and depth of our ability to probe genomes at the population and deep-time levels.

In the realm of personalized medicine, the XLRS read-sets generated from the methods disclosed herein represents a meaningful advance toward accurate, low-cost, phased, and rapidly produced personal genomes. Previous methods are insufficient in their ability to phase variants at long distances, thereby preventing the characterization of the phenotypic impact of compound heterozygous genotypes. Additionally, structural variants of substantial interest for genomic diseases are difficult to accurately identify and characterize with previous techniques due to their large size in comparison to the reads and read inserts used to study them. Read-sets spanning tens of kilobases to megabases or longer can help alleviate this difficulty, thereby allowing for highly parallel and personalized analyses of structural variation.

Basic evolutionary and biomedical research can be driven by technological advances in high-throughput sequencing. It is now relatively inexpensive to generate massive quantities of DNA sequence data. However, it is difficult in theory and in practice to produce high-quality, highly contiguous genome sequences with previous technologies. Further, many organisms, including humans, are diploid, wherein each individual has two haploid copies of the genome. At sites of heterozygosity (e.g. where the allele given by the mother differs from the allele given by the father), it is difficult to know which sets of alleles came from which parent (known as haplotype phasing). This information can be critically important for performing a number of evolutionary and biomedical studies such as disease and trait association studies.

The present disclosure provides methods for genome assembly that combine technologies for DNA preparation with tagged sequence reads for high-throughput discovery of short, intermediate and long term connections corresponding to sequence reads from a single physical nucleic acid molecule bound to a complex such as a chromatin complex within a given genome. The disclosure further provides methods using these connections to assist in genome assembly, for haplotype phasing, and/or for metagenomic studies. While the methods presented herein can be used to determine the assembly of a subject's genome, it should also be understood that in certain cases the methods presented herein are used to determine the assembly of portions of the subject's genome such as chromosomes, or the assembly of the subject's chromatin of varying lengths. It should also be understood that, in certain cases, the methods presented herein are used to determine or direct the assembly of non-chromosomal nucleic acid molecules. Indeed, any nucleic acid the sequencing of which is complicated by the presence of repetitive regions separating non-repetitive contigs may be facilitated using the methods disclosed herein.

In some cases, the methods disclosed herein comprise the step of generating a plurality of contigs from sequencing fragments of target DNA obtained from a subject. In some cases, long stretches of target DNA are fragmented by cutting the DNA with one or more restriction enzymes, incompletely digesting the DNA with one or more nonspecific endonucleases, shearing the DNA, or a combination thereof. The resulting fragments are sequenced using high throughput sequencing methods to obtain a plurality of sequencing reads. Cases of high throughput sequencing methods which are used with the methods of the disclosure include, but are not limited to, 454 pyrosequencing methods developed Roche Diagnostics, "clusters" sequencing methods developed by Illumina, SOLiD and Ion semiconductor sequencing methods developed by Life Technologies, and DNA nanoball sequencing methods developed by Complete Genomics. The overlapping ends of different sequencing reads are then assembled to form a contig. In other cases, fragmented target DNA are cloned into vectors. Cells or organisms are then transfected with the DNA vectors to form a library. After replicating the transfected cells or organisms, the vectors are isolated and sequenced to generate a plurality of sequencing reads. The overlapping ends of different sequencing reads are then assembled to form a contig.

Alternately or in combination with the above, in some cases, the methods disclosed herein are used with contig information previously generated. Contig information for a vast number of genomes, including the human genome, is publicly available (see, for example, sequence available at the National Center for Biotechnology Information, the Joint Genome Institute, the Eukaryotic Pathogen Database, or any number of species-specific genome web pages). Rather than generating contig information de novo, or in combination with de novo generated contig data, the methods disclosed herein may be used to assist in the chromosomal assembly, ordering and orientation of these previously generated contigs.

As shown in FIG. 1, genome assembly, especially with high-throughput sequencing technology can be problematic. Often, the assembly consists of thousands or tens of thousands of short contigs. The order and orientation of these contigs is generally unknown, limiting the usefulness of the genome assembly. Previous technologies for orienting these scaffolds often fail in discovering very long range interactions.

In some cases, a tissue or a DNA sample from a subject is provided and the method returns an assembled genome, alignments with called variants (including large structural variants), phased variant calls, and/or any additional analyses. In other embodiments, the methods disclosed herein provide XLRS libraries for the subject.

In some cases, samples comprising target DNA used to generate contigs are obtained from a subject by any number of means, including by taking bodily fluids (e.g., blood, urine, serum, lymph, saliva, anal and vaginal secretions, perspiration and semen), taking tissue, or by collecting cells/organisms. The sample obtained may be comprised of a single type of cell/organism, or may be comprised multiple types of cells/organisms. In some cases, the DNA are extracted and prepared from the subject's sample. For example, the sample are treated to lyse a cell comprising the polynucleotide, using known lysis buffers, sonication techniques, electroporation, and the like. In further cases, the target DNA is further purified to remove contaminants, such as proteins, by using alcohol extractions, cesium gradients, and/or column chromatography.

In further cases, the methods disclosed herein allow for accurate and predictive results for genotype assembly, haplotype phasing, and metagenomics with small amounts of materials. In some cases, less than about 0.1 µg, about 0.2 µg, about 0.3 µg, about 0.4 µg, about 0.5 µg, about 0.6 µg, about 0.7 µg, about 0.8 µg, about 0.9 µg, about 1.0 µg, about 1.2 µg, about 1.4 µg, about 1.6 µg, about 1.8 µg, about 2.0 µg, about 2.5 µg, about 3.0 µg, about 3.5 µg, about 4.0 µg, about 4.5 µg, about 5.0 µg, about 6.0 µg, about 7.0 µg, about 8.0 µg, about 9.0 µg, about 10 µg, about 15 µg, about 20 µg, about 30 µg, about 40 µg, about 50 µg, about 60 µg, about 70 µg, about 80 µg, about 90 µg, about 100 µg, about 150 µg, about 200 µg, about 300 µg, about 400 µg, about 500 µg, about 600 µg, about 700 µg, about 800 µg, about 900 µg, or about 1000 µg of DNA is used with the methods disclosed herein. In some cases, the DNA used in the methods disclosed herein is extracted from less than about 1,000,000, about 500,000, about 200,000, about 100,000, about 50,000, about 20,000, about 10,000, about 5,000, about 2,000, about 1,000, about 500, about 200, about 100, about 50, about 20, or about 10 cells.

In some cases, a method to extract very high molecular weight DNA is provided. In some cases, the data from an XLRS library is improved by increasing the fragment size of the input DNA. In some cases, extracting megabase-sized fragments of DNA from a cell produces read-sets comprising reads separated by megabases in the genome. In some cases, the read-sets provide sequence information over a span of greater than about 10 kB, about 50 kB, about 100 kB, about 200 kB, about 500 kB, about 1 Mb, about 2 Mb, about 5 Mb, about 10 Mb, or about 100 Mb. In some cases, the read-sets provide sequence information over a span of greater than about 500 kB. In further cases, the read-sets provide sequence information over a span of greater than about 2 Mb. In some cases, the very high molecular weight DNA is extracted by very gentle cell lysis (Teague, B. et al. (2010) *Proc. Nat. Acad. Sci. USA* 107(24), 10848-53) and agarose plugs (Schwartz, D. C., & Cantor, C. R. (1984) *Cell*, 37(1), 67-75). In other cases, commercially available machines that can purify DNA molecules up to megabases in length is used to extract very high molecular weight DNA.

In some cases, the methods disclosed herein are used with chromatin isolated from a cell/organism, or with reconstituted chromatin. Reconstituted chromatin is differentiated from chromatin formed within a cell/organism over various features. First, for many samples, the collection of naked DNA samples can be achieved by using a variety of noninvasive to invasive methods, such as by collecting bodily fluids, swabbing buccal or rectal areas, taking epithelial samples, etc. Second, reconstituting chromatin substantially prevents the formation of inter-chromosomal and other long-range interactions that generate artifacts for genome assembly and haplotype phasing. In some cases, a sample has less than about 20, 15, 12, 11, 10, 9, 8, 7, 6, 5, 4, 3, 2, 1, 0.5, 0.4, 0.3, 0.2, 0.1% or less inter-chromosomal or intermolecular crosslinking according to the methods and compositions of the disclosure. In some cases, the sample has less than about 5% inter-chromosomal or intermolecular crosslinking. In some cases, the sample has less than about 3% inter-chromosomal or intermolecular crosslinking. In further cases, the sample has less than about 1% inter-chromosomal or intermolecular crosslinking. Third, the frequency of sites that are capable of crosslinking and thus the frequency of intramolecular crosslinks within the polynucleotide can be adjusted. For example, the ratio of DNA to histones can be varied, such that the nucleosome density is adjusted to a desired value. In some cases, the nucleosome density is reduced below the physiological level. Accordingly, the distribution of crosslinks can be altered to favor longer-range interactions. In some embodiments, subsamples with varying cross-linking density may be prepared to cover both short- and long-range associations. In some cases, the crosslinking conditions is adjusted such that at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 40%, about 45%, about 50%, about 60%, about 70%, about 80%, about 90%, about 95%, or about 100% of the crosslinks occur between DNA segments that are at least about 50 kb, about 60 kb, about 70 kb, about 80 kb, about 90 kb, about 100 kb, about 110 kb, about 120 kb, about 130 kb, about 140 kb, about 150 kb, about 160 kb, about 180 kb, about 200 kb, about 250 kb, about 300 kb, about 350 kb, about 400 kb, about 450 kb, or about 500 kb apart on the sample DNA molecule. In some cases, the crosslinking is reversible. In certain cases, the crosslinking is reversed using heat. In other cases, the crosslinking is reversed using a chemical agent such as thiourea.

In some cases, the methods disclosed herein is used with DNA associated to nanoparticles. In further cases, the nanoparticles are positively charged. In some cases, the nanoparticles are coated with amine groups, and/or amine-containing molecules. In certain cases, the DNA and the nanoparticles aggregate and condense. In further cases, the nanoparticle-bound DNA is induced to aggregate in a fashion that mimics the ordered arrays of biological nucleosomes (e.g. chromatin). In some cases, the nanoparticle is a platinum-based nanoparticle. In other cases, the nanoparticle is a DNA intercalator, or any derivatives thereof. In further cases, the nanoparticle is a bisintercalator, or any derivatives thereof. In some cases, the nanoparticle-based method is less expensive, faster to assemble, provide a better recovery rate than using reconstituted chromatin, and/or allow for reduced DNA input requirements.

A number of factors can be varied to influence the extent and form of condensation including the concentration of nanoparticles in solution, the ratio of nanoparticles to DNA, and the size of nanoparticles used. In some cases, the nanoparticles is added to the DNA at a concentration greater than about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 15 ng/mL, 20 ng/mL, 25 ng/mL, 30 ng/mL, 40 ng/mL, 50 ng/mL, 60 ng/mL, 70 ng/mL, 80 ng/mL, 90 ng/mL, 100 ng/mL, 120 ng/mL, 140 ng/mL, 160 ng/mL, 180 ng/mL, 200 ng/mL, 250 ng/mL, 300 ng/mL, 400 ng/mL, 500 ng/mL, 600 ng/mL, 700 ng/mL, 800 ng/mL, 900 ng/mL, 1 µg/mL, 2 µg/mL, 3 µg/mL, 4 µg/mL, 5 µg/mL, 6 µg/mL, 7 µg/mL, 8 µg/mL, 9 µg/mL, 10 µg/mL, 15 µg/mL, 20 µg/mL, 25 µg/mL, 30 µg/mL, 40 µg/mL, 50 µg/mL, 60 µg/mL, 70 µg/mL, 80 µg/mL, 90 µg/mL, 100 µg/mL, 120 µg/mL, 140 µg/mL, 160 µg/mL, 180 µg/mL, 200 µg/mL, 250 µg/mL, 300 µg/mL, 400 µg/mL, 500 µg/mL, 600 µg/mL, 700 µg/mL, 800 µg/mL, 900 µg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 30 mg/mL, 40 mg/mL, 50 mg/mL, 60 mg/mL, 70 mg/mL, 80 mg/mL, 90 mg/mL, or 100 mg/mL. In some cases, the nanoparticles is added to the DNA at a concentration less than about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 15 ng/mL, 20 ng/mL, 25 ng/mL, 30 ng/mL, 40 ng/mL, 50 ng/mL, 60 ng/mL, 70 ng/mL, 80 ng/mL, 90 ng/mL, 100 ng/mL, 120 ng/mL, 140 ng/mL, 160 ng/mL, 180 ng/mL, 200 ng/mL, 250 ng/mL, 300 ng/mL, 400 ng/mL, 500 ng/mL, 600 ng/mL, 700 ng/mL, 800 ng/mL, 900 ng/mL, 1 µg/mL, 2 µg/mL, 3 µg/mL, 4 µg/mL, 5 µg/mL, 6 µg/mL, 7 µg/mL, 8 µg/mL, 9 µg/mL, 10 µg/mL, 15 µg/mL, 20 µg/mL, 25 µg/mL, 30 µg/mL, 40 µg/mL, 50 µg/mL, 60 µg/mL, 70 µg/mL, 80 µg/mL, 90 µg/mL, 100 µg/mL, 120 µg/mL, 140 µg/mL, 160 µg/mL, 180 µg/mL, 200 µg/mL, 250 µg/mL, 300 µg/mL, 400 µg/mL, 500 µg/mL, 600 µg/mL, 700 µg/mL, 800 µg/mL, 900 µg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 30 mg/mL, 40 mg/mL, 50 mg/mL, 60 mg/mL, 70 mg/mL, 80 mg/mL, 90 mg/mL, or 100 mg/mL. In some cases, the nanoparticles is added to the DNA at a weight-to-weight (w/w) ratio greater than about 1:10000, 1:5000, 1:2000, 1:1000, 1:500, 1:200, 1:100, 1:50, 1:20, 1:10, 1:5, 1:2, 1:1, 2:1, 5:1, 10:1, 20:1, 50:1, 100:1, 200:1, 500:1, 1000:1, 2000:1, 5000:1, or 10000:1. In some cases, the nanoparticles is added to the DNA at a weight-to-weight (w/w) ratio less than about 1:10000, 1:5000, 1:2000, 1:1000, 1:500, 1:200, 1:100, 1:50, 1:20, 1:10, 1:5, 1:2, 1:1, 2:1, 5:1, 10:1, 20:1, 50:1, 100:1, 200:1, 500:1, 1000:1, 2000:1, 5000:1, or 10000:1. In some cases, the nanoparticles have a diameter greater than about 1 nm 1 nm, 2 nm, 3 nm, 4 nm, 5 nm, 6 nm, 7 nm, 8 nm, 9 nm, 10 nm, 15 nm, 20 nm, 25 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 15 µm, 20 µm, 25 µm, 30 µm, 40 µm, 50 µm, 60 µm, 70 µm, 80 µm, 90 µm, or 100 µm. In some cases, the nanoparticles have a diameter less than about 1 nm 1 nm, 2 nm, 3 nm, 4 nm, 5 nm, 6 nm, 7 nm, 8 nm, 9 nm, 10 nm, 15 nm, 20 nm, 25 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 15 µm, 20 µm, 25 µm, 30 µm, 40 µm, 50 µm, 60 µm, 70 µm, 80 µm, 90 µm, or 100 µm.

Furthermore, the nanoparticles may be immobilized on solid substrates (e.g. beads, slides, or tube walls) by applying magnetic fields (in the case of paramagnetic nanoparticles) or by covalent attachment (e.g. by cross-linking to poly-lysine coated substrate). Immobilization of the nanoparticles may improve the ligation efficiency thereby increasing the number of desired products (signal) relative to undesired (noise).

In various cases, the methods disclosed herein are used to produce read-sets comprising reads that are separated by large distances. The upper limit of this distance may be improved by the ability to collect DNA samples of large size. In some cases, the reads are separated by up to 50, 60, 70, 80, 90, 100, 125, 150, 175, 200, 225, 250, 300, 400, 500, 600, 700, 800, 900, 1000, 1500, 2000, 2500, 3000, 4000, 5000 kbp or more in genomic distance. In some cases, the reads are separated by up to 500 kbp in genomic distance. In other cases, the reads are separated by up to 2000 kbp in genomic distance. The methods disclosed herein can integrate and build upon standard techniques in molecular biology, and are further well-suited for increases in efficiency, specificity, and genomic coverage. In some cases, the read-sets are generated in less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, or 90 days. In some cases, the read-sets are generated in less than about 14 days. In further cases, the read-sets are generated in less about 10 days. In some cases, the methods of the present disclosure provide greater than about 5%, about 10%, about 15%, about 20%, about 30%, about 40%, about 50%, about 60%, about 70%, about 80%, about 90%, about 95%, about 99%, or about 100% of the read pairs with at least about 50%, about 60%, about 70%, about 80%, about 90%, about 95%, about 99%, or about 100% accuracy in correctly ordering and/or orientating the plurality of contigs. In some cases, the methods provide about 90 to 100% accuracy in correctly ordering and/or orientating the plurality of contigs.

The methods disclosed herein can comprise probing the physical layout of chromosomes within living cells. In some cases, the methods utilize the fixation of chromatin in live cells to cement spatial relationships in the nucleus. Subsequent processing and sequencing of the products allows for recovery of a matrix of proximate associations among genomic regions. With further analysis, these associations can be used to produce a three-dimensional geometric map of the chromosomes as they are physically arranged in live nuclei. Such techniques describe the discrete spatial organization of chromosomes in live cells, and provide an accurate view of the functional interactions among chromosomal loci. In some cases, the nonspecific intrachromosomal interactions are captured by the methods presented herein so as to provide valuable information for assembly.

In some embodiments, sequence tag information is used to map sequence reads to a single nucleic acid molecule from which they originated. In some embodiments, this information is independent of distance information within a single nucleic acid molecule. In some cases, the nucleic acid molecule is obtained from a population of incompletely fragmented or sheared genomic DNA, which is sheared such that overlapping nucleic acid fragments are obtained. Upon sequencing the reads which correspond to each individual overlapping nucleic acid molecule, one may assemble larger 'read position contig' information to infer phase or physical linkage information across distances beyond single sheared nucleic acid size.

The intrachromosomal interactions can be used to correlate chromosomal connectivity. Similarly, the nucleic acid fragment mapping data can be used to correlate chromosomal connectivity. Further, the intrachromosomal data can aid genomic assembly. In some cases, the chromatin is reconstructed in vitro. This can be advantageous because chromatin—particularly histones, the major protein component of chromatin—is important for DNA fixation. In some cases, chromatin forms a stable complex with DNA to capture the spatial and sequence information, which is analyzed to aid genomic assembly. Chromatin is highly non-specific in terms of sequence and can be generally assemble uniformly across the genome. In some cases, the genomes of species that do not use chromatin is assembled on a reconstructed chromatin and thereby extend the horizon for the disclosure to all domains of life.

In some cases, cross-links is created between genome regions that are in close physical proximity. Crosslinking of proteins (e.g. histones) to the DNA molecule (e.g. genomic DNA), within chromatin is accomplished according to a suitable method described in further detail elsewhere herein or otherwise known in the art. In some cases, two or more nucleotide sequences is cross-linked via proteins bound to one or more nucleotide sequences. One approach is to expose the chromatin to ultraviolet irradiation (Gilmour et al., Proc. Nat'l. Acad. Sci. USA 81:4275-4279, 1984). Crosslinking of polynucleotide segments may also be performed utilizing other approaches, such as chemical or physical (e.g. optical) crosslinking. Suitable chemical crosslinking agents include, but are not limited to, formaldehyde and psoralen (Solomon et al., Proc. Natl. Acad. Sci. USA 82:6470-6474, 1985; Solomon et al., Cell 53:937-947, 1988). For example, cross-linking can be performed by adding a solution comprising about 2% formaldehyde to a mixture comprising the DNA molecule and chromatin proteins. Other cases of agents that are used to cross-link DNA include, but are not limited to, UV light, mitomycin C, nitrogen mustard, melphalan, 1,3-butadiene diepoxide, cis diaminedichloroplatinum(II) and cyclophosphamide. In further cases, the cross-linking agent forms cross-links that bridge relatively short distances-such as about 2 Å—thereby selecting intimate interactions that can be reversed.

In some cases, the DNA molecule is immunoprecipitated prior to or after crosslinking. In some cases, the DNA molecule is fragmented into two or more sequence segments. In further cases, sequence segments are contacted with a binding partner, such as an antibody that specifically recognizes and binds to acetylated histones, e.g., H3. Cases of such antibodies include, but are not limited to, Anti Acetylated Histone H3, available from Upstate Biotechnology, Lake Placid, N.Y. In some cases, the polynucleotides from the immunoprecipitate are subsequently collected from the immunoprecipitate. In some cases, prior to fragmenting the polynucleotide, the acetylated histones are cross-linked to adjacent polynucleotide sequences. In further cases, the mixture is then treated to fractionate polynucleotides in the mixture. Fractionation techniques are known in the art and include, for example, shearing techniques to generate smaller genomic fragments. Fragmentation can be accomplished using established methods for fragmenting chromatin, including, for example, sonication, shearing, contacting with enzymes or other chemicals having nonspecific endonuclease activity and/or the use of restriction enzymes. In some cases, the restriction enzyme has a restriction recognition site of 1, 2, 3, 4, 5, 6, 7, 8, or more than 8 bases long. Examples of restriction enzymes include, but are not limited to, AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BanHI, BanI, BanII, BbsI, BbvCI, BbvI, BccI, BceAI, BcgI, BciVI, BclI, BfaI, BfuAI, BfuCI, BglI, BglII, BipI, BmgBI, BmrI, BmtI, BpmI, Bpu10I, BpuEI, BsaAI, BsaBI, BsaHI, BsaI, BsaJI, BsaWI, BsaXI, BscRI, BscY, BsgI, BsiE, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssH-III, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdL, EacI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinPII, HpaI, HpaII, HphI, Hpy6II, Hpy188I, Hpy188III, Hpy99I, HpyAV, HpyCH4III, HpyCH4IV, FlpyCH4V, KasI, KpnI, MboI, MboII, MfeI, MluI, MlyI, MmeI, MnlI, MscI, MseI, MslI, MspA1I, MspI, MwoI, NaeI, NarI, Nb.BbvCI, Nb.BsmI, Nb.BsrDI, Nb.BtsI, NciI, NcoI, NdeI, NgoMIV, NheI, NlaIII, NlaAV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96II, SbfI, SeaI, ScrFI, SexAI, SfaNI, SfcI, SfiI, SfoI, SgrAI, SinaI, SmiII SnaBI, SpeI, SphI, SspI, StuI, StyD4I, StyI, SwaI, T, Taqαl, TfiI, TliI, TseI, Tsp45I, Tsp509I, TspMI, TspRI, Tth111I, XbaI, XcmI, XhoI, XmaI, XmnI, and ZraI. The resulting sequence segments can vary in size. The resulting sequence segments may also comprise a single-stranded overhand at the 5' or 3' end.

In some embodiments, using sonication techniques, sequence segments of about 100 to 5000 nucleotides are obtained. Alternatively, sequence segments of about 100 to 1000, about 150 to 1000, about 150 to 500, about 200 to 500, or about 200 to 400 nucleotides are obtained. The sample can be prepared for sequencing the cross-linked sequence segments. In some cases, sequence segments that were intramolecularly cross-linked are labeled with a common label. The common label can then be detected and analyzed to determine sequence segments that were intramolecularly cross-linked. The common label can, for example, be a barcode, which can optionally be detected by sequencing methods. In some cases, the reads of sequence segments labeled with a common label are binned into a read-set.

Sequence information may be obtained from the sample using any suitable sequencing technique described in further detail elsewhere herein or otherwise known in the art, such as a high throughput sequencing method. In some cases, the sequence segments are subject to a sequencing technique to generate sequence reads, which are used to identify sequence segments that are cross-linked and/or are labeled with a common label. In further cases, two or more sequence segments are represented in the obtained sequence information, associating haplotyping information over a linear distance separating the two sequence segments along the polynucleotide.

In some cases, the methods disclosed herein are used in combination with an existing sequencing technology. In further cases, the methods disclosed herein are used with technologies and approaches derived from any existing sequencing technology. Cases of sequencing technologies that can be used with the methods disclosed herein include, but are not limited to, the Illumina® sequencing-by-synthesis platform (Illumina, San Diego, Calif.), the SOLiD™ system (Applied Biosystems Corp.), pyrosequencing (e.g., 454 Life Sciences, subsidiary of Roche Diagnostics), a sequencing technique based on semiconductor detectors (e.g., the Ion Torrent® platform), nanopore sequencing (e.g., the Oxford Nanopore sequencing platform), DNA nanoball sequencing methods (e.g. Complete Genomics), sequencing by hybridization and any other suitable technology, or any technology that may be derived from any of the above technologies.

In addition to species-specific and cell type-specific chromatin interactions, two canonical interaction patterns have been observed in most chromatin capture techniques. One pattern, distance-dependent decay (DDD), is a general trend of decay in interaction frequency as a function of genomic distance. The second pattern, cis-trans ratio (CTR), is a significantly higher interaction frequency between loci located on the same chromosome, even when separated by tens of megabases of sequence, versus loci on different chromosomes. These patterns may reflect general polymer dynamics, where proximal loci have a higher probability of randomly interacting, as well as specific nuclear organization features such as the formation of chromosome territories, the phenomenon of interphase chromosomes tending to occupy distinct volumes in the nucleus with little mixing. Although the exact details of these two patterns may vary between species, cell types and cellular conditions, they are ubiquitous and prominent. These patterns are so strong and consistent that they are used to assess experiment quality and are usually normalized out of the data in order to reveal detailed interactions. However, in the methods disclosed herein, genome assembly can take advantage of the three-dimensional structure of genomes. In certain cases, the ubiquity, strength and consistency of these features are used as powerful tools for estimating the genomic position of contigs.

In particular cases, examination of the physical distance between intra-chromosomal read pairs indicates several useful features of the data with respect to genome assembly. First, shorter range interactions are more common than longer-range interactions (e.g., see FIG. 21). That is, each read of a read-pair is more likely to be mated with a region close by in the actual genome than it is to be with a region that is far away. Second, there is a long tail of intermediate and long-range interactions. That is, read-pairs carry information about intra-chromosomal arrangement at kilobase (kB) or even megabase (Mb) distances. In some cases, read-pairs provide sequence information over a span of greater than about 10 kB, about 50 kB, about 100 kB, about 200 kB, about 500 kB, about 1 Mb, about 2 Mb, about 5 Mb, about 10 Mb, or about 100 Mb. These features of the data simply indicate that regions of the genome that are nearby on the same chromosome are more likely to be in close physical proximity—an expected result because they are chemically linked to one another through the DNA backbone. It was speculated that genome-wide chromatin interaction data sets, such as those generated by chromatin capture methods, would provide long-range information about the grouping and linear organization of sequences along entire chromosomes.

The disclosure provides a variety of methods that enable the mapping of the plurality of read pairs to the plurality of contigs. There are several publicly available computer programs for mapping reads to contig sequences. These read-mapping programs data also provide data describing how unique a particular read-mapping is within the genome. From the population of reads that map uniquely, with high confidence within a contig, we can infer the distribution of distances between reads in each read pair. These are the data shown in FIG. 21. For read pairs whose reads map confidently to different contigs, this mapping data implies a connection between the two contigs in question. It also implies a distance between the two contigs that is proportional to the distribution of distances learned from the analysis described above. Thus, each read pair whose reads map to different contigs implies a connection between those two contigs in a correct assembly. The connections inferred from all such mapped read pairs can be summarized in an adjacency matrix wherein each contig is represented by both a row and column. Read pairs that connect contigs are marked as a non-zero value in the corresponding row and column denoting the contigs to which the reads in the read pair were mapped. Most of the read pairs will map within in a contig, and from which the distribution of distances between read pairs can be learned, and from which an adjacency matrix of contigs can be constructed using read pairs that map to different contigs.

The disclosure provides a variety of methods that enable the mapping of the plurality of read-sets to the plurality of contigs. There are several publicly available computer programs for mapping reads to contig sequences. In some cases, sequencing reads are used as queries to compare against datasets comprised of assembled or unassembled contig sequence, for example using a BLAST algorithm such as that described in any of the following references Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "Identification of protein coding regions by database similarity search." Nature Genet. 3:266-272; Madden, T. L., Tatusov, R. L. & Zhang, J. (1996) "Applications of network BLAST server" Meth. Enzymol. 266:131-141; Altschul, S. F., Madden, T. L., Schaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402; Zhang Z., Schwartz S., Wagner L., & Miller W. (2000), "A greedy algorithm for aligning DNA sequences", J Comput Biol 2000; 7(1-2):203-14; Zhang, J. & Madden, T. L. (1997) "PowerBLAST: A new network BLAST application for interactive or automated sequence analysis and annotation." Genome Res. 7:649-656.

Using Sequence Reads to Order and Orient Contigs

Traditional paired-end sequencing data sets comprise pairs of reads sampled from the genome so as to indicate approximately the probability distribution of their separation on the genome. Barcode Tagged sequence read data sets yield "sets" or "bins" of sequence tagged reads, where each set is defined in practice by sharing a ligated barcode molecular tag sequence. The reads in each "set" sample a particular nucleic acid molecule (a subset of the genome or other target sequence sample) approximately uniformly. The subset of the genome being sampled may be a single segment corresponding to a single molecule of input DNA, or it may be multiple input segments.

One way to define the ordering and orientation problem is: given a pair of sequence contigs, how can we distinguish whether (test the hypothesis that) they come from adjacent segments of the genome, with a particular choice of the four possible relative orientations?

Given a set of sequence reads sharing a common molecular tag and mapping to a common region of the target sequence or to two or more contigs in an obtained contig set (a common region of the genome, or a set of contigs known or believed to map to the same general vicinity, or even a set of contigs for which no mapping information is known), one may determine an order among the contigs as follows.

Provided that the nucleic acid molecules do not correspond directly to assembled contigs in content and in their endpoints, barcoded sequence sets derived from these nucleic acid molecules are in some embodiments used to assemble contig order and orientation as follows. Individual sequence reads on a sequence set are each individually mapped to a locus on a contig in the contig set corresponding to the target sequence of a sample. Commonly tagged sequences that derive from a single nucleic acid molecule are likely to map nearby to one another on a contig or contigs. If a commonly tagged set of sequence reads maps to more than one contig, in some embodiments the contigs are presumed to be near one another in the genomic sequence. In some embodiments, if a set of sequence reads maps to the ends of two contigs, the contigs are presumed to be adjacent and oriented such that the ends to which sequence reads map are adjacent to one another. In some embodiments, if a sequence read set spans three or more than three contigs, then the contig or contigs demonstrating complete coverage are placed in the interior of the contig order, and any one or two contigs demonstrating partial coverage, such as coverage biased toward an end of each contig, are positioned at an end or on opposite ends of the contig order. In some embodiments, middle contigs are unoriented. In some embodiments, if a sequence read set spans three or more than three contigs, then the contig or contigs demonstrating complete coverage are placed in the interior of the contig order and are unoriented, and any one or two contigs demonstrating partial coverage, such as coverage biased toward an end of each contig, are positioned at an end or on opposite ends of the contig order and are oriented such that the end of each contig demonstrating partial coverage is positioned adjacent to the internal contigs demonstrating full coverage.

As illustrated in FIG. 13A-B, one observes two contigs (black bars) with binned tagged sequence reads (horizontal bars) mapped to them, with reads from the same "set" drawn in the same horizontal file and differentially shaded. As illustrated here, contigs which derive from adjacent segments of the genome will be expected to share a number of barcodes. In various embodiments the expected number (and probability distribution of the number) will depend on the number of sets, the number of reads per set, the genome size, the size of the underlying molecule in each DNA complex read as a single set, the extent of nucleic acid shearing prior to DNA-complex assembly, the lengths of the contigs, the size of the gap separating the contigs, and possibly other factors, such as any sequence dependence of the library creation process.

In some embodiments each read set corresponds to a unique molecular tag or barcode. However, in some embodiments multiple sets may have the same molecular tag or barcode. Contigs that are unlinked on the genome may share barcode sets by chance, or because of read mapping errors, and the number of shared barcodes coming from these "noise" sources can also be calculated. In particular, sequence read sets that share a common molecular barcode or tag are nonetheless easily assembled without affecting final conclusions as to molecule phase or physical linkage, provided that the commonly tagged sets do not also overlap in their mapping to a single contig sequence. In cases of commonly tagged, genomically overlapping segments of disparate origins (for example a set from mom's chromosome and a set from dad's that overlap), the presence of overlap occurrence is nonetheless detectable and disentangleable by scanning for significant coverage density fluctuations (for example, twice as many reads mapping to a contig or set of contigs than expected or than observed elsewhere) or by detecting significant levels of heterozygosity in the region, such as levels of heterozygosity above those expected from sequencing error. Alternately, a single molecule or DNA complex can be multiply tagged with more than one tag sequence without affecting final physical linkage or phasing conclusions, as the sequence reads will map to a common contig or contigs, and the molecular tag or barcode sequence is likely to be randomly or fairly randomly distributed among the sets such that it becomes clear that the sequence reads correspond to a single molecule or DNA complex.

In some embodiments more quantitative approaches are used to order, orient or order and orient contigs. For example, the expected separation on the genome between consecutive (on the genome) reads sampled from the same molecule is approximately equal to L/n, where L is the mean length of input DNA fragments, and n in the mean number of reads sampled from each chromatin aggregate. This can be used to identify which relative orientation of a pair of contigs that share many barcodes is most consistent with the data. A misoriented contig manifests itself as unexpectedly long gaps between successive reads from many shared barcodes:

The expected separation between the most distant pair of reads sampled from the same input molecule is L (n−1)/n. This expression embodies on the of the advantages of sequence read sets or binned sequences over, for example, paired end sequences. When generating binned sequence sets, one may expect many chromatin aggregates to provide linking information on the same length scale as the input DNA.

Additional approaches to ordering contigs in light of molecular-tag sorted sequence read sets are contemplated and are consistent with the disclosure herein.

Figure 2A:
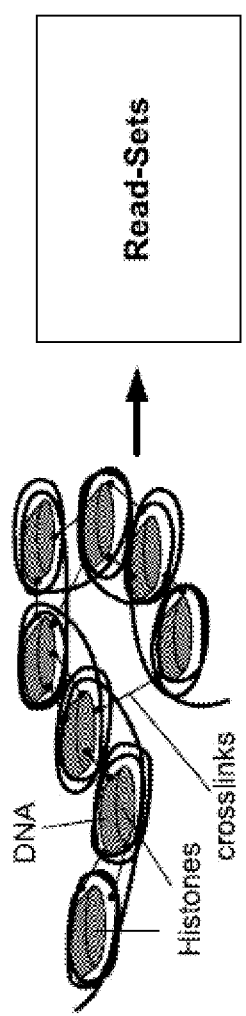
FIG. 2A-C provides a method of the disclosure to assist genome assembly.
Figure 2B:
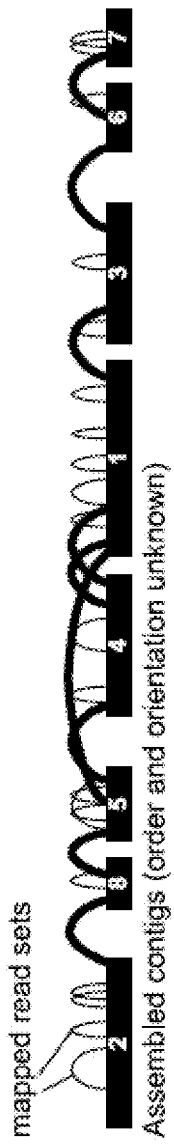
Figure 2C:
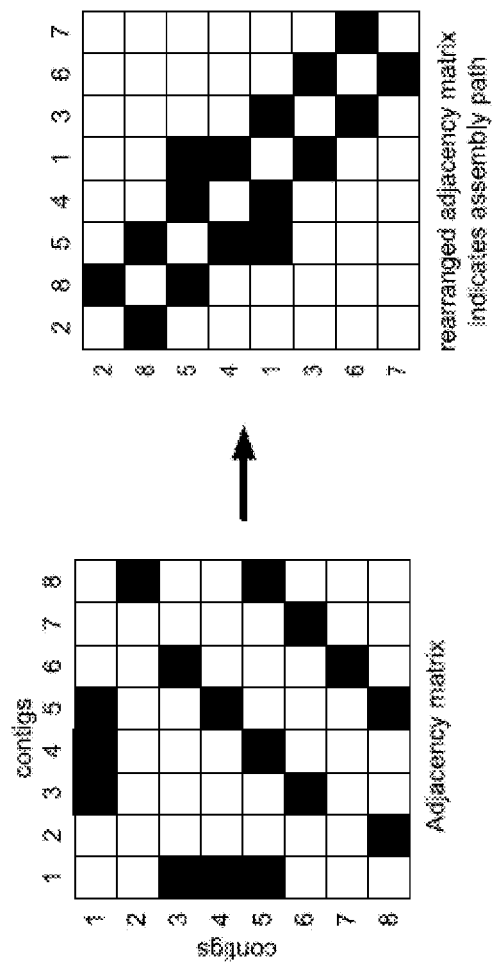

As some embodiments of the diversity of approaches for positioning and/or orienting contigs along a single physically linked nucleic acid molecule, the present disclosure further provides methods comprising constructing an adjacency matrix of contigs using the read-mapping data from the read-sets. In some embodiments, an adjacency matrix uses a weighting scheme for read-sets that incorporate the tendency for short-range interactions to occur more frequently than long-range interactions (e.g., see FIG. 2A-C). In some cases, a function describing the probability of a particular distance is fit using the read-mapping data that map to a single contig to learn this distribution. Therefore, one important feature of the reads within a read-set that map to different contigs is the position on the contig where they map. For sequence segments that both map near an end of their respective contigs, the inferred distance between these contigs can be short and therefore the distance between the joined reads may be inferred to be small. Since shorter distances between reads within a read-set are more common than longer distances, this configuration provides stronger evidence that these two contigs are adjacent than would reads mapping far from the edges of the contig. Therefore, in some embodiments the connections in the adjacency matrix are further weighted by the distance of the reads to the edge of the contigs. In further embodiments, the adjacency matrix is scaled to down-weigh the high number of contacts on some contigs that represent promiscuous regions of the genome. These regions of the genome, identifiable by having a high proportion of reads mapping to them, are a priori more likely to contain spurious read mappings that might misinform assembly. In yet further embodiments, this scaling is directed by searching for one or more conserved binding sites for one or more agents that regulate the scaffolding interactions of chromatin, such as transcriptional repressor CTCF, endocrine receptors, cohesins, or covalently modified histones.

In some embodiments, the methods disclosed herein comprise analyzing the adjacency matrix to determine a path through the contigs, or an ordering and/or orientation of the contigs that represents their order and/or orientation along a nucleic acid molecule, such as a chromosome. In some cases, the path through the contigs is chosen so that each contig is visited exactly once. In some cases, the path through the contigs is chosen so that the path through the adjacency matrix maximizes the sum of edge-weights visited. In this way, the most probable contig connections are proposed for the correct assembly. In further cases, the path through the contigs is chosen so that each contig is visited exactly once and that edge-weighting of adjacency matrix is maximized. In some embodiments an adjacency matrix is constructed to facilitate or to guide contig ordering or contig ordering and orientation, while in other embodiments contig ordering or contig ordering and orientation is determined using read-to-contig mapping information without the construction of an adjacency matrix.

Phase Data and Uses

In diploid genomes, it often important to know which allelic variants are physically linked on the same chromosome rather than mapping to the homologous position on a chromosome pair. Mapping an allele or other sequence to a specific physical chromosome of a diploid chromosome pair is known as the haplotype phasing. Short reads from high-throughput sequence data rarely allow one to directly observe which allelic variants are linked, particularly, as is most often the case, if the allelic variants are separated by a greater distance than the longest single read. Computational inference of haplotype phasing can be unreliable at long distances. Methods disclosed herein allow for determining which allelic variants are physically linked using allelic variants on read pairs.

In various cases, the methods and compositions of the disclosure enable the haplotype phasing of diploid or polyploid genomes with regard to a plurality of allelic variants. Methods described herein thus provide for the determination of linked allelic variants based on variant information from labeled sequence segments and/or assembled contigs using the same. Cases of allelic variants include, but are not limited to, those that are known from the 1000 genomes, UK10K, HapMap and other projects for discovering genetic variation among humans. In some cases, disease association to a specific gene are revealed more easily by having haplotype phasing data as demonstrated, for example, by the finding of unlinked, inactivating mutations in both copies SH3TC2 leading to Charcot-Marie-Tooth neuropathy (Lupski J R, Reid J G, Gonzaga-Jauregui C, et al. *N. Engl. J. Med.* 362:1181-91, 2010) and unlinked, inactivating mutations in both copies of ABCG5 leading to hypercholesterolemia 9 (Rios J, Stein E, Shendure J, et al. *Hum. Mol. Genet.* 19:4313-18, 2010).

Humans are heterozygous at an average of 1 site in 1,000. In some cases, a single lane of data using high throughput sequencing methods generates at least about 150,000,000 reads. In further cases, individual reads are about 100 base pairs long. If we assume input DNA fragments average 150 kbp in size and we get 100 paired-end reads per fragment, then we expect to observe 30 heterozygous sites per set, i.e., per 100 read-pairs. Every read-pair containing a heterozygous site within a set is in phase (i.e., molecularly linked) with respect to all other read-pairs within the same set. This property enables greater power for phasing with sets as opposed to singular pairs of reads in some cases. With approximately 3 billion bases in the human genome, and one in one-thousand being heterozygous, there are approximately 3 million heterozygous sites in an average human genome. With about 45,000,000 read pairs that contain heterozygous sites, the average coverage of each heterozygous site to be phased using a single lane of a high throughput sequence method is about (15×), using a typical high throughput sequencing machine. A diploid human genome can therefore be reliably and completely phased with one lane of a high-throughput sequence data relating sequence variants from a sample that is prepared using the methods disclosed herein. In some cases, a lane of data is a set of DNA sequence read data. In further cases, a lane of data is a set of DNA sequence read data from a single run of a high throughput sequencing instrument.

As the human genome consists of two homologous sets of chromosomes, understanding the true genetic makeup of an individual requires delineation of the maternal and paternal copies or haplotypes of the genetic material. Obtaining a haplotype in an individual is useful in several ways. For example, haplotypes are useful clinically in predicting outcomes for donor-host matching in organ transplantation. Haplotypes are increasingly used to detect disease associations. In genes that show compound heterozygosity, haplotypes provide information as to whether two deleterious variants are located on the same allele (that is, 'in cis', to use genetics terminology) or on two different alleles ('in trans'), greatly affecting the prediction of whether inheritance of these variants is harmful, and impacting conclusions as to whether an individual carries a functional allele and a single nonfunctional allele having two deleterious variant positions, or whether that individual carries two nonfunctional alleles, each with a different defect. Haplotypes from groups of individuals have provided information on population structure of interest to both epidemiologists and anthropologists and informative of the evolutionary history of the human race. In addition, widespread allelic imbalances in gene expression have been reported, and suggest that genetic or epigenetic differences between allele phase may contribute to quantitative differences in expression. An understanding of haplotype structure will delineate the mechanisms of variants that contribute to allelic imbalances.

In certain embodiments, the methods disclosed herein comprise an in vitro technique to fix and capture associations among distant regions of a genome as needed for long-range linkage and phasing. In some cases, the method comprises constructing and sequencing one or more read-sets to deliver very genomically distant read pairs. In further cases, each read-set comprises two or more reads that are labeled by a common barcode, which may represent two or more sequence segments from a common polynucleotide. In some cases, the interactions primarily arise from the random associations within a single polynucleotide. In some cases, the genomic distance between sequence segments are inferred because sequence segments near to each other in a polynucleotide interact more often and with higher probability, while interactions between distant portions of the molecule are less frequent. Consequently there is a systematic relationship between the number of pairs connecting two loci and their proximity on the input DNA. In some cases, the methods disclosed herein produce read pairs that span the largest DNA fragments in an extraction, as demonstrated in FIG. 19. The input DNA for this library had a maximum length of 150 kbp, which is the longest meaningful read pair we observe from the sequencing data. This suggests that the present method can link still more genomically distant loci if provided larger input DNA fragments. By applying improved assembly software tools that are specifically adapted to handle the type of data produced by the present method, a complete genomic assembly may be possible. Methods disclosed herein are used in some embodiments to label sequence segments that span the largest polynucleotide from an extraction.

In some aspects, the disclosure provides methods and compositions that produce data to achieve extremely high phasing accuracy. In comparison to previous methods, the methods described herein can phase a higher proportion of the variants. In some cases, phasing is achieved while maintaining high levels of accuracy. In further cases, this phase information is extended to longer ranges, for example greater than about 200 kbp, about 300 kbp, about 400 kbp, about 500 kbp, about 600 kbp, about 700 kbp, about 800 kbp, about 900 kbp, about 1 Mbp, about 2 Mbp, about 3 Mbp, about 4 Mbp, about 5 Mbp, or about 10 Mbp, or longer than about 10 Mbp, up to an d including the entire length of a chromosome. In some embodiments, more than 90% of the heterozygous SNPs for a human sample is phased at an accuracy greater than 99% using less than about 250 million reads, e.g. by using only 1 lane of Illumina HiSeq data. In other cases, more than about 40%, 50%, 60%, 70%, 80%, 90%, 95% or 99% of the heterozygous SNPs for a human sample is phased at an accuracy greater than about 70%, 80%, 90%, 95%, or 99% using less than about 250 million or about 500 million reads, e.g. by using only 1 or 2 lanes of Illumina HiSeq data. In some cases, more than 95% or 99% of the heterozygous SNPs for a human sample are phased at an accuracy greater than about 95% or 99% using less about 250 million or about 500 million reads. In further cases, additional variants are captured by increasing the read length to about 200 bp, 250 bp, 300 bp, 350 bp, 400 bp, 450 bp, 500 bp, 600 bp, 800 bp, 1000 bp, 1500 bp, 2 kbp, 3 kbp, 4 kbp, 5 kbp, 10 kbp, 20 kbp, 50 kbp, or 100 kbp.

Figure 21:
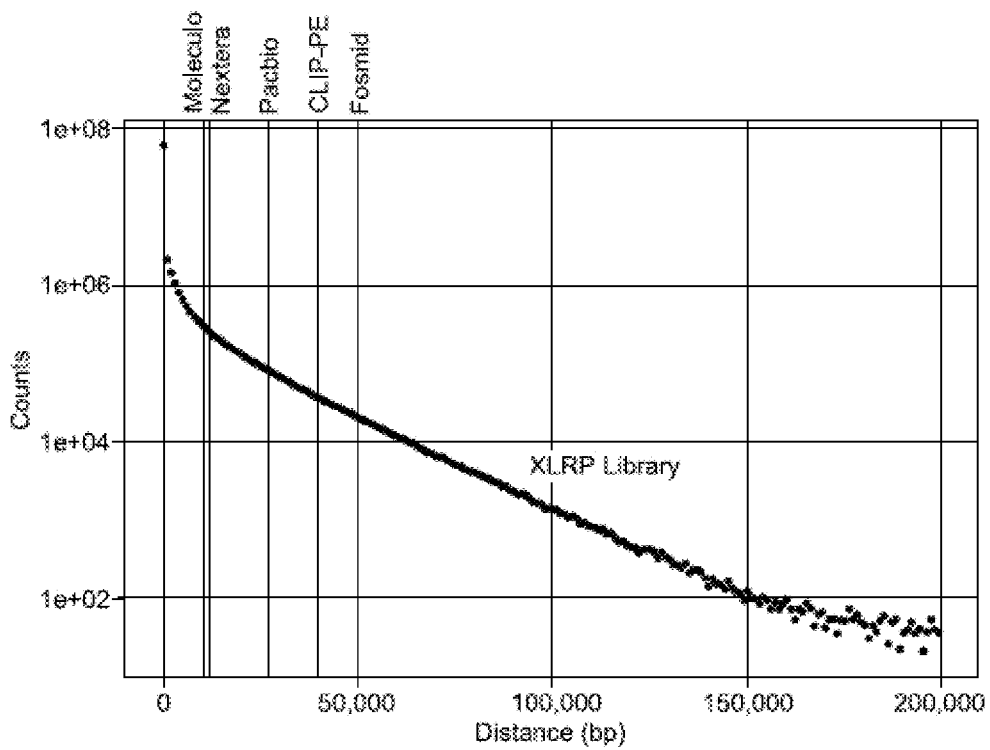
FIG. 21 illustrates the distribution of genomic distances between read pairs from a human XLRP library. Maximum distances achievable with other technologies are indicated for comparison.

In other embodiments of the disclosure, the data from an XLRP library are used to confirm the phasing capabilities of the long-range read pairs. As shown in FIG. 21, the accuracy of those results is on par with the best technologies previously available, but further extending to significantly longer distances. The current sample preparation protocol for a particular sequencing method recognizes variants located within a read-length, e.g. 150 bp, of a targeted restriction site for phasing. In one example, from an XLRP library built for NA12878, a benchmark sample for assembly, 44% of the 1,703,909 heterozygous SNPs present were phased with an accuracy greater than 99%. In some cases, this proportion is expanded to nearly all variable sites with the judicious choice of restriction enzyme or with combinations of different enzymes.

In another aspect, the methods and compositions disclosed herein allow for the investigation of meta-genomes, for example, those found in the human gut. In some cases, the partial or whole genomic sequences of some or all organisms that inhabit a given ecological environment are investigated. Cases include random sequencing of all gut microbes, the microbes found on certain areas of skin, and the microbes that live in toxic waste sites. In some cases, the composition of the microbe population in these environments is determined using the compositions and methods described herein and as well as the aspects of interrelated biochemistries encoded by their respective genomes. In further cases, the methods described herein enable metagenomic studies from complex biological environments, for example, those that comprise more than 2, 3, 4, 5, 6, 7, 8, 9, 10, 12, 15, 20, 25, 30, 40, 50, 60, 70, 80, 90, 100, 125, 150, 175, 200, 250, 300, 400, 500, 600, 700, 800, 900, 1000, 5000, 10000 or more organisms and/or variants of organisms.

Accordingly, methods disclosed herein may be applied to intact human genomic DNA samples but may also be applied to a broad diversity of nucleic acid samples, such as reverse-transcribed RNA samples, circulating free DNA samples, cancer tissue samples, crime scene samples, archaeological samples, nonhuman genomic samples, or environmental samples such as environmental samples comprising genetic information from more than one organism, such as an organism that is not easily cultured under laboratory conditions.

In some cases, high degrees of accuracy required by cancer genome sequencing are achieved using the methods and systems described herein. Inaccurate reference genomes make base-calling challenges when sequencing cancer genomes. Heterogeneous samples and small starting materials, for example a sample obtained by biopsy introduce additional challenges. Further, detection of large scale structural variants and/or losses of heterozygosity is often crucial for cancer genome sequencing, as well as the ability to differentiate between somatic variants and errors in base-calling.

The systems and methods described herein may generate accurate long sequences from complex samples containing 2, 3, 4, 5, 6, 7, 8, 9, 10, 12, 15, 20 or more than 20 varying genomes. Mixed samples of normal, benign, and/or tumor origin may be analyzed, optionally without the need for a normal control. In some embodiments, samples comprising less than about 1000 ng, about 500 ng, about 200 ng, about 100 ng, about 50 ng, about 20 ng, about 10 ng, or even as little as hundreds of genome equivalents, are utilized to generate accurate long sequences. Systems and methods described herein may allow for detection of large scale structural variants and rearrangements, Phased variant calls may be obtained over long sequences spanning about 1 kbp, about 2 kbp, about 5 kbp, about 10 kbp, 20 kbp, about 50 kbp, about 100 kbp, about 200 kbp, about 500 kbp, about 1 Mbp, about 2 Mbp, about 5 Mbp, about 10 Mbp, about 20 Mbp, about 50 Mbp, or about 100 Mbp or more nucleotides. For example, a phase variant call may be obtained over long sequences spanning about 1 Mbp or about 2 Mbp.

In certain aspects, the methods disclosed herein are used to assemble a plurality of contigs originating from a single DNA molecule. In some cases, the method comprises generating a plurality of read-pairs from the single DNA molecule that is cross-linked to a plurality of nanoparticles and assembling the contigs using the read-pairs. In certain cases, single DNA molecule is cross-linked outside of a cell. In some cases, at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% of the read-pairs span a distance greater than 1 kB, 2 kB, 3 kB, 4 kB, 5 kB, 6 kB, 7 kB, 8 kB, 9 kB, 10 kB, 15 kB, 20 kB, 30 kB, 40 kB, 50 kB, 60 kB, 70 kB, 80 kB, 90 kB, 100 kB, 150 kB, 200 kB, 250 kB, 300 kB, 400 kB, 500 kB, 600 kB, 700 kB, 800 kB, 900 kB, or 1 MB on the single DNA molecule. In certain cases, at least 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% of the read-pairs span a distance greater than 5 kB, 6 kB, 7 kB, 8 kB, 9 kB, 10 kB, 15 kB, 20 kB, 30 kB, 40 kB, 50 kB, 60 kB, 70 kB, 80 kB, 90 kB, 100 kB, 150 kB, or 200 kB on the single DNA molecule. In further cases, at least 0.5%, 0.6%, 0.7%, 0.8%, 0.9%, 1%, 2%, 3%, 4%, or 5% of the read-pairs span a distance greater than 20 kB, 30 kB, 40 kB, 50 kB, 60 kB, 70 kB, 80 kB, 90 kB, or 100 kB on the single DNA molecule. In particular cases, at least 1% or 5% of the read pairs span a distance greater than 50 kB or 100 kB on the single DNA molecule. In some cases, the read-pairs are generated within 1, 2, 3, 4, 5, 6, 7, 8, 9, 10, 11, 12, 13, 14, 15, 16, 17, 18, 19, 20, 30, 40, 50 or 60 days. In certain cases, the read-pairs are generated within 3, 4, 5, 6, 7, 8, 9, 10, 11, 12, 13, 14, 15, 16, 17 or 18 days. In further cases, the read-pairs are generated within 7, 8, 9, 10, 11, 12, 13, or 14 days. In particular cases, the read-pairs are generated within 7 or 14 days.

In other aspects, the methods disclosed herein are used for haplotype phasing. In some cases, the method comprises generating a plurality of read-pairs from a single DNA molecule that is cross-linked to plurality of nanoparticles and assembling a plurality of contigs of the DNA molecule using the read-pairs. In certain cases, single DNA molecule is cross-linked outside of a cell. In some cases, at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% of the read-pairs span a distance greater than 1 kB, 2 kB, 3 kB, 4 kB, 5 kB, 6 kB, 7 kB, 8 kB, 9 kB, 10 kB, 15 kB, 20 kB, 30 kB, 40 kB, 50 kB, 60 kB, 70 kB, 80 kB, 90 kB, 100 kB, 150 kB, 200 kB, 250 kB, 300 kB, 400 kB, 500 kB, 600 kB, 700 kB, 800 kB, 900 kB, or 1 MB on the single DNA molecule. In certain cases, at least 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% of the read-pairs span a distance greater than 5 kB, 6 kB, 7 kB, 8 kB, 9 kB, 10 kB, 15 kB, 20 kB, 30 kB, 40 kB, 50 kB, 60 kB, 70 kB, 80 kB, 90 kB, 100 kB, 150 kB, or 200 kB on the single DNA molecule. In further cases, at least 0.5%, 0.6%, 0.7%, 0.8%, 0.9%, 1%, 2%, 3%, 4%, or 5% of the read-pairs span a distance greater than 20 kB, 30 kB, 40 kB, 50 kB, 60 kB, 70 kB, 80 kB, 90 kB, or 100 kB on the single DNA molecule. In particular cases, at least 1% or 10% of the read pairs span a distance greater than 30 kB or 50 kB on the single DNA molecule. the haplotype phasing is performed at greater than 70% accuracy. In some embodiments, at least 10% of the read-pairs span a distance greater than 50 kB on the single DNA molecule. In other embodiments, wherein at least 1% of the read-pairs span a distance greater than 100 kB on the single DNA molecule. In some cases, the haplotype phasing is performed at greater than 50%, 60%, 70%, 75%, 80%, 85%, 90%, 95%, 96%, 97%, 98%, or 99% accuracy. In certain cases, the haplotype phasing is performed at greater than 70%, 75%, 80%, 85%, 90%, or 95% accuracy. In further cases, the haplotype phasing is performed at greater than 70%, or 90% accuracy.

Haplotypes determined using the methods and systems described herein may be assigned to computational resources, for example, computational resources over a network, such as a cloud system. Similarly, in certain cases, contig information are obtained using computational resources such as cloud system resources. Short variant calls are corrected, if necessary, using relevant information that is stored in the computational resources. In some cases, structural variants are detected based on the combined information from short variant calls and the information stored in the computational resources. In some cases, problematic parts of the genome, such as segmental duplications, regions prone to structural variation, the highly variable and medically relevant MHC region, centromeric and telomeric regions, and other heterochromatic regions including but limited to those with repeat regions, low sequence accuracy, high variant rates, ALU repeats, segmental duplications, or any other relevant problematic parts known in the art, are assembled or reassembled for increased accuracy.

In some cases, a sample type is assigned to the sequence information either locally or in a networked computational resource, such as a cloud. In cases where the source of the information is known, for example, when the source of the information is from a cancer or normal tissue, the source is assigned to the sample as part of a sample type. Other sample type cases generally include, but are not limited to, tissue type, sample collection method, presence of infection, type of infection, processing method, size of the sample, etc. In cases where a complete or partial comparison genome sequence is available, such as a normal genome in comparison to a cancer genome, the differences between the sample data and the comparison genome sequence is determined and optionally output.

In another aspect, the methods of the present disclosure is used in the analysis of genetic information of selective genomic regions of interest as well as genomic regions which may interact with the selective region of interest. In some cases, amplification methods as disclosed herein are used in the devices, kits, and methods known to the art for genetic analysis, such as, but not limited to those found in U.S. Pat. Nos. 6,449,562, 6,287,766, 7,361,468, 7,414,117, 6,225,109, and 6,110,709. In some cases, amplification methods of the present disclosure are used to amplify target nucleic acid for DNA hybridization studies to determine the presence or absence of polymorphisms. In further cases, the polymorphisms, or alleles, are associated with diseases or conditions such as genetic disease. In other cases, the polymorphisms are associated with susceptibility to diseases or conditions, for example, polymorphisms associated with addiction, degenerative and age related conditions, cancer, and the like. In other cases, the polymorphisms are associated with beneficial traits such as increased coronary health, or resistance to diseases such as HIV or malaria, or resistance to degenerative diseases such as osteoporosis, Alzheimer's or dementia.

In yet another aspect, the methods and compositions of the disclosure are used for diagnostic, prognostic, therapeutic, patient stratification, drug development, treatment selection, and screening purposes. In some cases, the methods of present disclosure provides the advantage that many different target molecules are analyzed at one time from a single biomolecular sample using the methods of the disclosure. This allows, for example, for several diagnostic tests to be performed on one sample.

In one aspect, the methods and compositions of the present disclosure are used in genomics. In some cases, the methods described herein provide an answer rapidly, which is very desirable for this application. In some cases, the methods and composition described herein are used in the process of finding biomarkers that may be used for diagnostics and/or prognostics, and/or as indicators of health and disease, or as part of a pharmaceutical selection regime. In further cases, the methods and compositions described herein are used to screen for drugs, e.g., drug development, selection of treatment, determination of treatment efficacy and/or identify targets for pharmaceutical development. The ability to test gene expression on screening assays involving drugs is very important because proteins are the final gene product in the body. In some embodiments, the methods and compositions described herein will measure both protein and gene expression simultaneously, which will provide the most information regarding the particular screening being performed.

In another aspect, the methods and compositions of the disclosure are used in gene expression analysis. In some cases, the methods described herein are used to discriminate between nucleotide sequences. In some cases, the difference between the target nucleotide sequences is a single nucleic acid base difference, a nucleic acid deletion, a nucleic acid insertion, or rearrangement. In further cases, such sequence differences involving more than one base are also detected. The process of the present disclosure is able to detect infectious diseases, genetic diseases, and cancer. It is also useful in environmental monitoring, forensics, and food science. Examples of genetic analyses that can be performed on nucleic acids include e.g., SNP detection, STR detection, RNA expression analysis, promoter methylation, gene expression, virus detection, viral subtyping and drug resistance.

In some cases, the present methods are applied to the analysis of biomolecular samples obtained or derived from a subject so as to determine whether a diseased cell type is present in the sample, the stage of the disease, the prognosis for the subject, the ability to the subject to respond to a particular treatment, or the best treatment for the subject. In further cases, the present methods are also applied to identify biomarkers for a particular disease.

In another aspect, the methods described herein are used in the diagnosis of a condition. As used herein, the term "diagnose" or "diagnosis" of a condition may include predicting or diagnosing the condition, determining predisposition to the condition, monitoring treatment of the condition, diagnosing a therapeutic response of the disease, or prognosis of the condition, condition progression, or response to particular treatment of the condition. In some cases, a blood sample are assayed according to any of the methods described herein to determine the presence and/or quantity of markers of a disease or malignant cell type in the sample, thereby diagnosing or staging the a disease or a cancer. In further examples, the methods and composition described herein are also used for the diagnosis and/or prognosis of a condition.

In numerous cases, immunologic, proliferative and malignant diseases and disorders are amenable to the methods described herein. Immunologic diseases and disorders include allergic diseases and disorders, disorders of immune function, and autoimmune diseases and conditions. Allergic diseases and disorders include but are not limited to allergic rhinitis, allergic conjunctivitis, allergic asthma, atopic eczema, atopic dermatitis, and food allergy. Immunodeficiencies include but are not limited to severe combined immunodeficiency (SCID), hypereosinophilic syndrome, chronic granulomatous disease, leukocyte adhesion deficiency I and II, hyper IgE syndrome, Chediak Higashi, neutrophilias, neutropenias, aplasias, Agammaglobulinemia, hyper-IgM syndromes, DiGeorge/Velocardial-facial syndromes and Interferon gamma-TH1 pathway defects. Autoimmune and immune dysregulation disorders include but are not limited to rheumatoid arthritis, diabetes, systemic lupus erythematosus, Graves' disease, Graves ophthalmopathy, Crohn's disease, multiple sclerosis, psoriasis, systemic sclerosis, goiter and struma lymphomatosa (Hashimoto's thyroiditis, lymphadenoid goiter), alopecia aerata, autoimmune myocarditis, lichen sclerosis, autoimmune uveitis, Addison's disease, atrophic gastritis, myasthenia gravis, idiopathic thrombocytopenic purpura, hemolytic anemia, primary biliary cirrhosis, Wegener's granulomatosis, polyarteritis nodosa, and inflammatory bowel disease, allograft rejection and tissue destructive from allergic reactions to infectious microorganisms or to environmental antigens.

Proliferative diseases and disorders that may be evaluated by the methods of the disclosure include, but are not limited to, hemangiomatosis in newborns; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Duputren's fibrosis, cirrhosis, atherosclerosis and vascular restenosis.

Malignant diseases and disorders that may be evaluated by the methods of the disclosure include both hematologic malignancies and solid tumors. In some cases, hematologic malignancies are amenable to the methods of the disclosure, especially when the sample is a blood sample, because such malignancies involve changes in blood-borne cells. Such malignancies include non-Hodgkin's lymphoma, Hodgkin's lymphoma, non-B cell lymphomas, and other lymphomas, acute or chronic leukemias, polycythemias, thrombocythemias, multiple myeloma, myelodysplastic disorders, myeloproliferative disorders, myelofibroses, atypical immune lymphoproliferations and plasma cell disorders. Plasma cell disorders that may be evaluated by the methods of the disclosure include multiple myeloma, amyloidosis and Waldenstrom's macroglobulinemia. Examples of solid tumors include, but are not limited to, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In some cases, genetic diseases are also detected by the process of the present disclosure. In some cases, this is carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

In one aspect, the methods described herein are used to diagnose pathogen infections (e.g. infections by intracellular bacteria and viruses) by determining the presence and/or quantity of markers of bacterium or virus, respectively, in the sample.

In further cases, a wide variety of infectious diseases are detected by the process of the present disclosure. In some cases, the infectious disease is caused by bacterial, viral, parasite, or fungal infectious agents. The resistance of various infectious agents to drugs can also be determined using the present disclosure.

Bacterial infectious agents which can be detected by the present disclosure include *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia*, B-Hemolytic strep., *Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes*.

Fungal infectious agents which can be detected by the present disclosure include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis*, and *Maduromycosis*.

Viral infectious agents which can be detected by the present disclosure include human immunodeficiency virus, human T-cell lymphocytotrophic virus, hepatitis viruses (e.g., Hepatitis B Virus and Hepatitis C Virus), Epstein-Barr virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present disclosure include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis, Trematodes, Diphyllobothrium latum, Taenia* spp., *Pneumocystis carinii*, and *Necator americanis*.

In one aspect, the present disclosure is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus may all be identified with the present disclosure. Thus, in some cases, the target molecules detected using the compositions and methods of the disclosure are either patient markers (such as a cancer marker) or markers of infection with a foreign agent, such as bacterial or viral markers.

In another aspect, the methods and compositions of the present disclosure are used to identify and/or quantify a target molecule whose abundance is indicative of a biological state or disease condition, for example, blood markers that are upregulated or downregulated as a result of a disease state.

In yet another aspect, the methods and compositions of the present disclosure is used for detecting cytokine expression. In some cases, the sensitivity of the methods described herein is helpful for early detection of cytokines, e.g., as biomarkers of a condition, diagnosis or prognosis of a disease such as cancer, and the identification of subclinical conditions.

Methods for Generating Labeled Polynucleotides

In some aspects, the present disclosure provides methods for generating labeled polynucleotides from a first DNA molecule comprising a first sequence segment and a second sequence segment. In some cases, the method comprises: a. crosslinking the first sequence segment and the second sequence segment outside of a cell; b. adding the first sequence segment and the second sequence segment to a first resolved locus comprising a plurality of binding probes; and c. generating a first labeled polynucleotide comprising a first label and a first complement sequence, and a second labeled polynucleotide comprising a second label and a second complement sequence.

Methods for Labeling DNA Segments

In one aspect, the present disclosure provides methods for labeling DNA segments. In some cases, the method comprises: a. crosslinking a first DNA molecule to yield a DNA complex; b. severing the DNA complex to form a plurality of sequence segments comprising a first sequence segment and a second sequence segment, wherein the first sequence segment comprises a first segment end and the second sequence segment comprises a second segment end; and c. attaching a first label to the first segment end and a second label to the second segment end.

In some cases, the first DNA molecule is severed by any known method in the art, including but not limited to the chemical, enzymatic, and mechanical fragmentation methods disclosed in the present application. In some examples, the first DNA molecule is severed using a restriction enzyme. In other examples, the first DNA molecule is severed by ultraviolet irradiation. The first segment end and the second segment end often comprise blunt ends. The first segment end and the second segment end can comprise overhang sequences. In some cases, the overhang sequences are filled in to generate blunt ends (e.g. using a DNA polymerase). In some cases, the overhangs are filled in by modified nucleotides, such as sulfated or biotinylated nucleotides. In some cases, the overhang sequences are cut with an exonuclease to generate blunt ends.

In some cases, the first DNA molecule is cross-linked within a cell. In some cases, the first DNA molecule is part of chromatin obtained from whole cell or nuclear extracts. In other examples, the first DNA molecule is cross-linked outside of a cell. For example, the first DNA molecule can be isolated and cross-linked in vitro. The cross-linking can be performed using photo-irradiation methods (e.g. UV irradiation) or chemical agents (e.g. formaldehyde).

In some cases, the first DNA molecule is cross-linked to a plurality of association molecules. In some cases, the association molecules comprise amino acids. In some cases, the association molecules comprise peptides or proteins (e.g. histones). In some cases, the association molecules comprise nanoparticles. In some cases, the nanoparticles are magnetic, which may facilitate the isolation of the cross-linked sequence segments. In some cases, the nanoparticle is a platinum-based nanoparticle. In other examples, the nanoparticle is a DNA intercalator, or any derivatives thereof. In further examples, the nanoparticle is a bisintercalator, or any derivatives thereof. In some cases, the association molecules are from a different source than the first DNA molecule. In some cases, the first DNA molecule is from a first human subject, whereas the association molecules are from a second human subject. In other examples, the first DNA molecule is from a mammal (e.g. human), whereas the association molecules are from another eukaryotic organism. In further examples, the first DNA molecule are from a plant cell or a prokaryote, whereas the association molecules are from a eukaryotic organism.

In some cases, the first label and the second label are identical. In other cases, the first label and the second label are different. In some cases, the first label and the second label are polynucleotides. In further examples, the first label and the second label each comprise one or more elements selected from the group consisting of a linker, a barcode and an adaptor.

In some cases, the first label comprises a first adaptor and the second label can comprise a second adaptor. In some cases, the first and second adaptor each comprises (1) an overhang sequence, which may be used to hybridize to a binding probe; (2) a double-stranded region, which may further comprise a barcode; and/or (3) a 3'-thymidine or 3'-adenine overhang, which may be used for TA ligation to the sequence segments. In some cases, the first adaptor is hybridized to a first binding probe on a resolved locus. In further examples, the first resolved locus can be located on a substrate. In some embodiments, the substrate comprises a solid support. In further embodiments, the substrate can also be any known array in the art, including but not limited to the substrates and/or arrays disclosed in the present application. In some cases, the substrate is a microarray such as a DNA microarray. In further examples, the substrate comprises more than about 10, about 20, about 50, about 100, about 200, about 500, about 1,000, about 2,000, about 5,000, about 10,000, about 20,000, about 50,000, about 100,000, about 200,000, about 500,000, about 1,000,000, about 2,000,000, about 5,000,000, about 10,000,000, about 20,000,000, about 50,000,000, or about 100,000,000 resolved loci. In some cases, the substrate comprises more than about 1,000 resolved loci. In further examples, the substrate comprises more than about 10,000 resolved loci.

In some cases, the resolved locus comprises a plurality of binding probes. In some cases, the resolve locus comprises more than about 10, about 20, about 50, about 100, about 200, about 500, about 1,000, about 2,000, about 5,000, about 10,000, about 20,000, about 50,000, about 100,000, about 200,000, about 500,000, about 1,000,000, about 2,000,000, about 5,000,000, about 10,000,000, about 20,000,000, about 50,000,000, or about 100,000,000 probes. In further examples, greater than about 50%, about 60%, about 70%, about 75%, about 80%, about 85%, about 90%, about 91%, about 92%, about 93%, about 94%, about 95%, about 96%, about 97%, about 98%, about 99%, about 99.9%, about 99.99%, about 99.999%, or about 99.9999% of the binding probes on the resolved locus are identical.

The binding probes can be any known probe in the art, including but not limited to the probes disclosed in the present application. In some cases, the binding probes comprise feature oligonucleotides. In some cases, the feature oligonucleotides comprise one or more elements selected from the group consisting of a linker, a primer, a barcode and a capture sequence. In some cases, the feature oligonucleotides comprise a linker, a primer, a barcode and/or a capture sequence. In some cases, the capture sequence can hybridize to the first sequence segment. In some cases, the barcode represents the resolved locus. In some cases, the resolved locus comprises a unique binding probe that is not found in any other resolved locus on the substrate. In some cases, the first sequence segment is extended using the binding probe as a template. In further cases, the second the second sequence segment is also extended using a binding probe as a template. In some cases, the first sequence segment and the second sequence segment comprise an identical label (i.e. the first label and the second label are identical), which may comprise the same barcode from the binding probes in the resolved locus.

In some cases, the methods comprise adding a first single nucleotide to the first segment end and a second single nucleotide to the second segment end. In some cases, the first and the second single nucleotides are added to the first and the second segment ends using a DNA polymerase that lacks 3'-5' exonuclease activity. In further examples, the first and the second single nucleotide are both adenosine. In some cases, the first label and the second label are attached to the first and the second segment ends using TA-based ligation.

In some cases, the first label comprises a first barcode and the second label can comprise a second barcode. In some cases, the first barcode and the second barcode are identical. In further examples, the first barcode and the second barcode are used to associate the first sequence segment and the second sequence segment.

In some cases, the method also comprises ligating a barcoded aggregate to the DNA complex. In some cases, the barcoded aggregate comprises a plurality of barcoded polynucleotides and a plurality of aggregate molecules. In further examples, the barcoded polynucleotides are generated using Rolling Circle Amplification (RCA). In some cases, each of the barcoded polynucleotides in the barcoded aggregate comprises an identical barcode. In further cases, each of the barcoded polynucleotides in the barcoded aggregate are identical. In some cases, the barcoded polynucleotides are ligated to the first sequence segment and the second sequence segment. In further cases, the first sequence segment and the second sequence segment are amplified using the barcoded polynucleotides as templates. In some cases, the barcoded polynucleotides comprise the first and the second label, which can comprise an identical barcode. In some cases, the aggregate molecules comprise amino acids. In further cases, the aggregate molecules comprise peptides or proteins (e.g. histones). In other cases, the aggregate molecules comprise nanoparticles. In some cases, the nanoparticle is a platinum-based nanoparticle. In other examples, the nanoparticle is a DNA intercalator, or any derivatives thereof. In further examples, the nanoparticle is a bisintercalator, or any derivatives thereof. In some cases, a sequencing adaptor is further linked to the first sequence segment and/or the second sequence segment. In some cases, the sequence information of the first sequence segment and the second sequence segment is obtained by a sequencing method. The sequencing method can be any known sequencing method in the art, including but not limited to the sequencing technologies disclosed in the present application. Using the sequence information, in some cases, the first sequence segment and the second sequence segment are associated to one another. In some cases, the first sequence segment and the second sequence segment comprise a same label and are binned into a read-set. In some cases, the sequence information is also used to assemble a plurality of contigs. In certain cases, the sequence information is used to assemble the first DNA molecule. In further cases, the sequence information is used to assemble a genome. In some cases, the genome is assembled by aligning reads to a reference genome, or by de novo assembly.

Methods for Associating Sequence Segments and Haplotype Phasing

In some embodiments, the present disclosure provides methods for associating a first sequence segment and a second sequence segment. In some cases, the methods comprise: a. crosslinking a DNA library comprising a first DNA molecule, wherein the first DNA molecule comprises the first sequence segment and the second sequence segment; b. isolating the first sequence segment and the second sequence segment in a first reaction volume; and c. attaching a first label to the first sequence segment and a second label to the second sequence segment. In some cases, the methods comprise: a. crosslinking a DNA library comprising a first DNA molecule, wherein the first DNA molecule comprises the first sequence segment and the second sequence segment; b. isolating the first sequence segment and the second sequence segment in a first reaction volume; c. releasing the first sequence segment and the second sequence segment from the crosslinking; and d. linking the first sequence segment and the second sequence segment.

In some cases, the methods further comprise severing the first DNA molecule. The first DNA molecule can be severed by any known method in the art, including but not limited to the chemical, enzymatic, and mechanical fragmentation methods disclosed in the present application. In some cases, the first DNA molecule can be severed using a restriction enzyme. In other examples, the first DNA molecule can be severed by ultraviolet irradiation. In some cases, the first DNA molecule is severed into the first sequence segment and the second sequence segment, which may have blunt-ends or overhangs. In some cases, the overhangs are filled in by modified nucleotides, such as sulfated or biotinylated nucleotides. In some cases, adaptor oligonucleotides are hybridized and/or ligated to the blunt-ends or overhangs. The adaptor oligonucleotides can be any known adaptor in the art, including but not limited to those disclosed in the present application.

In some cases, the first sequence segment and the second sequence segment are cross-linked within a cell. In some cases, the first sequence segment and the second sequence segment are part of chromatin obtained from whole cell or nuclear extracts. In other examples, the first sequence segment and the second sequence segment are cross-linked outside of a cell. In further examples, polynucleotides can be isolated and cross-linked in vitro. In some cases, the cross-linking is performed using photo-irradiation methods (e.g. UV irradiation) or chemical agents (e.g. formaldehyde).

In some cases, the first sequence segment and the second sequence segment are cross-linked to a plurality of association molecules. In some cases, the association molecules comprise amino acids. In further examples, the association molecules comprise peptides or proteins (e.g. histones, or packing proteins such as H1 and protamine). In other examples, the association molecules comprise nanoparticles. In certain cases, the nanoparticles can be magnetic, which may facilitate the isolation of the cross-linked sequence segments. In some cases, the nanoparticle is a platinum-based nanoparticle. In other examples, the nanoparticle is a DNA intercalator, or any derivatives thereof. In further examples, the nanoparticle is a bisintercalator, or any derivatives thereof. In further cases, the association molecules are from a different source than the first DNA molecule. In some cases, the first DNA molecule is from a first human subject, whereas the association molecules are from a second human subject. In other examples, the first DNA molecule is from a mammal (e.g. human), whereas the association molecules are from another eukaryotic organism. In further examples, the first DNA molecule is from a plant cell or a prokaryote, whereas the association molecules are from a eukaryotic organism.

Figure 17A:
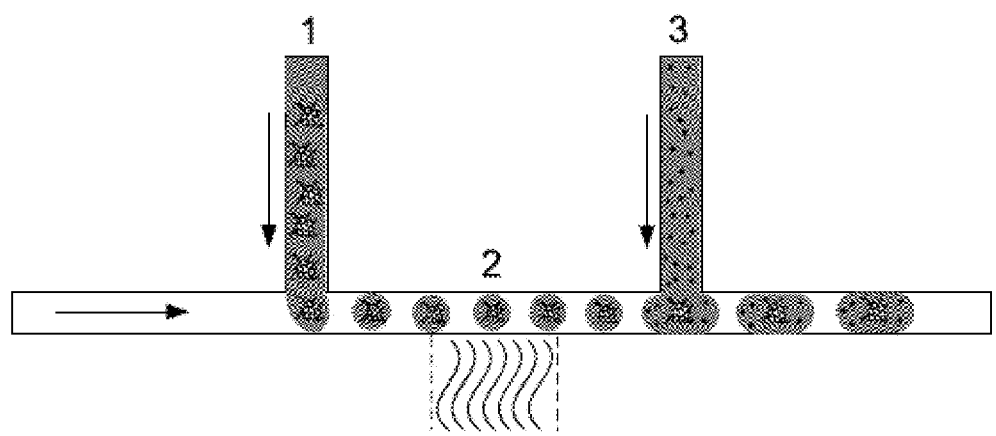
FIG. 17A-B provides an illustration of implementation of methods disclosed herein.
Figure 17B:
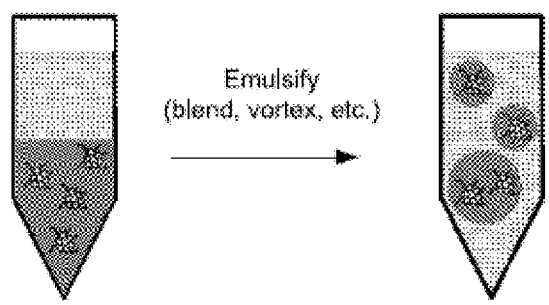
Figure 19A:
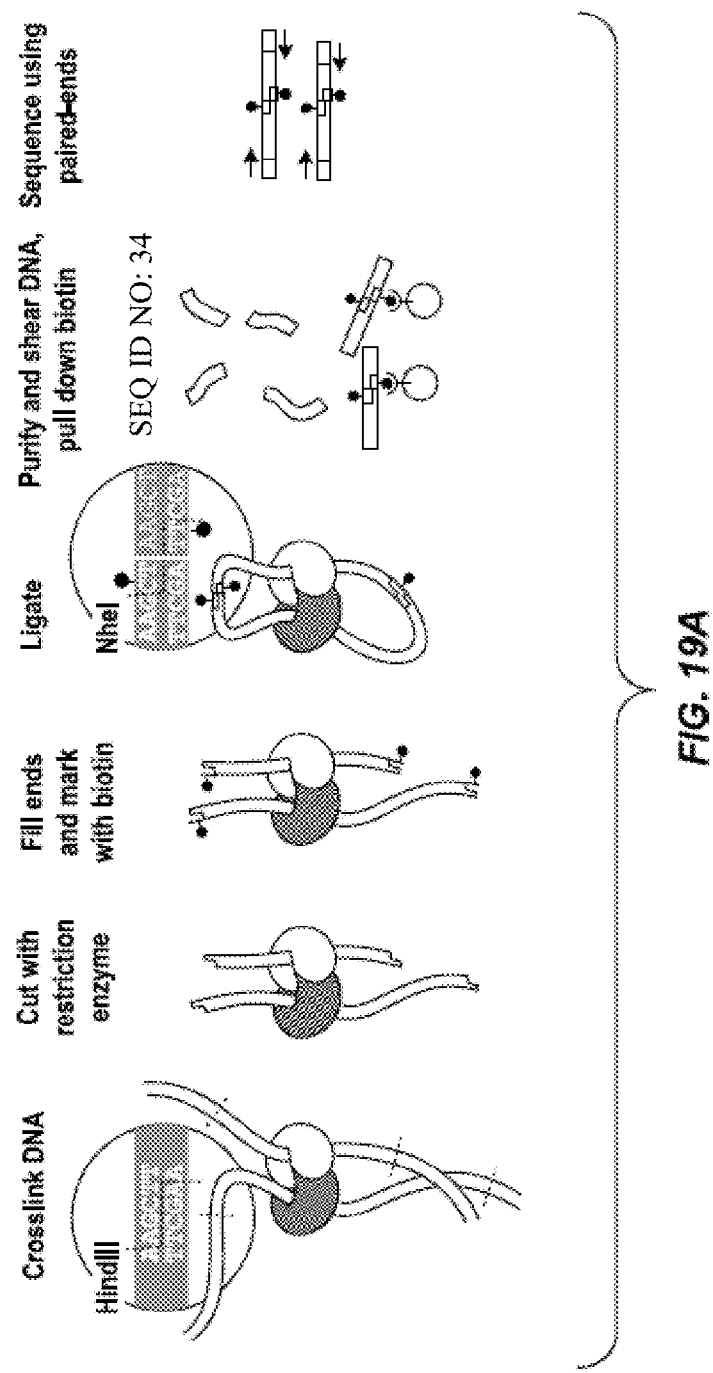
FIG. 19A-D illustrates a chromatin capture protocol of the disclosure.
Figure 19B:
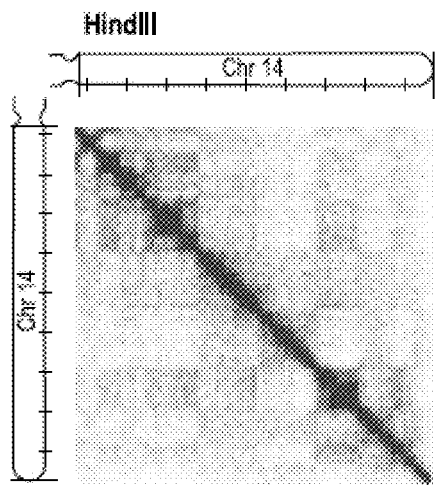
Figure 19C:
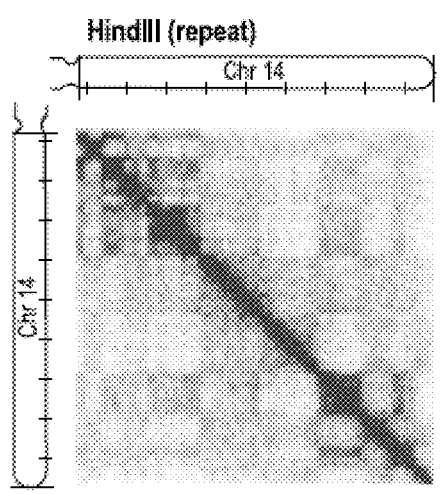
Figure 19D:
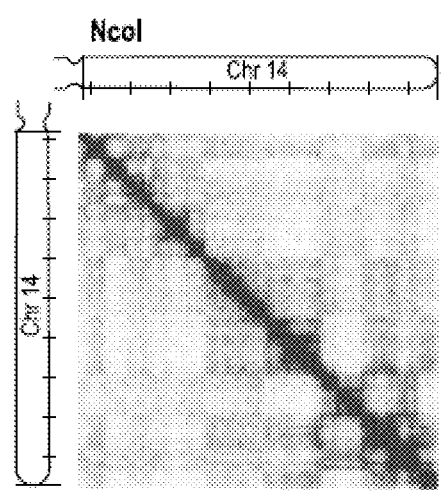
Figure 20:
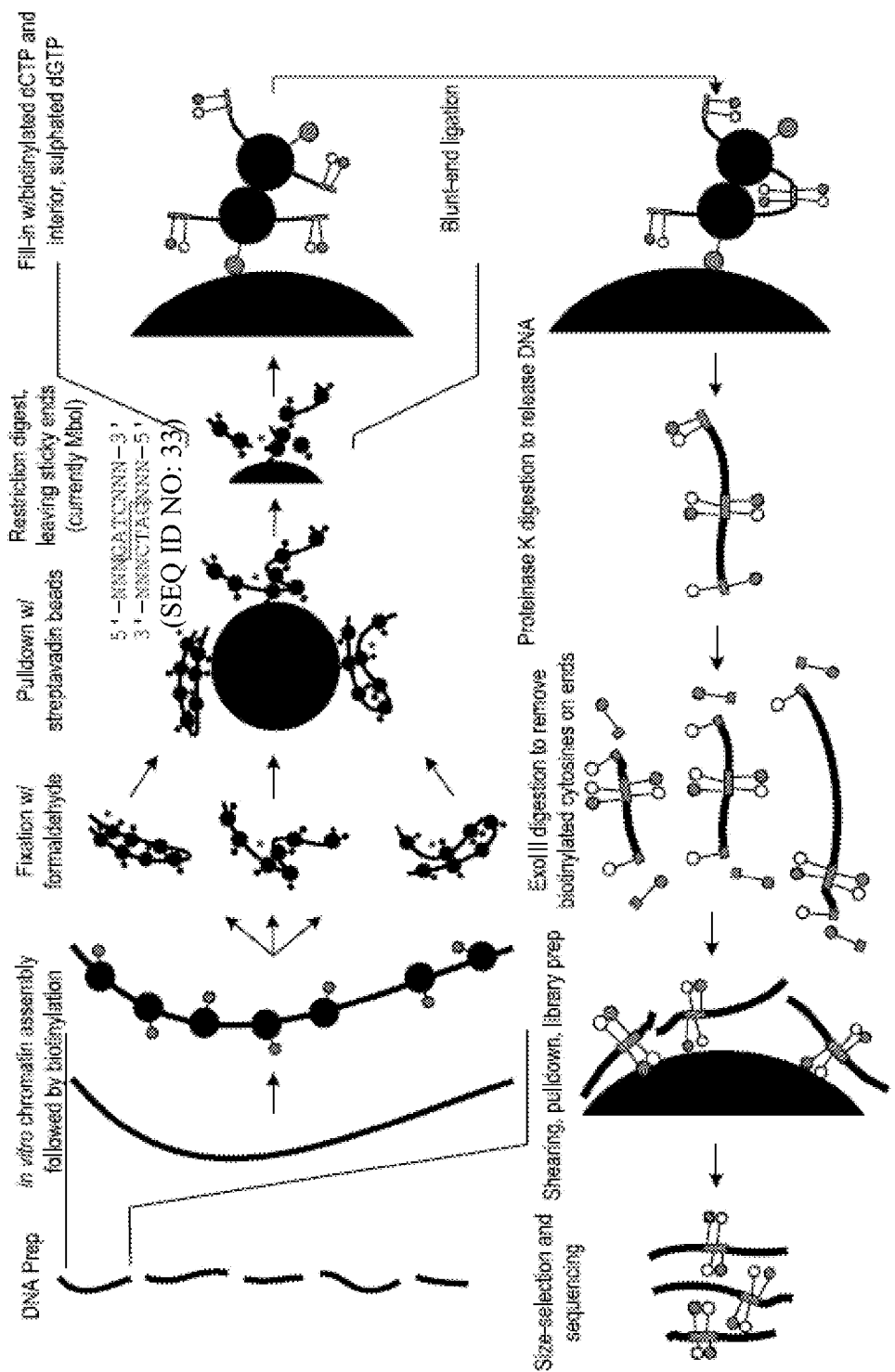
FIG. 20 illustrates an exemplary protocol of the disclosure: DNA fragments are first generated and prepared; followed by in vitro chromatin assembly and biotinylation; the chromatin/DNA complex is then fixed with formaldehyde and pulled down with streptavadin beads; the complexes are then restriction digested to generate sticky ends that are then filled with biotinylated dCTP and interior, sulfated GTP; following blunt-end ligation, the chromatin/DNA complex undergoes proteinase digestion, exonuclease digestion and shearing; after which the DNA fragments are pulled pulled-down with biotin and ligated with a sequencing adaptor; and finally, the DNA fragments are selected by size and sequenced.

In some embodiments, the first reaction volume is an aqueous droplet. In some cases, the first sequence segment and the second sequence segment are isolated in the first reaction volume using various techniques, including but not limited to emulsions, microfluidic devices, and liposomes, lipid bilayers and micelles. In some cases, the aqueous droplet comprising the first sequence segment and the second sequence segment are emulsified in an oil (FIG. 17B), such as in emulsion PCR (Williams, R. et al. (2006) *Nat. Methods,* 3(7), 545-550), or an organic solution. In other examples, the aqueous droplet is generated in an oil or organic phase using a microfluidic device by various approaches (Garstecki et al. (2005). "Formation of bubbles and droplets in microfluidic systems." *Technical sciences,* 53(4) 69). In some cases, an aqueous solution comprising the first sequence segment and the second sequence segment is injected into a flowing oil or organic phase, thereby creating the first reaction volume (FIG. 17A). In further examples, the various reactions within the reaction volume is controlled by varying the conditions (e.g. temperature, as in FIG. 17A, section 2) at various locations within the microfluidic device. A benefit of using the microfluidic approach is that additional reagents (e.g. polymerase, primer, restriction, ligase) may be introduced at various stages (FIG. 17A, section 3). The use of microfluidics may also allow for more precise control of the composition within the reaction volume, yielding greater control of the number of aggregates, reagents and enzymes in each reaction volume. In some cases, the linear nature of microfluidic channels allows for optical scanning of the reaction volume for various measurements related to the efficiency of reactions or the presence or absence of particular components. In some cases, junctions within the microfluidic channel are used to divert and/or discard compartments that do not meet certain criteria, based on optical scanning or other sensing. In other cases, the aqueous droplet are generated as a liposome or a micelle surrounded by relative thin lipid mono- (micelle) or bi- (liposome) layers. In some cases, the amphipathic layer(s) comprise phospholipids. However, nearly any amphipathic molecule may be used to form such compartments. In certain cases, using liposomes/micelles allows for substantially simpler and more feasible passing of reagents across the membrane, thus allowing for more flexibility in the reaction environment. In some cases, the lipid layer(s) comprise phospholipids. In some cases, anionic phospholipids are used to coat, rather than fully encapsulate, the cross-linked sequence segments to provide a more confined reaction environment at the expense of space for enzymes and reagents.

In some cases, the first reaction volume comprises a single DNA molecule and not any other DNA molecule. In some cases, the DNA library comprises a plurality of DNA molecules that are isolated in a plurality of reaction volumes. In further cases, the DNA molecules are isolated in the reaction volumes under conditions such that a substantial percentage of the reaction volumes comprise a single DNA molecule or no DNA molecules at all. In some cases, more than about 50%, about 60%, about 70%, about 75%, about 80%, about 85%, about 90%, about 91%, about 92%, about 93%, about 94%, about 95%, about 96%, about 97%, about 98%, about 99%, about 99.9%, about 99.99%, about 99.999%, or about 99.9999% of the reaction volumes comprise 0 or 1 DNA molecules.

In some cases, the first label and the second label are identical. In other cases, the first label and the second label are different. In some cases, the first label and the second label are polynucleotides. In further examples, the first label and the second label each comprise one or more elements selected from the group consisting of a primer, a barcode and a restriction site. In some cases, the first label and the second label each comprise a barcode. In further examples, the labels comprise specific sequences indicating the location of the barcode. In certain cases, the first label and the second label are produced from a template in the first reaction volume. In some cases, the first label and the second label are produced by amplification of a linear template (e.g. PCR). In other cases, the first label and the second label are produced by Rolling Circle Amplification (RCA) of a circular template. In further cases, the RCA product is further digested to yield a plurality of labels. In some cases, the labels are digested or modified (e.g. adenylated), such as to generate complementary overhangs for attachment to the sequence segments. In certain cases, the labels are attached to the sequence segments by ligation or by hybridization and extension with a DNA polymerase. In further cases, the labels are attached directly to the sequence segments, or indirectly to adaptor oligonucleotides that are ligated or hybridized to the sequence segments.

In some cases, the first sequence segment and the second sequence segment are released from the crosslinking using heat or chemical agents. In certain cases, the crosslinks are reversed. In some cases, the first sequence segment and the second sequence segment are further digested to generate new ends (e.g. with a different restriction enzyme). In further cases, the first sequence segment and the second sequence segment are hybridized and/or linked by a ligase. In some cases, the sequence segments within a single reaction volume link to one another and generate many hybrid molecules. In some cases, the linked sequence segments may be previously distant on the original DNA molecule.

In certain cases, sequencing adaptors are further linked to the first sequence segment and/or the second sequence segment. In some cases, the sequence information of the first sequence segment and/or the second sequence segment are obtained by a sequencing method. The sequencing method can be any known sequencing method in the art, including but not limited to the sequencing technologies disclosed in the present application. In some cases, the sequencing method is a microarray analysis (e.g. comparative hybridization) or a high-throughput sequencing technique. Using the sequence information, in some cases, the first sequence segment and the second sequence segment are associated to one another. In some cases, the first sequence segment and the second sequence segment comprise a same barcode and are binned into a read-set. In further examples, the first sequence segment and the second sequence segment are associated based on the first label and the second label. In some cases, the sequence information is also used to assemble a plurality of contigs. In certain cases, the sequence information is used to assemble the first DNA molecule. In further cases, the sequence information is used to assemble a genome. In some cases, the genome is assembled by aligning reads to a reference genome, or by de novo assembly.

In some cases, the labeled or linked sequence segments is analyzed and/or characterized. In some cases, the labeled or linked sequence segments are isolated (e.g. by phase separation), filtered and/or washed to retain only the sequence segments of interest. In some cases, the size of the DNA molecules in the DNA library are estimated (e.g. by gel electrophoresis or pulsed field gel electrophoresis (PFGE)) and used to calculate an expected range (in base pairs) of the sequence segments.

Bridge Amplification

In some cases, the plurality of binding probes is produced on the first resolved locus using bridge amplification. In some cases, the binding probes are feature oligonucleotides immobilized on the first resolved locus at a 5'end. In further cases, the first complement sequence is complementary to the first sequence segment and the second complement sequence is complementary to the second sequence segment.

In some embodiments, the substrate used is a solid surface, such as an array or a chip. In certain embodiments, the surface is coated with clusters of DNA, each of which contain many DNA molecules that can associate with appropriately prepared chromatin aggregates. In some embodiments, the surface is randomly coated, while in other embodiments the surface is systematically coated. In alternative embodiments, the surface is the exterior of a plurality of beads, such as beads having oligonucleotides corresponding to a single molecular tag or barcode attached to each bead surface, such that a plurality of beads differ in the barcode of the oligos attached thereon.

In some embodiments, each cluster, such as a cluster on an array or on a bead, is identified by a unique DNA barcode found within each DNA molecule of the cluster. In alternative embodiments, at least two clusters share a molecular tag or barcode. Provided that no barcode or molecular tag sequence is present in a majority of clusters, methods consistent with the disclosure herein are practicable. In exemplary embodiments, a molecular tag or barcode is present in at most 25%, 20%, 15%, 14%, 13%, 12%, 11%, 10%, 9%, 8%, 7%, 6%, 5%, 4%, 3%, 2%, 1%, or less than 1% of the clusters. In exemplary embodiments, each cluster comprises oligos having a molecular tag or barcode unique to that cluster, such that each cluster has its own barcode or molecular tag.

In some cases, the solid surface is a glass coverslip or a microbead, such as a magnetic microbead covered with a chemical that can form covalent bonds with appropriately modified oligonucleotides.

Throughout this discussion, reference is made to oligos having specific sequence representative of classes of oligos and, in some cases, conveying specific functionality to the methods. The sequences are provided for demonstrative purposes, and are not to be interpreted as indicative that alternatives do not exist. Alternatives to each nucleic acid having alternate sequence but conveying similar functionality are contemplated herein and are consistent with this disclosure and the practice of the methods herein.

Two sets of oligonucleotides are synthesized with a chemical reactive group on the 5' carbon of a terminal deoxyribose. An exemplary depiction of this, in which the oligos are synthesized for attachment to a silanized glass coverslip, is given in FIG. 6A.1.

The first set of oligonucleotides is termed the "adaptor oligonucleotide" and contains DNA sequence that serves three purposes: 1) to capture barcode oligonucleotides; 2) to provide an adaptor for high throughput sequencing; and 3) serve as a primer during bridge amplification.

The second set of oligonucleotides is termed the "chromatin capture oligonucleotide", or CCO, and has two purposes: 1) to provide a priming site for bridge amplification; and 2) to provide the capture sequence that is used to capture chromatin aggregates. A portion of the capture sequence contains a site that permits double stranded cleavage at a later step. An example of such a site is an EcoRV blunt-ended restriction endonuclease recognition site. Both sets of oligonucleotides have several spacer groups between the 5' reactive group and beginning of nucleotide sequence. An example of an appropriate spacer is hexaethylene glycol. The spacer will serve to provide enough distance between the nucleotide sequence and solid surface such that a polymerase may fully transcribe the attached nucleotides without being impeded by the glass surface. The spacer furthermore provides enough distance between the nucleotide sequence and solid surface in some cases for any type of enzymatic or chemical reaction.

These two sets of oligonucleotides are attached to a glass surface via complementary reaction groups found on the glass surface. An exemplary reaction group is given in FIG. 6A.2. For example, the glass surface may be coated with epoxysilane, which will covalently bind to oligonucleotides with an amino group attached to a terminal 5' deoxyribose via a phosphate group.

A third set of oligonucleotides is synthesized (FIG. 6A.3-4). Each oligonucleotide has the following functional domains of DNA sequence from 5' to 3': 1) the full capture sequence; 2) a randomized length of N nucleotides that serve as a barcode; and 3) the reverse complement of the adaptor oligonucleotide. The minimum length of N is such that the probability of selecting a uniquely barcoded oligonucleotide out of a given number of oligonucleotides is acceptable. A length of N=20 is elected in some embodiments as $4^{20}$ permutations are possible. In some embodiments N comprises 6 bases. In some embodiments N comprises 7 bases. In some embodiments N comprises 8 bases. In some embodiments N comprises 9 bases. In some embodiments N comprises 10 bases. In some embodiments N comprises 11 bases. In some embodiments N comprises 12 bases. In some embodiments N comprises 13 bases. In some embodiments N comprises 14 bases. In some embodiments N comprises 15 bases. In some embodiments N comprises 16 bases. In some embodiments N comprises 17 bases. In some embodiments N comprises 18 bases. In some embodiments N comprises 19 bases. In some embodiments N comprises 20 bases. In some embodiments N comprises 21 bases. In some embodiments N comprises 22 bases. In some embodiments N comprises 23 bases. In some embodiments N comprises 24 bases. In some embodiments N comprises 25 bases. In some embodiments N comprises greater than 25 bases.

This third set of oligonucleotides is applied at a given density to a glass surface that has a lawn of adaptor and CCO oligonucleotides. An example is given in FIG. 6A.4. Each individual, uniquely barcoded oligonucleotide is then copied onto the glass surface by DNA polymerase extension. An example is given in FIG. 6A.5. A number of clones of each barcoded oligonucleotide are then generated by bridge amplification PCR. An example is given in FIG. 6A.6-9. The number of oligonucleotide clones and the diameter of the clonal colony is controllable by the number of PCR cycles performed. A total of 10 PCR reaction cycles may be suitable to generate 1024 single-stranded templates, 512 of which will end with the capture sequence. The diameter of the cluster is likely to be no more than 1 micrometer in size.

After sufficient cycles of bridge amplification have been performed, the synthesized strands of DNA are allowed to base pair with their complement. An example is given in FIG. 6A.10. The capture sequence in the CCO is present in its double-stranded form and contains a recognition site for the blunt-end restriction endonuclease EcoRV, which is added to create a double strand break within the capture sequence. This effectively removes DNA strands that begin at the 5' end with the CCO and capture sequence. An example is given in FIG. 6A.11, which is important to ensure that the capture sequence present at the end of the adaptor oligonucleotide is available to bind only to chromatin aggregates.

As an alternative, and to demonstrate the sequence diversity that is consistent with the methods disclosed herein, a second bridge amplification protocol is presented. In the prior embodiments, above, the capture sequence is "hardwired" into the CCO (which is attached to the substrate), while in the embodiments discussed immediately below, the capture sequence is provided entirely by the barcode oligo. There is a restriction site in the CCO that will cut precisely between the capture sequence and CCO and provide a single strand ending with the capture sequence for interaction with DNA clusters. Providing the capture sequence in the barcoded oligo allows for maximum flexibility in designing the sequence to use while minimizing costs.

As emphasized above, throughout this discussion, reference is made to oligos having specific sequence representative of classes of oligos and in some cases conveying specific functionality to the methods. The sequences are provided for demonstrative purposes, and are not to be interpreted as indicative that alternatives do not exist. Alternatives to each nucleic acid having alternate sequence but conveying similar functionality are contemplated herein and are consistent with this disclosure and the practice of the methods herein.

Throughout this discussion, reference is made to oligos having specific sequence representative of classes of oligos and in some cases conveying specific functionality to the methods. The sequences are provided for demonstrative purposes, and are not to be interpreted as indicative that alternatives do not exist. Alternatives to each nucleic acid having alternate sequence but conveying similar functionality are contemplated herein and are consistent with this disclosure and the practice of the methods herein.

Figure 11C:
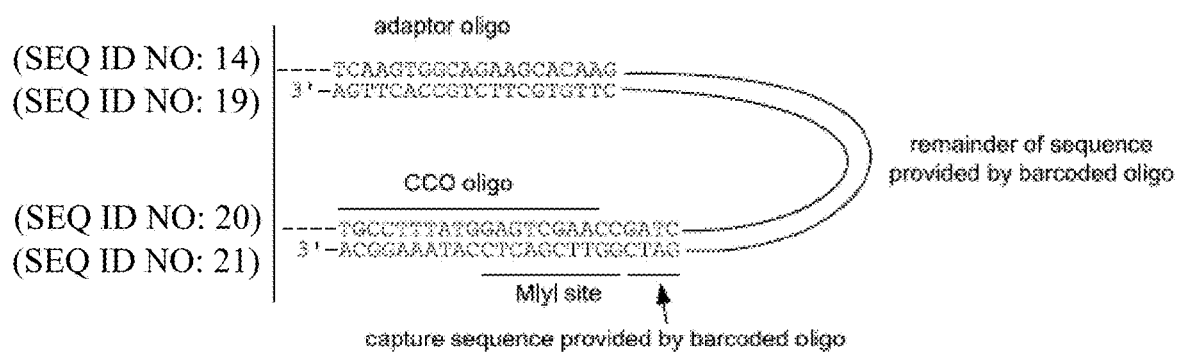

Two sets of oligonucleotides are synthesized with a chemical reactive group on the 5' carbon of a terminal deoxyribose. The first set is termed the "adaptor oligonucleotide" and contains DNA sequence that serves two purposes: 1) to capture barcode oligonucleotides; and 2) serve as a primer during bridge amplification. An example of such an oligonucleotide is given in FIG. 11A, top. The second set of oligonucleotides is termed the "chromatin capture oligonucleotide", or CCO, and has two purposes: 1) to provide a priming site for bridge amplification; and 2) to provide a restriction site that permits the generation of a single stranded oligonucleotide with a chromatin capture sequence at its 3' end. An example of such a restriction site is that recognized by the MlyI restriction endonuclease. An example of such an oligonucleotide is given in FIG. 11A, bottom.

Each set of oligonucleotides may comprise none to several spacer groups between the 5' reactive group and beginning of nucleotide sequence. In some embodiments the spacer will serve to provide enough distance between the nucleotide sequence and solid surface such that a polymerase may fully transcribe the attached nucleotides without being impeded by the glass surface. An example of a spacer consistent with the disclosure herein is hexaethylene glycol.

A third set of oligonucleotides is provided. Each oligonucleotide has the following functional domains of DNA sequence from 5' to 3': 1) the sequence of the CCO; 2) the capture sequence, which may be arbitrarily chosen and does not anneal directly to the CCO attached to the substrate; 3) a randomized length of N nucleotides that serve as a barcode; 4) adaptor sequence for use in high throughput sequencing; and 5) the reverse complement of the adaptor oligonucleotide.

The minimum length of N is such that the probability of selecting a uniquely barcoded oligonucleotide out of a given number of oligonucleotides is acceptable. An example of such an oligonucleotide set is given in FIG. 11B. A length of N=20 is elected in some embodiments as $4^{20}$ permutations are possible. In some embodiments N comprises 6 bases. In some embodiments N comprises 7 bases. In some embodiments N comprises 8 bases. In some embodiments N comprises 9 bases. In some embodiments N comprises 10 bases. In some embodiments N comprises 11 bases. In some embodiments N comprises 12 bases. In some embodiments N comprises 13 bases. In some embodiments N comprises 14 bases. In some embodiments N comprises 15 bases. In some embodiments N comprises 16 bases. In some embodiments N comprises 17 bases. In some embodiments N comprises 18 bases. In some embodiments N comprises 19 bases. In some embodiments N comprises 20 bases. In some embodiments N comprises 21 bases. In some embodiments N comprises 22 bases. In some embodiments N comprises 23 bases. In some embodiments N comprises 24 bases. In some embodiments N comprises 25 bases. In some embodiments N comprises greater than 25 bases.

Figure 11D:
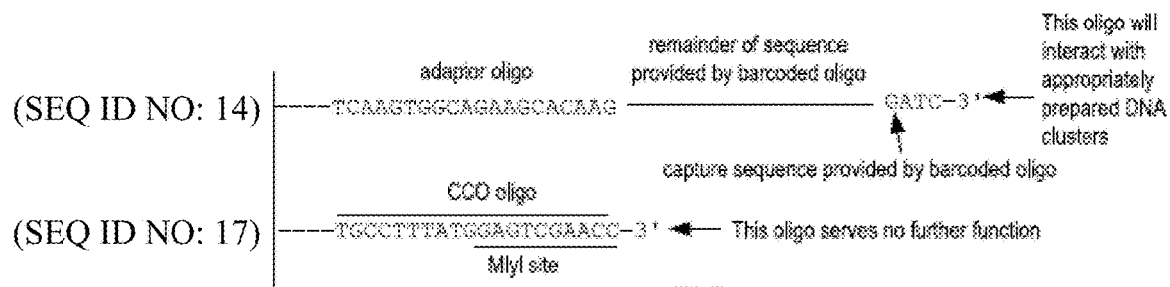

After sufficient cycles of bridge amplification have been performed, the synthesized strands of DNA are each allowed to base pair with their complement. An example of such a configuration set is given in FIG. 11C. The capture sequence in the CCO is present in its double-stranded form and contains a recognition site, which in the example given is for the blunt-end restriction endonuclease MlyI, but other restriction endonucleases and restriction site sequences are consistent with the methods herein. Treatment with the restriction endonuclease creates a double strand break within the capture sequence. Following introduction of this break, sequence 5' of the break site in each direction is held to the surface only by base pair interactions, and may be washed from the surface, for example after heating to melt any base pairing. In some embodiments, a wash step removes DNA strands that begin at the 5' end with the CCO and capture sequence, which in some embodiments is important to ensure that the capture sequence present at the end of the adaptor oligonucleotide is available to bind only to chromatin aggregates. An example of such a washed surface having oligonucleotides as described is given in FIG. 11D.

Other DNA sequences, whether arbitrary or a specific sequence such as a primer site may be placed within the barcoded oligonucleotide between the reverse complement of the adaptor oligonucleotide and capture sequence. These DNA sequences may serve any function. For example, they may make the final capture oligonucleotide longer, or they may provide a priming site for a primer.

As mentioned above, oligonucleotides as discussed in this section are characterized by at least one functional characteristic as disclosed herein. Specific sequences are provided in FIG. 6.A.1-8, and in FIGS. 11A-D for illustrative purposes, but are not limiting in some embodiments herein.

DNA Complex Formation

In some cases, the methods provided herein further comprise forming a complex comprising a nucleic acid and a nucleic acid binding agent.

In some embodiments, forming such a complex comprises severing the first DNA molecule. In some cases, the first DNA molecule is severed by any known method in the art, including but not limited to the chemical, enzymatic, and mechanical fragmentation methods disclosed in the present application. In some cases, the first DNA molecule is severed using a restriction enzyme. In other examples, the first DNA molecule is severed by ultraviolet irradiation. In some cases, the first DNA molecule is severed into the first sequence segment and the second sequence segment, which may have blunt-ends or overhangs. In some cases, the overhangs are filled in by modified nucleotides, such as sulfated or biotinylated nucleotides. In some cases, adaptor oligonucleotides are hybridized and/or ligated to the blunt-ends or overhangs. The adaptor oligonucleotides can be any known adaptor in the art, including but not limited to those disclosed in the present application.

In certain cases, the first sequence segment and the second sequence segment is cross-linked within a cell. In some cases, the first sequence segment and the second sequence segment are part of chromatin obtained from whole cell or nuclear extracts. In other cases, the first sequence segment and the second sequence segment are cross-linked outside of a cell. In some cases, polynucleotides can be isolated and cross-linked in vitro. In further examples, the crosslinking is performed using photo-irradiation methods (e.g. UV irradiation) or chemical agents (e.g. formaldehyde).

In some cases, the first sequence segment and the second sequence segment are cross-linked to a plurality of association molecules. In some cases, the association molecules comprise amino acids. In further cases, the association molecules comprise peptides or proteins (e.g. histones). In other cases, the association molecules comprise nanoparticles. In some cases, the nanoparticle is a platinum-based nanoparticle. In other examples, the nanoparticle is a DNA intercalator, or any derivatives thereof. In further examples, the nanoparticle is a bisintercalator, or any derivatives thereof. In some cases, the nanoparticles are magnetic, which may facilitate the isolation of the cross-linked sequence segments. In further examples, the association molecules are from a different source than the first DNA molecule. In some cases, the first DNA molecule is from a first human subject, whereas the association molecules are from a second human subject. In other examples, the first DNA molecule is from a mammal (e.g. human), whereas the association molecules are from another eukaryotic organism. In further examples, the first DNA molecule is from a plant cell or a prokaryote, whereas the association molecules are from a eukaryotic organism.

In certain cases, the first resolved locus is located on a substrate. In some cases, the substrate comprises a solid support. The substrate can also be any known array in the art, including but not limited to the substrates and/or arrays disclosed in the present application. In some cases, the substrate is a microarray such as a DNA microarray. In further examples, the substrate comprises more than about 10, about 20, about 50, about 100, about 200, about 500, about 1,000, about 2,000, about 5,000, about 10,000, about 20,000, about 50,000, about 100,000, about 200,000, about 500,000, about 1,000,000, about 2,000,000, about 5,000,000, about 10,000,000, about 20,000,000, about 50,000,000, or about 100,000,000 resolved loci. In some cases, the substrate comprises more than about 1,000 resolved loci. In further examples, the substrate comprises more than about 10,000 resolved loci.

In some cases, the first resolved locus comprises a plurality of binding probes. In some cases, the resolve loci comprises more than about 10, about 20, about 50, about 100, about 200, about 500, about 1,000, about 2,000, about 5,000, about 10,000, about 20,000, about 50,000, about 100,000, about 200,000, about 500,000, about 1,000,000, about 2,000,000, about 5,000,000, about 10,000,000, about 20,000,000, about 50,000,000, or about 100,000,000 probes. In some cases, greater than about 50%, about 60%, about 70%, about 75%, about 80%, about 85%, about 90%, about 91%, about 92%, about 93%, about 94%, about 95%, about 96%, about 97%, about 98%, about 99%, about 99.9%, about 99.99%, about 99.999%, or about 99.9999% of the binding probes on the first resolved loci comprises a common label. In further cases, greater than about 50%, about 60%, about 70%, about 75%, about 80%, about 85%, about 90%, about 91%, about 92%, about 93%, about 94%, about 95%, about 96%, about 97%, about 98%, about 99%, about 99.9%, about 99.99%, about 99.999%, or about 99.9999% of the binding probes on the first resolved loci are identical.

The binding probes can be any known probe in the art, including but not limited to the probes disclosed in the present application. In some cases, the binding probes comprise feature oligonucleotides. In some cases, the feature oligonucleotides comprise one or more elements selected from the group consisting of a linker, a primer, a barcode and a capture sequence. In some cases, the feature oligonucleotides comprise a linker, a primer, a barcode and/or a capture sequence. In some cases, the capture sequence can hybridize to the first sequence segment. In some cases, the barcode represents the resolved locus. In some cases, the first resolved locus comprises a unique binding probe that is not found in any other resolved locus on the substrate. In some cases, the first labeled polynucleotide is generated by extending the first sequence segment using the binding probe as a template. In further cases, the second labeled polynucleotide is generated by extending the second sequence segment by using a binding probe as a template. In some cases, the first labeled polynucleotide and the second labeled polynucleotide comprise the same label (i.e. the first label and the second label are identical), which may comprise the same barcode from the binding probes in the first resolved loci.

In certain cases, each of the resolved loci comprises a unique binding probe that is not found in any other resolved locus on the substrate. In some cases, sequence segments that are added to a common resolved locus are labeled with a same label, which can be generated by extending the sequence segments using the unique binding probe as a template. In further cases, DNA molecules comprising sequence segments are added to the substrate under conditions such that a substantial percentage of the resolved loci comprise binding probes that hybridize to sequence segments from a single DNA molecule or no sequence segments at all. In some cases, more than about 50%, about 60%, about 70%, about 75%, about 80%, about 85%, about 90%, about 91%, about 92%, about 93%, about 94%, about 95%, about 96%, about 97%, about 98%, about 99%, about 99.9%, about 99.99%, about 99.999%, or about 99.9999% of the resolved loci comprise binding probes that hybridize to sequence segments from 0 or 1 DNA molecules. In some cases, there is greater than about 50%, about 60%, about 70%, about 75%, about 80%, about 85%, about 90%, about 91%, about 92%, about 93%, about 94%, about 95%, about 96%, about 97%, about 98%, about 99%, about 99.9%, about 99.99%, about 99.999%, or about 99.9999% probability that sequence segments labeled with a same label originated from a common DNA molecule that hybridized to a common unique binding probe on a common resolved loci.

In some cases, a sequencing adaptor is further linked to the first labeled polynucleotide and/or the second labeled polynucleotide. In further cases, the sequence information of the first labeled polynucleotide and the second labeled polynucleotide are obtained by a sequencing method. The sequencing method can be any known sequencing method in the art, including but not limited to the sequencing technologies disclosed in the present application. Using the sequence information, in some cases, the first sequence segment and the second sequence segment are associated to one another. In some cases, the first labeled polynucleotide and the second labeled polynucleotide comprise a same label and are binned into a read-set. In further examples, the first complement sequence and the second complement sequence can be associated based on the first label and the second label. Using the sequence information of the first complement sequence and the second complement sequence, in some embodiments, the first sequence segment and the second sequence segment are associated. In some cases, the sequence information are used to assemble a plurality of contigs. In certain cases, the sequence information are used to assemble the first DNA molecule. In further cases, the sequence information are used to assemble a genome. In some cases, the genome is assembled by aligning reads to a reference genome, or by de novo assembly.

Compositions

In some aspects, the present disclosure provides a composition comprising: a. a first sequence segment and a second sequence segment; b. a plurality of association molecules cross-linked to the first and the second sequence segment; and c. a first binding probe attached to the first sequence segment, wherein the first binding probe is immobilized on a first resolved locus. The composition can further comprise a polymerase that is bound to the first binding probe. In some cases, the first sequence segment is hybridized to the first binding probe. In some cases, the first sequence segment is ligated to the first binding probe. In further cases, the second sequence segment is hybridized to a second binding probe. In some cases, the first binding probe and the second binding probe are identical. In some cases, the first sequence segment and the second sequence segment are part of a same polynucleotide. In other cases, the first sequence segment and the second sequence segment are part of different polynucleotides.

In another aspect, the present disclosure provides a composition comprising: a. a first sequence segment and a second sequence segment; b. a plurality of association molecules cross-linked to the first and the second sequence segment; and c. a first label attached to the first sequence segment and a second label attached to the second sequence segment. In some cases, the first label is ligated to the first sequence segment and the second label is ligated to the second sequence segment.

In some cases, the first label and the second label are identical. In other cases, the first label and the second label are different. In some cases, the first label and the second label are polynucleotides. In further examples, the first label and the second label each comprise one or more elements selected from the group consisting of a linker, a barcode and an adaptor. In certain examples, the first label comprises a first adaptor and the second label comprises a second adaptor.

In certain cases, the first adaptor is hybridized to a first binding probe on a resolved locus. In some cases, the resolved locus is located on a substrate. In further examples, the substrate comprises a solid support. The substrate can also be any known array in the art, including but not limited to the substrates and/or arrays disclosed in the present application. In some cases, the substrate is a microarray such as a DNA microarray. In certain examples, the substrate comprises more than about 10, about 20, about 50, about 100, about 200, about 500, about 1,000, about 2,000, about 5,000, about 10,000, about 20,000, about 50,000, about 100,000, about 200,000, about 500,000, about 1,000,000, about 2,000,000, about 5,000,000, about 10,000,000, about 20,000,000, about 50,000,000, or about 100,000,000 resolved loci. In some cases, the substrate comprises more than about 1,000 resolved loci. In further examples, the substrate comprises more than about 10,000 resolved loci.

In further cases, the resolved locus comprises a plurality of binding probes. In some cases, the resolved locus comprises more than about 10, about 20, about 50, about 100, about 200, about 500, about 1,000, about 2,000, about 5,000, about 10,000, about 20,000, about 50,000, about 100,000, about 200,000, about 500,000, about 1,000,000, about 2,000,000, about 5,000,000, about 10,000,000, about 20,000,000, about 50,000,000, or about 100,000,000 probes. In further examples, greater than about 50%, about 60%, about 70%, about 75%, about 80%, about 85%, about 90%, about 91%, about 92%, about 93%, about 94%, about 95%, about 96%, about 97%, about 98%, about 99%, about 99.9%, about 99.99%, about 99.999%, or about 99.9999% of the binding probes on the resolved locus are identical.

The binding probes can be any known probe in the art, including but not limited to the probes disclosed in the present application. In some cases, the binding probes comprise feature oligonucleotides. In some cases, the feature oligonucleotides comprises one or more elements selected from the group consisting of a linker, a primer, a barcode and a capture sequence. In certain examples, the feature oligonucleotides comprise a linker, a primer, a barcode and/or a capture sequence. In some cases, the capture sequence can hybridize to the first sequence segment. In some cases, the resolved locus comprise a unique binding probe that is not found in any other resolved locus on the substrate.

In some cases, the first resolved locus is located on a substrate. In some cases, the substrate comprises a solid support. The substrate can also be any known array in the art, including but not limited to the substrates and/or arrays disclosed in the present application. In some cases, the substrate is a microarray such as a DNA microarray. In further examples, the substrate comprises more than about 10, about 20, about 50, about 100, about 200, about 500, about 1,000, about 2,000, about 5,000, about 10,000, about 20,000, about 50,000, about 100,000, about 200,000, about 500,000, about 1,000,000, about 2,000,000, about 5,000,000, about 10,000,000, about 20,000,000, about 50,000,000, or about 100,000,000 resolved loci. In some cases, the substrate comprises more than about 1,000 resolved loci. In further examples, the substrate comprises more than about 10,000 resolved loci.

In certain cases, the first resolved locus comprises a plurality of binding probes. In some cases, the resolve loci comprise more than about 10, about 20, about 50, about 100, about 200, about 500, about 1,000, about 2,000, about 5,000, about 10,000, about 20,000, about 50,000, about 100,000, about 200,000, about 500,000, about 1,000,000, about 2,000,000, about 5,000,000, about 10,000,000, about 20,000,000, about 50,000,000, or about 100,000,000 probes. In some cases, greater than about 50%, about 60%, about 70%, about 75%, about 80%, about 85%, about 90%, about 91%, about 92%, about 93%, about 94%, about 95%, about 96%, about 97%, about 98%, about 99%, about 99.9%, about 99.99%, about 99.999%, or about 99.9999% of the binding probes on the first resolved loci comprise a common label. In further cases, greater than about 50%, about 60%, about 70%, about 75%, about 80%, about 85%, about 90%, about 91%, about 92%, about 93%, about 94%, about 95%, about 96%, about 97%, about 98%, about 99%, about 99.9%, about 99.99%, about 99.999%, or about 99.9999% of the binding probes on the first resolved loci are identical.

Resolved loci of a number of diameters and oligonucleotide densities are contemplated herein. In some embodiments, resolved loci have a diameter of about 60 micrometers and comprise 2.8 billion oligonucleotides. In some embodiments, resolved loci have a diameter of about 1 micrometer and comprise about 1,000 oligos. Resolved loci of a range of sizes are contemplated herein, such as resolved loci of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, or greater than about 60 micrometers. Exemplary resolved loci sizes are given in FIG. 12.

The binding probes can be any known probe in the art, including but not limited to the probes disclosed in the present application. In some cases, the binding probe comprises a feature oligonucleotide. In some cases, the feature oligonucleotide is immobilized on the first resolved locus at a 5'end. In some cases, the feature oligonucleotide comprises one or more elements selected from the group consisting of a linker, a primer, a barcode and a capture sequence. In some cases, the feature oligonucleotide comprises a linker, a primer, a barcode and/or a capture sequence. In some cases, a capture sequence hybridizes to the first sequence segment.

In certain cases, the first resolved locus comprises a plurality of feature oligonucleotides. In some cases, greater than about 50%, about 60%, about 70%, about 75%, about 80%, about 85%, about 90%, about 91%, about 92%, about 93%, about 94%, about 95%, about 96%, about 97%, about 98%, about 99%, about 99.9%, about 99.99%, about 99.999%, or about 99.9999% of the feature oligonucleotides in the first resolved locus comprise a same barcode. In some cases, greater than about 50%, about 60%, about 70%, about 75%, about 80%, about 85%, about 90%, about 91%, about 92%, about 93%, about 94%, about 95%, about 96%, about 97%, about 98%, about 99%, about 99.9%, about 99.99%, about 99.999%, or about 99.9999% of the feature oligonucleotides in the first resolved locus comprise a sequence adaptor.

In some cases, the association molecules comprise amino acids. In certain examples, the association molecules comprise peptides or proteins such as DNA binding proteins. Exemplary DNA binding proteins include native chromatin constituents such as histone, for example Histones 2A, 2B, 3A, 3B, 4A, or 4B. In some embodiments, the binding proteins comprise transcription factors. Non-protein organic molecules are also compatible with the disclosure herein, such as protamine, spermine, spermidine or other positively charged molecules. In some cases, the association molecules comprise nanoparticles, such as nanoparticles having a positively charged surface. A number of nanoparticle compositions are compatible with the disclosure herein. In some cases, the nanoparticle is a platinum-based nanoparticle. In other examples, the nanoparticle is a DNA intercalator, or any derivatives thereof. In further examples, the nanoparticle is a bisintercalator, or any derivatives thereof. In some embodiments, the nanoparticles comprise silicon, such as silicon coated with a positive coating so as to bind negatively charged nucleic acids. In some cases, the nanoparticles are magnetic, which may facilitate the isolation of the cross-linked sequence segments. In some embodiments the nanoparticles comprise silica, such as silica coated with a positive coating so as to bind negatively charged nucleic acids. In further examples, the nanoparticles are magnetic or paramagnetic, which may facilitate the isolation of the cross-linked sequence segments.

In further cases, the association molecules are from a different source than the first DNA molecule. In some cases, the first DNA molecule is from a first human subject, whereas the association molecules are from a second human subject. In other examples, the first DNA molecule is from a mammal (e.g. human), whereas the association molecules are from another eukaryotic organism. In further examples, the first DNA molecule is from a plant cell or a prokaryote, whereas the association molecules are from a eukaryotic organism.

In some cases, the first and the second sequence segments are produced by severing a first DNA molecule. In some cases, the first sequence segment comprises a first segment end and the second sequence segment comprises a second segment end. In some cases, the first segment end and the second segment end comprise blunt ends. In other cases, the first segment end and the second segment end comprise overhang sequences. In further cases, the overhang sequences are filled in by modified nucleotides, such as sulfated or biotinylated nucleotides.

In yet another aspect, the present disclosure provides a composition comprising: a. a plurality of barcoded polynucleotides each comprising a label; and b. a plurality of aggregate molecules attached to the plurality of barcoded polynucleotides. In some cases, each of the labels in the barcoded polynucleotides are identical. In some cases, the aggregate molecules comprise amino acids. In some cases, the aggregate molecules comprise peptides or proteins (e.g. histones). In other cases, the aggregate molecules comprise nanoparticles. In some cases, the nanoparticle is a platinum-based nanoparticle. In other examples, the nanoparticle is a DNA intercalator, or any derivatives thereof. In further examples, the nanoparticle is a bisintercalator, or any derivatives thereof.

In further cases, the barcoded polynucleotides are ligated to a DNA complex. In certain cases, the DNA complex comprises a first sequence segment and a second sequence segment cross-linked to a plurality of association molecules. In some cases, the first sequence segment and the second sequence segment are each ligated to the barcoded polynucleotides.

In some aspects, the present disclosure provides a composition comprising at least one aqueous droplet. In some cases, the aqueous droplet comprises a nucleic acid comprising a first sequence segment and a second sequence segment. In some embodiments the nucleic acid is not bound by any additional molecule, while in other embodiments the nucleic acid is bound by a nucleic acid binding molecule configured so as to bind the first sequence segment and the second sequence segment. In many embodiments, the additional molecule is covalently bound to the nucleic acid molecule, for example by formaldehyde or psoralin. The aqueous droplet can further comprise at least one amplification template, which can be linear or circular. In some cases, the first sequence segment is linked to a first label and the second sequence segment is linked to a second label. In certain cases, the first label and the second label each comprise a barcode, which may be identical. In further cases, the first sequence segment and the second sequence segment can be linked to an adaptor oligonucleotide.

In some embodiments, the aqueous droplet comprises a polymerase. In certain cases, the aqueous droplet further comprises a primer. In particular cases, the aqueous droplet comprises a restriction enzyme. In various cases, the aqueous droplet comprises a ligase. Examples of polymerases, primers, restriction enzymes and ligases are known in the art, including but not limited to those provided in the present disclosure.

In some cases, the aqueous droplet is surrounded by an oil or an organic phase. In further cases, the aqueous droplet is within a microfluidic device. The aqueous droplet in many embodiments is surrounded by an immiscible layer to form a micelle or an immiscible bilayer to form a liposome.

In some cases, the association molecule comprises amino acids. In some cases, the association molecule comprises peptides or proteins (e.g. histones, for example comprising at least one of H2A, H2B, H3A, H3B, H4A and H4B, a transcription factor, or packing proteins such as H1 and protamine). In some cases, the association molecule comprises a nonpolypeptide such as protamine, spermine, spermidine or other positively charged molecule. In some cases, the association molecules comprise nanoparticles. In some cases, the nanoparticle is a platinum-based nanoparticle. In other examples, the nanoparticle is a DNA intercalator, or any derivatives thereof. In further examples, the nanoparticle is a bisintercalator, or any derivatives thereof. In certain cases, the nanoparticles are magnetic, which may facilitate the isolation of the cross-linked sequence segments. In some cases The nanoparticles comprise silicon. In further cases, the nanoparticles are coated with a positively charged substance, a substance to facilitate cross-linking to a nucleic acid, or a substance that is both positively charged and capable of facilitating cross-linking to a nucleic acid.

In further embodiments, the association molecules are from a different source than the first DNA molecule. In some cases, the first DNA molecule is from a first human subject, whereas the association molecules are from a second human subject. In other examples, the first DNA molecule is from a mammal (e.g. human), whereas the association molecules are from another eukaryotic organism. In further examples, the first DNA molecule is from a plant cell or a prokaryote, whereas the association molecules are from a eukaryotic organism.

In certain cases, the aqueous droplet comprises a plurality of molecular tagged or barcoded oligonucleotides. In many cases, these molecularly tagged or barcoded oligonucleotide molecules have identical sequences. In further embodiments, the molecularly tagged or barcoded oligonucleotide molecules have identical molecular tag or barcode sequences. In other cases, the aqueous droplet comprises molecular tagged or barcoded oligonucleotides that sort into at least two populations, each population characterized by a distinct molecular tag or barcode sequence.

In various cases, the aqueous droplet comprises at least one template for the synthesis of a population of molecularly tagged or barcoded oligonucleotide molecules in some cases. In many examples, the at least one template is linear. In other examples, the at least one template is circular. The proportion of template to DNA complex is exactly one to one in each aqueous droplet of a population of aqueous droplets in some cases, particularly in cases where each droplet comprises exactly one DNA complex and exactly one circular or linear template molecule. However, these amounts and proportions are not absolutely required for operability of the methods disclosed herein. In some cases, at least one aqueous droplet comprises a plurality of non-identical circular or linear template molecules. In some cases, at least one aqueous droplet comprises a plurality of DNA complexes. In some cases, at least one droplet comprises a plurality of DNA complexes and at least one aqueous droplet comprises a plurality of non-identical circular or linear template molecules.

Samples

In some cases, the polynucleotides used in the methods disclosed herein are derived from multiple samples from the same individual, samples from different individuals, or combinations thereof. In some cases, a sample comprises a plurality of polynucleotides from a single individual. In some cases, a sample comprises a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. In further cases, sample polynucleotides are isolated from a subject, such as a cell sample, tissue sample, or organ sample derived therefrom, including, for example, cultured cell lines, biopsy, blood sample, or fluid sample containing a cell. In certain cases, the subject is an animal, including but not limited to, an animal such as a cow, a pig, a mouse, a rat, a chicken, a cat, a dog, etc., or a mammal, such as a human. In other cases, samples are artificially derived, such as by chemical synthesis. In some embodiments, the samples comprise DNA. In some embodiments, the samples comprise genomic DNA. In some embodiments, the samples comprise mitochondrial DNA, chloroplast DNA, plasmid DNA, bacterial artificial chromosomes, yeast artificial chromosomes, oligonucleotide tags, or combinations thereof. In some embodiments, the samples comprise DNA generated by primer extension reactions using any suitable combination of primers and a DNA polymerase, including but not limited to polymerase chain reaction (PCR), reverse transcription, and combinations thereof. In cases wherein the template for the primer extension reaction is RNA, the product of reverse transcription is referred to as complementary DNA (cDNA). In many cases, primers useful in primer extension reactions comprise sequences specific to one or more targets, random sequences, partially random sequences, and combinations thereof. Reaction conditions suitable for primer extension reactions are known in the art. In general, sample polynucleotides comprise any polynucleotide present in a sample, which may or may not include target polynucleotides.

In some embodiments, nucleic acid template molecules (e.g., DNA or RNA) are isolated from a biological sample containing a variety of other components, such as proteins, lipids and non-template nucleic acids. In many embodiments, nucleic acid template molecules are obtained from any cellular material, obtained from an animal, plant, bacterium, fungus, or any other cellular organism. Biological samples for use in the present disclosure include viral particles or preparations. In further embodiments, nucleic acid template molecules are obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the disclosure. In certain cases, nucleic acid template molecules are isolated from cultured cells, such as a primary cell culture or a cell line. In various cases, the cells or tissues from which template nucleic acids are obtained are infected with a virus or other intracellular pathogen. In many cases, a sample is total RNA extracted from a biological specimen, a cDNA library, viral, or genomic DNA. In other cases, a sample is isolated DNA from a non-cellular origin, e.g. amplified/isolated DNA from the freezer.

Methods for the extraction and purification of nucleic acids are well known in the art. In some cases, nucleic acids are purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. In other examples, nucleic acid isolation and/or purification comprises the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods are preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it is desirable to add a protein denaturation/digestion step to the protocol. In certain cases, purification methods are directed to isolate DNA, RNA, or both. When both DNA and RNA are isolated together during or subsequent to an extraction procedure, further steps may be employed to purify one or both separately from the other. In further cases, sub-fractions of extracted nucleic acids are generated, for example, purification by size, sequence, or other physical or chemical characteristic. In addition to an initial nucleic acid isolation step, in many cases, purification of nucleic acids are performed after any step in the methods of the disclosure, such as to remove excess or unwanted reagents, reactants, or products.

Nucleic acid template molecules can be obtained as described in U.S. Patent Application Publication Number US2002/0190663 A1, published Oct. 9, 2003. In various cases, nucleic acid are extracted from a biological sample by a variety of techniques such as those described by Maniatis, et al., Molecular Cloning: A Laboratory Manual, Cold Spring Harbor, N.Y., pp. 280-281 (1982). In some cases, the nucleic acids are first extracted from the biological samples and then cross-linked in vitro. In some cases, native association proteins (e.g. histones) are further removed from the nucleic acids.

In some cases, the methods disclosed herein are applied to any high molecular weight double stranded DNA including, for example, DNA isolated from tissues, cell culture, bodily fluids, animal tissue, plant, bacteria, fungi, viruses, etc.

In some cases, each of the plurality of independent samples independently comprise at least about 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 μg, 1.5 μg, 2 μg, 5 μg, 10 μg, 20 μg, 50 μg, 100 μg, 200 μg, 500 μg, or 1000 μg, or more of nucleic acid material. In some embodiments, each of the plurality of independent samples independently comprise less than about 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 μg, 1.5 μg, 2 μg, 5 μg, 10 μg, 20 μg, 50 μg, 100 μg, 200 μg, 500 μg, or 1000 μg, or more of nucleic acid.

Samples are prepared to regulate the density of the DNA complexes in solution. In some exemplary embodiments, samples are prepared to result in an equimolar concentration of DNA complexes and oligo loci on a support, such that when the DNA complexes are applied to the support a single DNA complex is bound to a single oligo locus. This proportion of DNA complexes to oligo loci has certain benefits for downstream analysis, because if each locus has a unique molecular tag or barcode, then each DNA complex is uniquely tagged, facilitating the mapping of sequence read sets onto contigs.

Figure 12:
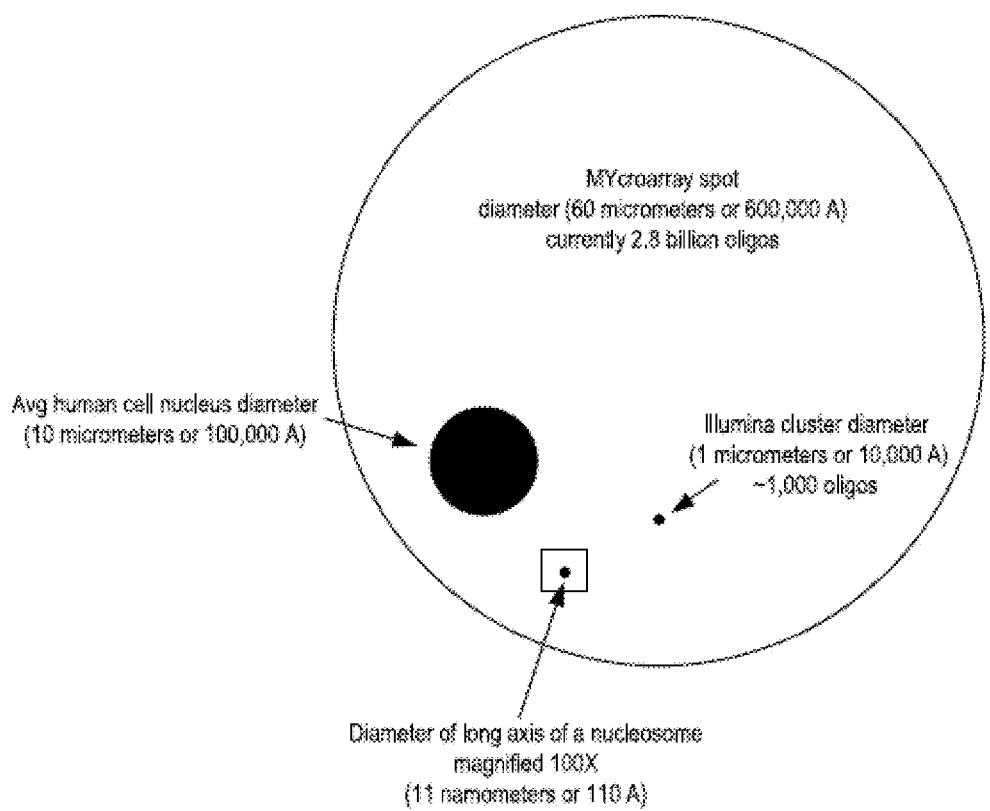
FIG. 12 provides examples of loci sizes in relation to nuclei and nucleosomes, which approximate the size of constituents of the chromatin complexes of DNA complexes as contemplated herein.

However, in some embodiments the ratio of DNA complexes to oligo loci is not one-to-one, and downstream analysis is still accomplished. If oligo loci are generated to be substantially larger than DNA complex diameter, as is the case in some oligo loci as indicated in FIG. 12, multiple DNA complexes may bind to a single locus. Provided that the DNA molecules of these DNA complexes are not homologous or overlapping, then the sequence read sets that are generated thereby will be distinguishable by the fact that read sets, even if tagged by a common molecular tag or barcode, will map to distinct contigs or contig populations. In certain cases, rare events of overlapping molecules tagged by the same molecular tag or barcode are excluded from a dataset if it is found that the read set includes dimorphisms at heterozygous loci (indicating the presence of more than one phase in a read set), or, optionally, if the read set maps to contig sequence that is longer than a pre-selected molecule size for the nucleic acids from which the DNA complexes are generated. Thus, an excess of DNA clusters per locus is only a computational challenge if there is an overabundance of DNA complexes such that individual loci have a substantial number of overlapping DNA molecules tagged thereby. In certain cases, later runs to sequence DNA complexes are performed on compositions diluted such that DNA complexes do not so abundantly anneal to loci. In other cases, smaller loci are used to decrease the ratio of DNA complexes per locus. In some embodiments, DNA complexes are prepared in a solution of a density such that there are not more than about 25 DNA complexes per locus.

In some exemplary embodiments, samples are prepared to result in an equimolar concentration of DNA complexes and barcoded aggregates, such that when the DNA complexes are in solution a single barcoded aggregate is bound to a single DNA complex. This proportion of DNA complex to barcoded aggregate has certain benefits for downstream analysis, because if each barcoded aggregate has a unique molecular tag or barcode, then each DNA complex is uniquely tagged, facilitating the mapping of sequence read sets onto contigs.

However, in some embodiments the ratio of DNA complexes to barcoded aggregates is not one-to-one, and downstream analysis is still accomplished. If the barcoded aggregates are in a substantially smaller quantity than the DNA complexes, multiple DNA complexes may bind to a single locus. Provided that the DNA molecules of these DNA complexes are not homologous or overlapping, then the sequence read sets that are generated thereby will be distinguishable by the fact that read sets, even if tagged by a common molecular tag or barcode, will map to distinct contigs or contig populations. In certain cases, rare events of overlapping molecules tagged by the same molecular tag or barcode are excluded from a dataset if it is found that the read set includes dimorphisms at heterozygous loci (indicating the presence of more than one phase in a read set), or, optionally, if the read set maps to contig sequence that is longer than a pre-selected molecule size for the nucleic acids from which the DNA complexes are generated. Thus, an excess of DNA complex per barcoded aggregate is only a computational challenge if there is an overabundance of DNA complexes such that individual aggregates have a substantial number of overlapping DNA molecules tagged thereby. In many cases, later runs to sequence DNA complexes are performed on compositions diluted such that DNA complexes do not so abundantly anneal to loci. In some cases, smaller loci are used to decrease the ratio of DNA complexes per locus. In some cases, DNA complexes are prepared in a solution of a density such that there are not more than about 25 DNA complexes per locus.

Adapters

As used herein, the term "adapter oligonucleotide" refers to any oligonucleotide having a sequence, at least a portion of which is known, that can be joined to a target polynucleotide. In some cases, adaptor oligonucleotides comprise DNA, RNA, nucleotide analogues, non-canonical nucleotides, labeled nucleotides, modified nucleotides, or combinations thereof. In certain cases, adaptor oligonucleotides are single-stranded, double-stranded, or partial duplex. In many cases, a partial-duplex adapter comprises one or more single-stranded regions and one or more double-stranded regions. In some cases, double-stranded adapters comprise two separate oligonucleotides hybridized to one another (also referred to as an "oligonucleotide duplex"). In further examples, the hybridization leaves one or more blunt ends, one or more 3' overhangs, one or more 5' overhangs, one or more bulges resulting from mismatched and/or unpaired nucleotides, or any combination of these. In some embodiments, a single-stranded adapter comprises two or more sequences that are able to hybridize with one another. When two such hybridizable sequences are contained in a single-stranded adapter, hybridization yields a hairpin structure (hairpin adapter). When two hybridized regions of an adapter are separated from one another by a non-hybridized region, a "bubble" structure results. In various cases, adaptors adopt aa bubble structure comprising a single adapter oligonucleotide that comprises internal hybridizations, or comprise two or more adapter oligonucleotides hybridized to one another. In certain cases, internal sequence hybridization, such as between two hybridizable sequences in an adapter, produce a double-stranded structure in a single-stranded adapter oligonucleotide.

In some cases, adaptors of different kinds can be used in combination, such as a hairpin adapter and a double-stranded adapter, or adapters of different sequences. Hybridizable sequences in a hairpin adapter may or may not include one or both ends of the oligonucleotide. When neither of the ends are included in the hybridizable sequences, both ends are "free" or "overhanging." When only one end is hybridizable to another sequence in the adapter, the other end forms an overhang, such as a 3' overhang or a 5' overhang. When both the 5'-terminal nucleotide and the 3'-terminal nucleotide are included in the hybridizable sequences, such that the 5'-terminal nucleotide and the 3'-terminal nucleotide are complementary and hybridize with one another, the end is referred to as "blunt." In some embodiments, end repair is performed to generate blunt end 5' phosphorylated nucleic acid ends using commercial kits, such as those available from Epicentre Biotechnologies (Madison, WI).

In certain cases, different adapters are joined to target polynucleotides in sequential reactions or simultaneously. In some cases, the first and second adapters are added to the same reaction. In certain examples, adaptors can be manipulated prior to combining with target polynucleotides. In further examples, terminal phosphates are added or removed.

In many cases, adaptors contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. In some cases, two or more sequence elements are non-adjacent to one another (e.g. separated by one or more nucleotides), adjacent to one another, partially overlapping, or completely overlapping. In certain examples, an amplification primer annealing sequence serves as a sequencing primer annealing sequence. In some cases, sequence elements are located at or near the 3' end, at or near the 5' end, or in the interior of the adapter oligonucleotide. In certain cases, when an adapter oligonucleotide is capable of forming secondary structure, such as a hairpin, sequence elements are located partially or completely outside the secondary structure, partially or completely inside the secondary structure, or in between sequences participating in the secondary structure. In some cases, when an adapter oligonucleotide comprises a hairpin structure, sequence elements are located partially or completely inside or outside the hybridizable sequences (the "stem"), including in the sequence between the hybridizable sequences (the "loop").

In some cases, the first adapter oligonucleotides in a plurality of first adapter oligonucleotides having different barcode sequences comprise a sequence element common among all first adapter oligonucleotides. In some embodiments, all second adapter oligonucleotides comprise a sequence element common among all second adapter oligonucleotides that is different from the common sequence element shared by the first adapter oligonucleotides. A difference in sequence elements can be any such that at least a portion of different adapters do not completely align, for example, due to changes in sequence length, deletion or insertion of one or more nucleotides, or a change in the nucleotide composition at one or more nucleotide positions (such as a base change or base modification).

In some embodiments, an adapter oligonucleotide comprises a 5' overhang, a 3' overhang, or both that is complementary to one or more target polynucleotides. In some cases, complementary overhangs are one or more nucleotides in length, including but not limited to 1, 2, 3, 4, 5, 6, 7, 8, 9, 10, 11, 12, 13, 14, 15, or more nucleotides in length. In further examples, the complementary overhangs are about 1, 2, 3, 4, 5 or 6 nucleotides in length. In some cases, complementary overhangs comprise a fixed sequence. In other cases, complementary overhangs comprise a random sequence of one or more nucleotides, such that one or more nucleotides are selected at random from a set of two or more different nucleotides at one or more positions, with each of the different nucleotides selected at one or more positions represented in a pool of adapters with complementary overhangs comprising the random sequence. In some embodiments, an adapter overhang is complementary to a target polynucleotide overhang produced by restriction endonuclease digestion. In some embodiments, an adapter overhang consists of an adenine or a thymine.

Adapter oligonucleotides can have any suitable length, at least sufficient to accommodate the one or more sequence elements of which they are comprised. In some embodiments, adapters are about, less than about, or more than about 10, 15, 20, 25, 30, 35, 40, 45, 50, 55, 60, 65, 70, 75, 80, 90, 100, 200, or more nucleotides in length. In some cases, the adaptors are be about 10 to about 50 nucleotides in length. In further examples, the adaptors are be about 20 to about 40 nucleotides in length.

Barcodes

As used herein, the term "barcode" or "molecular tag" refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes are at least 3, 4, 5, 6, 7, 8, 9, 10, 11, 12, 13, 14, 15, or more nucleotides in length. In some cases, barcodes are at least 10, 11, 12, 13, 14, or 15 nucleotides in length. In some embodiments, barcodes are shorter than 10, 9, 8, 7, 6, 5, or 4 nucleotides in length. In certain examples, barcodes are shorter than 10 nucleotides in length. In some embodiments, barcodes associated with some polynucleotides are of different length than barcodes associated with other polynucleotides.

In general, barcodes are of sufficient length and comprise sequences that are sufficiently different to allow the identification of samples based on barcodes with which they are associated. In some embodiments, a barcode, and the sample source with which it is associated, are identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some cases, 1, 2 or 3 nucleotides are mutated, inserted and/or deleted. In some embodiments, each barcode in a plurality of barcodes differ from every other barcode in the plurality at least two nucleotide positions, such as at least 2, 3, 4, 5, 6, 7, 8, 9, 10, or more positions. In some cases, each barcode differs from every other barcode by in at least 2, 3, 4 or 5 positions.

In some embodiments, both a first site and a second site comprise at least one of a plurality of barcode sequences. In some embodiments, barcodes for second sites are selected independently from barcodes for first adapter oligonucleotides. In some embodiments, first sites and second sites having barcodes are paired, such that sequences of the pair comprise the same or different one or more barcodes. In some embodiments, the methods of the disclosure further comprise identifying the sample from which a target polynucleotide is derived based on a barcode sequence to which the target polynucleotide is joined. In general, a barcode may comprise a nucleic acid sequence that when joined to a target polynucleotide serves as an identifier of the sample from which the target polynucleotide was derived.

Chromatin Reconstitution

In eukaryotes, genomic DNA is packed into chromatin to consist as chromosomes within the nucleus. The basic structural unit of chromatin is the nucleosome, which consists of 146 base pairs (bp) of DNA wrapped around a histone octamer. The histone octamer consists of two copies each of the core histone H2A-H2B dimers and H3-H4 dimers. Nucleosomes are regularly spaced along the DNA in what is commonly referred to as "beads on a string".

The assembly of core histones and DNA into nucleosomes is mediated by chaperone proteins and associated assembly factors. Nearly all of these factors are core histone-binding proteins. Some of the histone chaperones, such as nucleosome assembly protein-1 (NAP-1), exhibit a preference for binding to histones H3 and H4. It has also been observed that newly synthesized histones are acetylated and then subsequently deacetylated after assembly into chromatin. The factors that mediate histone acetylation or deacetylation therefore play an important role in the chromatin assembly process.

In general, two in vitro methods have been developed for reconstituting or assembling chromatin. One method is ATP-independent, while the second is ATP-dependent. The ATP-independent method for reconstituting chromatin involves the DNA and core histones plus either a protein like NAP-1 or salt to act as a histone chaperone. This method results in a random arrangement of histones on the DNA that does not accurately mimic the native core nucleosome particle in the cell. These particles are often referred to as mononucleosomes because they are not regularly ordered, extended nucleosome arrays and the DNA sequence used is usually not longer than 250 bp (Kundu, T. K. et al., Mol. Cell 6: 551-561, 2000). To generate an extended array of ordered nucleosomes on a greater length of DNA sequence, the chromatin must be assembled through an ATP-dependent process.

The ATP-dependent assembly of periodic nucleosome arrays, which are similar to those seen in native chromatin, requires the DNA sequence, core histone particles, a chaperone protein and ATP-utilizing chromatin assembly factors. ACF (ATP-utilizing chromatin assembly and remodeling factor) or RSF (remodeling and spacing factor) are two widely researched assembly factors that are used to generate extended ordered arrays of nucleosomes into chromatin in vitro (Fyodorov, D. V., and Kadonaga, J. T. Method Enzymol. 371: 499-515, 2003; Kundu, T. K. et al. Mol. Cell 6: 551-561, 2000).

In some embodiments, non-natural chromatin analogs are contemplated. Nanoparticles, such as nanoparticles having a positively coated outer surface to facilitate nucleic acid binding, or a surface activatable for cross-linking to nucleic acids, or both a positively coated outer surface to facilitate nucleic acid binding and a surface activatable for cross-linking to nucleic acids, are contemplated herein. In some cases, the nanoparticle is a platinum-based nanoparticle. In other examples, the nanoparticle is a DNA intercalator, or any derivatives thereof. In further examples, the nanoparticle is a bisintercalator, or any derivatives thereof. In some embodiments, nanoparticles comprise silicon.

Fragmentation

As used herein, the terms "fragment", "segment", or "sequence segment" can refer to a piece of polynucleotide derived or prepared from an original, larger nucleic acid molecule. Unless otherwise specified, the terms are used interchangeably herein.

The methods disclosed herein can be applied to any type of fragmented double stranded polynucleotide including but not limited to, for example, free DNA isolated from plasma, serum, and/or urine; apoptotic DNA from cells and/or tissues; DNA fragmented enzymatically in vitro (for example, by DNase I and/or restriction endonuclease); and/or DNA fragmented by mechanical forces (hydro-shear, sonication, nebulization, etc.).

Polynucleotides obtained from biological samples can be fragmented to produce suitable fragments or segments for analysis. Polynucleotides may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In some embodiments, nucleic acid from a biological sample is fragmented by sonication. In other embodiments, nucleic acid is fragmented by a hydroshear instrument. In certain cases, individual nucleic acid molecules are from about 2 kb to about 40 kb. In some cases, the nucleic acids are from about 6 kb to about 10 kb. In various cases, nucleic acid molecules are single-stranded, double-stranded, or double-stranded with single-stranded regions (for example, stem- and loop-structures).

In some cases, cross-linked polynucleotides are subjected to a size selection step. In some cases, size selection of the nucleic acids is performed to cross-linked polynucleotides below or above a certain size. In further examples, size selection is further affected by the frequency of cross-links and/or by the fragmentation method, for example by choosing a frequent or rare cutter restriction enzyme. In some embodiments, a composition is prepared comprising cross-linking a DNA molecule in the range of about 1 kb to 5 Mb, about 5 kb to 5 Mb, about 5 kB to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 150 kb to 1 Mb).

In some cases, sample polynucleotides are fragmented into a population of fragmented polynucleotides of one or more specific size range(s). In some cases, fragments are generated from at least about 1, about 2, about 5, about 10, about 20, about 50, about 100, about 200, about 500, about 1000, about 2000, about 5000, about 10,000, about 20,000, about 50,000, about 100,000, about 200,000, about 500,000, about 1,000,000, about 2,000,000, about 5,000,000, about 10,000,000, or more genome-equivalents of starting DNA. In certain cases, fragmentation is accomplished by methods known in the art, including chemical, enzymatic, and mechanical fragmentation.

In some cases, the fragments have an average length from about 10 to about 10,000, about 20,000, about 30,000, about 40,000, about 50,000, about 60,000, about 70,000, about 80,000, about 90,000, about 100,000, about 150,000, about 200,000, about 300,000, about 400,000, about 500,000, about 600,000, about 700,000, about 800,000, about 900,000, about 1,000,000, about 2,000,000, about 5,000,000, about 10,000,000, or more nucleotides. In some cases, the fragments have an average length from about 1 kb to about 10 Mb. In other examples, the fragments have an average length from about 1 kb to 5 Mb, about 5 kb to 5 Mb, about 5 kB to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 60 to 120 kb).

In some cases, the fragments have an average length less than about 10 Mb, less than about 5 Mb, less than about 1 Mb, less than about 500 kb, less than about 200 kb, less than about 100 kb, or less than about 50 kb. In other cases, the fragments have an average length more than about 5 kb, more than about 10 kb, more than about 50 kb, more than about 100 kb, more than about 200 kb, more than about 500 kb, more than about 1 Mb, more than about 5 Mb, or more than about 10 Mb.

In many cases, the fragmentation is accomplished mechanically, comprising subjection nucleic acid molecules to acoustic sonication. In some cases, the fragmentation comprises treating the polynucleotide with one or more enzymes under conditions suitable for the one or more enzymes to generate double-stranded nucleic acid breaks. Examples of enzymes useful in the generation of nucleic acid fragments include sequence specific and non-sequence specific nucleases. Non-limiting examples of nucleases include DNase I, Fragmentase, restriction endonucleases, variants thereof, and combinations thereof. In some cases, digestion with DNase I induces random double-stranded breaks in DNA in the absence of $Mg^{++}$ and in the presence of $Mn^{++}$.

In some cases, the fragmentation comprises treating the sample DNA molecules with one or more restriction endonucleases. In certain cases, fragmentation produces fragments having 5' overhangs, 3' overhangs, blunt ends, or a combination thereof. In some embodiments, the polynucleotide is cleaved to generate one or more overhangs with predictable sequence(s). In some embodiments, the method includes the step of size selecting the fragments via standard methods such as column purification or isolation from an agarose gel.

In some cases, the 5' and/or 3' end nucleotide sequences of fragmented polynucleotides are not modified prior to ligation. In some cases, fragmentation by a restriction endonuclease is used to leave a predictable overhang, followed by ligation with a nucleic acid end comprising an overhang complementary to the predictable overhang on a polynucleotide fragment. In other examples, cleavage by an enzyme that leaves a predictable blunt end is followed by ligation of blunt-ended polynucleotide fragments to nucleic acids, such as adapters, oligonucleotides, or polynucleotides, comprising a blunt end. In some embodiments, the fragmented polynucleotide is blunt-end polished (or "end repaired") to produce DNA fragments having blunt ends, prior to being joined to adapters. In some cases, the blunt-end polishing step is accomplished by incubation with a suitable enzyme, such as a DNA polymerase that has both 3' to 5' exonuclease activity and 5' to 3' polymerase activity, for example T4 polymerase. In some embodiments, end repair is followed by an addition of 1, 2, 3, 4, 5, 6, 7, 8, 9, 10, 11, 12, 13, 14, 15, 16, 17, 18, 19, 20 or more nucleotides, such as one or more adenine, one or more thymine, one or more guanine, or one or more cytosine, to produce an overhang. In certain examples, the end repair is followed by an addition of 1, 2, 3, 4, 5, or 6 nucleotides.

In certain cases, polynucleotide fragments having an overhang are joined to one or more nucleic acids, such as oligonucleotides, adapter oligonucleotides, or polynucleotides, having a complementary overhang, such as in a ligation reaction. In some cases, a single adenine is added to the 3' ends of end repaired DNA fragments using a template independent polymerase, followed by ligation to one or more adapters each having a thymine at a 3' end. In some cases, nucleic acids, such as oligonucleotides or polynucleotides is joined to blunt end double-stranded DNA molecules which have been modified by extension of the 3' end with one or more nucleotides followed by 5' phosphorylation. In some cases, extension of the 3' end is performed with a polymerase such as, Klenow polymerase or any of the suitable polymerases provided herein, or by use of a terminal deoxynucleotide transferase, in the presence of one or more dNTPs in a suitable buffer that can contain magnesium.

In some cases, polynucleotide fragments having blunt ends are joined to one or more adapters comprising a blunt end. In certain examples, phosphorylation of 5' ends of DNA fragment molecules is performed for example with T4 polynucleotide kinase in a suitable buffer containing ATP and magnesium. In further cases, the fragmented DNA molecules are treated to dephosphorylate 5' ends or 3' ends, for example, by using enzymes known in the art, such as phosphatases.

Ligation—Linking

As used herein, with respect to two polynucleotides such as an adapter oligonucleotide and a target polynucleotide, the terms "connecting", "joining" or "ligating" can refer to the covalent attachment of two separate nucleic acid segments to produce a single larger polynucleotide with a contiguous backbone. Methods for joining two nucleic acid segments are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, each of which is herein incorporated by reference in its entirety. In some embodiments, an adapter oligonucleotide is joined to a target polynucleotide by a ligase, for example a DNA ligase or RNA ligase. Multiple ligases, each having characterized reaction conditions, are known in the art, and include, without limitation $NAD^+$-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9°

N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof.

In some cases, ligation is between nucleic acid segments having hybridizable sequences, such as complementary overhangs. In certain cases, ligation is between two blunt ends. In many cases, a 5' phosphate is utilized in a ligation reaction. In various cases, the 5' phosphate is provided by the target polynucleotide, the adapter oligonucleotide, or both. In further cases, 5' phosphates are added to or removed from sequence segments to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some cases, both of the two ends joined in a ligation reaction (e.g. an adapter end and a target polynucleotide end) provide a 5' phosphate, such that two covalent linkages are made in joining the two ends. In other cases, only one of the two ends joined in a ligation reaction (e.g. only one of an adapter end and a target polynucleotide end) provides a 5' phosphate, such that only one covalent linkage is made in joining the two ends.

In some cases, only one strand at one or both ends of a target polynucleotide is joined to an adapter oligonucleotide. In other cases, both strands at one or both ends of a target polynucleotide are joined to an adapter oligonucleotide. In some cases, 3' phosphates are removed prior to ligation. In some cases, an adapter oligonucleotide is added to both ends of a target polynucleotide, wherein one or both strands at each end are joined to one or more adapter oligonucleotides. In certain cases, when both strands at both ends are joined to an adapter oligonucleotide, joining is followed by a cleavage reaction that leaves a 5' overhang that can serve as a template for the extension of the corresponding 3' end, which 3' end may or may not include one or more nucleotides derived from the adapter oligonucleotide. In some cases, a target polynucleotide is joined to a first adapter oligonucleotide on one end and a second adapter oligonucleotide on the other end. In other cases, two ends of a target polynucleotide are joined to the opposite ends of a single adapter oligonucleotide. In some cases, the target polynucleotide and the adapter oligonucleotide to which it is joined comprise blunt ends. In some cases, separate ligation reactions are carried out for each sample, using a different first adapter oligonucleotide comprising at least one barcode sequence for each sample, such that no barcode sequence is joined to the target polynucleotides of more than one sample. A sequence segment or a polynucleotide that has an adapter oligonucleotide joined to it is considered "tagged" by the joined adapter.

In some cases, the ligation reaction is performed at a sequence segment or polynucleotide concentration of about less than about 0.1 ng/μL, about 0.2 ng/μL, about 0.3 ng/μL, about 0.4 ng/μL, about 0.5 ng/μL, about 0.6 ng/μL, about 0.7 ng/μL, about 0.8 ng/μL, about 0.9 ng/μL, about 1.0 ng/μL, about 1.2 ng/μL, about 1.4 ng/μL, about 1.6 ng/μL, about 1.8 ng/μL, about 2.0 ng/μL, about 2.5 ng/μL, about 3.0 ng/μL, about 3.5 ng/μL, about 4.0 ng/μL, about 4.5 ng/μL, about 5.0 ng/μL, about 6.0 ng/μL, about 7.0 ng/μL, about 8.0 ng/μL, about 9.0 ng/μL, about 10 ng/μL, about 15 ng/μL, about 20 ng/μL, about 30 ng/μL, about 40 ng/μL, about 50 ng/μL, about 60 ng/μL, about 70 ng/μL, about 80 ng/μL, about 90 ng/μL, about 100 ng/μL, about 150 ng/μL, about 200 ng/μL, about 300 ng/μL, about 400 ng/μL, about 500 ng/μL, about 600 ng/μL, about 800 ng/μL, or about 1000 ng/μL. In some cases, the ligation reaction is performed at a sequence segment or polynucleotide concentration of about greater than about 0.1 ng/μL, about 0.2 ng/μL, about 0.3 ng/μL, about 0.4 ng/μL, about 0.5 ng/μL, about 0.6 ng/μL, about 0.7 ng/μL, about 0.8 ng/μL, about 0.9 ng/μL, about 1.0 ng/μL, about 1.2 ng/μL, about 1.4 ng/μL, about 1.6 ng/μL, about 1.8 ng/μL, about 2.0 ng/μL, about 2.5 ng/μL, about 3.0 ng/μL, about 3.5 ng/μL, about 4.0 ng/μL, about 4.5 ng/μL, about 5.0 ng/μL, about 6.0 ng/μL, about 7.0 ng/μL, about 8.0 ng/μL, about 9.0 ng/μL, about 10 ng/μL, about 15 ng/μL, about 20 ng/μL, about 30 ng/μL, about 40 ng/μL, about 50 ng/μL, about 60 ng/μL, about 70 ng/μL, about 80 ng/μL, about 90 ng/μL, about 100 ng/μL, about 150 ng/μL, about 200 ng/μL, about 300 ng/μL, about 400 ng/μL, about 500 ng/μL, about 600 ng/μL, about 800 ng/μL, or about 1000 ng/μL. In some cases, the ligation is performed at a sequence segment or polynucleotide concentration of about 100 ng/μL, about 150 ng/μL, about 200 ng/μL, about 300 ng/μL, about 400 ng/μL, or about 500 ng/μL. In further examples, the ligation reaction is performed at a sequence segment or polynucleotide concentration of about 0.1 to 1000 ng/μL, about 1 to 1000 ng/μL, about 1 to 800 ng/μL, about 10 to 800 ng/μL, about 10 to 600 ng/μL, about 100 to 600 ng/μL, or about 100 to 500 ng/μL.

In some cases, the ligation reaction is performed for more than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. In certain cases, the ligation reaction is performed for less than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. In some cases, the ligation reaction is performed for about 30 minutes to about 90 minutes. In certain examples, joining of an adapter to a polynucleotide produces a joined polynucleotide having a 3' overhang comprising a nucleotide sequence derived from the adapter.

In some cases, after joining at least one adapter oligonucleotide to a polynucleotide, the 3' end of one or more polynucleotides is extended using the one or more joined adapter oligonucleotides as template. For example, an adapter comprising two hybridized oligonucleotides that is joined to only the 5' end of a polynucleotide allows for the extension of the unjoined 3' end of the polynucleotide using the joined strand of the adapter as template, concurrently with or following displacement of the unjoined strand. In some cases, both strands of an adapter comprising two hybridized oligonucleotides are joined to a polynucleotide such that the joined product has a 5' overhang, and the complementary 3' end is extended using the 5' overhang as template. In further examples, a hairpin adapter oligonucleotide is joined to the 5' end of a polynucleotide. In some cases, the 3' end of the polynucleotide that is extended comprises one or more nucleotides from an adapter oligonucleotide. In some cases, for target polynucleotides to which adapters are joined on both ends, extension is carried out for both 3' ends of a double-stranded polynucleotide having 5' overhangs. This 3' end extension, or "fill-in"

reaction, generates a complementary sequence, or "complement," to the adapter oligonucleotide template that is hybridized to the template, thus filling in the 5' overhang to produce a double-stranded sequence region. Where both ends of a double-stranded target polynucleotide have 5' overhangs that are filled in by extension of the complementary strands' 3' ends, the product is completely double-stranded. In certain cases, extension is carried out by any suitable polymerase known in the art, such as a DNA polymerase, many of which are commercially available. In some cases, DNA polymerases comprise DNA-dependent DNA polymerase activity, RNA-dependent DNA polymerase activity, or DNA-dependent and RNA-dependent DNA polymerase activity. In certain examples, DNA polymerases are thermostable or non-thermostable. Examples of DNA polymerases include, but are not limited to, Taq polymerase, Tth polymerase, Tli polymerase, Pfu polymerase, Pfutubo polymerase, Pyrobest polymerase, Pwo polymerase, KOD polymerase, Bst polymerase, Sac polymerase, Sso polymerase, Poc polymerase, Pab polymerase, Mth polymerase, Pho polymerase, ES4 polymerase, VENT polymerase, DEEPVENT polymerase, EX-Taq polymerase, LA-Taq polymerase, Expand polymerases, Platinum Taq polymerases, Hi-Fi polymerase, Tbr polymerase, Tfl polymerase, Tru polymerase, Tac polymerase, Tne polymerase, Tma polymerase, Tih polymerase, Tfi polymerase, Klenow fragment, and variants, modified products and derivatives thereof. In certain cases, 3' end extension is performed before or after pooling of polynucleotides from independent samples.

Enrichment

The disclosure further provides methods for the enrichment and/or analysis of nucleic acids. In some cases, the enrichment method is a solution-based format. In certain cases, the nucleic acid is labeled with a labeling agent. In various cases, the nucleic acid is cross-linked to one or more association molecules that are labeled with a labeling agent. Examples of labeling agents include but are not limited to biotin, polyhistidine tags, and chemical tags (e.g. alkyne and azide derivatives used in Click Chemistry methods). In further cases, the labeled target nucleic acid is captured and thereby enriched by using a capturing agent. In some cases, the capturing agent is streptavidin and/or avidin, an antibody, a chemical moiety (e.g. alkyne, azide), or any biological, chemical, physical, or enzymatic agents used for affinity purification known in the art.

In some cases, immobilized or non-immobilized nucleic acid probes are used to capture the nucleic acids. In some cases, the polynucleotides are enriched from a sample by hybridization to the probes on a solid support or in solution. In some cases, the sample is a genomic sample. In some cases, the probes comprise an amplicon. In further examples, the amplicon comprises a predetermined sequence. In further cases, the hybridized nucleic acids can be washed and/or eluted off of the probes. In some cases, the nucleic acid is a DNA, RNA, cDNA, or mRNA molecule.

In some cases, the enrichment method comprises contacting the sample comprising the nucleic acid to the probes and binding the nucleic acid to a solid support. In some cases, the sample is fragmented using chemical, physical or enzymatic methods to yield the nucleic acids. In some cases, the probes are specifically hybridized to the nucleic acids. In some cases, the nucleic acids have an average size of about 50 to 5000, about 50 to 2000, about 100 to 2000, about 100 to 1000, about 200 to 1000, about 200 to 800, or about 300 to 800, about 300 to 600, or about 400 to 600 nucleotide residues. In further cases, the nucleic acids are separated from the unbound nucleic acids in the sample. In certain examples, the solid support are washed and/or eluted to provide the enriched nucleic acids. In some cases, the enrichment steps are repeated for about 1, 2, 3, 4, 5, 6, 7, 8, 9, or 10 times. In further examples, the enrichment steps are repeated for about 1, 2, or 3 times.

In some cases, the enrichment method comprises providing probe derived amplicons wherein the probes for amplification are attached to a solid support. In some cases, the solid support comprises support-immobilized nucleic acid probes to capture specific polynucleotides from a sample. In certain examples, the probe derived amplicons can hybridize to the nucleic acids. In certain cases, following hybridization to the probe amplicons, the nucleic acids in the sample is enriched by capturing (e.g., via capturing agents as biotin, antibodies, etc.) and washing and/or eluting the hybridized nucleic acids from the captured probes (FIG. 4A-D and FIG. 20). In further cases, the nucleic acid sequence(s) is amplified using, for example, PCR methods to produce an amplified pool of enriched PCR products.

In some cases, the solid support is a microarray, a slide, a chip, a microwell, a column, a tube, a particle or a bead. In some cases, the solid support is coated with streptavidin and/or avidin. In some cases, the solid support is coated with an antibody. In further examples, the solid support comprises a glass, metal, ceramic or polymeric material. In some embodiments, the solid support is a nucleic acid microarray (e.g. a DNA microarray). In other embodiments, the solid support is a paramagnetic bead.

In certain cases, the enrichment method comprises digestion with a secondary restriction enzyme, self-ligation (e.g. self-circularization), and re-digestion with the original restriction enzyme. In some cases, the ligation products are linearized and available for adapter-ligation and sequencing. In other examples, the ligation junction sequence itself is used for hybridization based enrichment using a bait-probe complimentary to the junction sequence.

Amplification

As used herein, the term "amplification" refers to any process by which the copy number of a nucleic acid sequence is increased. The disclosure further provides methods for amplifying polynucleotides. In some cases, the polynucleotides comprise a label. The labeled polynucleotide(s) can be obtained by the methods of the present disclosure.

In some cases, the one or more amplification and/or replication steps are used for the preparation of a library or read-set to be sequenced. Any amplification method known in the art may be used. Examples of amplification techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polonony PCR, in situ rolling circle amplification (RCA), bridge PCR, ligation mediated PCR, Qb replicase amplification, inverse PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

In some cases, an amplification reaction produces only a single complimentary copy/replica of a polynucleotide. Methods for primer-directed amplification of target polynucleotides are known in the art, and include without limitation, methods based on the polymerase chain reaction (PCR). Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles.

In particular cases, PCR is used to amplify polynucleotides after they are dispensed into individual partitions. In some cases, one or more specific priming sequences within amplification adapters are utilized for PCR amplification. The amplification adapters may be ligated to fragmented polynucleotides before or after dispensing into individual partitions. In some cases, polynucleotides comprising amplification adapters with suitable priming sequences on both ends are PCR amplified exponentially. Polynucleotides with only one suitable priming sequence due to, for example, imperfect ligation efficiency of amplification adapters comprising priming sequences, may only undergo linear amplification. Further, polynucleotides can be eliminated from amplification, for example, PCR amplification, altogether, if no adapters comprising suitable priming sequences are ligated. In some embodiments, the number of PCR cycles varies among 10-30 cycles, but is as low as 9, 8, 7, 6, 5, 4, 3, 2 or less or as high as 40, 45, 50, 55, 60 or more. As a result, in some cases, exponentially amplifiable fragments carrying amplification adapters with a suitable priming sequence is present in much higher (1000 fold or more) concentration compared to linearly amplifiable or un-amplifiable fragments, after a PCR amplification. Benefits of PCR, as compared to whole genome amplification techniques (such as amplification with randomized primers or Multiple Displacement Amplification using phi29 polymerase) can include, but are not limited to, a more uniform relative sequence coverage—as each fragment can be copied at most once per cycle and as the amplification is controlled by thermocycling program, a substantially lower rate of forming chimeric molecules than for example MDA (Lasken et al., 2007, BMC Biotechnology)—as chimeric molecules pose significant challenges for accurate sequence assembly by presenting nonbiological sequences in the assembly graph, which may result in higher rate of misassemblies or highly ambiguous and fragmented assembly, reduced sequence specific biases that may result from binding of randomized primers commonly used in MDA versus using specific priming sites with a specific sequence, a higher reproducibility in the amount of final amplified DNA product, which can be controlled by selection of the number of PCR cycles, and a higher fidelity in replication with the polymerases that are commonly used in PCR as compared to common whole genome amplification techniques known in the art.

In some cases, a fill-in reaction is followed by or performed as part of amplification of one or more target polynucleotides using a first primer and a second primer, wherein the first primer comprises a sequence that is hybridizable to at least a portion of the complement of one or more of the first adapter oligonucleotides, and further wherein the second primer comprises a sequence that is hybridizable to at least a portion of the complement of one or more of the second adapter oligonucleotides. Each of the first and second primers may be of any suitable length, such as about, less than about, or more than about 10, 15, 20, 25, 30, 35, 40, 45, 50, 55, 60, 65, 70, 75, 80, 90, 100, or more nucleotides, any portion or all of which may be complementary to the corresponding target sequence (e.g. about, less than about, or more than about 5, 10, 15, 20, 25, 30, 35, 40, 45, 50, or more nucleotides). In some cases, about 10 to 50 nucleotides is complementary to the corresponding target sequence.

In some embodiments, an amplification reaction comprises at least about 1, 2, 3, 4, 5, 6, 7, 8, 9, 10, 11, 12, 13, 14, 15, 20, 25, 30, 35, 40, 50, 60, 70, 80, 90, 100, 150, 200 or more cycles. In some cases, an amplification reaction comprises at least about 20, 25, 30, 35 or 40 cycles. In some embodiments, an amplification reaction comprises no more than about 1, 2, 3, 4, 5, 6, 7, 8, 9, 10, 11, 12, 13, 14, 15, 20, 25, 30, 35, 40, 50, 60, 70, 80, 90, 100, 150, 200 or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, 3' end extension (e.g. adapter fill-in), primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, 1200, 1800, or more seconds, including indefinitely until manually interrupted. In some cases, cycles of any number comprising different steps are combined in any order. In some embodiments, different cycles comprising different steps are combined such that the total number of cycles in the combination is about, less that about, or more than about 5, 10, 15, 20, 25, 30, 35, 40, 50, 60, 70, 80, 90, 100, 150, 200 or more cycles. In some embodiments, amplification is performed following the fill-in reaction.

In some cases, the amplification reaction is carried out on at least about 1, 2, 3, 4, 5, 6, 7, 8, 9, 10, 12, 14, 16, 18, 20, 25, 30, 40, 50, 100, 200, 300, 400, 500, 600, 800, 1000 ng of the target DNA molecule. In some cases, the amplification reaction is carried out on less than about 1, 2, 3, 4, 5, 6, 7, 8, 9, 10, 12, 14, 16, 18, 20, 25, 30, 40, 50, 100, 200, 300, 400, 500, 600, 800, 1000 ng of the polynucleotide. In further examples, amplification is performed before or after pooling of target polynucleotides from independent samples.

In certain cases, the methods disclosed herein comprise determining an amount of amplifiable nucleic acid present in a sample. Any known method may be used to quantify amplifiable nucleic acid, and an exemplary method is the polymerase chain reaction (PCR), specifically quantitative polymerase chain reaction (qPCR). qPCR is a technique based on the polymerase chain reaction, and is used to amplify and simultaneously quantify a targeted nucleic acid molecule. qPCR allows for both detection and quantification (as absolute number of copies or relative amount when normalized to DNA input or additional normalizing genes) of a specific sequence in a DNA sample. The procedure follows the general principle of polymerase chain reaction, with the additional feature that the amplified DNA is quantified as it accumulates in the reaction in real time after each amplification cycle. QPCR is described, for example, in Kurnit et al. (U.S. Pat. No. 6,033,854), Wang et al. (U.S. Pat. Nos. 5,567,583 and 5,348,853), Ma et al. (The Journal of American Science, 2(3), 2006), Heid et al. (Genome Research 986-994, 1996), Sambrook and Russell (Quantitative PCR, Cold Spring Harbor Protocols, 2006), and Higuchi (U.S. Pat. Nos. 6,171,785 and 5,994,056). The contents of these are incorporated by reference herein in their entirety.

Other methods of quantification include use of fluorescent dyes that intercalate with double-stranded DNA, and modified DNA oligonucleotide probes that fluoresce when hybridized with a complementary DNA. These methods can be broadly used but are also specifically adapted to real-time PCR as described in further detail as an example.

In some cases, a DNA-binding dye binds to double-stranded (ds)DNA in PCR, resulting in fluorescence of the dye. An increase in DNA product during PCR therefore leads to an increase in fluorescence intensity and is measured at each cycle, thus allowing DNA concentrations to be quantified. The reaction is prepared similarly to a standard PCR reaction, with the addition of fluorescent (ds)DNA dye. The reaction is run in a thermocycler, and after each cycle, the levels of fluorescence are measured with a detector; the dye only fluoresces when bound to the (ds)DNA (i.e., the PCR product). In some cases, with reference to a standard dilution, the (ds)DNA concentration in the PCR is determined. Like other real-time PCR methods, the values obtained do not have absolute units associated with it. A comparison of a measured DNA/RNA sample to a standard dilution gives a fraction or ratio of the sample relative to the standard, allowing relative comparisons between different tissues or experimental conditions. In certain cases, to ensure accuracy, the quantification and/or expression of a target gene is normalized with respect to a stably expressed gene. In some cases, copy numbers of unknown genes are normalized relative to genes of known copy number.

In some cases, a sequence-specific RNA or DNA-based probe is used to quantify only the DNA containing a probe sequence; therefore, use of the reporter probe significantly increases specificity, and allows quantification even in the presence of some non-specific DNA amplification. This allows for multiplexing, i.e., assaying for several genes in the same reaction by using specific probes with differently colored labels, provided that all genes are amplified with similar efficiency.

In some cases, these methods are carried out with a DNA-based probe with a fluorescent reporter (e.g. 6-carboxyfluorescein) at one end and a fluorescence quencher (e.g., 6-carboxy-tetramethylrhodamine) at the opposite end of the probe. The close proximity of the reporter to the quencher prevents detection of its fluorescence. Breakdown of the probe by the 5' to 3' exonuclease activity of a polymerase (e.g., Taq polymerase) breaks the reporter-quencher proximity and thus allows unquenched emission of fluorescence, which can be detected. An increase in the product targeted by the reporter probe at each PCR cycle results in a proportional increase in fluorescence due to breakdown of the probe and release of the reporter. The reaction is prepared similarly to a standard PCR reaction, and the reporter probe is added. As the reaction commences, during the annealing stage of the PCR both probe and primers anneal to the DNA target. Polymerization of a new DNA strand is initiated from the primers, and once the polymerase reaches the probe, its 5'-3'-exonuclease degrades the probe, physically separating the fluorescent reporter from the quencher, resulting in an increase in fluorescence. Fluorescence is detected and measured in a real-time PCR thermocycler, and geometric increase of fluorescence corresponding to exponential increase of the product is used to determine the threshold cycle in each reaction.

Relative concentrations of DNA present during the exponential phase of the reaction are determined by plotting fluorescence against cycle number on a logarithmic scale (so an exponentially increasing quantity will give a straight line). A threshold for detection of fluorescence above background is determined. The cycle at which the fluorescence from a sample crosses the threshold is called the cycle threshold, $C_t$. Since the quantity of DNA doubles every cycle during the exponential phase, relative amounts of DNA can be calculated, e.g. a sample with a $C_t$ of 3 cycles earlier than another has $2^3=8$ times more template. Amounts of nucleic acid (e.g., RNA or DNA) are then determined by comparing the results to a standard curve produced by a real-time PCR of serial dilutions (e.g. undiluted, 1:4, 1:16, 1:64) of a known amount of nucleic acid.

In certain cases, the qPCR reaction involves a dual fluorophore approach that takes advantage of fluorescence resonance energy transfer (FRET), e.g., LIGHTCYCLER hybridization probes, where two oligonucleotide probes anneal to the amplicon (e.g. see U.S. Pat. No. 6,174,670). The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: SCORPIONS probes (e.g., Whitcombe et al., Nature Biotechnology 17:804-807, 1999, and U.S. Pat. No. 6,326,145), Sunrise (or AMPLI-FLOUR) primers (e.g., Nazarenko et al., Nuc. Acids Res. 25:2516-2521, 1997, and U.S. Pat. No. 6,117,635), and LUX primers and MOLECULAR BEACONS probes (e.g., Tyagi et al., Nature Biotechnology 14:303-308, 1996 and U.S. Pat. No. 5,989,823).

In other cases, a qPCR reaction uses fluorescent Taqman methodology and an instrument capable of measuring fluorescence in real time (e.g., ABI Prism 7700 Sequence Detector). The Taqman reaction uses a hybridization probe labeled with two different fluorescent dyes. One dye is a reporter dye (6-carboxyfluorescein), the other is a quenching dye (6-carboxy-tetramethylrhodamine). When the probe is intact, fluorescent energy transfer occurs and the reporter dye fluorescent emission is absorbed by the quenching dye. During the extension phase of the PCR cycle, the fluorescent hybridization probe is cleaved by the 5'-3' nucleolytic activity of the DNA polymerase. On cleavage of the probe, the reporter dye emission is no longer transferred efficiently to the quenching dye, resulting in an increase of the reporter dye fluorescent emission spectra. Any nucleic acid quantification method, including real-time methods or single-point detection methods may be used to quantify the amount of nucleic acid in the sample. The detection can be performed several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment), as well as any other suitable detection method known in the art for nucleic acid quantification. The quantification may or may not include an amplification step.

Labels

In some embodiments, the disclosure provides labels for identifying or quantifying the polynucleotides and/or sequence segments. In some cases, the segments is labeled in order to assist in downstream applications, such as array hybridization. In some cases, the segments are labeled using random priming or nick translation.

A wide variety of labels (e.g. reporters) may be used to label the nucleotide sequences described herein, which may be used before, during, or after an amplification step. Suitable labels include radionuclides, enzymes, fluorescent, chemiluminescent, or chromogenic agents as well as ligands, cofactors, inhibitors, magnetic particles and the like. Examples of such labels are included in U.S. Pat. Nos. 3,817,837; 3,850,752; 3,939,350; 3,996,345; 4,277,437; 4,275,149 and 4,366,241, which are incorporated by reference in its entirety.

Additional labels include but are not limited to 3-galactosidase, invertase, green fluorescent protein, luciferase, chloramphenicol, acetyltransferase, 0-glucuronidase, exoglucanase and glucoamylase. Fluorescent labels may also be used, as well as fluorescent reagents specifically synthesized with particular chemical properties. A wide variety of ways to measure fluorescence are available. For example, some fluorescent labels exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements.

In some cases, in order to obtain sufficient material for labeling, multiple amplifications are pooled, instead of increasing the number of amplification cycles per reaction. In other cases, labeled nucleotides are incorporated in to the last cycles of the amplification reaction, e.g. 30 cycles of PCR (no label)+10 cycles of PCR (plus label).

Probes

In particular cases, the disclosure provides probes that attach to polynucleotides and/or sequence segments. As used herein, the term "probe" refers to a molecule (e.g., an oligonucleotide, whether occurring naturally as in a purified restriction digest or produced synthetically, recombinantly or by PCR amplification), that is capable of hybridizing to another molecule of interest (e.g., another oligonucleotide). When probes are oligonucleotides, they may be single-stranded or double-stranded. Probes are useful in the detection, identification and isolation of particular targets (e.g., gene sequences). In some cases, the probes may be associated with a label so that is detectable in any detection system, including, but not limited to enzyme (e.g., ELISA, as well as enzyme-based histochemical assays), fluorescent, radioactive, and luminescent systems With respect to substrates, arrays and microarrays, the term "probe" is used to refer to any hybridizable material that is affixed to the array for the purpose of detecting a nucleotide sequence that has hybridized to the probe. In some cases, the probes are about 10 bp to 500 bp, about 10 bp to 250 bp, about 20 bp to 250 bp, about 20 bp to 200 bp, about 25 bp to 200 bp, about 25 bp to 100 bp, about 30 bp to 100 bp, or about 30 bp to 80 bp. In some cases, the probes are greater than about 10 bp, about 20 bp, about 30 bp, about 40 bp, about 50 bp, about 60 bp, about 70 bp, about 80 bp, about 90 bp, about 100 bp, about 150 bp, about 200 bp, about 250 bp, about 300 bp, about 400 bp, or about 500 bp in length. In further cases, the probes are about 20 to about 50 bp in length. Examples and rationale for probe design can be found in WO95/11995, EP 717,113 and WO97/29212

In some cases, one or more probes are designed such that they can hybridize close to the sites that are digested by a restriction enzyme. In some cases, the probe(s) are within about 10 bp, about 20 bp, about 30 bp, about 40 bp, about 50 bp, about 60 bp, about 70 bp, about 80 bp, about 90 bp, about 100 bp, about 150 bp, about 200 bp, about 250 bp, about 300 bp, about 400 bp, or about 500 bp of the restriction enzyme recognition site.

In other cases, a single, unique, probe is designed within about 10 bp, about 20 bp, about 30 bp, about 40 bp, about 50 bp, about 60 bp, about 70 bp, about 80 bp, about 90 bp, about 100 bp, about 150 bp, about 200 bp, about 250 bp, about 300 bp, about 400 bp, or about 500 bp at each side of the sites that are digested by the restriction enzyme. In certain examples, the probes are designed such that they can hybridize at either side of the sites that are digested by the restriction enzyme. In further examples, a single probe at each side of the primary restriction enzyme recognition site is used.

In further cases, 2, 3, 4, 5, 6, 7, 8, or more probes are designed at each side of the restriction enzyme recognition site, which can then be used to investigate the same ligation event. In some cases, 2 or 3 probes are designed at each side of the restriction enzyme recognition site. In some cases, the use of multiple (e.g. 2, 3, 4, 5, 6, 7 or 8 or more) probes per primary restriction enzyme recognition site are useful to minimize the problem of obtaining false negative results from individual probes.

In certain cases, the probes are immobilized on a support. Supports (e.g. solid supports) can be made of a variety of materials-such as glass, silica, plastic, nylon or nitrocellulose. Supports are preferably rigid and have a planar surface. In some cases, supports have from about 1 to 10,000,000 resolved loci. In some cases, a support has about 10 to 10,000,000, about 10 to 5,000,000, about 100 to 5,000,000, about 100 to 4,000,000, about 1000 to 4,000,000, about 1000 to 3,000,000, about 10,000 to 3,000,000, about 10,000 to 2,000,000, about 100,000 to 2,000,000, or about 100,000 to 1,000,000 resolved loci. In further examples, the density of resolved loci is at least about 10, about 100, about 1000, about 10,000, about 100,000 or about 1,000,000 resolved loci within a square centimeter. In some cases, each resolves loci is occupied by >95% of a single type of oligonucleotide. In other cases, each resolved locus is occupied by pooled mixtures of probes or a set of probes. In further cases, some resolved loci are occupied by pooled mixtures of probes or a set of probes, and other resolved loci are occupied by >95% of a single type of oligonucleotide.

In some cases, the number of probes for a given nucleotide sequence on the array is in large excess to the polynucleotide sample to be hybridized to such array. In some cases, the array has about 10, about 100, about 1000, about 10,000, about 100,000, about 1,000,000, about 10,000,000, or about 100,000,000 times the number of probes relative to the amount of polynucleotide in the input sample. In some cases, an array has about 10, about 100, about 1000, about 10,000, about 100,000, about 1,000,000, about 10,000,000, about 100,000,000, or about 1,000,000,000 probes.

Arrays of probes or sets of probes may be synthesized in a step-by-step manner on a support or can be attached in presynthesized form. One method of synthesis is VLSIPS™

(as described in U.S. Pat. No. 5,143,854 and EP 476,014), which entails the use of light to direct the synthesis of oligonucleotide probes in high-density, miniaturized arrays. Algorithms for design of masks to reduce the number of synthesis cycles are described in U.S. Pat. Nos. 5,571,639 and 5,593,839. In some cases, arrays are synthesized in a combinatorial fashion by delivering monomers to cells of a support by mechanically constrained flow paths, as described in EP 624,059. In further cases, arrays are synthesized by spotting reagents on to a support using an ink jet printer (see, for example, EP 728,520).

Substrates and Arrays

The present disclosure provides methods for hybridizing polynucleotides onto an array. A "substrate" or an "array" is an intentionally created collection of nucleic acids which are prepared either synthetically or biosynthetically in a variety of different formats (e.g., libraries of soluble molecules; and libraries of oligonucleotides tethered to resin beads, silica chips, or other solid supports). Additionally, the term "array" includes those libraries of nucleic acids which are prepared by spotting nucleic acids of essentially any length (e.g., from 1 to about 1000 nucleotide monomers in length) onto a substrate.

Array technology and the various associated techniques and applications are described generally in numerous textbooks and documents. For example, these include Lemieux et al., 1998, *Molecular Breeding* 4, 277-289; Schena and Davis, *Parallel Analysis with Biological Chips*. in *PCR Methods Manual* (eds. M. Innis, D. Gelfand, J. Sninsky); Schena and Davis, 1999, *Genes, Genomes and Chips*. In *DNA Microarrays: A Practical Approach* (ed. M. Schena), Oxford University Press, Oxford, U K, 1999); *The Chipping Forecast* (Nature Genetics special issue; January 1999 Supplement); Mark Schena (Ed.), *Microarray Biochip Technology*, (Eaton Publishing Company); Cortes, 2000, *The Scientist* 14[17]: 25; Gwynn and Page, *Microarray analysis: the next revolution in molecular biology, Science,* 1999 Aug. 6; and Eakins and Chu, 1999, *Trends in Biotechnology,* 17, 217-218.

In general, any library may be arranged in an orderly manner into an array, by spatially separating the members of the library. Examples of suitable libraries for arraying include nucleic acid libraries (including genomic DNA, cDNA, oligonucleotide, and other libraries), peptide, polypeptide and protein libraries, as well as libraries comprising any molecules, such as ligand libraries, among others.

In some cases, the library is fixed or immobilized onto a solid phase (e.g. a solid substrate), to limit diffusion and admixing of the members. In some cases, libraries of DNA binding probes (e.g. oligonucleotides) are prepared. In particular cases, the libraries are immobilized to a substantially planar solid phase, including membranes and non-porous substrates such as plastic and glass. In further cases, the library is arranged in such a way that indexing (i.e., reference or access to a particular member) is facilitated. In some cases, the members of the library are applied as spots in a grid formation. Common assay systems may be adapted for this purpose. In certain examples, an array is immobilized on the surface of a microplate, either with multiple members in a well, or with a single member in each well. In further examples, the solid substrate is a membrane, such as a nitrocellulose or nylon membrane (for example, membranes used in blotting experiments). Alternative substrates include glass, or silica based substrates. Thus, the library can be immobilized by any suitable method known in the art, for example, by charge interactions, or by chemical coupling to the walls or bottom of the wells, or the surface of the membrane. Other means of arranging and fixing may be used, for example, pipetting, drop-touch, piezoelectric means, ink-jet and bubblejet technology, electrostatic application, etc. In the case of silicon-based chips, photolithography may be utilized to arrange and fix the libraries on the chip.

In some cases, the library is arranged by being "spotted" onto the solid substrate; this may be done by hand or by making use of robotics to deposit the members. In general, arrays may be described as macroarrays or microarrays, the difference being the size of the spots. Macroarrays can contain spot sizes of about 300 microns or larger and may be easily imaged by existing gel and blot scanners. The spot sizes in microarrays can be less than 200 microns in diameter and these arrays usually contain thousands of spots. Thus, microarrays may require specialized robotics and imaging equipment, which may need to be custom made. Instrumentation is described generally in a review by Cortese, 2000, *The Scientist* 14[11]: 26.

Techniques for producing immobilized libraries of DNA molecules have been described in the art. Generally, most prior art methods described how to synthesize single-stranded nucleic acid molecule libraries, using for example masking techniques to build up various permutations of sequences at the various discrete positions on the solid substrate. U.S. Pat. No. 5,837,832 describes an improved method for producing DNA arrays immobilized to silicon substrates based on very large scale integration technology. In particular, U.S. Pat. No. 5,837,832 describes a strategy called "tiling" to synthesize specific sets of probes at spatially-defined locations on a substrate which may be used to produce the immobilized DNA libraries of the present disclosure. U.S. Pat. No. 5,837,832 also provides references for earlier techniques that may also be used. In other cases, arrays may also be built using photo deposition chemistry.

Arrays of peptides (or peptidomimetics) may also be synthesized on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a target or probe) and reactive library members occur is determined, thereby identifying the sequences of the reactive library members on the basis of spatial location. These methods are described in U.S. Pat. No. 5,143,854; WO90/15070 and WO92/10092; Fodor et al. (1991) *Science,* 251: 767; Dower and Fodor (1991) *Ann. Rep. Med. Chem.,* 26: 271

In some cases, to aid detection, labels are used (as discussed above)—such as any readily detectable reporter, for example, a fluorescent, bioluminescent, phosphorescent, radioactive, etc. reporter. Such reporters, their detection, coupling to targets/probes, etc. are discussed elsewhere in this document. Labelling of probes and targets is also disclosed in Shalon et al., 1996, *Genome Res* 6(7):639-45.

Examples of some commercially available microarray formats are set out in Table 1 below (see also Marshall and Hodgson, 1998, *Nature Biotechnology,* 16(1), 27-31).

TABLE 1

Examples of currently available hybridization microarray formats

| Company | Product name | Arraying method | Hybridization step | Readout |
|---|---|---|---|---|
| Affymetrix, Inc., Santa Clara California | Genechip ® | In situ (on-chip) photolithographic synthesis of ~20-25-mer oligos onto silicon wafers, which are diced into 1.25 cm² or 5.25 cm² chips | 10,000-260,000 oligo features probed with labeled 30-40 nucleotide fragments of sample cDNA or antisense RNA | Fluorescence |
| Brax, Cambridge, UK | | Short synthetic oligo, synthesized off-chip | 1000 oligos on a "universal chip" probed with tagged nucleic acid | Mass spectrometry |
| Gene Logic, Inc., Columbia, Maryland | READS ™ | | | |
| Genometrix Inc., The Woodlands, Texas | Universal Arrays ™ | | | |
| GENSET, Paris, France | | | | |
| Hyseq Inc., Sunnyvale, California | HyChip ™ | 500-2000 nt DNA samples printed onto 0.6 cm² (HyGnostics) or ~18 cm² (Gene Discovery) membranes | 64 sample cDNA spots probed with 8,000 7-mer oligos (HyGnostics) or <= 55,000 sample cDNA spots probed with 300 7-mer oligo (Gene Discovery) | Radioisotope |
| | | Fabricated 5-mer oligos printed as 1.15 cm² arrays onto glass (HyChip) | Universal 1024 oligo spots probed 10 kb sample cDNAs, labeled 5-mer oligo, and ligase | Fluorescence |
| Incyte Pharmaceuticals, Inc., Palo Alto, California | GEM | Piezoelectric printing for spotting PCR fragments and on-chip synthesis of oligos | <=1000 (eventually 10,000) oligo/ PCR fragment spots probed with labeled RNA | Fluorescence and radioisotope |
| Molecular Dynamics, Inc., Sunnyvale, California | Storm ® Fluorimager ® | 500-5000 nt cDNAs printed by pen onto ~10 cm² on glass slide | ~10.000 cDNA spots probed with 200-400 nt labeled sample cDNAs | Fluorescence |
| Nanogen, San Diego, California | Semiconductor Microchip | Prefabricated ~20-mer oligos, captured onto electroactive spots on silicon wafers, which are diced into <=1 cm² chips | 25, 64, 400 (and eventually 10,000) oligo spots polarized to enhance hybridization to 200-400 nt labeled sample cDNAs | Fluorescence |
| Protogene Laboratories, Palo Alto, California | | On-chip synthesis of 40-50-mer oligos onto 9 cm² glass chip via printing to a surface-tension array | <=8,000 oligo spots probed with 200-400 nt labeled sample nucleic acids | Fluorescence |
| Sequenom, Hamburg, Germany, and San Diego, California | MassArray SpectroChip | Off-set printing of array; around 20-25-mer oligos | 250 locations per SpectroChip interrogated by laser desorbtion and mass spectrometry | Mass spectrometry |

TABLE 1-continued

Examples of currently available hybridization microarray formats

| Company | Product name | Arraying method | Hybridization step | Readout |
|---|---|---|---|---|
| Synteni, Inc., Fremont, California | UniGEM ™ | 500-5,000 nt cDNAs printed by tip onto ~4 cm² glass chip | <=10,000 cDNA spots probed with 200-400 nt labeled smaple cDNAs | Fluorescence |
| Nimblegen Systems Inc., Madison | Homo sapiens Whole-Genome 60mer Microarray | 38,000 transcripts with 5 probes per gene 17.4 mm × 13 mm | | 5-micron scanning platform |
| The German Cancer Institute, Heidelberg, Germany | | Prototypic PNA macrochip with on-chip synthesis of probes using f-moc or t-moc chemistry | Around 1,000 spots on a 8 × 12 cm chip | Fluorescence/ mass spectrometry |

In certain cases, in order to generate data from array-based assays, a signal is detected to signify the presence of or absence of hybridization between a probe and a nucleotide sequence. In further cases, direct and indirect labeling techniques are utilized. In some cases, direct labeling incorporates fluorescent dyes directly into the nucleotide sequences that hybridize to the array associated probes (e.g., dyes are incorporated into nucleotide sequence by enzymatic synthesis in the presence of labeled nucleotides or PCR primers). In some cases, direct labeling schemes yield strong hybridization signals, for example by using families of fluorescent dyes with similar chemical structures and characteristics, and can be simple to implement. In certain cases, when nucleic acids are directly labelled, cyanine or alexa analogs are utilized in multiple-fluor comparative array analyses. In other cases, indirect labeling schemes are utilized to incorporate epitopes into the nucleic acids either prior to or after hybridization to the microarray probes. In some cases, one or more staining procedures and reagents is used to label the hybridized complex (e.g., a fluorescent molecule that binds to the epitopes, thereby providing a fluorescent signal by virtue of the conjugation of dye molecule to the epitope of the hybridized species).

Sequencing Technologies

In one aspect, suitable sequencing methods described herein or otherwise known in the art are used to obtain sequence information from nucleic acid molecules within a sample. In some cases, sequencing is accomplished through classic Sanger sequencing methods, which are well known in the art. In other cases, sequencing is accomplished using high-throughput systems some of which allow detection of a sequenced nucleotide immediately after or upon its incorporation into a growing strand, i.e., detection of sequence in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour. In some cases, the sequencing reads are at least about 50, about 60, about 70, about 80, about 90, about 100, about 120, about 150, about 180, about 210, about 240, about 270, about 300, about 350, about 400, about 450, about 500, about 600, about 700, about 800, about 900, about 1000, about 1500, about 2000, about 2500, about 3000, about 4000, about 5000, about 6000, about 7000, about 8000, about 9000, or about 10000 bases per read.

In some cases, high-throughput sequencing is performed using technology available by Illumina's Genome Analyzer IIX, MiSeq personal sequencer, or HiSeq systems, such as those using HiSeq 2500, HiSeq 1500, HiSeq 2000, or HiSeq 1000 machines. These machines use reversible terminator-based sequencing by synthesis chemistry. These machines can produce 200 billion DNA reads or more in eight days. Alternatively, smaller systems may be utilized for runs within 3, 2, 1 days or less time.

In some cases, high-throughput sequencing is performed using technology available by ABI Solid System. This genetic analysis platform that enables massively parallel sequencing of clonally-amplified DNA fragments linked to beads. The sequencing methodology is based on sequential ligation with dye-labeled oligonucleotides.

In some cases, high-throughput sequencing is performed using ion semiconductor sequencing (e.g., using technology from Life Technologies (Ion Torrent)). Ion semiconductor sequencing can take advantage of the fact that when a nucleotide is incorporated into a strand of DNA, an ion can be released. In some cases, to perform ion semiconductor sequencing, a high density array of micromachined wells is formed. In some cases, each well holds a single DNA template. In further examples, an ion sensitive layer is beneath the well, and beneath the ion sensitive layer can be an ion sensor. In certain cases, when a nucleotide is added to a DNA, H+ is released, which can be measured as a change in pH. In further cases, the H+ ion is converted to voltage and recorded by the semiconductor sensor. In some cases, an array chip is sequentially flooded with one nucleotide after another. In some cases, no scanning, light, or cameras is required. In some cases, an IONPROTON™ Sequencer is used to sequence nucleic acid. In some cases, an IONPGM™ Sequencer is used. In certain examples, the Ion Torrent Personal Genome Machine (PGM) can do 10 million reads in two hours.

In some cases, high-throughput sequencing is performed using technology available by Helicos BioSciences Corporation (Cambridge, Massachusetts) such as the Single Molecule Sequencing by Synthesis (SMSS) method. SMSS is unique because it allows for sequencing the entire human genome in up to 24 hours. Finally, SMSS is described in part in US Publication Application Nos. 20060024711; 20060024678; 20060012793; 20060012784; and 20050100932.

In some cases, high-throughput sequencing is performed using technology available by 454 Lifesciences, Inc. (Branford, Connecticut) such as the PicoTiterPlate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density pricolitre reactors Nature 437, 376-380 (15 Sep. 2005), doi: 10.1038/nature03959; and well as in US Application Publication Nos. 20020012930; 20030068629; 20030100102; 20030148344; 20040248161; 20050079510, 20050124022; and 20060078909.

In some cases, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106110; 20030064398; 20030022207; and Constans, A., The Scientist 2003, 17(13):36.

In some cases, high-throughput sequencing is performed using real-time (SMRT™) technology by Pacific Biosciences. In certain examples of SMRT, each of four DNA bases is attached to one of four different fluorescent dyes. In further examples, these dyes are phospho linked. In some cases, a single DNA polymerase is immobilized with a single molecule of template single stranded DNA at the bottom of a zero-mode waveguide (ZMW). In certain cases, a ZMW is a confinement structure which enables observation of incorporation of a single nucleotide by DNA polymerase against the background of fluorescent nucleotides that can rapidly diffuse in an out of the ZMW (in microseconds). In some cases, it takes several milliseconds to incorporate a nucleotide into a growing strand. During this time, the fluorescent label can be excited and produce a fluorescent signal, and in some cases the fluorescent tag is further cleaved off. In certain cases, the ZMW is illuminated from below. Attenuated light from an excitation beam can penetrate the lower 20-30 nm of each ZMW. In some cases, a microscope with a detection limit of 20 zepto liters (10" liters) is created. In certain examples, the tiny detection volume provides 1000-fold improvement in the reduction of background noise. In further examples, detection of the corresponding fluorescence of the dye indicates which base was incorporated. In many cases, the process is repeated.

In some cases, high-throughput sequencing is performed using nanopore sequencing (See, e.g., Soni G V and Meller A. (2007) Clin Chem 53: 1996-2001). In various cases, a nanopore is a small hole, of the order of about one nanometer in diameter. In certain cases, immersion of a nanopore in a conducting fluid and application of a potential across it results in a slight electrical current due to conduction of ions through the nanopore. In further cases, the amount of current which flows is sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore may represent a reading of the DNA sequence. In some cases, the nanopore sequencing technology is from Oxford Nanopore Technologies; e.g., a GridION system. In certain examples, a single nanopore is inserted in a polymer membrane across the top of a microwell. In various examples, each microwell has an electrode for individual sensing. In further examples, the microwells are fabricated into an array chip, with 100,000 or more microwells (e.g., more than 200,000, 300,000, 400,000, 500,000, 600,000, 700,000, 800,000, 900,000, or 1,000,000) per chip. In some cases, an instrument (or node) is used to analyze the chip. In certain cases, data is analyzed in real-time. In many cases, one or more instruments are operated at a time. In some cases, the nanopore is a protein nanopore, e.g., the protein alpha-hemolysin, a heptameric protein pore. In certain examples, the nanopore is a solid-state nanopore made, e.g., a nanometer sized hole formed in a synthetic membrane (e.g., $SiN_x$, or $SiO_2$). In other examples, the nanopore is a hybrid pore (e.g., an integration of a protein pore into a solid-state membrane). In further examples, the nanopore is a nanopore with an integrated sensors (e.g., tunneling electrode detectors, capacitive detectors, or graphene based nano-gap or edge state detectors (see e.g., Garaj et al. (2010) Nature vol. 67, doi: 10.1038/nature09379)). In some cases, a nanopore is functionalized for analyzing a specific type of molecule (e.g., DNA, RNA, or protein). In certain cases, nanopore sequencing comprises "strand sequencing" in which intact DNA polymers can be passed through a protein nanopore with sequencing in real time as the DNA translocates the pore. In many cases, an enzyme separates strands of a double stranded DNA and feed a strand through a nanopore. In further cases, the DNA has a hairpin at one end, and the system can read both strands. In some cases, nanopore sequencing is "exonuclease sequencing" in which individual nucleotides are cleaved from a DNA strand by a processive exonuclease, and the nucleotides are passed through a protein nanopore. In certain examples, the nucleotides transiently bind to a molecule in the pore (e.g., cyclodextran). In various examples, a characteristic disruption in current is used to identify bases.

In further cases, nanopore sequencing technology from GENIA is used. In some cases. an engineered protein pore is embedded in a lipid bilayer membrane. In certain examples, "Active Control" technology is used to enable efficient nanopore-membrane assembly and control of DNA movement through the channel. In some cases, the nanopore sequencing technology is from NABsys. In some cases, genomic DNA is fragmented into strands of average length of about 100 kb. In certain examples, the 100 kb fragments are made single stranded and subsequently hybridized with a 6-mer probe. In many examples, the genomic fragments with probes are driven through a nanopore, which can create a current-versus-time tracing. In further examples, the current tracing provides the positions of the probes on each genomic fragment. In some cases, the genomic fragments are lined up to create a probe map for the genome. In certain cases, the process is done in parallel for a library of probes. In further cases, a genome-length probe map for each probe is generated. In many cases, errors are fixed with a process termed "moving window Sequencing By Hybridization (mwSBH)." In some cases, the nanopore sequencing technology is from IBM/Roche. In certain examples, an electron beam is used to make a nanopore sized opening in a microchip. In some cases, an electrical field is used to pull or thread DNA through the nanopore. In various examples, a DNA transistor device in the nanopore comprises alternating nanometer sized layers of metal and dielectric. In some cases, discrete charges in the DNA backbone are trapped by electrical fields inside the DNA nanopore. In further cases, turning off and on gate voltages allows the DNA sequence to be read.

In some cases, high-throughput sequencing is performed using DNA nanoball sequencing (as performed, e.g., by Complete Genomics; see e.g., Drmanac et al. (2010) Science 327: 78-81). In certain cases, DNA is isolated, fragmented, and size selected. In some cases, DNA is fragmented (e.g., by sonication) to a mean length of about 500 bp. Adaptors (Ad1) can be attached to the ends of the fragments. In certain examples, the adaptors are used to hybridize to anchors for sequencing reactions. In various examples, DNA with adaptors bound to each end is PCR amplified. In further examples, the adaptor sequences are modified so that complementary single strand ends bind to each other forming circular DNA. In some cases, the DNA is methylated to protect it from cleavage by a type IIS restriction enzyme used in a subsequent step. In certain cases, an adaptor (e.g., the right adaptor) has a restriction recognition site, and the restriction recognition site remains non-methylated. In other cases, the non-methylated restriction recognition site in the adaptor is recognized by a restriction enzyme (e.g., Acu1), and the DNA is cleaved by Acu1 13 bp to the right of the right adaptor to form linear double stranded DNA. In further cases, a second round of right and left adaptors (Ad2) is ligated onto either end of the linear DNA, and all DNA with both adapters bound are PCR amplified (e.g., by PCR). In some cases, Ad2 sequences are modified to allow them to bind each other and form circular DNA. In certain examples, the DNA is methylated, but a restriction enzyme recognition site remains non-methylated on the left Ad1 adapter. In various examples, a restriction enzyme (e.g., Acu1) is applied, and the DNA is cleaved 13 bp to the left of the Ad1 to form a linear DNA fragment. In further examples, a third round of right and left adaptor (Ad3) is ligated to the right and left flank of the linear DNA, and the resulting fragment is PCR amplified. In some embodiments, the adaptors are modified so that they bind to each other and form circular DNA. In certain embodiments, a type III restriction enzyme (e.g., EcoP15) is added; EcoP15 cleaves the DNA 26 bp to the left of Ad3 and 26 bp to the right of Ad2. In various embodiments, this cleavage removes a large segment of DNA and linearizes the DNA once again. In further embodiments, a fourth round of right and left adaptors (e.g., Ad4) is ligated to the DNA, the DNA is amplified (e.g., by PCR), and modified so that they bind each other and form the completed circular DNA template.

In certain cases, rolling circle replication (e.g., using Phi 29 DNA polymerase) is used to amplify small fragments of DNA. In some cases, the four adaptor sequences contain palindromic sequences that can hybridize and a single strand can fold onto itself to form a DNA nanoball (DNB™) which can be approximately 200-300 nanometers in diameter on average. In certain examples, a DNA nanoball is attached (e.g., by adsorption) to a microarray (sequencing flowcell). In further examples, the flow cell is a silicon wafer coated with silicon dioxide, titanium and hexamehtyldisilazane (HMDS) and a photoresist material. In some cases, sequencing is performed by unchained sequencing by ligating fluorescent probes to the DNA. In certain cases, the color of the fluorescence of an interrogated position is visualized by a high resolution camera. In further cases, the identity of nucleotide sequences between adaptor sequences is determined.

In some cases, high-throughput sequencing is performed using AnyDot.chips (Genovoxx, Germany). In particular, the AnyDot.chips allow for 10×-50× enhancement of nucleotide fluorescence signal detection. AnyDot.chips and methods for using them are described in part in International Publication Application Nos. WO 02088382, WO 03020968, WO 03031947, WO 2005044836, PCT/EP 05/05657, PCT/EP 05/05655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al. Science 24 Mar. 2000; and M. J. Levene, et al. Science 299:682-686, January 2003; as well as US Publication Application No. 20030044781 and 2006/0078937. Overall such system involve sequencing a target nucleic acid molecule having a plurality of bases by the temporal addition of bases via a polymerization reaction that is measured on a molecule of nucleic acid, i.e. the activity of a nucleic acid polymerizing enzyme on the template nucleic acid molecule to be sequenced is followed in real time. In some cases, the sequence is deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishable type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

Kits

In yet another aspect, the present disclosure provides kits comprising one or more components of the disclosure. In some cases, the kits are used for any application apparent to those of skill in the art, including those described above. In some cases, the kits comprise a plurality of association molecules, a fixative agent, a restriction endonuclease, a ligase, and/or a combination thereof. In some cases, the association molecules are proteins including, for example, histones. In some cases, the fixative agent is formaldehyde or any other DNA crosslinking agent.

In some cases, the kit further comprises a substrate. In some cases, the substrate comprises a plurality of resolved loci. In further examples, the substrate comprises more than about 10, about 20, about 50, about 100, about 200, about 500, about 1,000, about 2,000, about 5,000, about 10,000, about 20,000, about 50,000, about 100,000, about 200,000, about 500,000, about 1,000,000, about 2,000,000, about 5,000,000, about 10,000,000, about 20,000,000, about 50,000,000, or about 100,000,000 resolved loci. In certain examples, each of the resolved loci comprises a plurality of binding probes. In further examples, the resolve loci comprise more than about 10, about 20, about 50, about 100, about 200, about 500, about 1,000, about 2,000, about 5,000, about 10,000, about 20,000, about 50,000, about 100,000, about 200,000, about 500,000, about 1,000,000, about 2,000,000, about 5,000,000, about 10,000,000, about 20,000,000, about 50,000,000, or about 100,000,000 probes.

In some cases, the kit comprises adaptor polynucleotides. In other cases, the kit comprises barcoded polynucleotides or a barcoded template that can be used to generate barcoded polynucleotides. In some examples, the template is linear or circular.

In some cases, the kit further comprises a plurality of beads. In some cases, the beads are paramagnetic and/or are coated with a capturing agent. In further examples, the beads are coated with streptavidin and/or an antibody.

In some cases, the kit comprises adaptor oligonucleotides and/or sequencing primers. In further cases, the kit comprises a device capable of amplifying the read-pairs using the adaptor oligonucleotides and/or sequencing primers.

In some cases, the kit comprises sequencing adaptors and/or sequencing primers. In further cases, the kit comprises a device capable of amplifying the read-sets using the sequencing adaptors and/or sequencing primers.

In some cases, the kit comprises other reagents including but not limited to lysis buffers, ligation reagents (e.g. dNTPs, polymerase, polynucleotide kinase, and/or ligase buffer, etc.), and PCR reagents (e.g. dNTPs, polymerase, and/or PCR buffer, etc.), In certain cases, the kit includes instructions for using the components of the kit and/or for generating the read-sets.

Computer Systems

Figure 7:
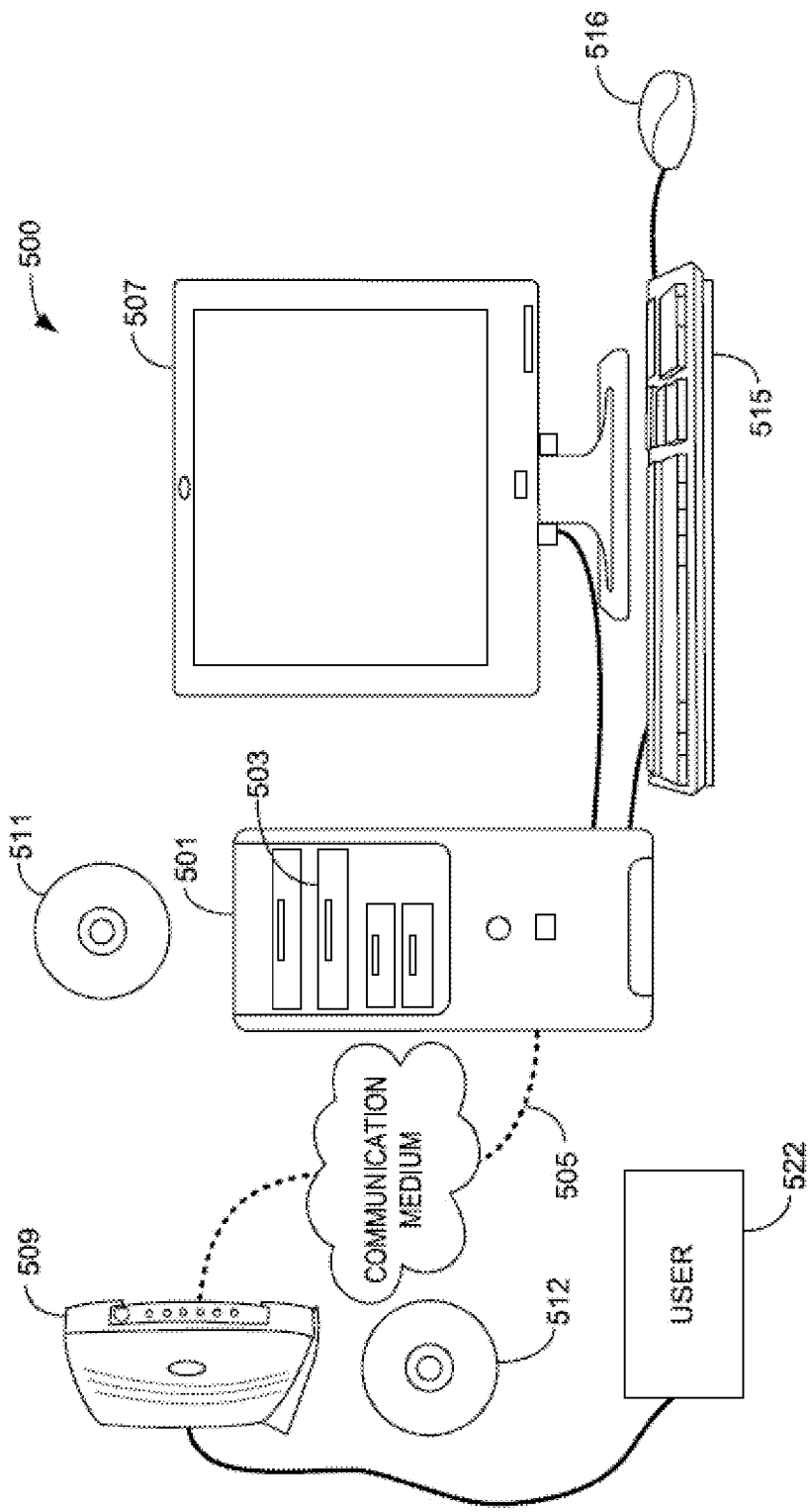
FIG. 7 illustrates various components of an exemplary computer system according to various embodiments of the present disclosure.

The computer system 500 illustrated in FIG. 7 may be understood as a logical apparatus that can read instructions from media 511 and/or a network port 505, which is optionally connected to server 509 having fixed media 512. In some cases, the system, such as shown in FIG. 7 includes a CPU 501, disk drives 503, optional input devices such as keyboard 515 and/or mouse 516 and optional monitor 507. In certain cases, data communication is achieved through the indicated communication medium to a server at a local or a remote location. In further cases, the communication medium includes any means of transmitting and/or receiving data. In some cases, the communication medium is a network connection, a wireless connection or an internet connection. In certain examples, such a connection provides for communication over the World Wide Web. It is envisioned that data relating to the present disclosure can be transmitted over such networks or connections for reception and/or review by a party 522 as illustrated in FIG. 7.

Figure 8:
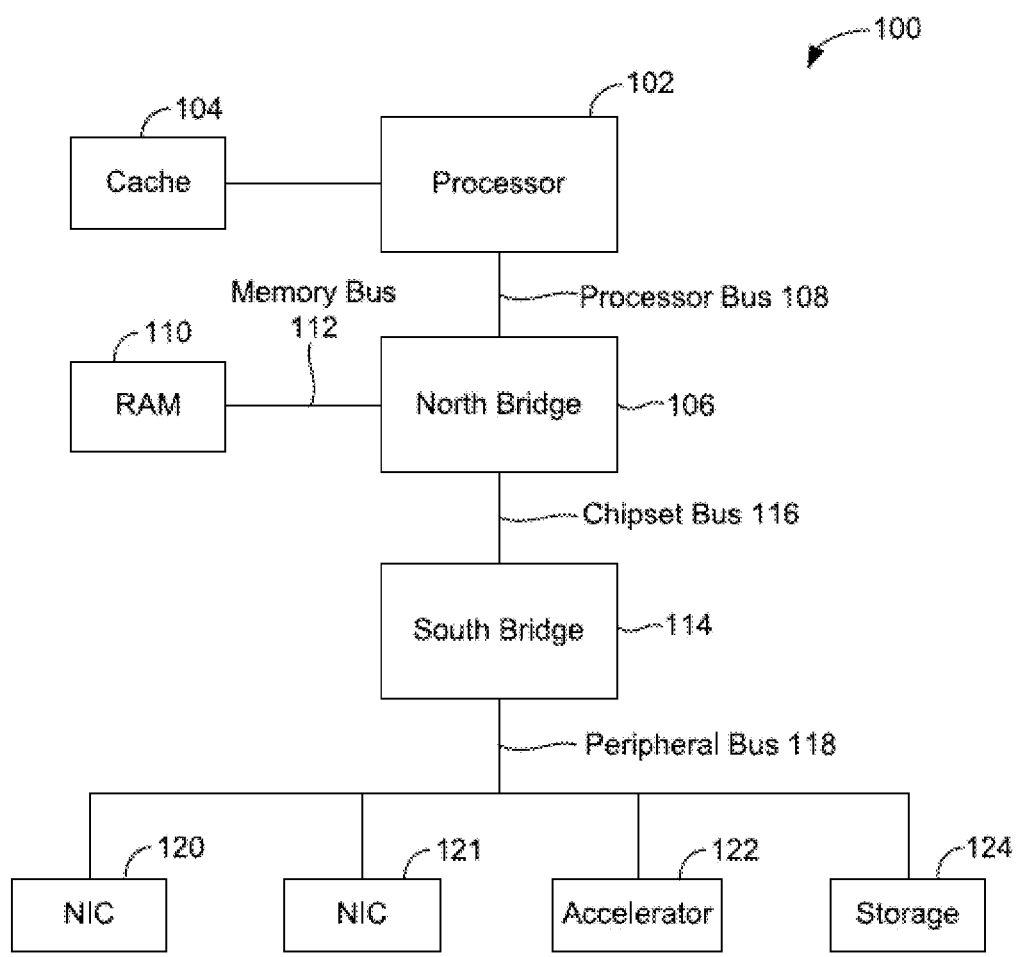
FIG. 8 is a block diagram illustrating the architecture of an exemplary computer system that can be used in connection with various embodiments of the present disclosure.

FIG. 8 is a block diagram illustrating a first example architecture of a computer system 100 that can be used in connection with example embodiments of the present disclosure. In certain cases, as depicted in FIG. 8, the example computer system includes a processor 102 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC 100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores are used, whether in a single computer system, in a cluster, or distributed across systems over a network comprising a plurality of computers, cell phones, and/or personal data assistant devices.

In various cases, as illustrated in FIG. 8, a high speed cache 104 is connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 includes an accelerator card 122 attached to the peripheral bus 118. In some cases, the accelerator includes field programmable gate arrays (FPGAs) or other hardware for accelerating certain processing. In further examples, an accelerator is used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present disclosure.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 9:
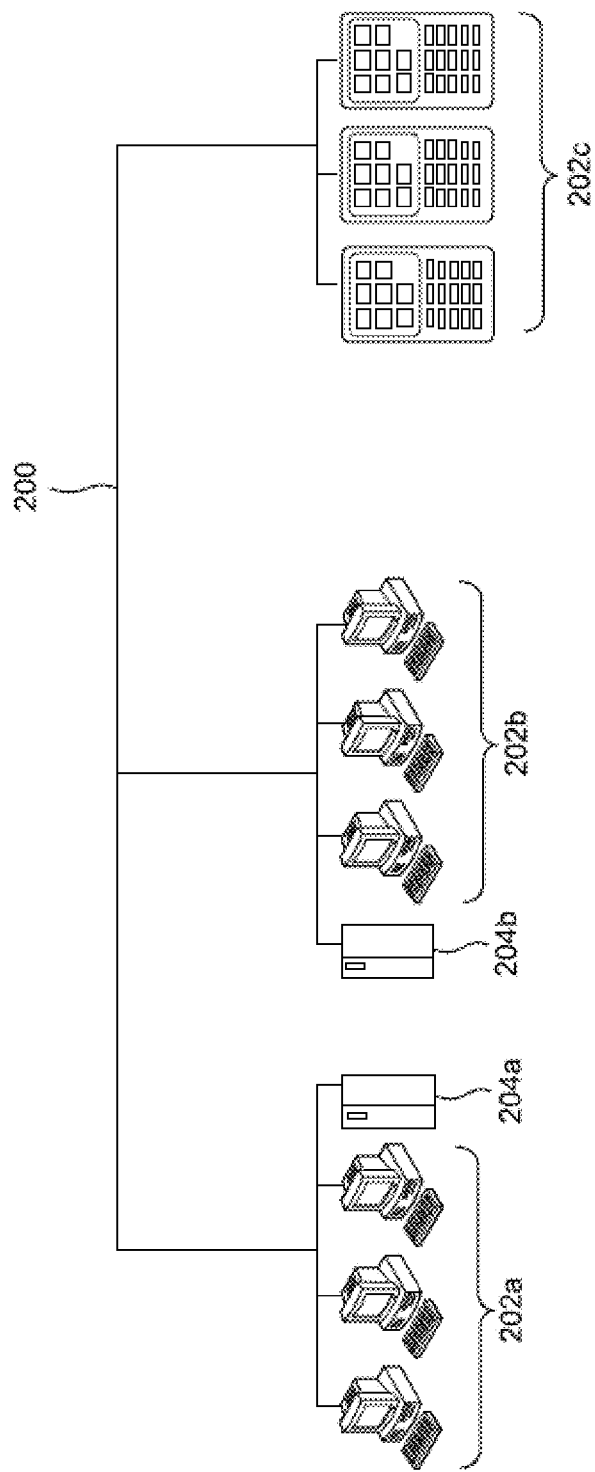
FIG. 9 is a diagram illustrating an exemplary computer network that can be used in connection with various embodiments of the present disclosure.

FIG. 9 is a diagram showing a network 200 with a plurality of computer systems 202a, and 202b, a plurality of cell phones and personal data assistants 202c, and Network Attached Storage (NAS) 204a, and 204b. In certain examples, systems 202a, 202b, and 202c manage data storage and optimize data access for data stored in Network Attached Storage (NAS) 204a and 204b. In some cases, a mathematical model is used for the data and evaluated using distributed parallel processing across computer systems 202a, and 202b, and cell phone and personal data assistant systems 202c. In certain cases, computer systems 202a, and 202b, and cell phone and personal data assistant systems 202c also provide parallel processing for adaptive data restructuring of the data stored in Network Attached Storage (NAS) 204a and 204b. FIG. 9 illustrates an example only, and a wide variety of other computer architectures and systems are used in conjunction with the various embodiments of the present disclosure. In some cases, a blade server is used to provide parallel processing. In further examples, processor blades are connected through a back plane to provide parallel processing. In certain examples, storage is connected to the back plane or as Network Attached Storage (NAS) through a separate network interface.

In some cases, processors maintain separate memory spaces and transmit data through network interfaces, back plane or other connectors for parallel processing by other processors. In other embodiments, some or all of the processors use a shared virtual address memory space.

Figure 10:
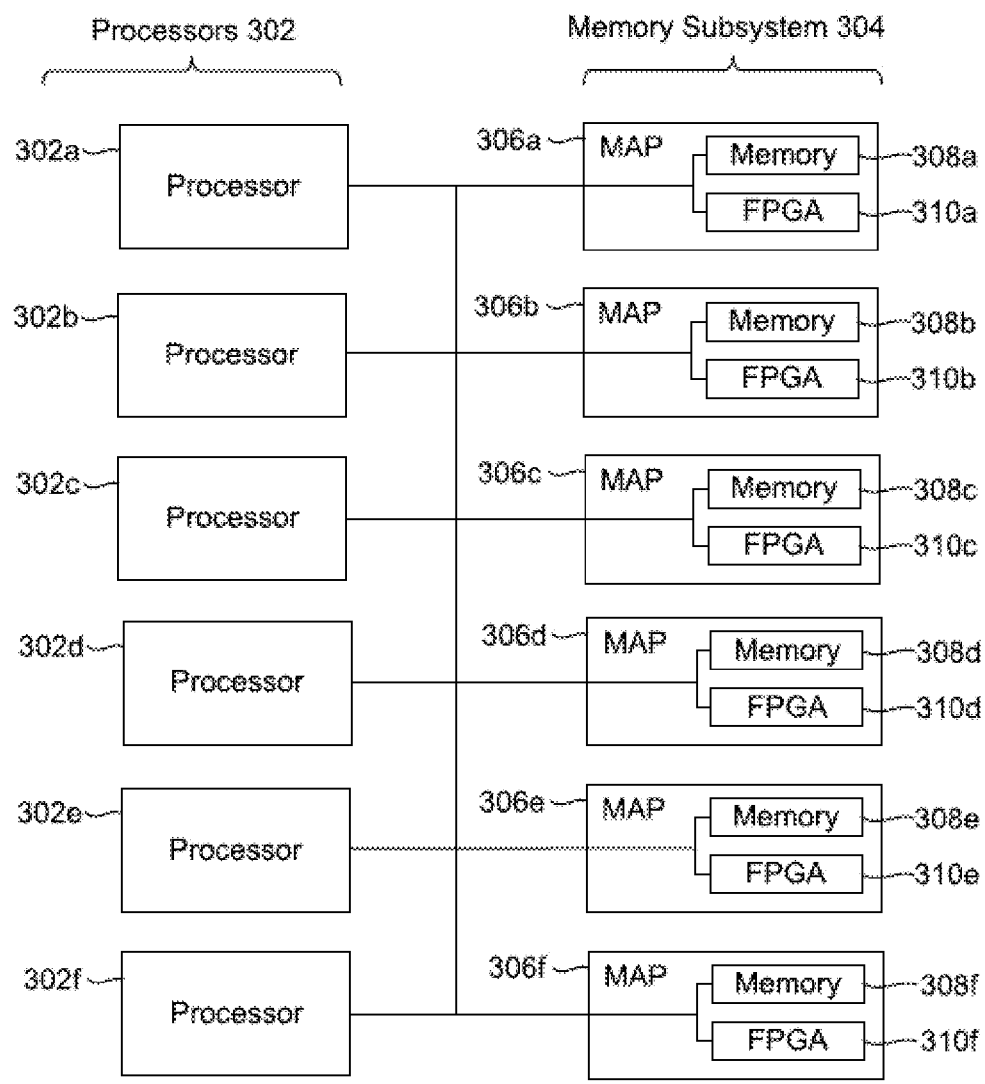
FIG. 10 is a block diagram illustrating the architecture of another exemplary computer system that can be used in connection with various embodiments of the present disclosure.

FIG. 10 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. In some cases, each MAP 306a-f comprises a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. In some cases, the MAPs are used to evaluate algebraic expressions regarding the data model and to perform adaptive data restructuring in example embodiments. In this example, each MAP is globally accessible by all of the processors for these purposes. In one configuration, each MAP uses Direct Memory Access (DMA) to access an associated memory 308a-f, allowing it to execute tasks independently of, and asynchronously from, the respective microprocessor 302a-f. In this configuration, a MAP feeds results directly to another MAP for pipelining and parallel execution of algorithms.

The above computer architectures and systems are examples only, and a wide variety of other computer, cell phone, and personal data assistant architectures and systems can be used in connection with exemplary embodiments, including systems using any combination of general processors, co-processors, FPGAs and other programmable logic devices, system on chips (SOCs), application specific integrated circuits (ASICs), and other processing and logic elements. In some embodiments, all or part of the computer system is implemented in software or hardware. In certain cases, any variety of data storage media is used in connection with example embodiments, including random access memory, hard drives, flash memory, tape drives, disk arrays, Network Attached Storage (NAS) and other local or distributed data storage devices and systems.

In some cases, the computer system is implemented using software modules executing on any of the above or other computer architectures and systems. In other embodiments, the functions of the system are implemented partially or completely in firmware, programmable logic devices such as field programmable gate arrays (FPGAs) as referenced in FIG. 10, system on chips (SOCs), application specific integrated circuits (ASICs), or other processing and logic elements. In some cases, the Set Processor and Optimizer is implemented with hardware acceleration through the use of a hardware accelerator card, such as accelerator card 122 illustrated in FIG. 8.

The following examples are intended to illustrate but not limit the disclosure. While they are typical of those that might be used, other procedures known to those skilled in the art may alternatively be used.

EXAMPLES

Example 1. Methods for Preparing the Substrate

The substrate used herein is a solid surface randomly coated with clusters of DNA, each of which contain many DNA molecules that can associate with appropriately prepared chromatin aggregates. Each cluster can be identified by a unique DNA barcode found within each DNA molecule of the cluster. In some cases, the solid surface is a glass coverslip or a magnetic microbead covered with a chemical that can form covalent bonds with appropriately modified oligonucleotides.

Two sets of oligonucleotides are synthesized with a chemical reactive group on the 5' carbon of a terminal deoxyribose (FIG. 6A.1) The first set is termed the "adaptor oligonucleotide" and contains DNA sequence that serves three purposes: 1) to capture barcode oligonucleotides; 2) to provide an adaptor for high throughput sequencing; and 3) serve as a primer during bridge amplification. The second set of oligonucleotides is termed the "chromatin capture oligonucleotide", or CCO, and has two purposes: 1) to provide a priming site for bridge amplification; and 2) to provide the capture sequence that is used to capture chromatin aggregates. A portion of the capture sequence contains a site that permits double stranded cleavage at a later step. An example of such a site is an EcoRV blunt-ended restriction endonuclease recognition site. Both sets of oligonucleotides have several spacer groups between the 5' reactive group and beginning of nucleotide sequence. An example of an appropriate spacer is hexaethylene glycol. The spacer will serve to provide enough distance between the nucleotide sequence and solid surface such that a polymerase may fully transcribe the attached nucleotides without being impeded by the glass surface.

These two sets of oligonucleotides are attached to a glass surface via complementary reaction groups found on the glass surface (FIG. 6A.2). For example, the glass surface may be coated with epoxysilane, which will covalently bind to oligonucleotides with an amino group attached to a terminal 5' deoxyribose via a phosphate group.

A third set of oligonucleotides is synthesized (FIG. 6A.3). Each oligonucleotide has the following functional domains of DNA sequence from 5' to 3': 1) the full capture sequence; 2) a randomized length of N nucleotides that serve as a barcode; and 3) the reverse complement of the adaptor oligonucleotide. The minimum length of N is such that the probability of selecting a uniquely barcoded oligonucleotide out of a given number of oligonucleotides is acceptable. A length of N=20 is likely appropriate as $4^{20}$ permutations are possible.

This third set of oligonucleotides is applied at a given density to a glass surface that has a lawn of adaptor and CCO oligonucleotides (FIG. 6A.4). Each individual, uniquely barcoded oligonucleotide is then copied onto the glass surface by DNA polymerase extension (FIG. 6A.5). A number of clones of each barcoded oligonucleotide are then generated by bridge amplification PCR (FIG. 6A.6-9). The number of oligonucleotide clones and the diameter of the clonal colony is controllable by the number of PCR cycles performed. For example, a total of 10 PCR reaction cycles may be suitable to generate 1024 single-stranded templates, 512 of which will end with the capture sequence. The diameter of the cluster is likely to be no more than 1 micrometer in size.

After sufficient cycles of bridge amplification have been performed, the synthesized strands of DNA are allowed to base pair with their complement (FIG. 6A.10). The capture sequence in the CCO is present in its double-stranded form and contains a recognition site for the blunt-end restriction endonuclease EcoRV, which is added to create a double strand break within the capture sequence. This effectively removes DNA strands that begin at the 5' end with the CCO and capture sequence (FIG. 6A.11), which is important to ensure that the capture sequence present at the end of the adaptor oligonucleotide is available to bind only to chromatin aggregates.

Other DNA sequences, whether arbitrary or a specific sequence such as a primer site may be placed within the barcoded oligonucleotide between the reverse complement of the adaptor oligonucleotide and capture sequence. These DNA sequences may serve any function. For example, they may make the final capture oligonucleotide longer, or they may provide a priming site for a primer.

Example 2. Methods for Generating Labeled Polynucleotides

In vitro chromatin is assembled from genomic DNA and histone proteins, cross-linked and digested with a restriction enzyme. Alternatively, the chromatin may be fragmented using any restriction enzyme or any appropriate method. The digested ends are blunt-ended, the 3'-ends are adenylated, and an adaptor sequence is linked using TA-mediated ligation (FIG. 6B.1). This adaptor sequence has a single-stranded 3' segment that is the reverse complement of the chromatin capture sequence.

This prepared chromatin is added to the substrate containing clusters of barcoded DNA. Individual chromatin aggregates are ligated to individual clonal clusters on the substrate (FIG. 6B.2). DNA polymerase is provided to add a second strand to the full length of the adaptor oligonucleotide (FIG. 6B.3). Chromatin is removed, and the free end of the duplexes is treated to become blunt ended (FIG. 6B.4). The blunt ends are adenylated at the 3' deoxyribose carbon and ligated to a dsDNA adaptor with a 3' thymidine overhang (FIG. 6B.5). This adaptor contains additional sequences for high-throughput sequencing.

In some cases, the chromatin DNA attached to the substrate may be too long for sequencing without further treatment prior to adenylating blunt ends and attaching an adaptor. A number of alternative processes are available to shorten DNA prior to adenylation and attaching an adaptor. One method is to use a restriction enzyme that will cut only within the sample DNA, not the DNA provided by the substrate oligonucleotides. In certain cases, this modified DNA is blunt-ended prior to 3' adenylation and adaptor ligation. In other cases, a specific restriction enzyme recognition sequence is engineered into the very 5' end of the adaptor sequence and a restriction enzyme used to free DNA from the substrate. In further cases, chemical methods are used directly on the substrate to liberate DNA from the substrate. In various cases, the liberated DNA is then shortened by shearing methods, including sonication, nebulization or enzymatic digestion.

The common adaptors on both ends of the duplex DNA on the duplex on the substrate allow for PCR amplification. PCR is performed in the presence of the substrate. Alternatively, the synthesized second strand may be melted off the substrate and transferred to a separate PCR reaction. After appropriate PCR amplification reactions, high-throughput DNA sequencing is conducted to identify genomic sequences, which are grouped into individual chromatin aggregates or read-sets based on the sequenced barcode. These grouped sequences provide useful data for more accurate de novo genome assembly.

Example 3. Surface Loci Preparation

Two distinct oligonucleotides are synthesized as appropriate for attachment to a solid surface. Reference is made to FIG. 6.A.1-6.A.9. To aid in describing this method, oligonucleotides for attachment to a silanized glass coverslip will be described.

The following are codes for use with Integrated DNA Technologies for ordering oligonucleotides/5AmMC 12/ is a 12-carbon group with an amino moiety for attachment to an epoxysilane glass surface. /iSp18/ is a hexaethyleglycol group intended for increasing the distance between a solid surface and the DNA sequence of an oligonucleotide attached to the surface.

Adaptor Oligonucleotide.

The adaptor oligonucleotide contains an amino group at its 5' end for attachment to an epoxysilane-coated glass surface. This amino group is separated from DNA sequence by a sequence of 1 to 10 18-carbon spacers. There will be a number (#) of these spacers present, which is to be determined but likely will not be more than 5. The spacers function to provide spatial distance between the solid glass surface and DNA sequence to prevent steric hindrance of enzymes used in later steps.

There are three functions of the adaptor oligonucleotide: 1. Provide common adapter sequence that will be needed for later high throughput DNA sequencing; 2. Serve as the anneal sites for barcoded oligonucleotides in a later step; 3. Serve as a primer for bridge amplification.

Chromatin Capture Oligonucleotide (CCO).

The chromatin capture oligonucleotide contains an amino group at its 5' end for attachment to an epoxysilane coated glass surface. This amino group is separated from DNA sequence by a sequence of 1 to 10 18-carbon spacers. There will be a number (#) of these spacers present, which is to be determined but likely will not be more than 5. The spacers function to provide spatial distance between the solid glass surface and DNA sequence to prevent steric hindrance of enzymes used in later steps. It will be necessary to remove this oligo and extended sequence later to prevent stable bridge products that would inhibit association with chromatin. One method described here involves the use of the blunt end restriction endonuclease EcoRV (GAT^ATC). There are other analogous methods that may be used as appropriate. Note that the DNA sequence of the CCO is an example; alternatives are consistent with the methods herein.

There are two functions of the chromatin capture oligo: 1. Serve as a primer for bridge amplification; 2. Provide the DNA sequence (termed "capture sequence") that will be copied onto DNA molecules within a cluster during bridge amplification. The 3' end of these DNA molecules will contain the reverse complement of this capture sequence and will anneal to its reverse complement found in 5' ssDNA overhangs present in appropriately prepared chromatin aggregates. The capture sequence found within the first set of sequence in the 5' end of the CCO, after the 18-carbon spacer.

Oligonucleotides are Attached to a Silanized Glass Surface.

Epoxysilanized cover slips can be prepared or purchased. The structure and reaction with an amine are summarized in FIG. 6A.2. The P5 and CCO oligos that have an amino group attached to their 5' end are mixed together in equimolar amounts and applied to a silanized cover slip. The amino group will react with the epoxy ring and covalenty attach the oligonucleotides to the glass surface.

Shown in FIG. 6A.3 is a representation of the two oligos covalently attached to a glass surface. The spacer groups are present but are left out for clarity.

Barcoded Oligonucleotides are Synthesized.

Barcoded oligonucleotides of the following sequence are synthesized as indicated in FIG. 6A.3. Note that the sequence may vary based on the final sequences chosen for the adaptor and chromatin capture oligonucleotides:

This oligonucleotide has 3 important features, from 5' to 3': 1. The reverse complement of the CCO; 2. A 20-mer randomized sequence that serves as a barcode. There are $4^{20}$ possible permutations, and the probability that two randomly chosen oligos have the same barcode sequence is exceedingly low; 3. The reverse complement of the P5 oligo. This will anneal to the P5 oligo attached to the glass surface, and later strand extension is possible.

Barcoded oligonucleotides are annealed to the P5 oligo on the glass surface. These oligos are added to the surface at an appropriate concentration to ensure generation of optimally spaced clonal clusters as indicated in FIG. 6A.4. During the same annealing reaction, strand extension with DNA Polymerase, Klenow fragment is conducted as indicated in FIG. 6.A.5.

PCR Thermocycling is Performed.

One cycle of PCR is performed as indicated in FIG. 6A.6-6A.9. In FIG. 6A.6, the original barcoded oligos are removed during the initial denaturation step of the PCR. In FIG. 6A.7, primer annealing occurs. In FIG. 6A.8. Strand extension is accomplished using a thermostable polymerase such as Taq. In FIG. 6A.9, one sees the end result of one cycle of PCR after melting the duplexes. After multiple cycles of bridge PCR amplification are performed, two types of strands are generated and represented in FIG. 6A.9. At the point depicted in FIG. 6A.10, it is possible for stable bridges to form, which will hinder association with chromatin aggregates. Stable bridges are allowed to form, which is Tm dependent, and EcoRV is added to create a blunt end, as illustrated in FIG. 6A.11.

The platform is now ready to be ligated to appropriately prepared chromatin.

Example 4. DNA Complex Ligation and Library Preparation

The platform is incubated with chromatin aggregates, and each cluster interacts with one chromatin aggregate. DNA fragments found within each chromatin aggregate are ligated to the platform, and a series of enzymatic processes are conducted to prepare a library of DNA fragments for high-throughput sequencing. As described elsewhere, and as seen in FIG. 6B.1, chromatin is prepared and ligated to an universal adaptor that has 3' ssDNA which has its reverse complement at the 3' end of the Pittsburgh clusters. Shown below is a chromatin aggregate. For simplicity, the grey circle is a chromatin aggregate with all nucleosomes and DNA associated with it. There are be a number of adaptor-ligated DNA fragments, but only one is shown.

As seen in FIG. 6B.2, Chromatin (DNA complexes) are ligated to the capture sequence on the Pittsburgh platform. As seen in FIG. 6B.3, the 3' end of the ligated chromatin is extended with a DNA polymerase such as Klenow fragment. As seen in FIG. 6B.4, Chromatin is removed. As seen in FIG. 6B.5, the free 3' end is adenylated with a polymerase such as Klenow (3'-5' exo-). As seen in FIG. 6B.6, a sequencing adaptor is ligated by TA ligation with a DNA ligase such as T4 DNA ligase. The adaptor shown here is a P7 adaptor. As seen in FIG. 6B.7, PCR may now be performed to obtain sufficient quantities of product for high-throughput sequencing. It should not be necessary to remove the Pittsburgh platform from the PCR reaction.

Example 5. Contig Ordering Using Sequence Read Information

An example using the methods herein to assemble contigs into a linear order is provided. Contig information for the sequenced non-diploid human genome is obtained from a publicly available source such as the National Center for Biotechnology Information. Individuals harboring at least one wild-type allele of the full length version of the gene are able to metabolize the drug, while individuals lacking a wild-type allele of the gene accumulate the drug to levels detrimental to individual health. The gene comprises a 100 kb region of the human genome, and the coding region is interrupted by a number of long, AT-dinucleotide repetitive introns that complicate assembly of the locus.

Two deleterious mutation sites are known in the gene in many populations. The two deleterious mutations are separated by 10s of thousands of kb of sequence, spanning a number of introns harboring the repeat sequence. One of the two deleterious mutations is in the coding region, while the other is in the putative promoter region and affects transcript accumulation only when the drug is administered.

An individual's genomic sample is sequenced using locus-targeted PCR spanning two regions of the gene known to harbor deleterious mutations in some individuals. Sequences of the PCR amplicons indicate that, at each region of the gene, the individual is heterozygous for a deleterious mutation.

A genomic DNA sample is obtained from a single individual identified as being heterozygous for deleterious mutations at two positions in the gene relevant to the metabolism of the drug. Nucleic acids are extracted, separated from native chromatin, partially sheared by treatment with an endonuclease and then artificial chromatin is reassembled by the addition of nucleosomes to the partially sheared nucleic acid sample. The nucleic acid-artificial chromatin complexes are cross-linked by treatment with formaldehyde and contacted with the restriction endonuclease MboI.

A surface to which DNA may bind is provided, upon which are synthesized a plurality of features, each being a population of millions of identical custom-designed DNA oligomers comprising a 3' MboI-compatible complementary end, a feature specific barcode that varies for each feature (spot) on the array, and a P5 Illumina adapter joined to the array at a 5' end.

The cross-linked, MboI digested nucleic acid-artificial chromatin complexes are contacted to the array and their complementary ends are allowed to hybridize to the DNA array features. The complexes are treated with ligase and then agitated to allow the nucleic acids to break upstream of the ligation point, such that sheared DNA complexes are removed, and nucleic acids comprising the original oligo sequence and a stretch of target sample nucleic acid sequence ligated thereto remain on the array. Cleaved ends are repaired and a second sequencing adapter is ligated to the free end of the oligonucleotides. Molecules are converted to an Illumina library by PCR using primers that anneal to the first and second sequencing adapter sequences, and sequence sets are generated. Sequences are mapped to the contigs obtained as discussed above.

It is observed that sequence read sets sharing a common molecular tag/barcode sequence map to a common set of contigs. In some instances a sequence read set comprises sequence reads that map to two distinct sets of contigs believed to map to distinct regions of the genome. This outcome indicates that two separate DNA complexes, representing two distinct nucleic acid molecules, annealed to the same olio locus on the array. The molecules, or the distinct read subsets among the population of sequence reads having the molecular tag, are easily distinguished in light of their mapping to two distinct sets of contigs.

It is observed that a sequence read indicating a mutant coding region maps to a contig corresponding to the locus of the drug resistance gene. Similarly, a sequence read indicating a wild-type coding region also maps to a contig corresponding to the locus of the drug resistance gene. A sequence corresponding to a mutant promoter region maps to a contig corresponding to the promoter of the drug resistance gene, and a sequence corresponding to a wild-type promoter region maps to a contig corresponding to the promoter of the drug resistance gene.

The feature-specific barcode of each sequence read is investigated. No two feature-specific reads match, indicating that no two reads resulted from the same post-shearing nucleic acid molecule.

However, it is found that the read corresponding to the mutant coding region shares a feature-specific barcode with a number reads spanning single-nucleotide polymorphisms (SNPs) of unknown function that also map to the drug resistance gene, 5' of the coding region mutation, indicating that the coding region mutation and the SNPs are physically linked, or in phase, with one another. It is also found that the read corresponding to the mutant promoter region shares a feature-specific barcode with a number of reads spanning of single-nucleotide polymorphisms of unknown function that also map to the drug resistance gene, 3' of the coding region mutation, indicating that the coding region mutation and the SNPs are physically linked, or in phase, with one another.

The sequences of the two inferred physically linked molecules are compared and found to share SNP sequences in common. It is inferred that the gene of interest was cut during the endonuclease/shearing process multiple times, generating multiple overlapping fragments.

It is concluded that the drug-resistance gene coding region mutation and the drug resistance gene promoter mutation map to a single allele of the drug resistance gene on a single physical chromosome.

Similarly, it is found that the read corresponding to the wild-type coding region shares a feature-specific barcode with a number reads spanning single-nucleotide polymorphisms (SNPs) of unknown function, different from those mentioned above, that also map to the drug resistance gene, 5' of the coding region site, indicating that the coding region mutation and the SNPs are physically linked, or in phase, with one another. It is also found that the read corresponding to the wild-type promoter region shares a feature-specific barcode with a number of reads spanning the single-nucleotide polymorphisms of unknown function mentioned immediately above, that also map to the drug resistance gene, 3' of the promoter region, indicating that the wild-type coding region and the second set of SNPs are physically linked, or in phase, with one another.

The sequences of the two inferred physically linked molecules are compared and found to share SNP sequences in common. It is inferred that the gene of interest was cut during the endonuclease/shearing process multiple times, generating multiple overlapping fragments.

It is concluded that the drug-resistance gene coding region wild-type sequence and the drug resistance gene wild-type promoter map to a single allele of the drug resistance gene on a single physical chromosome.

It is further concluded that the individual's genome encodes a functional drug-resistance gene.

Example 6. Methods for Attaching a Universal Adaptor to Crosslinked Chromatin

Chromatin aggregates are cross-linked with formaldehyde and digested with the MboI restriction enzyme. The recessed 3' ends are filled in with DNA polymerase (FIG. 14A.1). Using Klenow (3'-5' exo), the 3' ends are adenylated (FIG. 14A.2). Adaptors are ligated via TA-mediated ligation using DNA ligase. The adapters have 3 sections: 1) a single-stranded 5' overhang suitable for a chromatin capture platform; 2) a double-stranded region that functions to form an adaptor and further comprises a barcode region; and 3) a 3' T overhang for TA ligation (FIG. 14A.3). The free 5' ends are phoshorylated and ligated to the downstream chromatin capture platform, which has multiple resolved loci each comprising binding probes that share a locus-specific barcode. Each of the adaptors are extended using the binding probes as templates to generate extension products that comprise the locus-specific barcodes. Illumina sequencing adaptors are ligated to the extension products, which are subsequently amplified and characterized by high-throughput sequencing. Based on the sequencing information, the extension products that share the same locus-specific are binned together to form a read-set. The read-sets are used to determine the order and orientation of known contigs, and thereby assemble a genome.

Example 7. Using Barcoded Aggregates to Label Crosslinked DNA Complexes

Figure 15A:
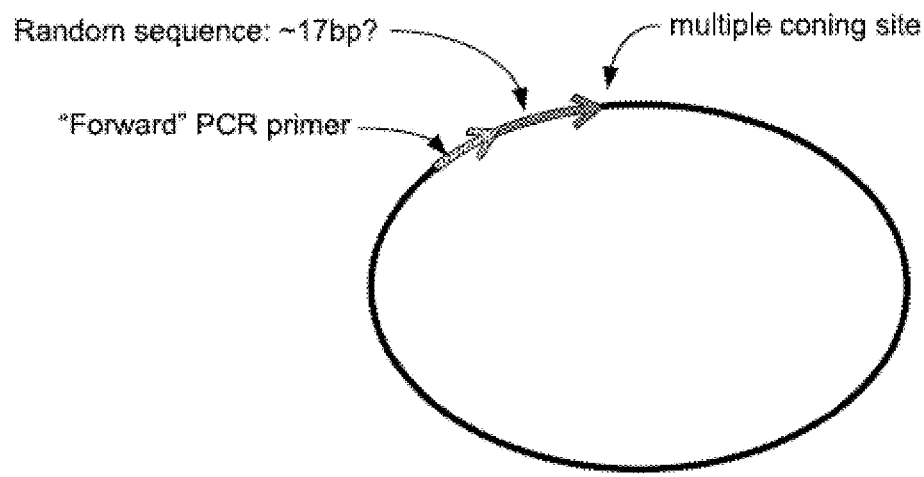
FIG. 15A-F provides an exemplary demonstration of implementation of methods disclosed herein.
Figure 15B:
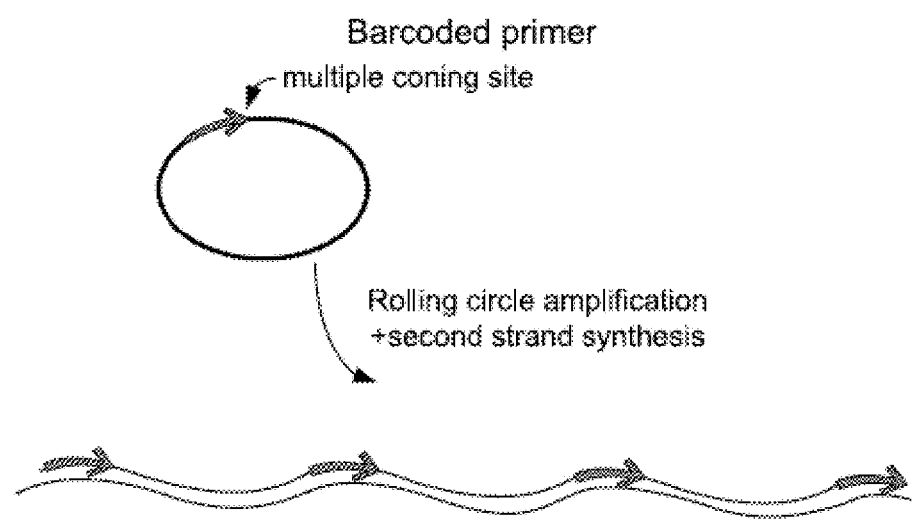
Figure 15C:
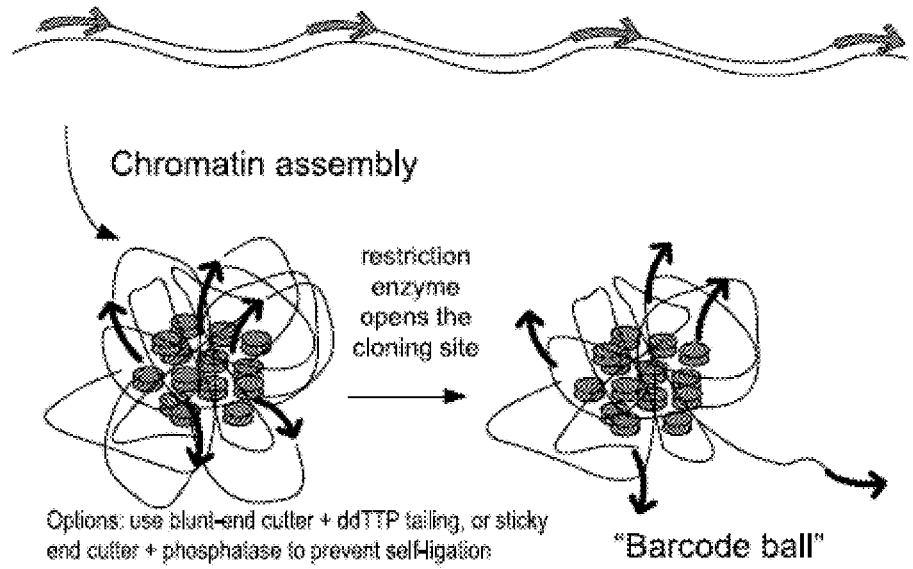
Figure 15D:
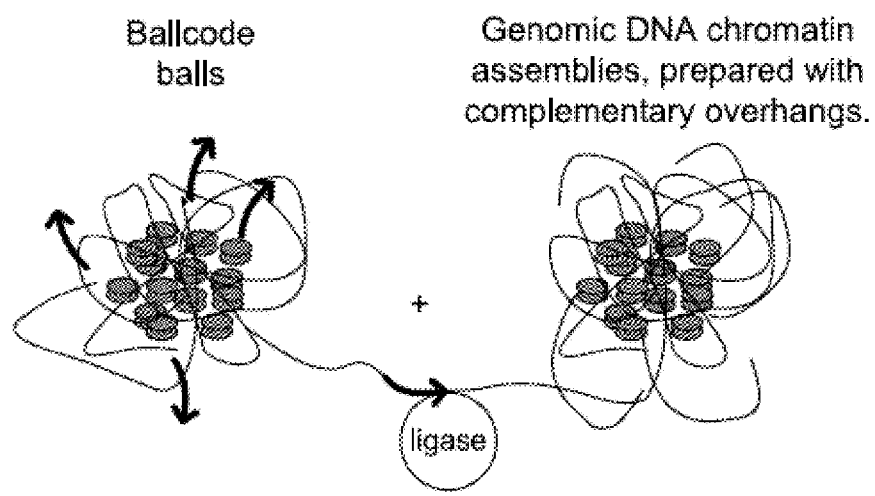
Figure 15E:
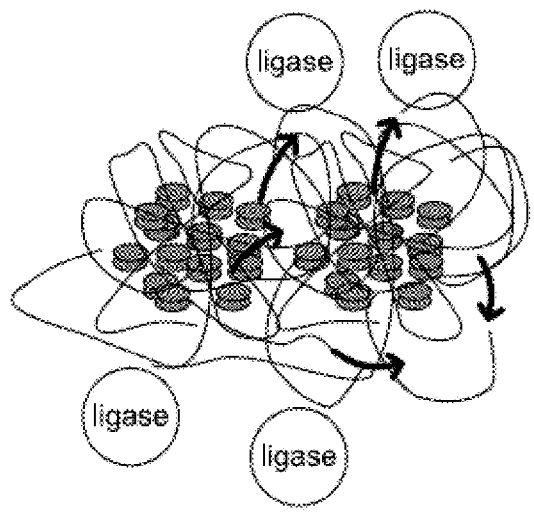
Figure 15F:
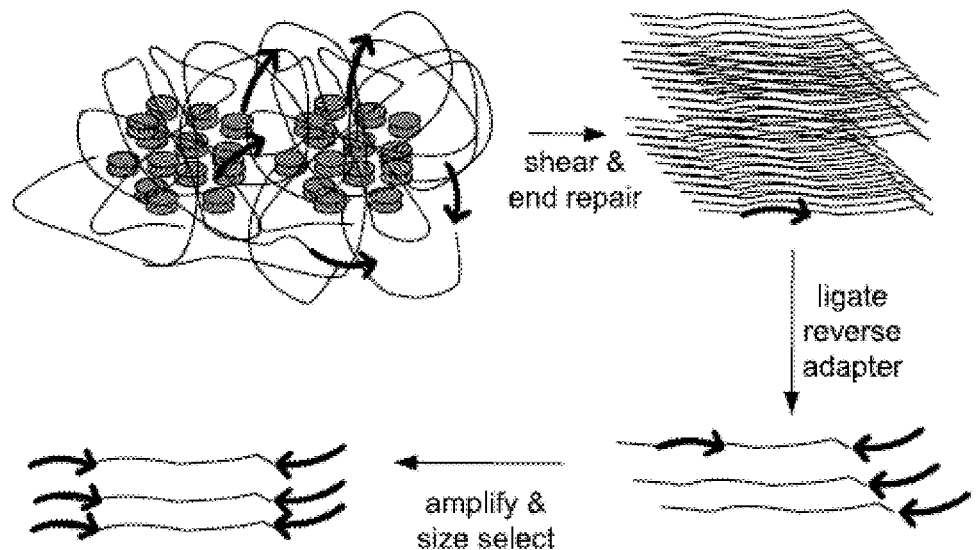
Figures 16A, 16B:
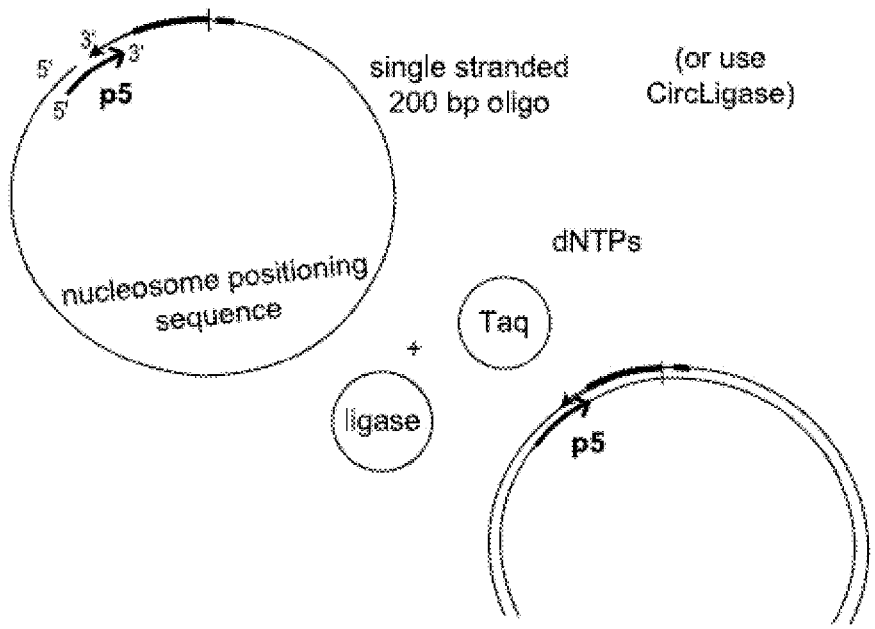
Figure 16C:
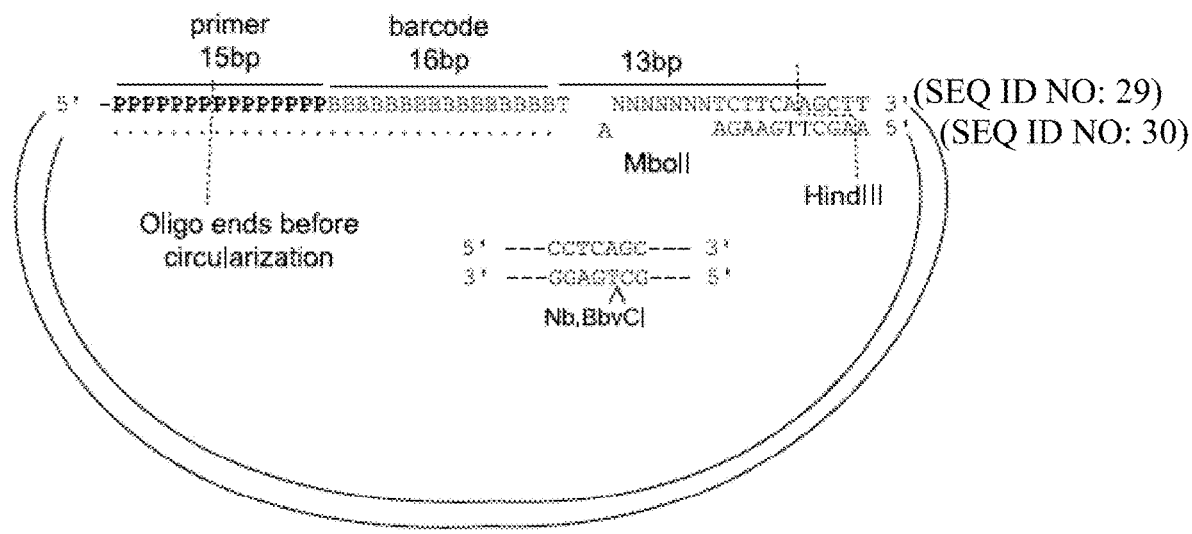
Figure 16D:
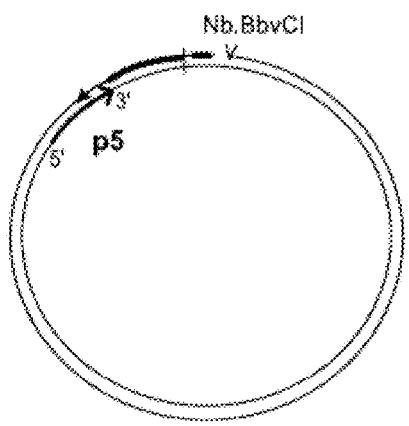

Single-stranded DNA molecules each comprising a restriction enzyme recognition site and a barcode sequence are designed and synthesized. The linear DNA molecules are circularized directly using CircLigase (from epobio.com), which catalyzes intramolecular ligation (FIG. 15A). The circularized ssDNAs are amplified using Rolling Circle Amplification (RCA) and the second strands are synthesized (FIG. 15B). The resulting double-stranded DNA molecules are purified and assembled into chromatin in vitro using the Active Motif kit (#102074). The chromatin complexes are fixed in 1% formaldehyde solution and digested with MboI and HindIII to generate the barcoded aggregates (i.e. "barcode balls") (FIG. 15C). MboI exposes a 3' T base immediate adjacent to the barcode, while HindIII removes the complementary A and thus preventing re-ligation within the barcoded aggregate. The barcoded aggregates are ligated to cross-linked DNA complexes in sufficiently dilute conditions such that the barcoded aggregates are each ligated to at most one DNA complex (FIGS. 15D & 15E). The ligated barcoded aggregate-DNA complex is sheared and end repaired to generate sequence segments, some of which are labeled with the barcode (FIG. 15F). A reverse adaptor is ligated to the sequence segments, which are subsequently amplified, size selected, and characterized by high-throughput sequencing. Based on the sequencing information, the extension products that share the same locus-specific are binned together to form a read-set. The read-sets are used to determine the order and orientation of known contigs, and thereby assemble a genome.

Example 8. Methods for Associating Sequence Segments in an Emulsion

An example using an emulsion is provided, but other methods of isolation (e.g., microfluidics) or treatment (e.g., not tagging but directly ligating genomic fragments) may be easily employed for the same purpose. Consequently, the example is simply provided for illustrative purposes and is by no means exhaustive.

The reconstituted chromatin used herein is procured by in vitro assembly of histones on naked DNA. The chromatin is then cross-linked with formaldehyde and treated with the restriction enzyme NlaIII, which leaves a 4 bp 3' overhang. The digested chromatin is treated with phosphatase to remove 5' and 3' phosphates to prevent re-ligation of native fragments. The treated chromatin is added to an aqueous droplet (FIG. 18A), along with a. a synthetic rolling circle amplification (RCA) construct consisting of circularized, double-stranded DNA with one of the strands nicked (FIG. 18E); b. a warm start polymerase (e.g., NEB's Bst 2.0 WarmStart DNA Polymerase); c. a primer for second strand synthesis, which is complementary to a priming site on the first strand product of the RCA product; d. a restriction enzyme BstXI for shearing the double-stranded second strand products into tags with complementarity to the DNA overhangs (FIG. 18E); and e. a thermostable Taq ligase. The RCA construct sequence comprises a random barcode, forward and reverse priming sites, a compound restriction site, and a known sequence to mark the position of the barcode.

Oil and other reagents required for the emulsion are added to the prepared solution and an emulsion is generated through blending, vortexing, etc. This yields many "nanoreactors", or reaction volumes, which are solution compartments in the emulsion containing some number of aggregates and synthetic constructs. A substantial percentage of the reaction volumes contain a single aggregate and a single construct (FIG. 18B).

RCA is then begun by raising the temperature of the emulsion to the activation temperature of the polymerase, which is 65° C. in the case of Bst 2.0 WarmStart. A single long product is produced from the initial circular RCA construct, which then becomes double-stranded with the second strand primer and further polymerization (FIG. 18C).

After a period of time, the temperature is lowered to the optimal temperature for the restriction enzyme, which is 37° C. in the case of BstXI. This slows down further template polymerization while allowing the restriction enzyme time to cut up synthesized templates to produce many tags. The polymerization, restriction digestion, and ligation, should all be occurring simultaneously, but the relative efficiency of each process is modified by altering the temperature.

After some time the temperature is raised to 80° C. for 20 minutes to completely inactivate the polymerase and restriction enzyme. The temperature is then lowered to the optimal temperature of the ligase, which is 45° C. in the case of Taq ligase, to complete ligation of tags to subject DNA (FIG. 18D).

The emulsion is broken and the products collected and characterized by high throughput sequencing. Connections between segments of fragments are recovered by gathering all reads with identical barcodes, which are analyzed as reads from the same initial aggregate.

Example 9. Methods to Generate Chromatin In Vitro

Two approaches to reconstitute chromatin are of particular attention: one approach is to use ATP-independent random deposition of histones onto DNA, while the other approach uses ATP-dependent assembly of periodic nucleosomes. The disclosure allows the use of either approach with one or more methods disclosed herein. Examples of both approaches to generate chromatin can be found in Lusser et al. ("Strategies for the reconstitution of chromatin," Nature Methods (2004), 1(1): 19-26), which is incorporated herein by reference in its entirety, including the references cited therein.

Example 10. Genome Assembly Using Chromatin Capture Techniques

A genome from a human subject was fragmented into pseudo-contigs having a size of 500 kb. Using a chromatin capture method, a plurality of read pairs were generated by probing the physical layout of chromosomes within living cells. Any number of chromatin capture methods can be used to generate read pairs, including the method presented in Lieberman-Aiden et al. ("Comprehensive mapping of long range interactions reveals folding principles of the human genome," Science (2009), 326(5950):289-293), which is incorporated herein in-full, including the references cited therein. Read pairs were mapped to all pseudo-contigs and those pairs that mapped to two separate pseudo-contigs, were used to construct an adjacency matrix based upon the mapping data. At least about 50%, about 60%, about 70%, about 80%, about 90%, about 95% or about 99% of the read pairs were weighted by taking a function of the read's distance to the edge of the pseudo-contig so as to mathematically incorporate the empirically known higher probability of shorter contacts than longer contacts. Then, for each pseudo-contig, the adjacency matrix was analyzed to determine a path through the pseudo-contigs by finding the single best neighbor pseudo-contig, which was determined by having the highest sum-of-weights. By performing these methods, it was found that >97% of all pseudo-contigs identified their correct neighbor. In some cases, additional experiments are performed to test the impact of shorter contigs and alternate weighting and path-finding schemes.

Alternatively, genome assembly using data generated from chromatin capture can include computational methods that exploit the signal of genomic proximity in chromatin capture data sets for ultra-long scaffolding of de novo genome assemblies. Examples of such computational methods that can used with the methods disclosed herein, include the ligating adjacent chromatin method by Burton et al. (*Nature Biotechnology* 31:1119-1125 (2013)); and a DNA triangulation method by Kaplan et al. (*Nature Biotechnology* 31:1143-47 (2013)), which references are incorporated herein in-full, and any references cited therein. Further, it should be understood that these computational methods can be used in combination, including with the other genome assembly methods presented herein.

For example, a ligating adjacent chromatin method based on Burton et al. comprising the steps of (a) clustering contigs to chromosome groups, (b) ordering the contigs within one or more chromosome group, and then (c) assigning relative orientations to individual contigs, can be used with the methods disclosed herein. For step (a), contigs are placed into groups using hierarchical clustering. A graph is built, with each node initially representing one contig, and each edge between nodes having a weight equal to the number of chromatin capture read-pairs linking the two contigs. The contigs are merged together using hierarchical agglomerative clustering with an average-linkage metric, which is applied until the number of groups are reduced to the expected number of distinct chromosomes (counting only groups with more than one contig). Repetitive contigs (contigs whose average link density with other contigs, normalized by number of restriction fragment sites, is greater than two times the average link density) and contigs with too few restriction fragment sites are not clustered. However, after clustering, each of these contigs is assigned to a group if its average link density with that group is greater than four times its average link densities with any other group. For step (b), a graph is built as in the clustering step, but with the edge weights between nodes equal to the inverse of the number of chromatin capture links between the contigs, normalized by the number of restriction fragment sites per contig. Short contigs are excluded from this graph. A minimum spanning tree is calculated for this graph. The longest path in this tree, the "trunk", is found. The spanning tree is then modified so as to lengthen the trunk by adding to it contigs adjacent to the trunk, in ways that keep the total edge weight heuristically low. After a lengthened trunk is found for each group, it is converted into a full ordering as follows. The trunk is removed from the spanning tree, leaving a set of "branches" containing all contigs not in the trunk. These branches are reinserted into the trunk, the longest branches first, with the insertion sites chosen so as to maximize the number of links between adjacent contigs in the ordering. Short fragments are not reinserted; as a result, many small contigs that were clustered are left out of the final assembly. For step (c), the orientation of each contig within its ordering is determined by taking into account the exact position of the chromatin capture link alignments on each contig. It is assumed that the likelihood of a chromatin capture link connecting two reads at a genomic distance of x is roughly 1/x for $x \geq \sim 100$ Kb. A weighted, directed, acyclic graph (WDAG) is built representing all possible ways to orient the contigs in the given order. Each edge in the WDAG corresponds to a pair of adjacent contigs in one of their four possible combined orientations, and the edge weight is set to the log-likelihood of observing the set of chromatin capture link distances between the two contigs, assuming they are immediately adjacent with the given orientation. For each contig, a quality score for its orientation is calculated as follows. The log-likelihood of the observed set of chromatin capture links between this contig, in its current orientation, and its neighbors, is found. Then the contig is flipped and the log-likelihood is calculated again. The first log-likelihood is guaranteed to be higher because of how the orientations are calculated. The difference between the log-likelihoods is taken as a quality score.

An alternative DNA triangulation method similar to Kaplan et al. can also be used in the methods disclosed herein to assemble a genome from contigs and read pairs. DNA triangulation is based upon the use of high-throughput in vivo genome-wide chromatin interaction data to infer genomic location. For the DNA triangulation method, the CTR pattern is first quantified by partitioning a genome into 100-kb bins, each representing a large virtual contig, and calculating for each placed contig its average interaction frequency with each chromosome. To evaluate localization over long ranges, interaction data of a contig with its flanking 1 mb on each side is omitted. The average interaction frequency strongly separates inter—from intrachromosomal interactions, and is highly predictive of which chromosome a contig belongs to. Next, a simple multiclass model, a naive Bayes classifier, is trained to predict the chromosome of each contig based on its average interaction frequency with each chromosome. The assembled portion of the genome is used to fit a probabilistic single-parameter exponential decay model describing the relationship between chromatin capture interaction frequency and genomic distance (the DDD pattern). In each turn, a contig is removed from the chromosome, along with a flanking region of 1 Mb on each side. It is then estimated the most likely position for each contig based upon the interaction profile and decay model. The prediction error is quantified as the absolute value of the distance between the predicted position and the actual position.

By combining the DNA triangulation method with long-insert libraries the predictability for each contig can be further improved. By knowing the chromosomal assignment and approximate location of each contig could significantly reduce the computational complexity of long-insert scaffolding, as each contig need only be paired with contigs in its vicinity; thereby resolving ambiguous contig joining, and reduce assembly errors where contigs which are located at distant regions of a chromosome or on different chromosomes, are incorrectly joined.

Example 11. Methods for Haplotype Phasing

Because the read pairs generated by the methods disclosed herein are generally derived from intra-chromosomal contacts, any read pairs that contain sites of heterozygosity will also carry information about their phasing. Using this information, reliable phasing over short, intermediate and even long (megabase) distances can be performed rapidly and accurately. Experiments designed to phase data from one of the 1000 genomes trios (a set of mother/father/offspring genomes) have reliably inferred phasing. Additionally, haplotype reconstruction using proximity-ligation similar to Selvaraj et al. (*Nature Biotechnology* 31:1111-1118 (2013)) can also be used with haplotype phasing methods disclosed herein.

For example, a haplotype reconstruction using proximity-ligation based method can also be used in the methods disclosed herein in phasing a genome. A haplotype reconstruction using proximity-ligation based method combines a proximity-ligation and DNA sequencing with a probabilistic algorithm for haplotype assembly. First, proximity-ligation sequencing is performed using a chromosome capture protocol, such as a chromatin capture protocol. These methods can capture DNA fragments from two distant genomic loci that looped together in three-dimensional space. After shotgun DNA-sequencing of the resulting DNA library, paired-end sequencing reads have 'insert sizes' that range from several hundred base pairs to tens of millions of base pairs. Thus, short DNA fragments generated in a chromatin capture experiment can yield small haplotype blocks, long fragments ultimately can link these small blocks together. With enough sequencing coverage, this approach has the potential to link variants in discontinuous blocks and assemble every such block into a single haplotype. This data is then combined with a probabilistic algorithm for haplotype assembly. The probabilistic algorithm utilizes a graph in which nodes correspond to heterozygous variants and edges correspond to overlapping sequence fragments that may link the variants. This graph might contain spurious edges resulting from sequencing errors or trans interactions. A max-cut algorithm is then used to predict parsimonious solutions that are maximally consistent with the haplotype information provided by the set of input sequencing reads. Because proximity ligation generates larger graphs than conventional genome sequencing or mate-pair sequencing, computing time and number of iterations are modified so that the haplotypes can be predicted with reasonable speed and high accuracy. The resulting data can then be used to guide local phasing using Beagle software and sequencing data from the genome project to generate chromosome-spanning haplotypes with high resolution and accuracy.

Example 12. Methods for Meta-Genomic Assembly

Microbes are collected from an environment and fixed with a fixative agent, such as formaldehyde, in order to form cross-links within the microbial cells. A plurality of contigs from the microbes is generated by using high-throughput sequencing. A plurality of read pairs are generated by using chromatin capture techniques. Read pairs that map to different contigs indicate which contigs are from the same species.

Example 13. Methods for Producing Extremely Long-Range Read Pairs (XLRPs)

Using commercially available kits, DNA was extracted to fragments sizes up to 150 kbp. The DNA was assembled into a reconstituted chromatin structure in vitro using a commercial kit from Activ Motif. The chromatin was biotinylated, fixed with formaldehyde, and immobilized onto streptavidin beads. The DNA fragments were digested with a restriction enzyme and incubated overnight. The resulting sticky ends were filled-in with an alpha-thio-dGTP and a biotinylated dCTP to generate blunt ends. The blunt ends were ligated with T4 ligase. The reconstituted chromatin was digested with a proteinase to recover the ligated DNA. The DNA was extracted from the beads and subject to an exonuclease digestion to remove biotin from unligated ends. The DNA recovered was sheared and the ends are filled-in with dNTPs. The biotinylated fragments were purified by a pull-down with streptavidin beads. Sequencing adaptors were ligated to the DNA fragments, which were PCR amplified for high-throughput sequencing to generate the extremely long-range read pairs.

Figure 22:
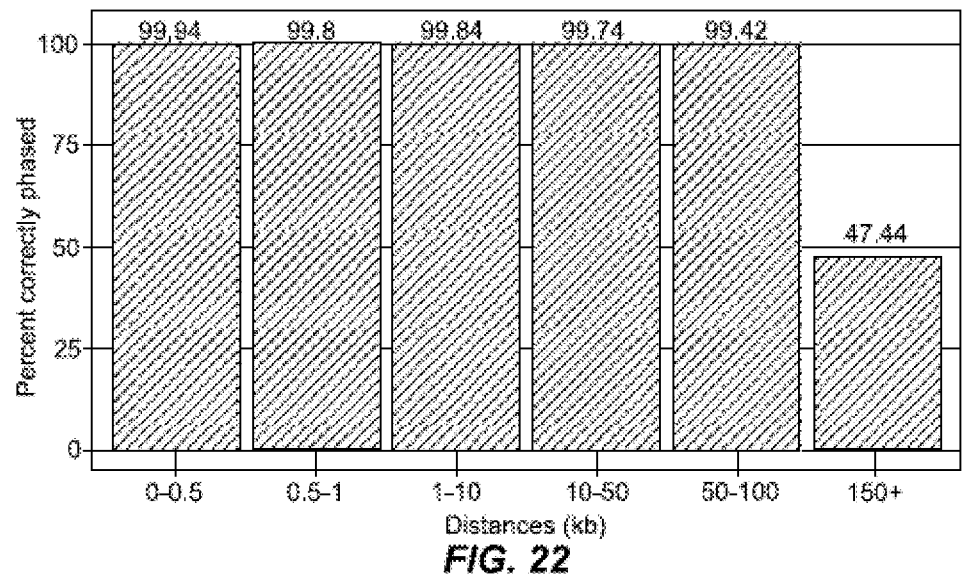
FIG. 22 illustrates the phasing accuracy for a sample with well-characterized haplotypes, NA12878. Indicated distances are those between the SNPs being phased.

The insert distribution of the extremely long-range read pairs were analyzed (FIG. 21). Further, the read pairs were used to phase heterozygous SNPs, with a greater than 99% accuracy for read pairs spanning up to 150 kb (FIG. 22).

In another example, the DNA was assembled onto nanoparticles ("Baldwin" nanoparticles) in vitro to form a DNA complex, which was then cross-linked with di-tert-butyl peroxide (DTBP). The DNA complex was digested with a restriction enzyme and incubated overnight. The resulting sticky ends were filled-in with alpha-thio-dGTP and biotinylated dCTP to generate blunt ends. The blunt ends were ligated with T4 ligase. The DNA complex was incubated in a DTT solution to reverse the crosslinks. The DNA was extracted from the nanoparticles and subject to an exonuclease digestion to remove biotin from unligated ends. The DNA recovered was sheared and the ends were filled-in with dNTPs. The biotinylated fragments were purified by a pull-down with streptavidin beads. Sequencing adaptors were ligated to the DNA fragments, which were PCR amplified for high-throughput sequencing to generate the extremely long-range read pairs.

Figure 23:
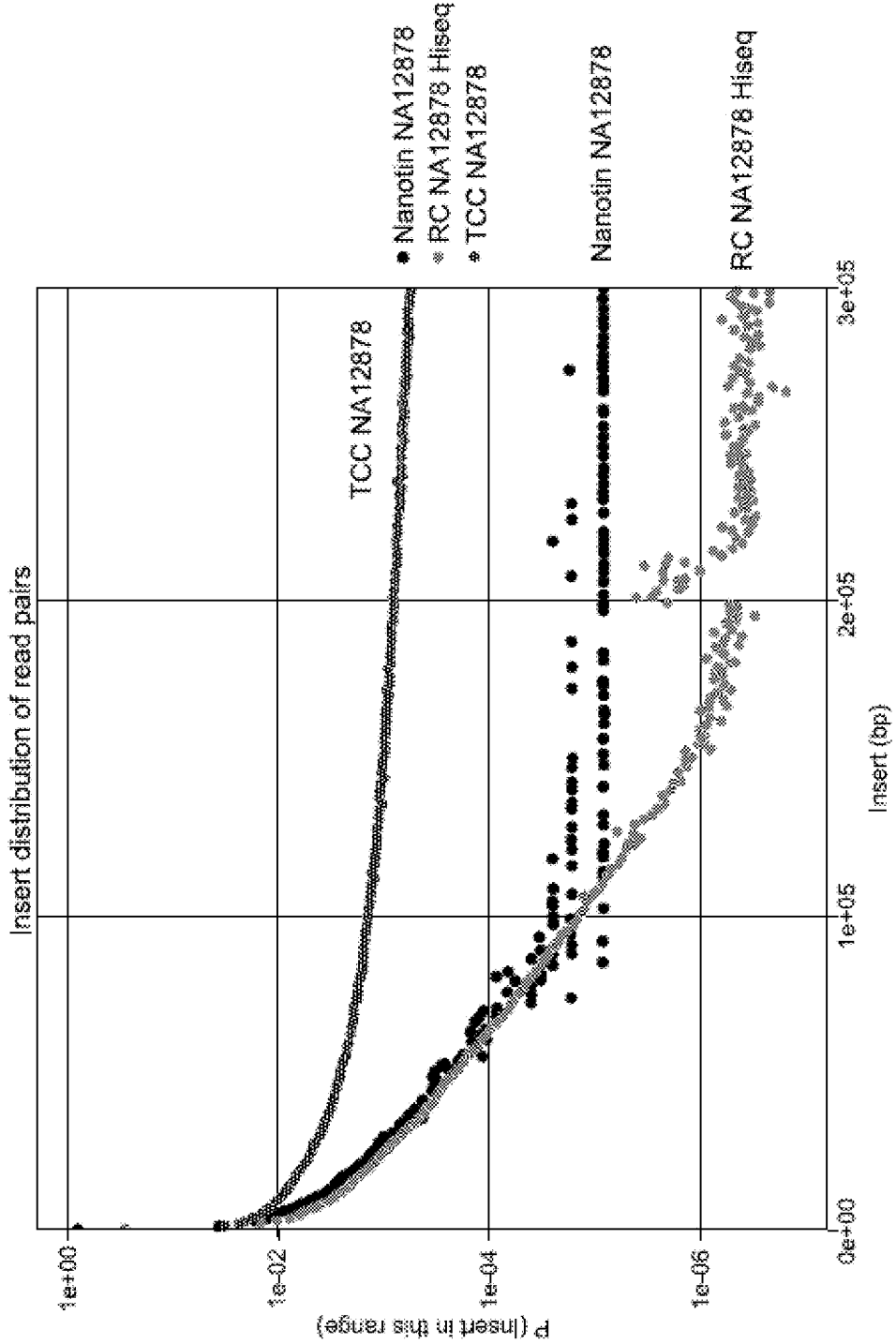
FIG. 23 illustrates the distribution of genomic distances between read pairs from a human XLRP library generated using nanoparticle-DNA complexes. The distribution of the read pairs generated using previous techniques such as TCC (tethered chromatin capture) and using reconstituted chromatin (RC) are indicated for comparison.

The read pairs generated from the nanoparticle complex (i.e. "nanotin") were analyzed (FIG. 23-25). The insert size (i.e. the distance spanned by the read pairs) for the nanoparticle complex and the reconstituted chromatin spanned up to the maximum estimated length of the input DNA fragments, suggesting that input DNA fragment size is the limiting factor in read pair separation for this method (FIG. 23). The read pairs were used to phase heterozygous SNPs, with a greater than 99% accuracy for read pairs spanning up to 100 kb (FIG. 24).

Example 14. Methods for Producing a High Quality Human Genome Assembly

With the knowledge that read pairs spanning considerable genomic distances can be generated by the disclosure, the utilization of this information for genomic assembly can be tested. The disclosure can significantly improve the linkage of de novo assemblies, potentially to chromosome-length scaffolds. An assessment can be performed on how complete an assembly can be produced and how much data will be required using the disclosure. To evaluate the efficacy of the present method for producing data that is valuable for assembly, a standard Illumina shotgun library and XLRP libraries can be built and sequenced. In one case, data from 1 Illumina HiSeq lane each of a standard shotgun library and an XLRP library are used. The data generated from each method is tested and compared with various existing assemblers. Optionally, a new assembler is also written to specifically tailor to the unique data produced by the disclosure. Optionally, a well-characterized human sample is used to provide a reference to compare the assembly produced by the present method against to assess its accuracy and completeness. Using the knowledge gained in the previous analyses, an assembler is produced to increase efficient and effective utilization the XLRP and shotgun data. A genome assembly of the quality of the December 2002 mouse genome draft, or better is generated using methods described herein.

One sample that can be used for this analysis is NA12878. DNA from sample cells are extracted using a variety of published techniques designed to maximize DNA fragment length. A standard Illumina TruSeq shotgun library and an XLRP library are each built. A single HiSeq lane of 2×150 bp sequence is obtained for each library, which may yield approximately 150 million read pairs per library. The shotgun data are assembled into contigs using algorithms for whole genome assembly. Examples of such algorithms include: Meraculous as described in Chapman et al. (PLOS ONE 6(8):e2350 (2011)) or SGA as described in Simpson et al. (Genome research 22(3):549-56 (2012)). The XLRP library reads are aligned to the contigs produced by the initial assembly. The alignments are used to further link the contigs. Once the effectiveness of the XLRP library for connecting contigs is ascertained, the Meraculous assembly is extended to integrate both the shotgun and XLRP libraries simultaneously into a single assembly process. Meraculous provides a strong foundation for the assembler. Optionally, an all-in-one assembler is produced to suit the specific needs of the disclosure. The human genome assembled by the disclosure is compared to any known sequence to evaluate the quality in the assembly of the genome.

Example 15. Methods for Phasing of Heterozygous SNPs for a Human Sample at High Accuracy from a Small Data Set In one experiment, approximately 44% of the heterozygous variants in a test human sample dataset are phased. All or nearly all phasing variants that are within one read-length's distance of a restriction site are captured. By using in silico analysis, more variants for phasing can be captured by using longer read lengths and using one or more combinations restriction enzymes for digestion. Using a combination of restriction enzymes with different restriction sites increases the proportion of the genome (and therefore heterozygous sites) that is within range of one of the two restriction sites that participate in each read pair. In silico analysis shows that the methods of the disclosure can phase more than 95% of known heterozygous positions using various combinations of two restriction enzymes. Additional enzymes and greater read lengths further increase the fraction of heterozygous sites that are observed and phased, up to a complete coverage and phasing.

Heterozygous site coverages achievable with various combinations of two restriction enzymes are calculated. The top three combinations, in terms of heterozygous sites in read proximity, are tested with the protocol. For each of these combinations, an XLRP library is produced and sequenced. The resulting reads are aligned to a human reference genome and compared to the known haplotypes of the sample to determine the accuracy of the protocol. Up to 90% or more of the heterozygous SNPs for a human sample are phased at an accuracy of 99% or greater using only 1 lane of Illumina HiSeq data. In addition, further variants are captured by increasing the read length to 300 bp. The read area around the observable restriction sites is effectively doubled. Additional restriction enzyme combinations are implemented increasing the coverage and accuracy.

Example 16. Extraction and Effects of High Molecular Weight DNA

NA up to 150 kbp was extracted with commercially available kits. FIG. 22 demonstrates that XLRP libraries can be generated from capture read pairs up to maximum fragment lengths of the extracted DNA. Accordingly, the methods disclosed herein can be expected to be capable of generating read pairs from even longer stretches of DNA. There are numerous well-developed processes for high molecular weight DNA recovery, and these methods can be used with the methods or protocols disclose herein. Using an extraction method to produce large fragment lengths of DNA, an XLRP library is created from these fragments and the read pairs that are produced can be evaluated. For example, large molecular weight DNA can be extracted by, (1) gentle lysis of the cells according to Teague et al. (Proc. Nat. Acad. Sci. USA 107(24): 10848-53 (2010)) or Zhou et al. (PLOS Genetics, 5(11):e1000711 (2009)); and (2) agarose gel plugs according to Wing et al. (The Plant Journal: for Cell and Molecular Biology, 4(5):893-8 (1993)), which references are incorporated herein in-full, including any references cited therein, or by using the Aurora System from Boreal Genomics. These methods are capable of generating long DNA fragments beyond what is routinely required for next generation sequencing; however, any other suitable methods known in the art can be substituted for achieving similar results. The Aurora System provides exceptional results and can separate and concentrate DNA from tissue or other preparations up to, and beyond, a megabase in length. DNA extractions are prepared using each of these methodologies, beginning from a single GM12878 cell culture to control for possible differences at the sample level. The size distribution of the fragments can be evaluated by pulsed field gel electrophoresis according to Herschleb et al. (*Nature Protocols* 2(3):677-84 (2007)). Using the foregoing methods, extremely large stretches of DNA can be extracted and used to build XLRP libraries. The XLRP library is then sequenced and aligned. The resulting read data are analyzed by comparing the genomic distance between read pairs to the fragment sizes observed from the gel.

Example 17. Reducing Read-Pairs from Undesired Genomic Regions

RNA complementary to the undesired genomic regions is produced by in vitro transcription and added to the reconstructed chromatin prior to crosslinking. As the supplemented RNA binds to one or more undesired genomic regions, RNA binding decreases the crosslinking efficiency at these regions. The abundance of DNA from these regions in the cross-linked complexes is thereby reduced. The reconstructed chromatin is biotinylated and immobilized, and used as described above. In some cases, the RNA is designed to target repetitive regions in the genome.

Example 18. Increasing Read-Pairs from Desired Chromatin Regions

DNA from desired chromatin regions is produced in double stranded form for gene assembly or haplotyping. Representation of DNA from undesired regions is accordingly reduced. Double-stranded DNA from desired chromatin regions is generated by primers that tile at such regions in multi-kilobase intervals. In other implementations of the method, the tiling intervals are varied to address desired regions of different sizes with desired replication efficiency. Primer binding sites across the desired regions are contacted with primers, optionally by melting the DNA. New strands of DNA are synthesized using the tiled primers. Undesired regions are reduced or eliminated, for example by targeting these regions with an endonuclease specific to singlestranded DNA. The remaining desired regions can be optionally amplified. The prepared sample is subjected to the sequencing library preparation methods as described elsewhere herein. In some implementations, read-pairs spanning distances up to the length of each desired chromatin regions are generated from each such desired chromatin region.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of mapping a sequence to a nucleic acid molecule, comprising the steps of:
obtaining a nucleic acid sample comprising a first nucleic acid molecule comprising a first region and a second region;
crosslinking said nucleic acid sample outside of a cell such that said first region and said second region of said first nucleic acid molecule are bound independently of a phosphodiester backbone of said first nucleic acid molecule;
fragmenting said nucleic acid sample to produce at least one double strand break between said first region and said second region of said first nucleic acid molecule;
contacting said nucleic acid sample to a population of oligonucleotides comprising a first plurality of oligonucleotides,
wherein each of said first plurality of oligonucleotides comprises a) a 3' annealing region capable of annealing to said double strand break, and b) a first molecular tag sequence 5' of said 3' annealing region, and
wherein at least one of said first plurality of oligonucleotides anneals to one or more nucleotides on either side of said double strand break of said first nucleic acid molecule;
ligating each side of said double strand break to at least one of said first plurality of oligonucleotides to form a ligation product;
recovering said first nucleic acid molecule; and
sequencing said ligation product;
wherein a first sequence read comprising said first molecular tag sequence corresponds to a sequence of said first nucleic acid molecule.

2. The method of claim 1, wherein a second sequence comprising said first molecular tag corresponds to a sequence of said first nucleic acid molecule.

3. The method of claim 1, wherein said nucleic acid sample is subjected to fragmentation prior to said crosslinking.

4. The method claim 1, wherein said population of oligonucleotides comprises a second plurality of oligonucleotides, wherein each of said second plurality of oligonucleotides comprises
a) a 3' annealing region capable of annealing to said double strand break, and b) a second molecular tag sequence 5' of said 3' annealing region, having a sequence different from that of said first molecular tag.

5. The method of claim 4, wherein said second plurality of oligonucleotides is spatially separate from said first plurality of oligonucleotides.

6. The method claim 1, wherein said population of oligonucleotides is attached to a solid surface.

7. The method of claim 6, wherein said solid surface is a nucleic acid array.

8. The method of claim 1, wherein said fragmenting is conducted enzymatically.

9. The method of claim 8, wherein said fragmenting is conducted enzymatically in vitro.

10. The method of claim 8, wherein said fragmenting is conducted enzymatically with one or more restriction enzymes.

11. The method of claim 8, wherein said fragmenting is conducted enzymatically with a DNase.

12. The method of claim 8, wherein said fragmenting is conducted enzymatically with a transposase.

13. The method of claim 8, wherein said fragmenting is conducted enzymatically with a nicking enzyme.

14. The method of claim 1, wherein said fragmenting is conducted mechanically.

15. The method of claim 14, wherein said fragmenting is conducted mechanically with hydro-shear.

16. The method of claim 14, wherein said fragmenting is conducted mechanically with sonication.

17. The method of claim 14, wherein said fragmenting is conducted mechanically with nebulization.

18. The method of claim 1, further comprising, prior to said recovering said first nucleic acid molecule, ligating said ligation product to a second double strand break of said first nucleic acid molecule.

19. The method of claim 1, wherein said recovering comprises protein removal.

20. The method of claim 19, wherein said protein removal comprises protease treatment.

21. The method of claim 1, wherein said recovering comprises crosslink reversal.

22. The method of claim 1, wherein said recovering comprises capturing.

23. The method of claim 22, wherein said capturing comprises capturing via affinity label.

* * * * *